(12) United States Patent
Warrington et al.

(10) Patent No.: US 11,890,260 B2
(45) Date of Patent: Feb. 6, 2024

(54) COMPOSITIONS FOR TREATING ACNE AND DERMATOLOGICAL CONDITIONS

(71) Applicant: Ilera Derm LLC, Plymouth Meeting, PA (US)

(72) Inventors: Brian Warrington, Plymouth Meeting, PA (US); Karyn Grossman, Plymouth Meeting, PA (US); Oludare Odumosu, Plymouth Meeting, PA (US); Zoltan Kerekes, Plymouth Meeting, PA (US)

(73) Assignee: Ilera Derm LLC, Plymouth Meeting, PA (US)

( * ) Notice: Subject to any disclaimer, the term of this patent is extended or adjusted under 35 U.S.C. 154(b) by 0 days.

(21) Appl. No.: 17/385,454

(22) Filed: Jul. 26, 2021

(65) Prior Publication Data

US 2021/0361591 A1    Nov. 25, 2021

Related U.S. Application Data

(63) Continuation of application No. PCT/US2021/033908, filed on May 24, 2021.

(60) Provisional application No. 63/162,850, filed on Mar. 18, 2021, provisional application No. 63/028,857, filed on May 22, 2020.

(51) Int. Cl.
| | | |
|---|---|---|
| A61K 31/05 | (2006.01) | |
| A61K 31/455 | (2006.01) | |
| A61P 17/10 | (2006.01) | |
| A61K 31/366 | (2006.01) | |
| A61K 31/4172 | (2006.01) | |

(52) U.S. Cl.
CPC ............ *A61K 31/05* (2013.01); *A61K 31/366* (2013.01); *A61K 31/4172* (2013.01); *A61K 31/455* (2013.01); *A61P 17/10* (2018.01)

(58) Field of Classification Search
CPC .... A61K 31/05; A61K 31/366; A61K 31/455; A61P 17/10
See application file for complete search history.

(56) References Cited

U.S. PATENT DOCUMENTS

| | | |
|---|---|---|
| 2,798,053 A | 7/1957 | Brown |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,087,445 A | 2/1992 | Haffey et al. |
| 5,100,660 A | 3/1992 | Hawe et al. |
| 7,344,736 B2 | 3/2008 | Whittle et al. |
| 9,447,019 B2 | 9/2016 | Mechoulam et al. |
| 9,814,670 B2 | 11/2017 | Gan et al. |
| 2007/0072939 A1 | 3/2007 | Kupper |
| 2008/0182234 A1 | 7/2008 | Van Eyk et al. |
| 2010/0080764 A1 | 4/2010 | Fox |
| 2014/0248379 A1* | 9/2014 | Mueller .............. A61K 36/185 424/725 |
| 2015/0320698 A1 | 11/2015 | Whalley et al. |
| 2016/0010126 A1 | 1/2016 | Poulos et al. |
| 2016/0120781 A1 | 5/2016 | Powell |
| 2017/0008868 A1 | 1/2017 | Dialer et al. |
| 2018/0021247 A1 | 1/2018 | Ghalili et al. |
| 2018/0042890 A1 | 2/2018 | Sinai et al. |
| 2019/0031601 A1 | 1/2019 | ElSohly et al. |
| 2019/0040031 A1 | 2/2019 | Nakajima |
| 2019/0078168 A1 | 3/2019 | Sayre et al. |
| 2019/0160393 A1 | 5/2019 | Marshall et al. |
| 2019/0231833 A1 | 8/2019 | Garti et al. |

FOREIGN PATENT DOCUMENTS

| | | |
|---|---|---|
| CN | 110812304 A | 2/2020 |
| EP | 2 578 561 A1 | 4/2013 |
| WO | WO 2004/016277 A2 | 2/2004 |
| WO | WO 2008/010241 A1 | 1/2008 |
| WO | WO 2017/139496 A1 | 8/2017 |
| WO | WO 2018/094183 A1 | 5/2018 |
| WO | WO 2019/020738 A1 | 1/2019 |

OTHER PUBLICATIONS

Hill et al. "Meat Intake and the Dose of Vitamin B3—Nicotinamide: Cause of the Causes of Disease Transitions, Health Divides, and Health Futures?", International Journal of Tryptophan Research. 2017; 10:1-22. (Year: 2017).*
Ey et al. "Dietary Sources and Antioxidant Effects of Ergothioneine". Journal of Agricultural and Food Chemistry. 2007; 55:6466-6474. (Year: 2007).*
Aon et al., "Mitochondrial and cellular mechanisms for managing lipid excess," *Frontiers in Physiology* 5(282), 2014. (13 pages).
Bastian et al., Anti-aging effects of ellagitannin metabolites, urolithins, on the skin, Department of Nutritional Science—Conference: 8th International Conference on Polyphenols and HealthAt: Quebec, CanadaAffiliation: Okayama Prefectural University, Oct. 2017. (21 pages).
Beere, "'The stress of dying': the role of heat shock proteins in the regulation of apoptosis," *Journal of Cell Science* 117(13):2641-2651, 2004.
Benet et al., "BDDCS, the Rule of 5 and drugability," *Advanced Drug Delivery Reviews* 101:89-98, 2016.
Berenbaum, "What is Synergy?" *Pharmacological Reviews* 41(2):93-141, 1989.
Bih et al., "Molecular Targets of Cannabidiol in Neurological Disorders," *Neurotherapeutics* 12:699-730, 2015.
Bingol et al., "The mitochondrial deubiquitinase USP30 opposes parkin-mediated mitophagy," *Nature* 510, 2014. (27 pages).
Bliss, C. I., "The Toxicity of Poisons Applied Jointly," *Annals of Applied Biology* 26(3):585-615, 1939.
Bloomfield et al., "The effects of acute cannabidiol on cerebral blood flow and its relationship to memory: An arterial spin labelling magnetic resonance imaging study," *Journal of Psychopharmacology* 34(9):981-989, 2020.

(Continued)

*Primary Examiner* — Kamal A Saeed

(57) ABSTRACT

The present disclosure generally relates to compositions comprising unique combinations of cannabinoids, antioxidants, and cofactors. The present disclosure also provides methods of making the compositions and methods for using the compositions for the treatment of mitochondrial ATP deficit disorders.

5 Claims, 38 Drawing Sheets

(56) References Cited

OTHER PUBLICATIONS

Canto et al., "The NAD+ Precursor Nicotinamide Riboside Enhances Oxidative Metabolism and Protects against High-Fat Diet-Induced Obesity," *Cell Metabolism* 15:838-847, 2012.

Carter et al., "Methods to detect mitophagy in neurons during disease," *Journal of Neuroscience Methods* 325:108351, 2019. (7 pages).

CBD Serum—Be. Clinical Spa: Medical Spa & Skin Care, Be. Clinical Spa | Medical Spa & Skin Care, published on Sep. 13, 2021, retrieved from https://beclinicalspa.com/product/cbd-serum/ on Oct. 18, 2021. (7 pages).

Chakravorty et al., "Dysfunctional Mitochondria and Mitophagy as Drivers of Alzheimer's Disease Pathogenesis," *Frontiers in Aging Neuroscience* 11(311), 2019. (16 pages).

Cheah et al., "Administration of Pure Ergothioneine to Healthy Human Subjects: Uptake, Metabolism, and Effects on Biomarkers of Oxidative Damage and Inflammation," *Antioxidants & Redox Signaling* 26(5), 2017. (14 pages).

Colica et al., "Antioxidant Effects of a Hydroxytyrosol-Based Pharmaceutical Formulation on Body Composition, Metabolic State, and Gene Expression: A Randomized Double-Blinded, Placebo-Controlled Crossover Trial," *Hindawi, Oxidative Medicine and Cellular Longevity* 2017(2473495), 2017. (14 pages).

Cornelissen et al., "The deubiquitinase USP15 antagonizes Parkin-mediated mitochondrial ubiquitination and mitophagy," *Human Molecular Genetics* 23(19): 5227-5242, 2014.

Di Marzo, "New approaches and challenges to targeting the endocannabinoid system," *Nature Reviews, Drug Discovery*, Advance Online Publication, 2018. (17 pages).

Fang et al., "Defective Mitophagy in XPA via PARP-1 Hyperactivation and NAD+/SIRT1 Reduction," *Cell* 157:882-896, 2014.

Fang et al., "Mitophagy inhibits amyloid-β and tau pathology and reverses cognitive deficits in models of Alzheimer's disease," *Nature Neuroscience* 22: 401-412, 2019.

Fišar et al., "Cannabinoid-induced changes in respiration of brain mitochondria," *Toxicology Letters* 231: 62-71, 2014.

Fivenson et al., "Mitophagy in neurodegeneration and aging," *Neurochemistry International* 109: 202-209, 2017.

Gerö et al., "The novel mitochondria-targeted hydrogen sulfide (H2S) donors AP123 and AP39 protect against hyperglycemic injury in microvascular endothelial cells in vitro," *Pharmacological Research* 113: 186-198, 2016.

Gong et al., "Nicotinamide riboside restores cognition through an upregulation of proliferator-activated receptor-g coactivator la regulated b-secretase 1 degradation and mitochondrial gene expression in Alzheimer's mouse models," *Neurobiology of Aging*, 34(6):1581-1588, 2013.

Ianevski et al., "SynergyFinder: a web application for analyzing drug combination dose-response matrix data," *Bioinformatics*, 33(15):2413-2415, 2017.

Ianevski et al., "SynergyFinder 2.0: visual analytics of multi-drug combination synergies," *Nucleic Acids Research* 48: W488-W493, 2020.

International Search Report and Written Opinion dated Aug. 25, 2021, for International Application No. PCT/US2021/033908, 14 pages.

Jeong et al., "Cannabidiol promotes apoptosis via regulation of XIAP/Smac in gastric cancer," *Cell Death and Disease* 10:846, 2019. (13 pages).

Katsyuba et al., "NAD+ homeostasis in health and disease," *Nature Metabolism* 2: 9-31, 2020.

Kerr et al., "Mitophagy and Alzheimer's disease: cellular and molecular mechanisms," *Trends Neurosci.* 40(3): 151-166, 2017.

Kluge et al., "Novel highly selective inhibitors of ubiquitin specific protease 30 (USP30) accelerate mitophagy," *Bioorganic & Medicinal Chemistry Letters* 28:2655-2659, 2018.

Lanevski et al., "SynergyFinder: a web application for analyzing drug combination dose-response matrix data," *Bioinformatics*, 33(15):2413-2415, 2017.

Lee et al., "Cannabidiol regulation of emotion and emotional memory processing: relevance for treating anxiety-related and substance abuse disorders," *British Journal of Pharmacology* 174: 3242-3256, 2017.

Lipinski et al., "Experimental and computational approaches to estimate solubility and permeability in drug discovery and development settings," *Advanced Drug Delivery Reviews* 46:3-26, 2001.

Lipinski, "Drug-like properties and the causes of poor solubility and poor permeability," *Journal of Pharmacological and Toxicological Methods* 44:235-249, 2000.

Liu et al., "Nicotinamide forestalls pathology and cognitive decline in Alzheimer mice: evidence for improved neuronal bioenergetics and autophagy procession," *Neurobiology of Aging* 34:1564-1580, 2013.

Loewe, S. "The problem of synergism and antagonism of combined drugs." *Arzneimittelforschung* 3: 285-290, 1953.

Markova et al., "Skin cells and tissue are capable of using L-ergothioneine as an integral component of their antioxidant defense system," *Free Radical Biology & Medicine* 46:1168-1176, 2009.

McPartland et al., "Are cannabidiol and Δ9-tetrahydrocannabivarin negative modulators of the endocannabinoid system? A systematic review," *British Journal of Pharmacology* 172: 737-753, 2015.

Miller et al., "Therapeutic approaches to enhance PINK1/Parkin mediated mitophagy for the treatment of Parkinson's disease," *Neuroscience Letters* 705: 7-13, 2019.

Namdar et al., "Medical Cannabis for the Treatment of Inflammation," *Natural Product Communications* 13(3): 249-254, 2018.

Oláh et al., "Cannabidiol exerts sebostatic and anti-inflammatory effects on human sebocytes," *The Journal of Clinical Investigation*, 124(9):3713-3724, 2014.

Palikaras et al., "Mechanisms of mitophagy in cellular homeostasis, physiology and pathology," *Nature Cell Biology* 20:1013-1022, 2018.

Palikaras et al., "Mitophagy Modulators," *Encyclopedia of Biomedical Gerontology*, 2018. (13 pages).

Partridge et al., "The quest to slow ageing through drug discovery," *Nature Reviews, Drug Discovery*19, Aug. 2020.

Pellati et al., "*Cannabis sativa* L. and Nonpsychoactive Cannabinoids: Their Chemistry and Role against Oxidative Stress, Inflammation, and Cancer," *Hindawi, BioMed Research International* 1691428, 2018. (16 pages).

Rimmerman et al., "Direct modulation of the outer mitochondrial membrane channel, voltage-dependent anion channel 1 (VDAC1) by cannabidiol: a novel mechanism for cannabinoid-induced cell death," *Cell Death and Disease* 4: e949, 2013. (11 pages).

Russo et al., "A tale of two cannabinoids: The therapeutic rationale for combining tetrahydrocannabinol and cannabidiol," *Medical Hypotheses* 66:234-246, 2006.

Ryan et al., "Cannabidiol Targets Mitochondria to Regulate Intracellular Ca2+ Levels," *The Journal of Neuroscience* 29(7):2053-2063, 2009.

Schuetz et al., "Cannabigerol (CBG): The Mother of Cannabinoids Demonstrates a Broad Spectrum of Anti-inflammatory, Antioxidant and Antimicrobial Properties Important for Skin Health," Willow Biosciences, Suite 202, 1201 5th Street SW, Calgary, Alberta, Canada; Signum Biosciences Inc., Monmouth Junction, NJ, USA, 2021. (1 page.).

Sephora, Enlightenment Serum with Niacinamide + 100mg CBD—Prima, retreaved from https://www.sephora.com/product/prima-enlightenment-serum-concentrated-cbd-serum-booster-for-vital-hydranon even-skin-toner-P456214 Oct. 18, 2021. (5 pages).

Singh et al., "Cannabinoid-Induced Changes in the Activity of Electron Transport Chain Complexes of Brain Mitochondria," *J. Mol. Neurosci.* 56:926-931, 2015.

Snaidr et al., "Nicotinamide for photoprotection and skin cancer chemoprevention: A review of efficacy and safety," *Experimental Dermatology* 28:15-22, 2019.

Snigdha et al., "Effect of mitochondrial cofactors and antioxidants supplementation on cognition in the aged canine," *Neurobiology of Aging* 37:171-178, 2016.

Sorci et al., "Nicotinamide mononucleotide synthetase is the key enzyme for an alternative route of NAD biosynthesis in Francisella tularensis," *PNAS* 106(9):3083-3088, 2009.

(56) References Cited

OTHER PUBLICATIONS

Sun et al., "Measuring In Vivo Mitophagy," *Molecular Cell* 60: 685-696, 2015.

Ter Chemicals, Sun protection & care, UV-filters & Care Ingredients, Formulation brochure, 124, 129 Apr. 2015 [retrieved on Jul. 21, 2021]. Retrieved from the Internet:URL:https://www.terchemicals.com/fileadmin/downloads/product_information/Sun-Protection-Care-Formulation-Brochure-WEB-version.pdf . (20 pages).

Varkuti et al., "Neuron-based high-content assay and screen for CNS active mitotherapeutics," *Science Advances*, Jan. 8, 2020. (17 pages).

Yadav et al., "Searching for Drug Synergy in Complex Dose-Response Landscapes Using an Interaction Potency Model," *Computational and Structural Biotechnology Journal* 13:504-513, 2015.

Zapata-Perez et al., "Enzyme engineering to fight mitochondrial diseases," *Nature Metabolism*, Feb. 17, 2020. (2 pages).

\* cited by examiner

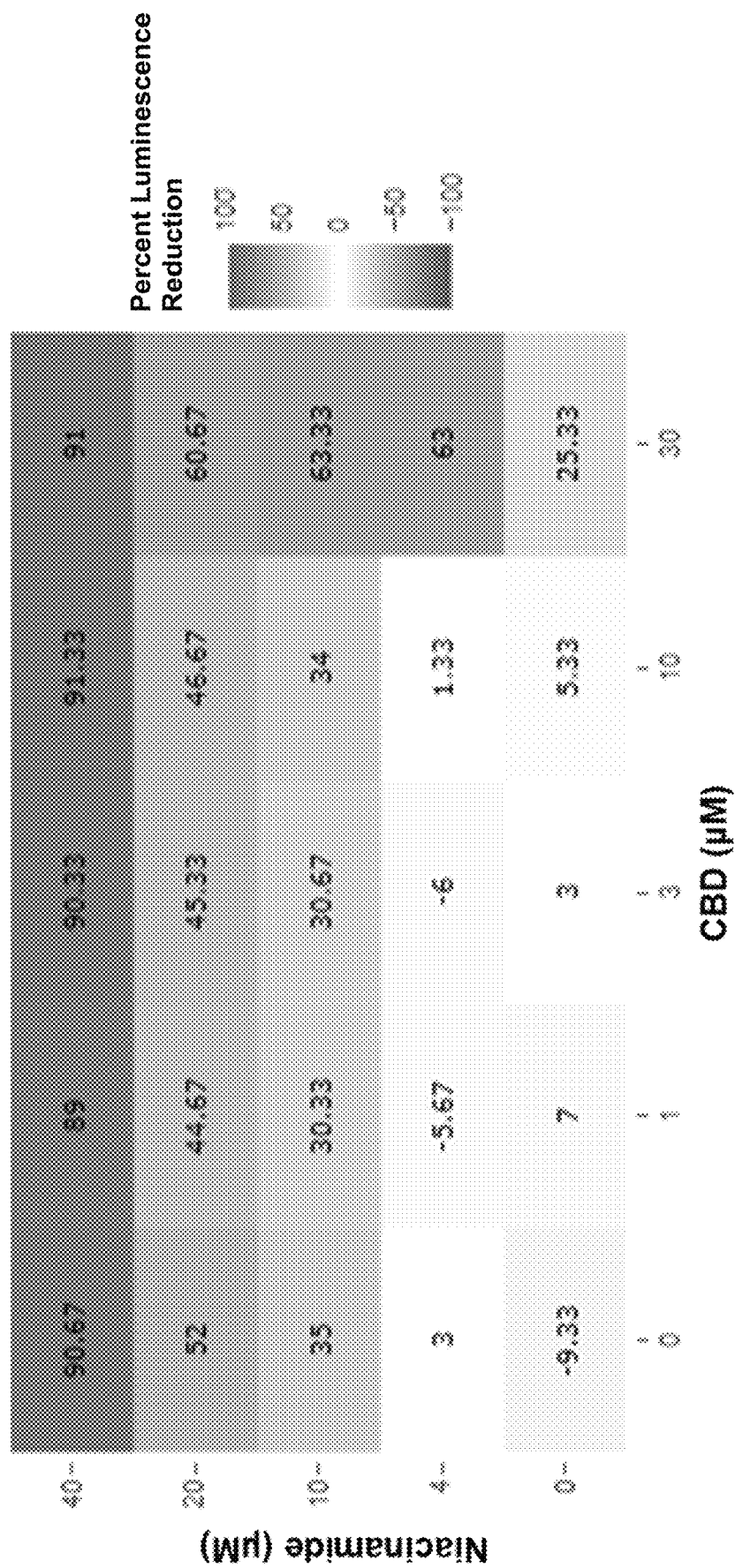

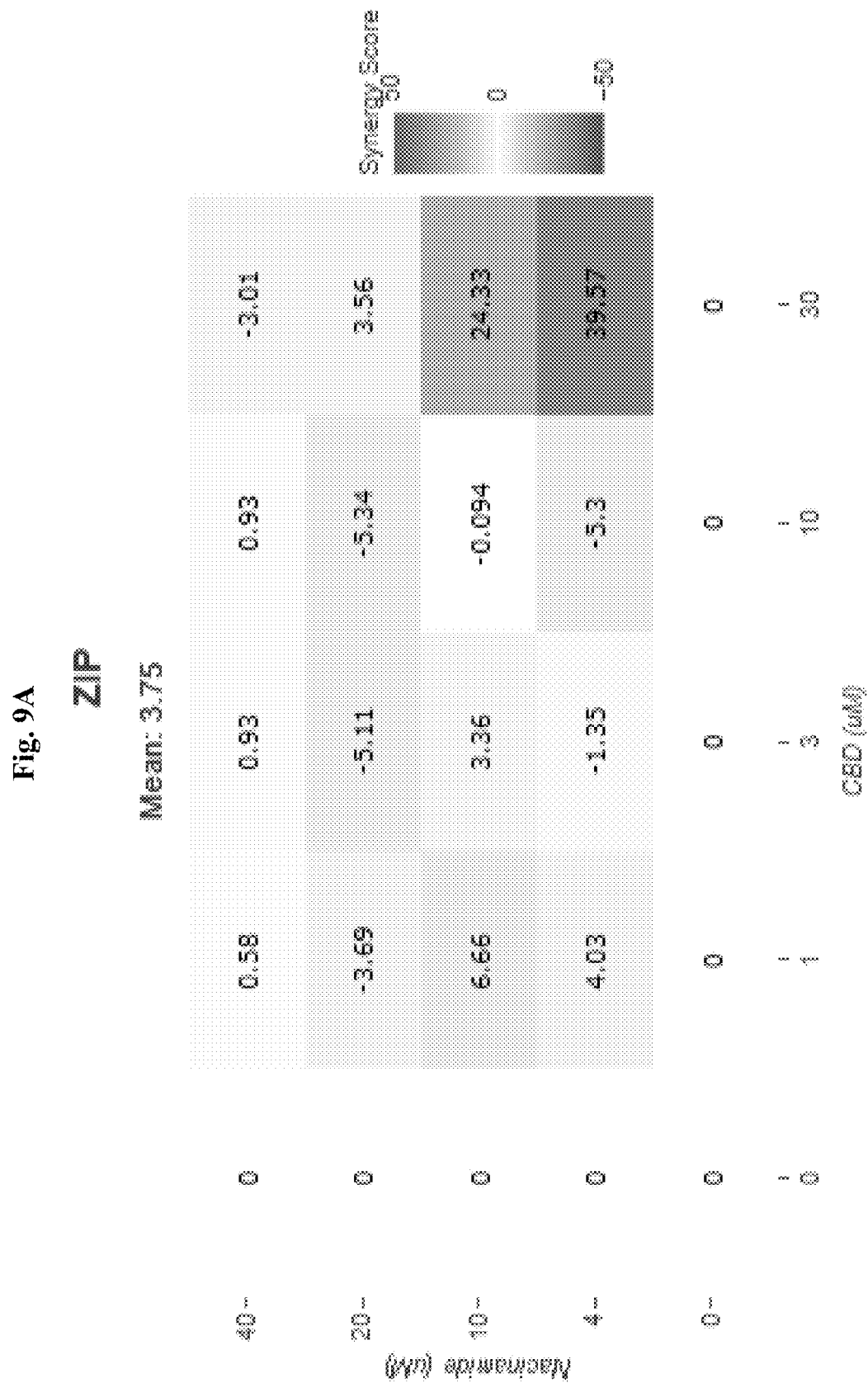

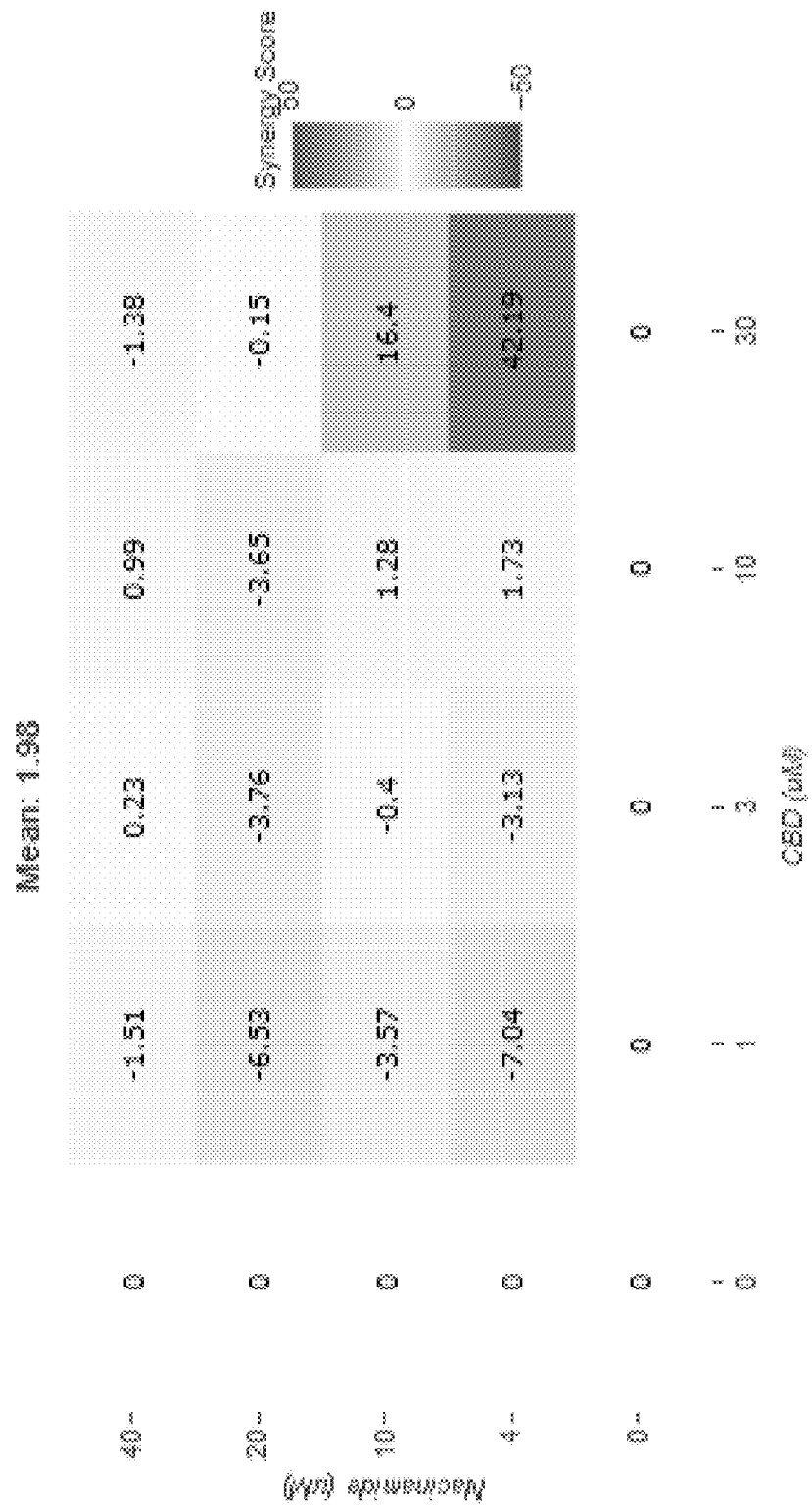

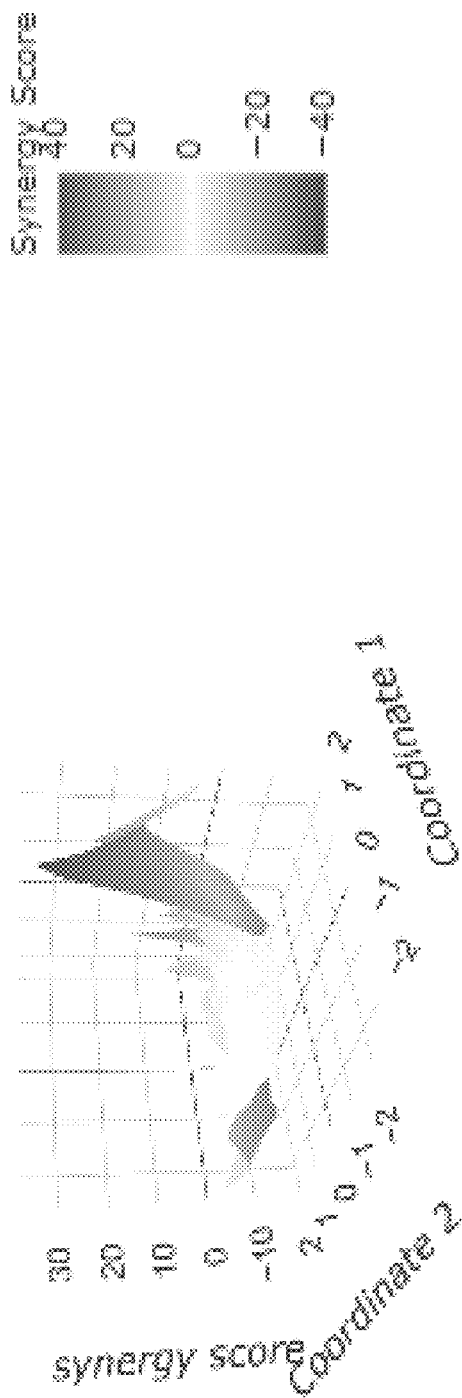
Fig. 10A ZIP

Fig. 12A
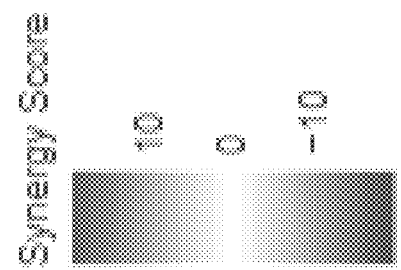
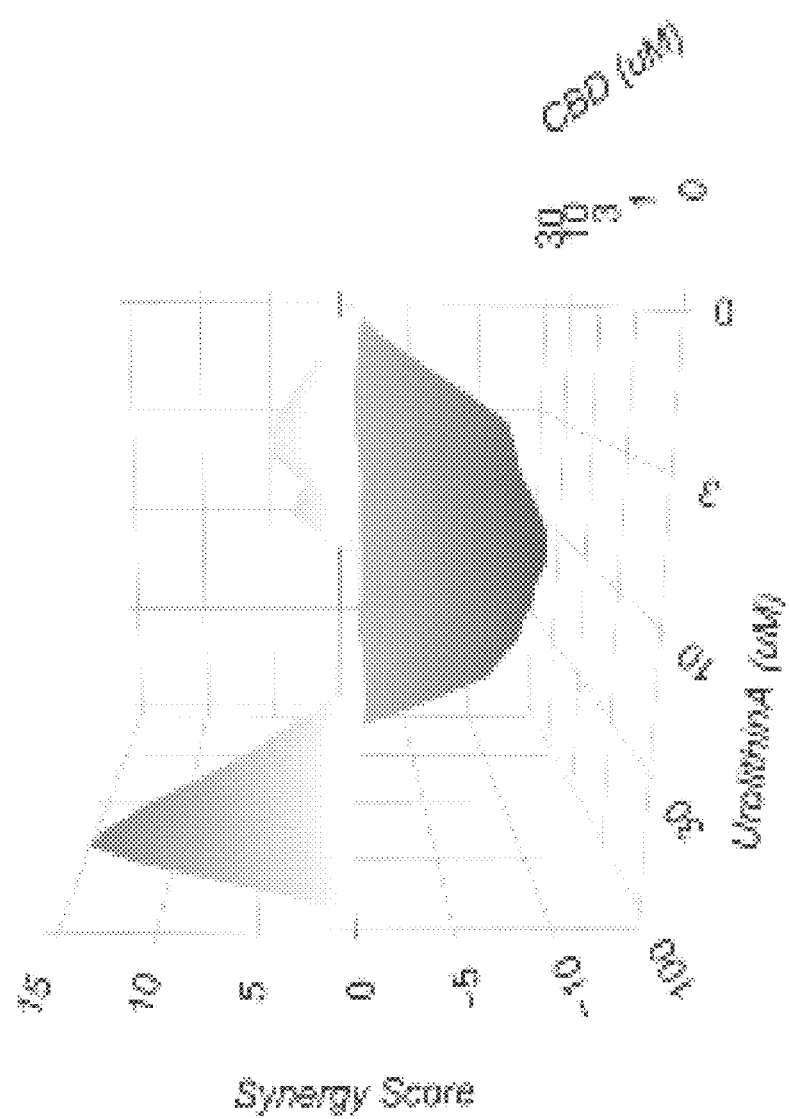

Fig. 12D
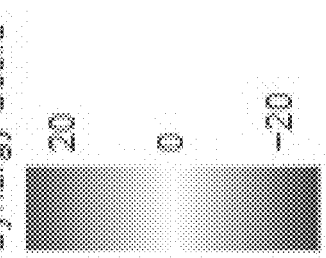
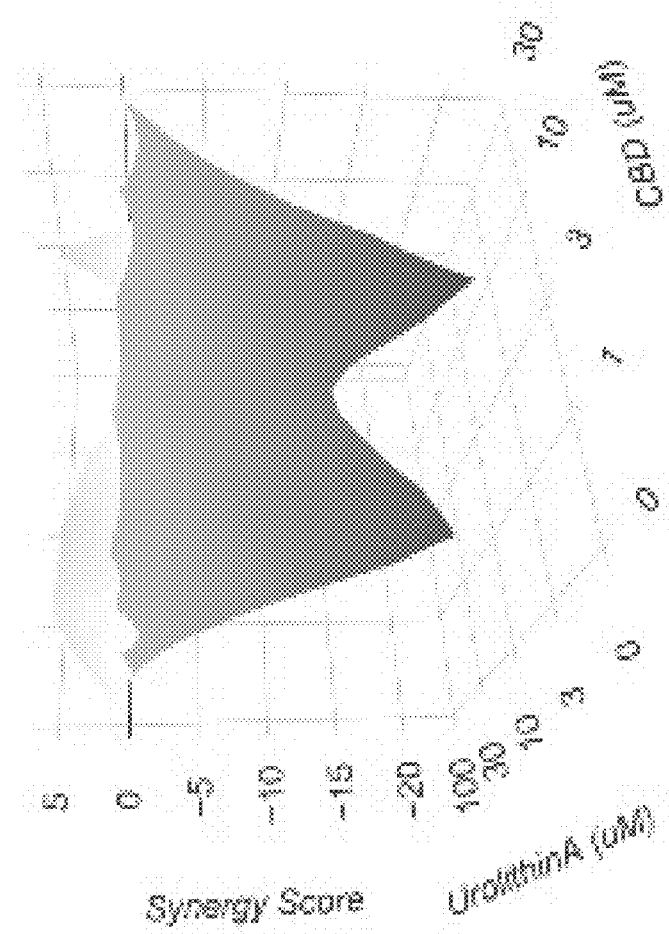

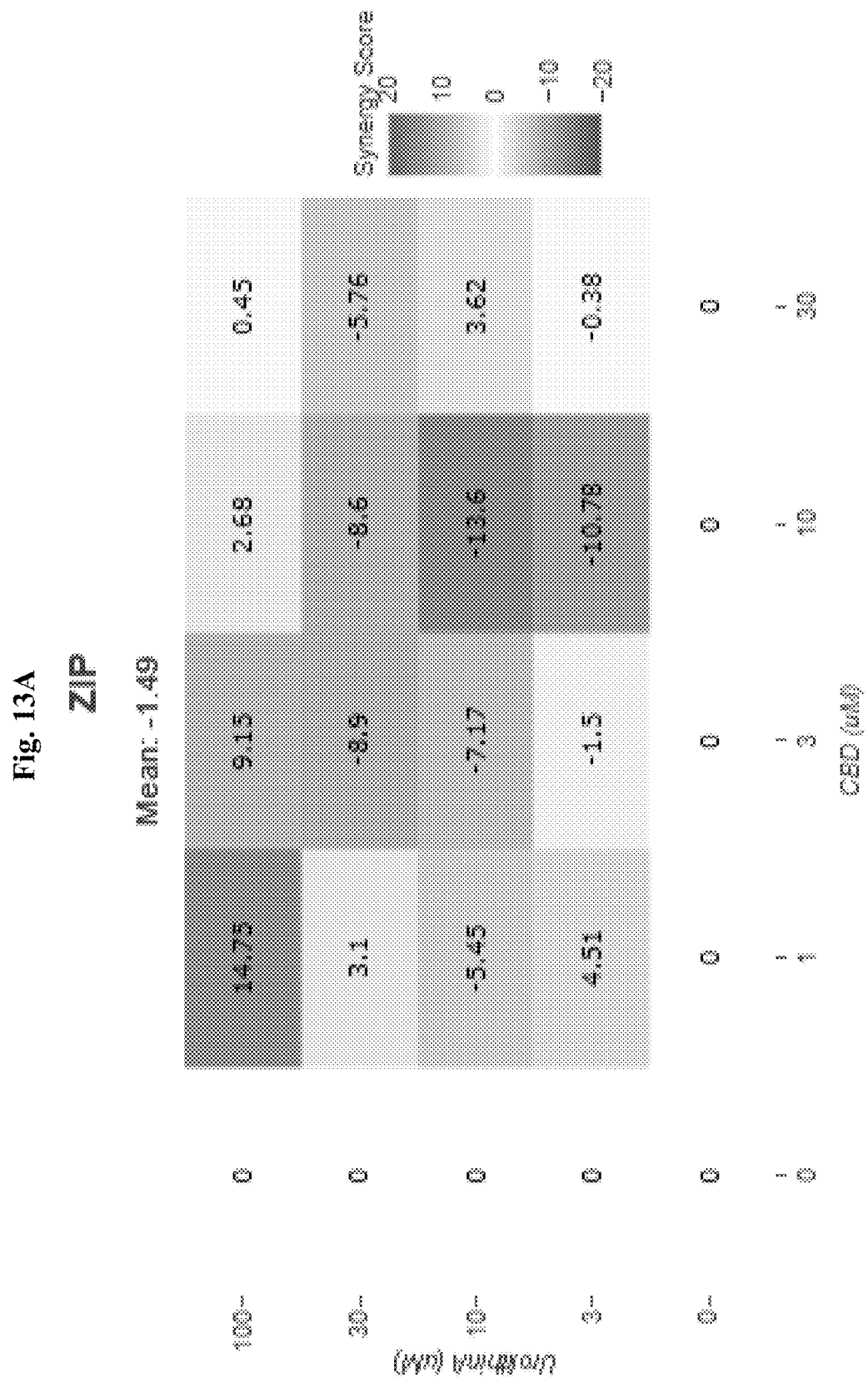

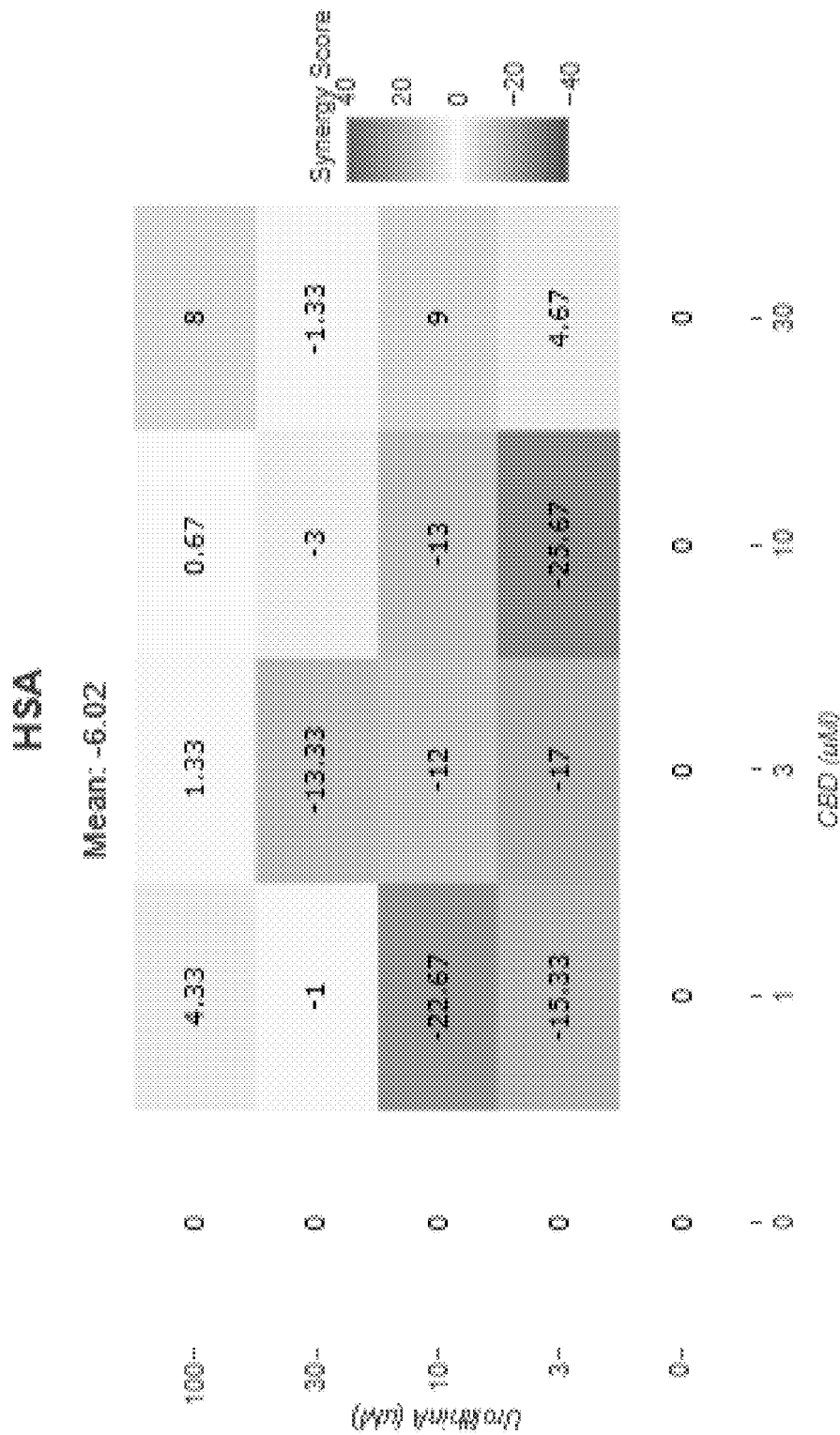

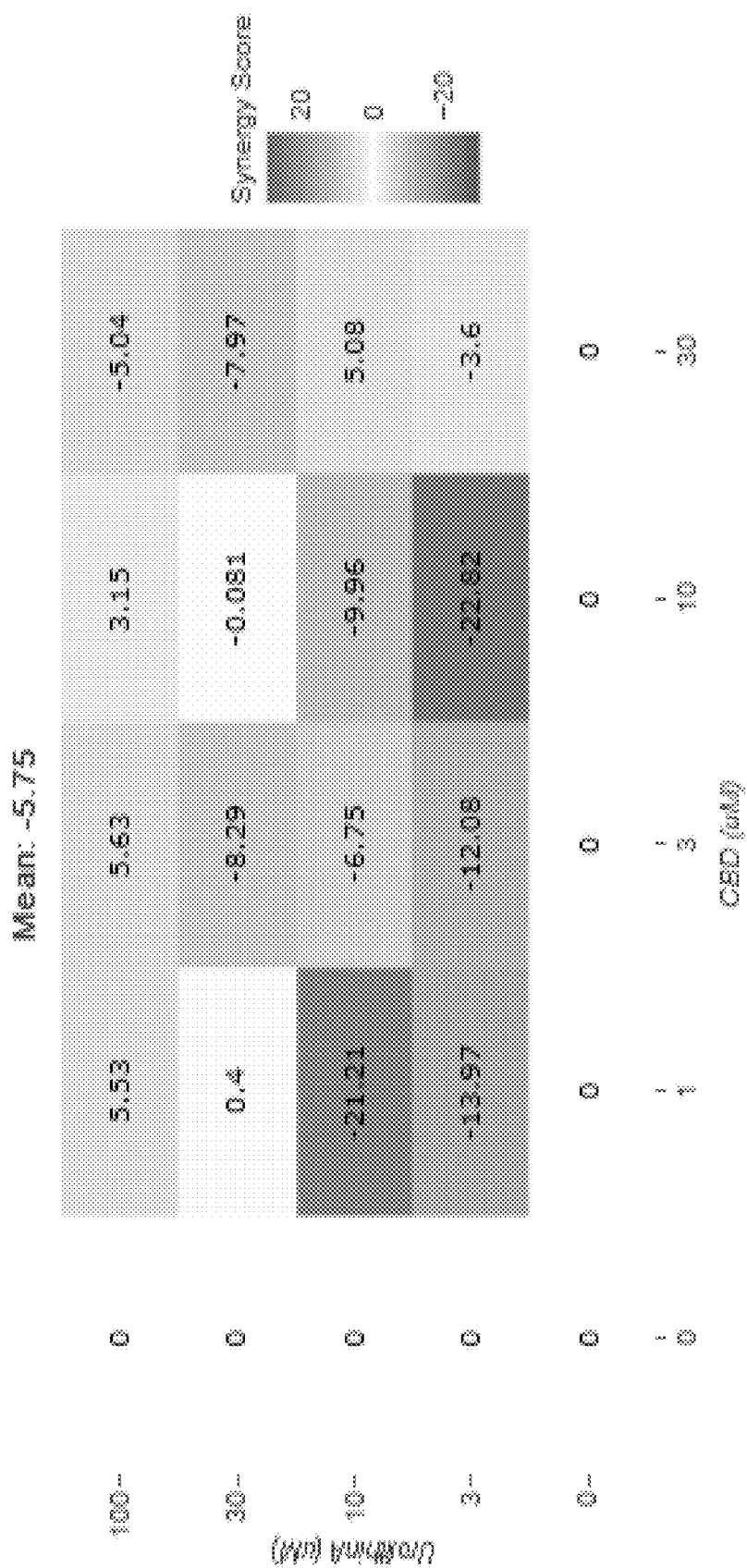

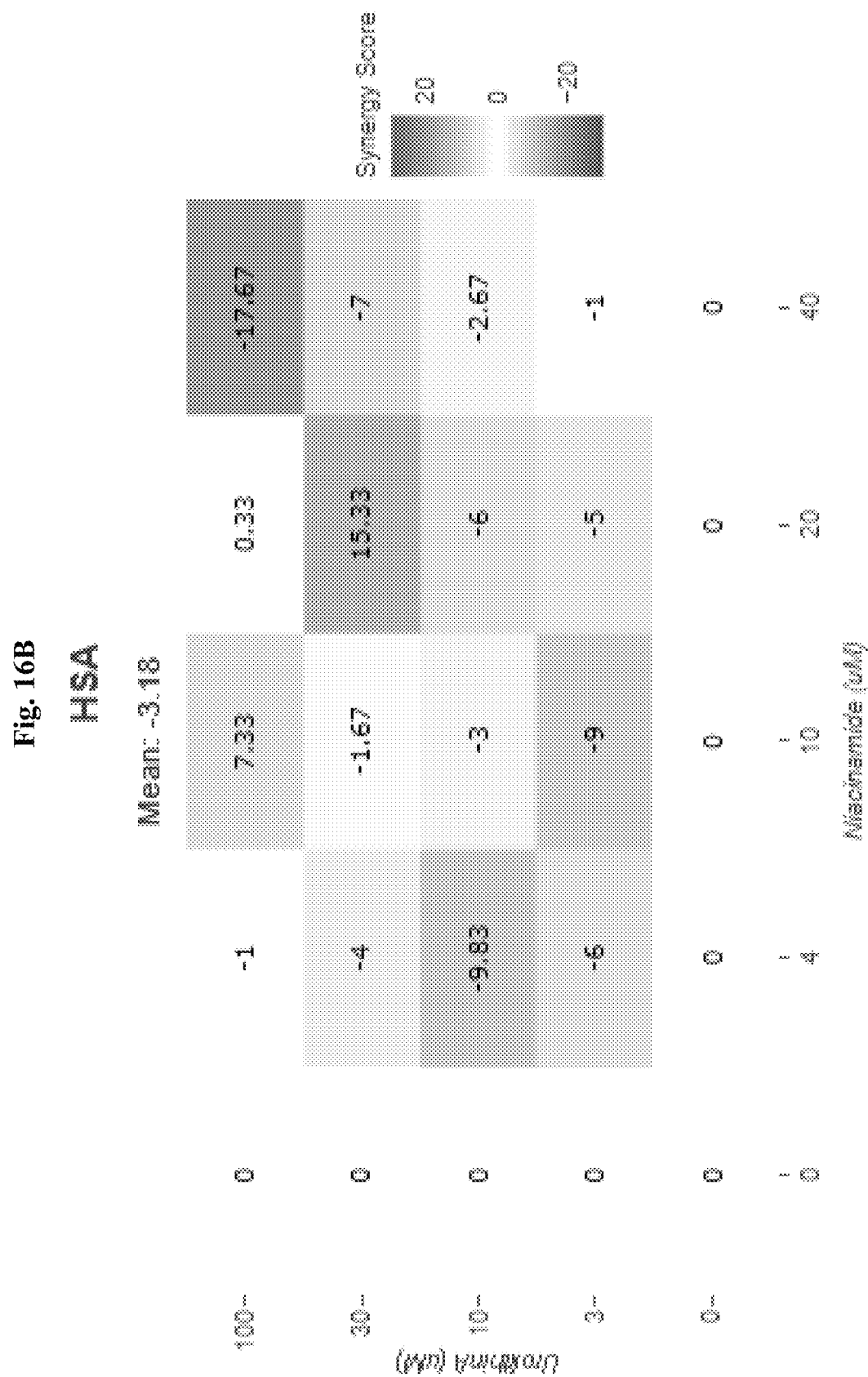

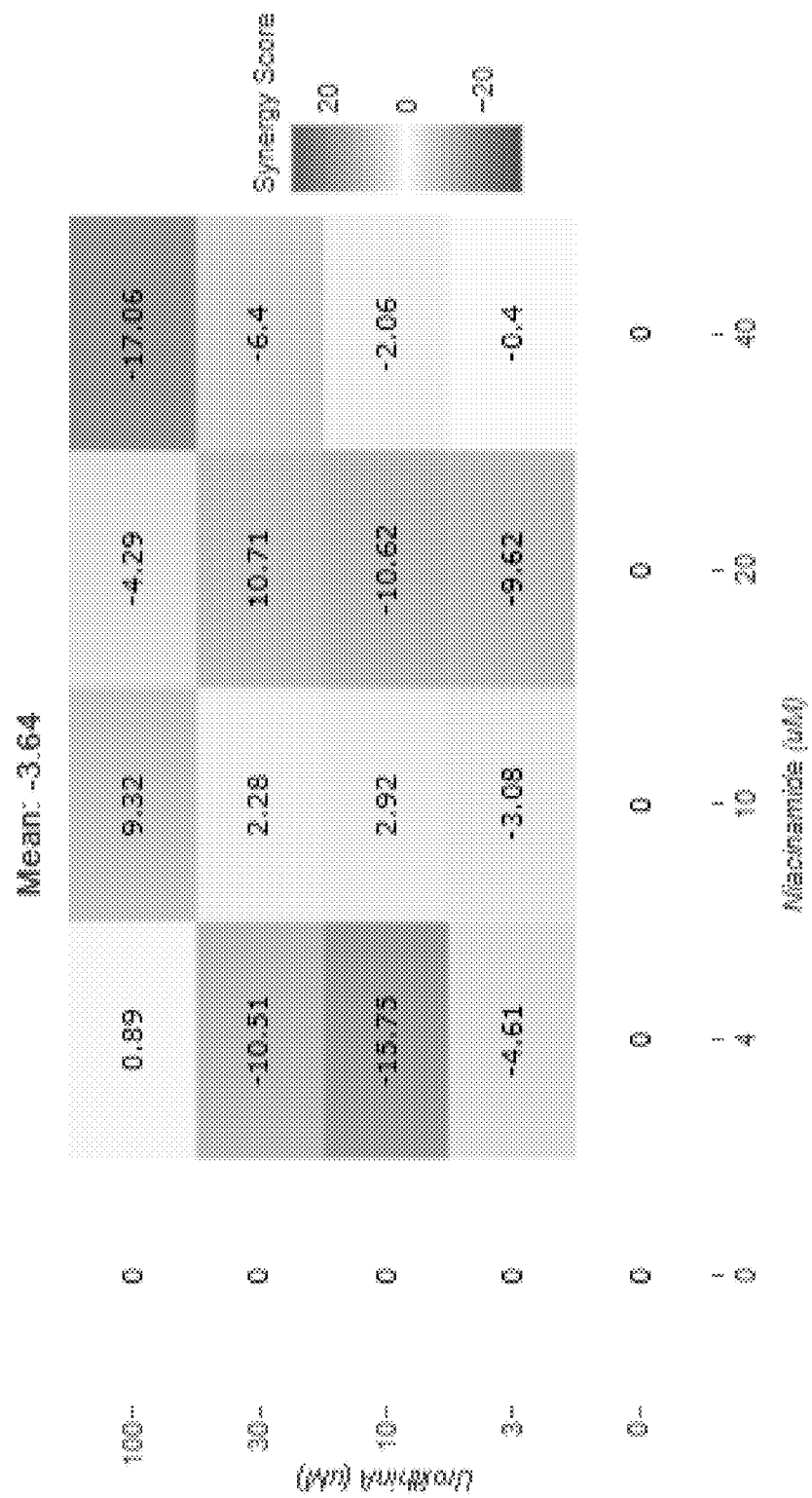

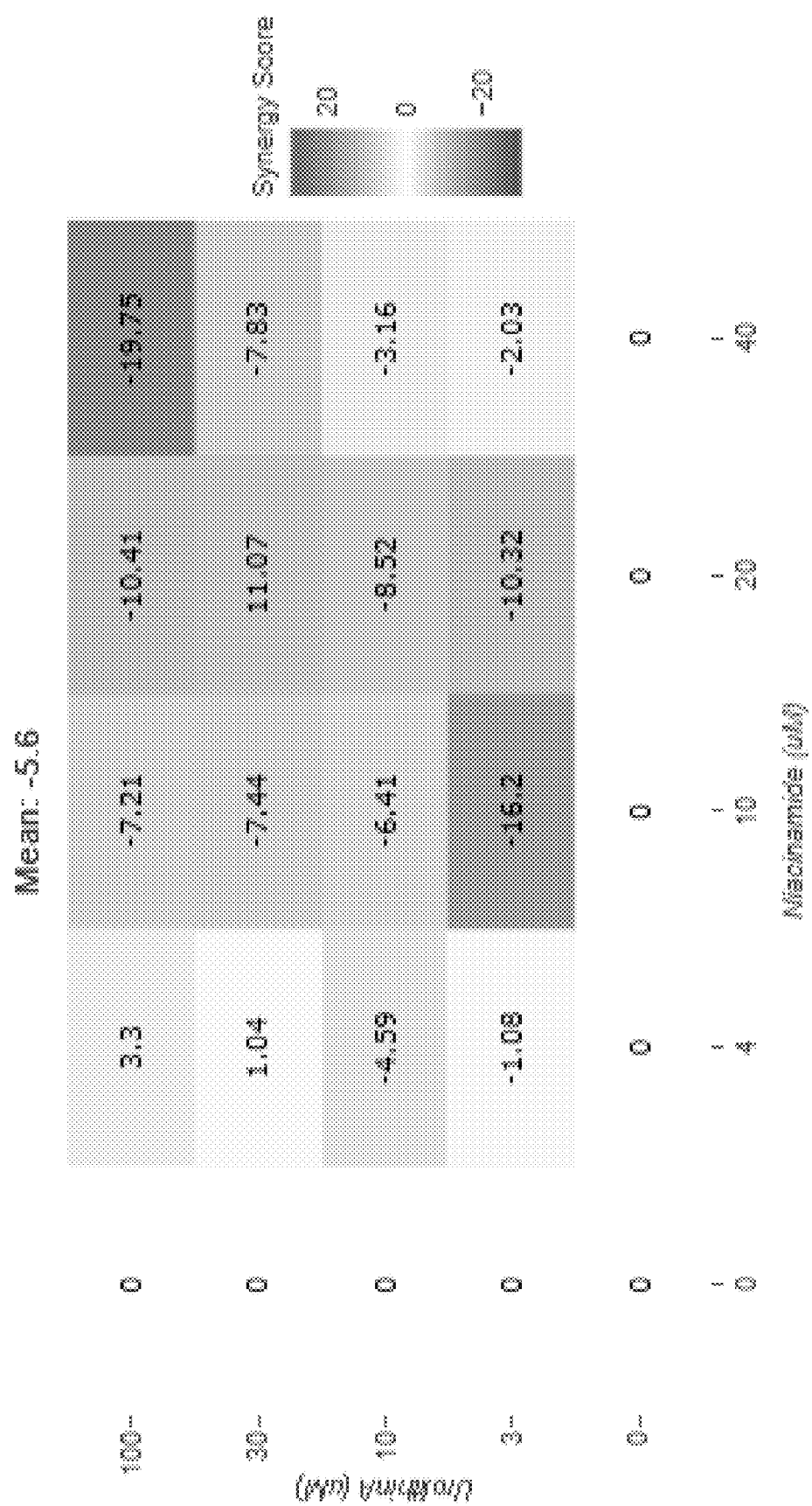

COMPOSITIONS FOR TREATING ACNE AND DERMATOLOGICAL CONDITIONS

CROSS-REFERENCE TO RELATED APPLICATIONS

This application is a continuation of International Application No. PCT/US2021/033908, filed May 24, 2021. International Application No. PCT/US2021/033908 claims priority to U.S. Provisional Application No. 63/028,857, filed May 22, 2020 and U.S. Provisional Application No. 63/162,850, filed Mar. 18, 2021. Each of the aforementioned applications is incorporated by reference herein in its entirety for all purposes.

FIELD

The present disclosure generally relates to compositions and formulations thereof comprising unique combinations of cannabinoids, antioxidants, cofactors and other biochemical agents, methods of making the compositions, and methods for using the compositions for the treatment of mitochondrial ATP deficit disorders.

BACKGROUND OF THE INVENTION

Adenosine triphosphate (ATP) is produced via cellular respiration in mitochondria, organelles that are present in animal cells, by processes described in (FIGS. 1, 2 and 3A). Functionally, ATP can store, transport and deliver chemical energy to support all cellular activities. It can also act as an intra- and extra-cellular signaling molecule in the maintenance of cellular homeostasis.

Some people suffer from sub-normal ATP metabolism, due to various genetic and environmental causes. Temporary reductions in ATP metabolism can also occur due to non-inherited, patient-specific physiological or pathological factors such as hormonal imbalance and/or rapid growth. In all cases, reduced ability to produce and/or utilize ATP can result in many disease symptoms, particularly ones related to an enhanced inflammatory response.

Acne is one such manifestation of reduced local ATP levels and is detrimental to an individual's self-image. Therefore, there exists a need in the art for new treatments for low levels of ATP metabolism.

SUMMARY OF THE INVENTION

The present disclosure provides topical compositions for the treatment of mitochondrial ATP deficit disorders. In some embodiments, the compositions comprise a cannabinoid, a cofactor or precursor thereof, optionally, an antioxidant, and, optionally, a mitophagy stimulant. In some embodiments, the compositions described herein cause metabolism of ATP to ADP. In some embodiments, the compositions described herein treat acne by increasing ATP levels and/or restoring local mitochondrial health. In some embodiments, the compositions described herein treat acne indirectly, by increasing the availability of ATP for metabolism to ADP and reducing reactive oxygen species (ROS).

In some embodiments, provided herein is a composition for the treatment of mitochondrial ATP deficit disorders, comprising:
(a) a cannabinoid;
(b) a cofactor or precursor thereof;
(c) an antioxidant; and
(d) optionally, a mitophagy stimulant.

In some embodiments, the compositions provided herein treat a mitochondrial ATP deficit disorder, wherein the mitochondrial ATP deficit disorder is a dermatological concern.

In some embodiments, the compositions provided herein increase the level of ATP in a cell. In some embodiments, the increase in the level of ATP compared to prior to said treating is in the skin, muscle, or fat. In some embodiments, the compositions provided herein optimize mitochondrial health.

In some embodiments, the compositions provided herein treat a mitochondrial ATP deficit disorder, wherein the mitochondrial ATP deficit disorder is acne.

In some embodiments, the cannabinoid of the compositions described herein is CBD.

In some embodiments, the cannabinoid of the compositions described herein is THC.

In some embodiments, the cannabinoid of the compositions described herein is CBD and THC.

In some embodiments, the cofactor or precursor thereof of the compositions described herein is a redox cofactor or precursor thereof.

In some embodiments, the cofactor or precursor thereof of the compositions described herein is involved in the mitochondrial electron transfer chain.

In some embodiments, the cofactor or precursor thereof of the compositions described herein is niacinamide.

In some embodiments, the cofactor or precursor thereof of the compositions described herein comprises niacinamide.

In some embodiments, the antioxidant of the compositions described herein comprises sulfur.

In some embodiments, the antioxidant of the compositions described herein comprises a thiol group.

In some embodiments, the antioxidant of the compositions described herein is an amino acid.

In some embodiments, the antioxidant of the compositions described herein is L-ergothioneine.

In some embodiments, the compositions comprise a mitophagy modulator, wherein the mitophagy modulator is a benzo-coumarin or dibenzo-α-pyrone.

In some embodiments, the compositions comprise a mitophagy stimulant, wherein the mitophagy modulator is a metabolite of an ellagic acid or ellagitannin.

In some embodiments, the compositions comprise a mitophagy stimulant, wherein the mitophagy modulator is a urolithin.

In some embodiments, the compositions comprise a mitophagy stimulant, wherein the mitophagy modulator is urolithin A.

In some embodiments, the compositions comprise a cannabinoid, cofactor or precursor thereof, and antioxidant, wherein the cannabinoid is CBD, the cofactor or precursor thereof is niacinamide, and the antioxidant is L-ergothioneine.

In some embodiments, the compositions comprise a cannabinoid, cofactor or precursor thereof, and antioxidant, wherein the cannabinoid is THC, the cofactor or precursor thereof is niacinamide, and the antioxidant is L-ergothioneine.

In some embodiments, the compositions comprise a cannabinoid, cofactor or precursor thereof, and antioxidant, wherein the cannabinoid is CBD and THC, the cofactor or precursor thereof is niacinamide, and the antioxidant is L-ergothioneine.

In some embodiments, the compositions comprise a cannabinoid, cofactor or precursor thereof, and antioxidant, and a mitophagy stimulant, wherein the cannabinoid is CBD, the cofactor or precursor thereof is niacinamide, the antioxidant is L-ergothioneine, and the mitophagy stimulant is urolithin A.

In some embodiments, the compositions comprise a cannabinoid, cofactor or precursor thereof, and antioxidant, and a mitophagy stimulant, wherein the cannabinoid is THC, the cofactor or precursor thereof is niacinamide, the antioxidant is L-ergothioneine, and the mitophagy stimulant is urolithin A.

In some embodiments, the compositions comprise a cannabinoid, cofactor or precursor thereof, and antioxidant, and a mitophagy stimulant, wherein the cannabinoid is CBD and CBD, the cofactor or precursor thereof is niacinamide, the antioxidant is L-ergothioneine, and the mitophagy stimulant is urolithin A.

In some embodiments, a composition comprises about 0.01 milligrams (mg) to about 10 mg of cannabinoid, about 0.5 mg to about 50 mg cofactor or precursor thereof, and about 0.1 mg and 100 mg antioxidant per milliliter of composition.

In some embodiments, a composition comprises about 0.01 milligrams (mg) to about 10 mg of CBD, about 0.5 mg to about 50 mg niacinamide, and about 0.1 mg and 100 mg L-ergothioneine per milliliter of composition.

In some embodiments, a composition comprises about 0.01 milligrams (mg) to about 10 mg of CBD, about 0.5 mg to about 50 mg niacinamide, and about 0.1 mg and 100 mg L-ergothioneine per milliliter of composition and a mitophagy stimulant wherein the mitophagy stimulant is urolithin A.

In some embodiments, the composition comprises about 0.42 mg cannabinoid, about 10 mg cofactor or precursor thereof, and about 1 mg antioxidant per milliliter of composition.

In some embodiments, the composition comprises about 0.42 mg cannabinoid, about 10 mg cofactor or precursor thereof, and about 1 mg antioxidant per milliliter of composition, wherein the cannabinoid is CBD, the cofactor or precursor thereof is niacinamide, and the antioxidant is L-ergothioneine.

In some embodiments, the composition comprises about 0.42 mg cannabinoid, about 10 mg cofactor or precursor thereof, and about 1 mg antioxidant per milliliter of composition, wherein the cannabinoid is CBD, the cofactor or precursor thereof is niacinamide, and the antioxidant is L-ergothioneine, and a mitophagy stimulant wherein the mitophagy stimulant is urolithin A.

In some embodiments, the composition comprises about 2.3 mg cannabinoid, about 20 mg cofactor or precursor thereof, and about 1 mg antioxidant per milliliter of composition.

In some embodiments, the composition comprises about 2.3 mg cannabinoid, about 20 mg cofactor or precursor thereof, and about 1 mg antioxidant per milliliter of composition, wherein the cannabinoid is CBD, the cofactor or precursor thereof is niacinamide, and the antioxidant is L-ergothioneine.

In some embodiments, the composition comprises about 2.3 mg cannabinoid, about 20 mg cofactor or precursor thereof, and about 1 mg antioxidant per milliliter of composition, wherein the cannabinoid is CBD, the cofactor or precursor thereof is niacinamide, and the antioxidant is L-ergothioneine, and a mitophagy stimulant wherein the mitophagy stimulant is urolithin A.

In some embodiments, the composition comprises about 6.8 mg cannabinoid, about 30 mg cofactor or precursor thereof, and about 10 mg antioxidant per milliliter of composition.

In some embodiments, the composition comprises about 6.8 mg cannabinoid, about 30 mg cofactor or precursor thereof, and about 10 mg antioxidant per milliliter of composition, wherein the cannabinoid is CBD, the cofactor or precursor thereof is niacinamide, and the antioxidant is L-ergothioneine.

In some embodiments, the composition comprises about 6.8 mg cannabinoid, about 30 mg cofactor or precursor thereof, and about 10 mg antioxidant per milliliter of composition, wherein the cannabinoid is CBD, the cofactor or precursor thereof is niacinamide, and the antioxidant is L-ergothioneine, and a mitophagy stimulant wherein the mitophagy stimulant is urolithin A.

In some embodiments, the composition comprises about 4 mg cannabinoid, about 2 mg cofactor or precursor thereof, and about 10 mg antioxidant per milliliter of composition.

In some embodiments, the composition comprises about 4 mg cannabinoid, about 2 mg cofactor or precursor thereof, and about 10 mg antioxidant per milliliter of composition, wherein the cannabinoid is CBD, the cofactor or precursor thereof is niacinamide, and the antioxidant is L-ergothioneine.

In some embodiments, the composition comprises about 4 mg cannabinoid, about 2 mg cofactor or precursor thereof, and about 10 mg antioxidant per milliliter of composition, wherein the cannabinoid is CBD, the cofactor or precursor thereof is niacinamide, and the antioxidant is L-ergothioneine, and a mitophagy stimulant wherein the mitophagy stimulant is urolithin A.

In some embodiments, the composition comprises an additional ingredient selected from the group consisting of an avenanthramide, lilac stem cells, and salicylic acid.

In some embodiments, provided herein is a method for treatment of a mitochondrial ATP deficit disorder, comprising: administering to a patient in need thereof, a composition comprising:
 (a) a cannabinoid;
 (b) a cofactor or precursor thereof;
 (c) an antioxidant; and
 (d) optionally, a mitophagy stimulant.

In some embodiments, the method comprises treating a mitochondrial ATP deficit disorder, wherein the mitochondrial ATP deficit disorder is a dermatological concern.

In some embodiments, the method comprises treating a mitochondrial ATP deficit disorder, wherein the mitochondrial ATP deficit disorder is a dermatological concern, wherein the dermatological concern is selected from the group consisting of: acne, psoriasis, eczema, rosacea, ichthyosis, vitiligo, seborrheic dermatitis, actinic keratosis, stretch mark, wrinkles, fine lines, carbuncle, aging, and cellulitis. In some embodiments, these dermatological conditions are caused by viruses, such as SARS-CoV-2.

In some embodiments, the method comprises treating a dermatological concern, wherein the dermatological concern is acne.

In some embodiments, the method comprises administering a composition comprising a cannabinoid, wherein the cannabinoid is CBD.

In some embodiments, the method comprises administering a composition comprising a cannabinoid, wherein the cannabinoid is THC.

In some embodiments, the method comprises administering a composition comprising a cannabinoid, wherein the cannabinoid is CBD and THC.

In some embodiments, the method comprises administering a composition comprising a cofactor or precursor thereof, wherein the cofactor or precursor thereof is a redox cofactor or precursor thereof.

In some embodiments, the method comprises administering a composition comprising a cofactor or precursor thereof, wherein the cofactor or precursor thereof is involved in the mitochondrial electron transfer chain.

In some embodiments, the method comprises administering a composition comprising a cofactor or precursor thereof, wherein the cofactor or precursor thereof is niacinamide.

In some embodiments, the method comprises administering a composition comprising a cofactor or precursor thereof, wherein the cofactor or precursor thereof comprises niacinamide.

In some embodiments, the method comprises administering a composition comprising an antioxidant, wherein the antioxidant comprises sulfur.

In some embodiments, the method comprises administering a composition comprising an antioxidant, wherein the antioxidant comprises a thiol group.

In some embodiments, the method comprises administering a composition comprising an antioxidant, wherein the antioxidant is an amino acid.

In some embodiments, the method comprises administering a composition comprising an antioxidant, wherein the antioxidant is L-ergothioneine.

In some embodiments, the method comprises administering a composition comprising an antioxidant, wherein the antioxidant is L-ergothioneine.

In some embodiments, the method comprises administering a composition comprising a mitophagy modulator, wherein the mitophagy modulator is a benzo-coumarin or dibenzo-α-pyrone.

In some embodiments, the method comprises administering a composition comprising a mitophagy stimulant, wherein the mitophagy stimulant is a metabolite of an ellagic acid or ellagitannin.

In some embodiments, the method comprises administering a composition comprising a mitophagy stimulant, wherein the mitophagy stimulant is a urolithin.

In some embodiments, the method comprises administering a composition comprising a mitophagy stimulant, wherein the mitophagy stimulant is urolithin A.

In some embodiments, the method comprises administering a composition comprising a cannabinoid, cofactor or precursor thereof, and antioxidant, wherein the cannabinoid is CBD, the cofactor or precursor thereof is niacinamide, and the antioxidant is L-ergothioneine.

In some embodiments, the method comprises administering a composition comprising a cannabinoid, cofactor or precursor thereof, and antioxidant, wherein the cannabinoid is THC, the cofactor or precursor thereof is niacinamide, and the antioxidant is L-ergothioneine.

In some embodiments, the method comprises administering a composition comprising a cannabinoid, cofactor or precursor thereof, and antioxidant, wherein the cannabinoid is CBD and THC, the cofactor or precursor thereof is niacinamide, and the antioxidant is L-ergothioneine.

In some embodiments, the method comprises administering a composition comprising a cannabinoid, cofactor or precursor thereof, and antioxidant, and a mitophagy stimulant, wherein the cannabinoid is CBD, the cofactor or precursor thereof is niacinamide, the antioxidant is L-ergothioneine, and the mitophagy stimulant is urolithin A.

In some embodiments, the method comprises administering a composition comprising a cannabinoid, cofactor or precursor thereof, and antioxidant, and a mitophagy stimulant, wherein the cannabinoid is THC, the cofactor or precursor thereof is niacinamide, the antioxidant is L-ergothioneine, and the mitophagy stimulant is urolithin A.

In some embodiments, the method comprises administering a composition comprising a cannabinoid, cofactor or precursor thereof, and antioxidant, and a mitophagy stimulant, wherein the cannabinoid is CBD and CBD, the cofactor or precursor thereof is niacinamide, the antioxidant is L-ergothioneine, and the mitophagy stimulant is urolithin A.

In some embodiments, the method comprises administering a composition comprising about 0.01 milligrams (mg) to about 10 mg of cannabinoid, about 0.5 mg to about 50 mg cofactor or precursor thereof, and about 0.1 mg and 100 mg antioxidant per milliliter of composition.

In some embodiments, the method comprises administering a composition comprising about 0.01 milligrams (mg) to about 10 mg of CBD, about 0.5 mg to about 50 mg niacinamide, and about 0.1 mg and 100 mg L-ergothioneine per milliliter of composition.

In some embodiments, the method comprises administering a composition comprising about 0.01 milligrams (mg) to about 10 mg of CBD, about 0.5 mg to about 50 mg niacinamide, and about 0.1 mg and 100 mg L-ergothioneine per milliliter of composition and a mitophagy stimulant wherein the mitophagy stimulant is urolithin A.

In some embodiments, the method comprises administering a composition comprising about 0.42 mg cannabinoid, about 10 mg cofactor or precursor thereof, and about 1 mg antioxidant per milliliter of composition.

In some embodiments, the method comprises administering a composition comprising about 0.42 mg cannabinoid, about 10 mg cofactor or precursor thereof, and about 1 mg antioxidant per milliliter of composition, wherein the cannabinoid is CBD, the cofactor or precursor thereof is niacinamide, and the antioxidant is L-ergothioneine.

In some embodiments, the method comprises administering a composition comprising about 0.42 mg cannabinoid, about 10 mg cofactor or precursor thereof, and about 1 mg antioxidant per milliliter of composition, wherein the cannabinoid is CBD, the cofactor or precursor thereof is niacinamide, and the antioxidant is L-ergothioneine, and a mitophagy stimulant wherein the mitophagy stimulant is urolithin A.

In some embodiments, the method comprises administering a composition comprising about 2.3 mg cannabinoid, about 20 mg cofactor or precursor thereof, and about 1 mg antioxidant per milliliter of composition.

In some embodiments, the method comprises administering a composition comprising about 2.3 mg cannabinoid, about 20 mg cofactor or precursor thereof, and about 1 mg antioxidant per milliliter of composition, wherein the cannabinoid is CBD, the cofactor or precursor thereof is niacinamide, and the antioxidant is L-ergothioneine.

In some embodiments, the method comprises administering a composition comprising about 2.3 mg cannabinoid, about 20 mg cofactor or precursor thereof, and about 1 mg antioxidant per milliliter of composition, wherein the cannabinoid is CBD, the cofactor or precursor thereof is niacinamide, and the antioxidant is L-ergothioneine, and a mitophagy stimulant wherein the mitophagy stimulant is urolithin A.

In some embodiments, the method comprises administering a composition comprising about 6.8 mg cannabinoid, about 30 mg cofactor or precursor thereof, and about 10 mg antioxidant per milliliter of composition.

In some embodiments, the method comprises administering a composition comprising comprises about 6.8 mg cannabinoid, about 30 mg cofactor or precursor thereof, and about 10 mg antioxidant per milliliter of composition, wherein the cannabinoid is CBD, the cofactor or precursor thereof is niacinamide, and the antioxidant is L-ergothioneine.

In some embodiments, the method comprises administering a composition comprising about 6.8 mg cannabinoid, about 30 mg cofactor or precursor thereof, and about 10 mg antioxidant per milliliter of composition, wherein the cannabinoid is CBD, the cofactor or precursor thereof is niacinamide, and the antioxidant is L-ergothioneine, and a mitophagy stimulant wherein the mitophagy stimulant is urolithin A.

In some embodiments, the method comprises administering a composition comprising about 4 mg cannabinoid, about 2 mg cofactor or precursor thereof, and about 10 mg antioxidant per milliliter of composition.

In some embodiments, the method comprises administering a composition comprising about 4 mg cannabinoid, about 2 mg cofactor or precursor thereof, and about 10 mg antioxidant per milliliter of composition, wherein the cannabinoid is CBD, the cofactor or precursor thereof is niacinamide, and the antioxidant is L-ergothioneine.

In some embodiments, the method comprises administering a composition comprising about 4 mg cannabinoid, about 2 mg cofactor or precursor thereof, and about 10 mg antioxidant per milliliter of composition, wherein the cannabinoid is CBD, the cofactor or precursor thereof is niacinamide, and the antioxidant is L-ergothioneine, and a mitophagy stimulant wherein the mitophagy stimulant is urolithin A.

In some embodiments, the method comprises administering a composition comprising an additional ingredient selected from the group consisting of an avenanthramide, lilac stem cells, and salicylic acid.

In some embodiments, the method comprises applying the composition to a face.

In some embodiments, the method comprises applying the composition to acne.

In some embodiments, the method comprises a composition, wherein the composition is incorporated into a product selected from the group consisting of an acne cleanser, an acne toner, an acne spot treatment, an acne day/night moisturizer, and a sunscreen.

Provided herein is a composition, comprising: a cannabinoid; and a redox cofactor or precursor thereof. In some embodiments, the composition comprises an antioxidant. In some embodiments, the composition comprises a mitophagy stimulant. In some embodiments, the composition is effective at treating a dermatological mitochondrial ATP deficit disorder or concern. In some embodiments, the composition increases ATP metabolism in sebocyte cells. In some embodiments, the composition is capable of treating acne. In some embodiments, the composition comprises cannabidiol (CBD). In some embodiments, the composition comprises delta 9 tetrahydrocannabinol (THC). In some embodiments, the composition comprises CBD and THC. In some embodiments, the composition comprises a cannabinoid selected from the group consisting of cannabidiol (CBD), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM), Tetrahydrocannabinol (THC), cannabidiolic acid (CBDA), tetrahydrocannabinolic acid (THCA), Cannabichromenic acid (CBCA), cannabigerolic acid (CBGA), tetrahydrocannabivarin acid (THCVA), cannabidivarinic acid (CBDVA), and any combinations thereof. In some embodiments, the redox cofactor or precursor thereof is involved in the mitochondrial electron transfer chain. In some embodiments, the redox cofactor or precursor thereof comprises niacinamide. In some embodiments, the antioxidant does not affect ATP homeostasis of cells. In some embodiments, the antioxidant is selected from the group consisting of: L-ergothioneine, butylated hydroxytoluene (BHT), butylated hydroxy anisole (BHA), tert-Butylhydroquinone (TBHQ), pyrogallol, propylgallate, N,N'-Di-sec-butyl-p-phenylenediamine, coenzyme $Q_{10}$, astaxanthin, ellagic acid, picrocrocin, lycopene, lutein/zeaxanthin, lutein, zeaxanthin, quercetin, vitamin C, IP-6, beta-carotene, epicatechin, ECGC-epigallocatechin gallate, safranal, proanthocyanidins, resveratrol, vitamin E, melatonin, and mitoQ. In some embodiments, the antioxidant is an amino acid. In some embodiments, the antioxidant is L-ergothioneine. In some embodiments, the mitophagy stimulant is a urolithin. In some embodiments, the urolithin is selected from urolithin A, urolithin B, urolithin C, urolithin E, urolithin M7, urolithin M5, urolithin D, isourolithin A, urolithin M4, urolithin M6, urolithin M3, and isourolithin B. In some embodiments, the mitophagy stimulant is a metabolite of an ellagic acid or ellagitannin. In some embodiments, the cannabinoid is CBD and the cofactor or precursor thereof is niacinamide. In some embodiments, the CBD and niacinamide are at a molar ratio between 2:1 to 10:1. In some embodiments, the CBD and niacinamide are at a molar ratio between 3:1 to 10:1. In some embodiments, the CBD and niacinamide are at a molar ratio between 1:10 to 1:55. In some embodiments, the CBD and niacinamide are at a molar ratio between 1:10 to 1:15. In some embodiments, the CBD and urolithin are at a molar ratio of 1:10 to 10:1. In some embodiments, the CBD and urolithin are at a molar ratio of 1:3 to 10:1. In some embodiments, the cannabinoid is CBD, the cofactor or precursor thereof is niacinamide, and the antioxidant is L-ergothioneine. In some embodiments, the cannabinoid is THC, the cofactor or precursor thereof is niacinamide, and the antioxidant is L-ergothioneine. In some embodiments, the cannabinoid is CBD and THC, the cofactor or precursor thereof is niacinamide, and the antioxidant is L-ergothioneine. In some embodiments, the cannabinoid is CBD, the cofactor or precursor thereof is niacinamide, the antioxidant is L-ergothioneine, and the mitophagy stimulant is urolithin A. In some embodiments, the cannabinoid is THC, the cofactor or precursor thereof is niacinamide, the antioxidant is L-ergothioneine, and the mitophagy stimulant is urolithin A. In some embodiments, the cannabinoid is CBD and THC, the cofactor or precursor thereof is niacinamide, the antioxidant is L-ergothioneine, and the mitophagy stimulant is urolithin A. In some embodiments, the composition comprises about 0.01 milligrams (mg) to about 10 mg of cannabinoid, about 0.5 mg to about 50 mg cofactor or precursor thereof, and about 0.1 mg and 100 mg antioxidant per milliliter of composition. In some embodiments, the composition comprises the mitophagy stimulant urolithin A, about 0.01 milligrams (mg) to about 10 mg of cannabinoid, about 0.5 mg to about 50 mg cofactor or precursor thereof, and about 0.1 mg and 100 mg antioxidant per milliliter of composition. In some embodiments, the composition comprises about 0.01 milligrams (mg) to about 10 mg of CBD, about 0.5 mg to about 50 mg niacinamide, and about 0.1 mg and 100 mg L-ergothioneine per milliliter of composition. In some embodiments, the composition comprises about 0.01 milligrams (mg) to about 10 mg of CBD, about 0.5 mg to about 50 mg niacinamide, about 0.1 mg and 100 mg L-ergothioneine per milliliter of composition, and a mitophagy stimulant, wherein the mitophagy stimulant is urolithin A. In some embodiments, the composition comprises about 0.42 mg cannabinoid, about 10 mg cofactor or precursor thereof, and about 1 mg antioxidant per milliliter of composition. In some embodiments, the composition comprises the mitophagy stimulant urolithin A and about 0.42 mg cannabinoid, about 10 mg cofactor or precursor thereof, and about 1 mg antioxidant per milliliter of composition. In some embodiments, the composition comprises about 0.42 mg CBD, about 10 mg niacinamide, and about 1 mg L-ergothioneine per milliliter of composition. In some embodiments, the composition comprises about 0.42 mg CBD, about 10 mg niacinamide, about 1 mg L-ergothioneine per milliliter of composition, and a mitophagy stimulant, wherein the mitophagy stimulant is urolithin A. In some embodiments, the composition comprises about 2.3 mg cannabinoid, about 20 mg cofactor or precursor thereof, and about 1 mg antioxidant per milliliter of composition. In some embodiments, the composition comprises the mitophagy stimulant urolithin A, about 2.3 mg cannabinoid, about 20 mg cofactor or precursor thereof, about 1 mg antioxidant per milliliter of composition. In some embodiments, the composition comprises about 2.3 mg CBD, about 20 mg niacinamide, and about 1 mg L-ergothioneine per milliliter of composition. In some embodiments, the composition comprises about 2.3 mg CBD, about 20 mg niacinamide, about 1 mg L-ergothioneine, and the mitophagy stimulant urolithin A per milliliter of composition. In some embodiments, the composition comprises about 6.8 mg cannabinoid, about 30 mg cofactor or precursor thereof, and about 10 mg antioxidant per milliliter of composition. In some embodiments, the composition comprises the mitophagy stimulant urolithin A and about 6.8 mg cannabinoid, about 30 mg cofactor or precursor thereof, and about 10 mg antioxidant per milliliter of composition. In some embodiments, the composition comprises about 6.8 mg CBD, about 30 mg niacinamide, and about 10 mg L-ergothioneine per milliliter of composition. In some embodiments, the composition comprises the mitophagy stimulant urolithin A and about 6.8 mg CBD, about 30 mg niacinamide, and about 10 mg L-ergothioneine per milliliter of composition. In some embodiments, the composition comprises an additional ingredient selected from the group consisting of an avenanthramide, lilac stem cells, and salicylic acid.

In some embodiments, provided herein is a method for increasing ATP metabolism in a cell, comprising: administering to a patient in need thereof, a therapeutically effective amount of a composition comprising: a cannabinoid; and a redox cofactor or precursor thereof. In some embodiments, provided herein is a method for increasing ATP metabolism in a cell, comprising: contacting the cell with a therapeutically effective amount of a composition comprising: a therapeutically effective amount of a composition comprising: a cannabinoid; and a redox cofactor or precursor thereof. In some embodiments, the composition comprises an antioxidant. In some embodiments, the composition comprises a mitophagy stimulant. In some embodiments, the patient suffers from a dermatological concern. In some embodiments, the dermatological concern is selected from the group consisting of acne, psoriasis, eczema, rosacea, ichthyosis, vitiligo, hives, seborrheic dermatitis, actinic keratosis, carbuncle, and cellulitis. In some embodiments, the dermatological concern is acne. In some embodiments, the composition comprises the cannabinoid cannabidiol (CBD). In some embodiments, the composition comprises the cannabinoid delta 9 tetrahydrocannabinol (THC). In some embodiments, the composition comprises the cannabinoids CBD and THC. In some embodiments, the composition comprises a cannabinoid selected from the group consisting of cannabidiol (CBD), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM), Tetrahydrocannabinol (THC), cannabidiolic acid (CBDA), tetrahydrocannabinolic acid (THCA), Cannabichromenic acid (CBCA), cannabigerolic acid (CBGA), tetrahydrocannabivarin acid (THCVA), cannabidivarinic acid (CBDVA), and any combinations thereof. In some embodiments, the redox cofactor or precursor thereof of the composition is involved in the mitochondrial electron transfer chain. In some embodiments, the redox cofactor or precursor thereof of the composition comprises niacinamide. In some embodiments, the antioxidant of the composition does not affect ATP homeostasis of cells. In some embodiments, the antioxidant of the composition is selected from the group consisting of: L-ergothioneine, butylated hydroxytoluene (BHT), butylated hydroxy anisole (BHA), tert-Butylhydroquinone (TBHQ), pyrogallol, propylgallate, N,N'-Di-sec-butyl-p-phenylenediamine, coenzyme $Q_{10}$, astaxanthin, ellagic acid, picrocrocin, lycopene, lutein/zeaxanthin, lutein, zeaxanthin, quercetin, vitamin C, IP-6, beta-carotene, epicatechin, ECGC-epigallocatechin gallate, safranal, proanthocyanidins, resveratrol, vitamin E, melatonin, and mitoQ. In some embodiments, the antioxidant of the composition is an amino acid. In some embodiments, the antioxidant of the composition is L-ergothioneine. In some embodiments, the mitophagy stimulant of the composition is a urolithin. In some embodiments, the urolithin of the composition is selected from urolithin A, urolithin B, urolithin C, urolithin E, urolithin M7, urolithin M5, urolithin D, isourolithin A, urolithin M4, urolithin M6, urolithin M3, and isourolithin B. In some embodiments, the mitophagy stimulant of the composition is a metabolite of an ellagic acid or ellagitannin. In some embodiments, the mitophagy stimulant of the composition is urolithin A. In some embodiments, the composition comprises the cannabinoid CBD and the cofactor or precursor thereof niacinamide. In some embodiments, the composition comprises CBD and niacinamide at a molar ratio between 2:1 to 10:1. In some embodiments, the composition comprises CBD and niacinamide at a molar ratio between 3:1 to 10:1. In some embodiments, the composition comprises CBD and niacinamide at a molar ratio between 1:10 to 1:55. In some embodiments, the composition comprises CBD and niacinamide at a molar ratio between 1:10 to 1:15. In some embodiments, the composition comprises CBD and urolithin at a molar ratio of 1:10 to 10:1. In some embodiments, the composition comprises CBD and urolithin at a molar ratio of 1:3 to 10:1. In some embodiments, the composition comprises the cannabinoid CBD, the cofactor or precursor thereof niacinamide, and the antioxidant L-ergothioneine. In some embodiments, the composition comprises the cannabinoid CBD, the cofactor or precursor thereof niacinamide, and the antioxidant L-ergothioneine, wherein the CBD and niacinamide are at a molar ratio between 2:1 to 10:1. In some embodiments, the composition comprises the cannabinoid CBD, the cofactor or precursor thereof niacinamide, and the antioxidant L-ergothioneine, wherein the CBD and niacinamide are at a molar ratio between 3:1 to 10:1. In some embodiments, the composition comprises the cannabinoid CBD, the cofactor or precursor thereof niacinamide, and the antioxidant L-ergothioneine, wherein the CBD and niacinamide are at a molar ratio between 1:10 to 1:55. In some embodiments, the composition comprises the cannabinoid CBD, the cofactor or precursor thereof niacinamide, and the antioxidant L-ergothioneine, wherein the CBD and niacinamide are at a molar ratio between 1:10 to 1:15. In some embodiments, the composition comprises the cannabinoid CBD, the cofactor or precursor thereof niacinamide, and the antioxidant L-ergothioneine, wherein the CBD and urolithin are at a molar ratio of 1:10 to 10:1. In some embodiments, composition comprises the cannabinoid CBD, the cofactor or precursor thereof niacinamide, and the antioxidant is L-ergothioneine, wherein the CBD and urolithin are at a molar ratio of 1:3 to 10:1. In some embodiments, the composition comprises the cannabinoid THC, the cofactor or precursor thereof niacinamide, and the antioxidant L-ergothioneine. In some embodiments, the composition comprises the cannabinoid CBD and THC, the cofactor or precursor thereof niacinamide, and the antioxidant L-ergothioneine. In some embodiments, the composition comprises the cannabinoid CBD, the cofactor or precursor thereof niacinamide, the antioxidant L-ergothioneine, and the mitophagy stimulant urolithin A. In some embodiments, the composition comprises the cannabinoid THC, the cofactor or precursor thereof niacinamide, the antioxidant L-ergothioneine, and the mitophagy stimulant urolithin A. In some embodiments, the composition comprises the cannabinoid CBD and THC, the cofactor or precursor thereof niacinamide, the antioxidant L-ergothioneine, and the mitophagy stimulant urolithin A. In some embodiments, the composition comprises about 0.01 milligrams (mg) to about 10 mg of cannabinoid, about 0.5 mg to about 50 mg cofactor or precursor thereof, and about 0.1 mg and 100 mg antioxidant per milliliter of composition. In some embodiments, the composition comprises about 0.01 milligrams (mg) to about 10 mg of cannabinoid, about 0.5 mg to about 50 mg cofactor or precursor thereof, and about 0.1 mg and 100 mg antioxidant per milliliter of composition, wherein the cannabinoid is CBD, the cofactor or precursor thereof is niacinamide, and the antioxidant is L-ergothioneine. In some embodiments, the composition comprises about 0.01 milligrams (mg) to about 10 mg of cannabinoid, about 0.5 mg to about 50 mg cofactor or precursor thereof, and about 0.1 mg and 100 mg antioxidant per milliliter of composition, wherein the cannabinoid is CBD, the cofactor or precursor thereof is niacinamide, the antioxidant is L-ergothioneine, and the mitophagy stimulant is present and is urolithin A. In some embodiments, the composition comprises about 0.42 mg cannabinoid, about 10 mg cofactor or precursor thereof, and about 1 mg antioxidant per milliliter of composition. In some embodiments, the composition comprises about 0.42 mg cannabinoid, about 10 mg cofactor or precursor thereof, and about 1 mg antioxidant per milliliter of composition, wherein the cannabinoid is CBD, the cofactor or precursor thereof is niacinamide, and the antioxidant is L-ergothioneine. In some embodiments, the composition comprises about 0.42 mg cannabinoid, about 10 mg cofactor or precursor thereof, and about 1 mg antioxidant per milliliter of composition, wherein the cannabinoid is CBD, the cofactor or precursor thereof is niacinamide, the antioxidant is L-ergothioneine, and the mitophagy stimulant is present and is urolithin A. In some embodiments, the composition comprises about 2.3 mg cannabinoid, about 20 mg cofactor or precursor thereof, and about 1 mg antioxidant per milliliter of composition. In some embodiments, the composition comprises about 2.3 mg cannabinoid, about 20 mg cofactor or precursor thereof, and about 1 mg antioxidant per milliliter of composition, wherein the cannabinoid is CBD, the cofactor or precursor thereof is niacinamide, and the antioxidant is L-ergothioneine. In some embodiments, the composition comprises about 2.3 mg cannabinoid, about 20 mg cofactor or precursor thereof, and about 1 mg antioxidant per milliliter of composition wherein the cannabinoid is CBD, the cofactor or precursor thereof is niacinamide, the antioxidant is L-ergothioneine, and the mitophagy stimulant is present and is urolithin A. In some embodiments, the composition comprises about 6.8 mg cannabinoid, about 30 mg cofactor or precursor thereof, and about 10 mg antioxidant per milliliter of composition. In some embodiments, the composition comprises about 6.8 mg cannabinoid, about 30 mg cofactor or precursor thereof, and about 10 mg antioxidant per milliliter of composition, wherein the cannabinoid is CBD, the cofactor or precursor thereof is niacinamide, and the antioxidant is L-ergothioneine. In some embodiments, the composition comprises about 6.8 mg cannabinoid, about 30 mg cofactor or precursor thereof, and about 10 mg antioxidant per milliliter of composition wherein the cannabinoid is CBD, the cofactor or precursor thereof is niacinamide, the antioxidant is L-ergothioneine, and the mitophagy stimulant is present and is urolithin A. In some embodiments, the composition comprises about 4 mg cannabinoid, about 2 mg cofactor or precursor thereof, and about 10 mg antioxidant per milliliter of composition. In some embodiments, the composition comprises about 4 mg cannabinoid, about 2 mg cofactor or precursor thereof, and about 10 mg antioxidant per milliliter of composition, wherein the cannabinoid is CBD, the cofactor or precursor thereof is niacinamide, and the antioxidant is L-ergothioneine. In some embodiments, the composition comprises about 4 mg cannabinoid, about 2 mg cofactor or precursor thereof, and about 10 mg antioxidant per milliliter of composition wherein the cannabinoid is CBD, the cofactor or precursor thereof is niacinamide, the antioxidant is L-ergothioneine, and the mitophagy stimulant is present and is urolithin A. In some embodiments, the composition comprises an additional ingredient selected from the group consisting of an avenanthramide, lilac stem cells, and salicylic acid. In some embodiments, the method comprises applying the composition to skin of a patient. In some embodiments, the method comprises applying the composition to acne. In some embodiments, the composition is incorporated into a product selected from the group consisting of an acne cleanser, an acne toner, an acne spot treatment, an acne day/night moisturizer, and a sunscreen.

In some embodiments, provided herein is a composition comprising all the ingredients of Formulation K. In some embodiments, provided herein is a composition comprising all the ingredients of Formulation L. In some embodiments, provided herein is a composition comprising all the ingredients of Formulation M. In some embodiments, provided herein is a composition comprising all the ingredients of Formulation N. In some embodiments, provided herein is a composition comprising all the ingredients of Formulation O. In some embodiments, provided herein is a composition comprising all the ingredients of Formulation U. In some embodiments, provided herein is a composition comprising all the ingredients of Formulation V. In some embodiments, provided herein is a composition comprising all the ingredients of Formulation W. In some embodiments, provided herein is a composition comprising all the ingredients of Formulation X. In some embodiments, provided herein is a composition comprising all the ingredients of Formulation Y. In some embodiments, provided herein is a composition comprising all the ingredients of Formulation Z. In some embodiments, provided herein is a composition comprising all the ingredients of Formulation AA. In some embodiments, provided herein is a composition comprising all the ingredients of Formulation BB. In some embodiments, provided herein is a composition comprising all the ingredients of Formulation CC. In some embodiments, provided herein is a composition comprising all the ingredients of Formulation DD.

In some embodiments, provided herein is a method for increasing ATP metabolism comprising exposing a cell to any composition described herein. In some embodiments, provided herein is a method for treating acne, comprising applying to skin of a patient in need thereof, a therapeutically effective amount of any composition described herein.

DESCRIPTION OF THE DRAWINGS

In a continuous process, energy released by matrix-based conversion of $^1O_2$ to $H_2O$ ($\Delta G = -418$ kJ/mol $H_2O$ activates and induces a cofactor-coupled flow of electrons from the TCA through ETC complexes I to IV and back to the mitochondrial matrix. The electrical gradient so established induces a counter-flow of protons from the matrix through ETC complexes I, II, and IV into the inter-membrane space to return to the matrix via ADP synthase causing a chemiosmotic transformation ADP to energy-rich ATP and heat. This life-compatible conversion of $O_2$ to $H_2O$ is (by Hund's Rules and the Pauli principle) available only through a rate-limiting partial reduction of single $O_2$ to the superoxide radical ion $O_2 \cdot^-$. This intermediate, wherever it occurs is also able to competitively interact with its environment to produce highly damaging reactive oxygen species (ROS). The abbreviations in FIG. 2 refer to the following: ATP: adenosine triphosphate; ETC: electron transport chain; ROS: Reactive oxygen species; TCA: tri-carboxylic acid cycle; NADH & NAD+: Nicotinamide adenine dinucleotide reduced and oxidized forms; FADH$_2$ & FAD: Flavin adenine dinucleotide reduced and oxidized forms; ADP: adenosine diphosphate; CoQ: coenzyme Q; Cyt c: cytochrome C; UCP: uncoupling protein; SOD1: superoxide dismutase; $^1O_2$: singlet oxygen FIGS. 3A-C show further measures that deploy an optimized mitochondrial ATP synthesis process.

Maintaining an adequate physiological ATP levels at all degrees of demand requires a competent mitochondrial ATP synthesis system responding exquisitely to human need but, as these systems are largely reflexive isolation of single fault points almost impossible. User-applied formulations must therefore be able to provide correction at all possible intervention points. In considering the basic ATP synthesis system, formation of the critical superoxide radical ion depends on the probability of the quantum occurrence of singlet oxygen molecules and $^1O_2$ and its single electron conversion is conserved. At the other end of the process the 'proton flow' is a reactive transfer from electron flow generated by reduction of $O_2$ to $H_2O$.

Figure 3A:
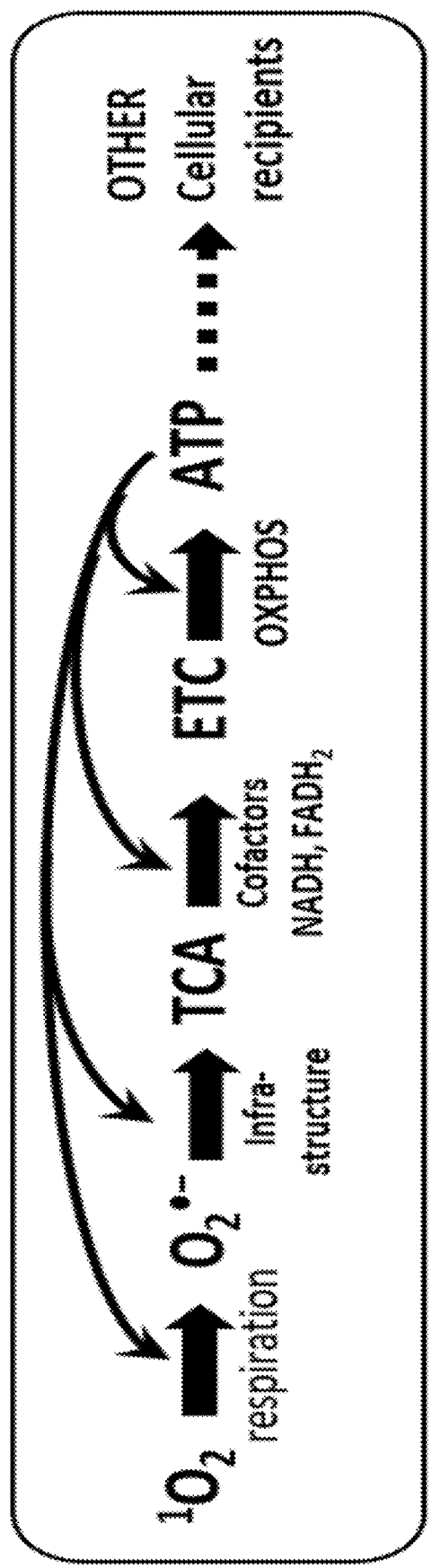
FIG. 3A shows a schema of cellular respiration and transfer of the energy stored within ATP to cellular recipients including those infrastructures that support the stages of ATP synthesis.
Figure 3B:
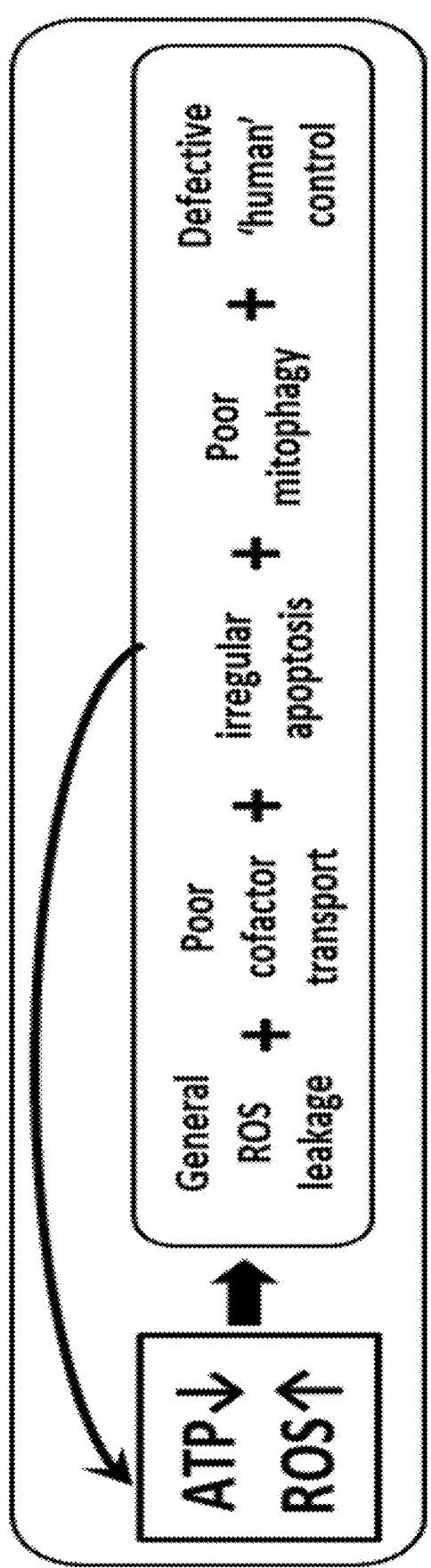
FIG. 3B shows exemplary processes that contribute to poor ATP synthesis.

For the core ATP synthesis process (FIG. 3A) to be effective, issues resulting from low levels conversion of $O_2 \cdot^-$ into ATP resulting in increased ROS activity must be addressed, not least for the benefit of the ATP-supported, ATP synthesis process itself. Further issues (FIG. 3B) are that apoptosis becomes irregular and untimely with the result decrepit mitochondria are not replaced new and their debris obstructs the ETC in the matrix cristae. However, at low ATP levels this is a stalemate. The resolution is the inclusion of a mitophagy stimulant which should clear the pathway for the 'primed' ATP synthesis process. Recovery may also require the neutralization of the damaging actions of ROS emanating from products of the human genome such as ATP-compromised components of the immune system FIG. 3B. In some embodiments, this requires an antioxidant that will not interfere with ATP synthesis.

Regarding human control of mitochondrial response, the endocannabinoid system is known to play prominent role in signalling ATP demands to mitochondria. However, the evolved basis of the signal seems to be that hormesis will be in full play i.e. the mitochondrial oxidative phosphorylation process will be operating optimally at a point just short of "oxidative stress". However, this state rare in modern and unfit individuals and a shift from the sharply biphasic hormesis operating point leads to low ATP as a 'norm'. Compounds that can modulate the behaviour of the endocannabinoid and related systems are included in our comprehensive formulations which are also designed to complete and safe enough for patient self-management.

Figure 4:
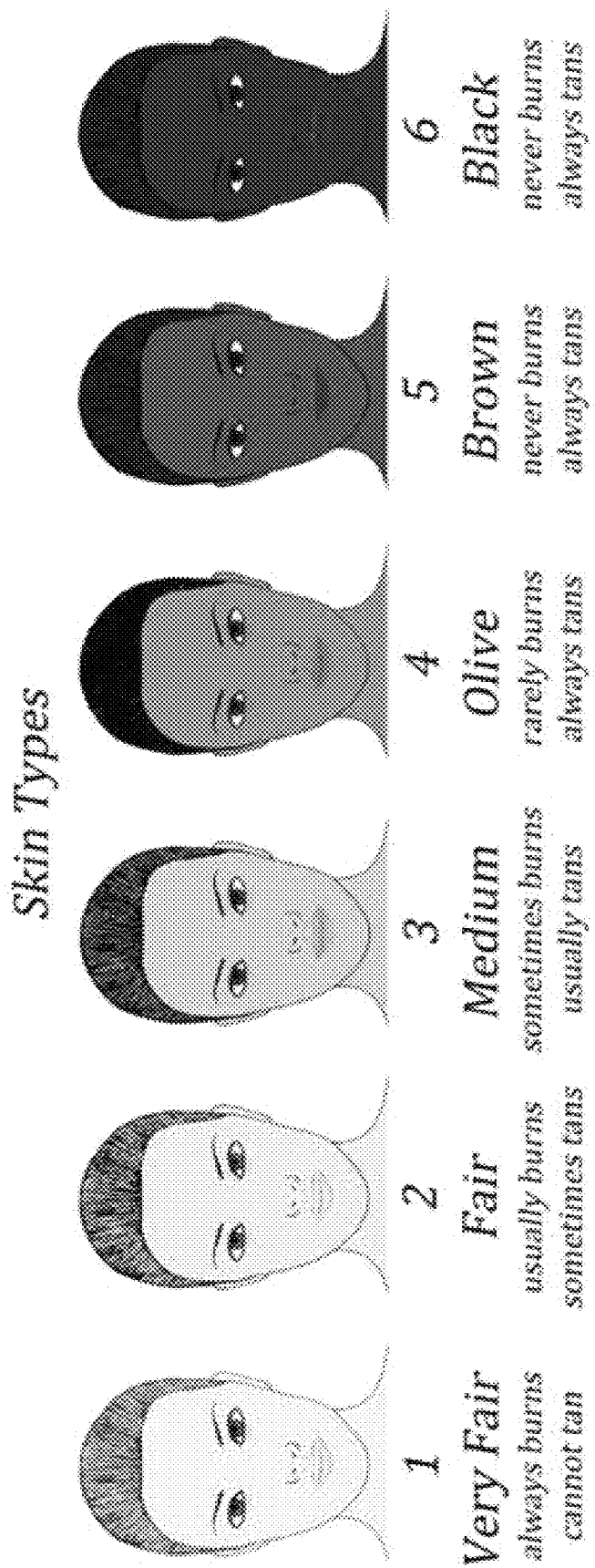

FIG. 4 shows possible complexions (e.g., very fair, fair, medium, olive, brown, black) of the participants evaluated in the study described in Example 3.

Figure 5:
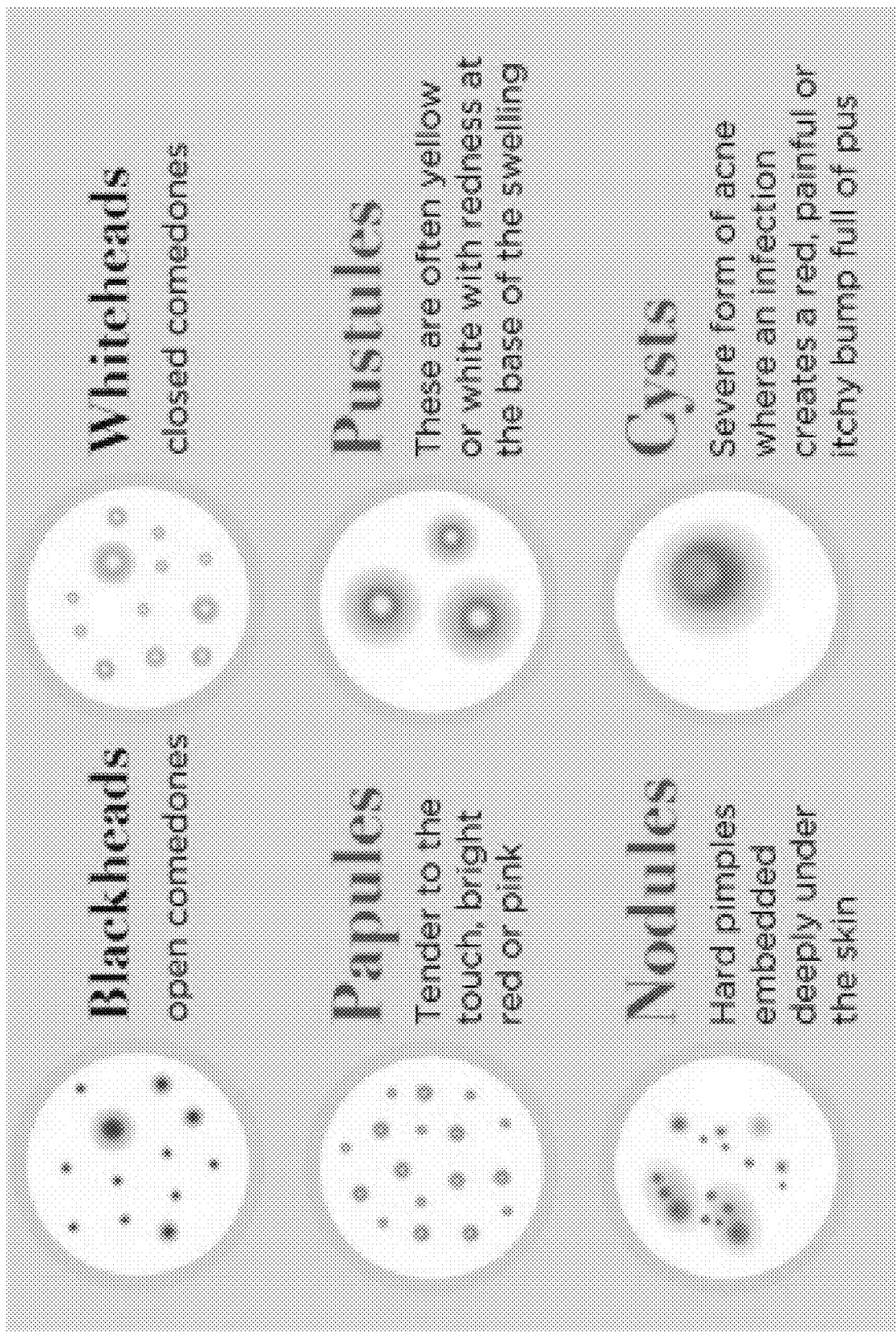

FIG. 5 shows exemplary types of acne (e.g., blackheads, whiteheads, papules, pustules, nodules, and cysts).

Figure 6:
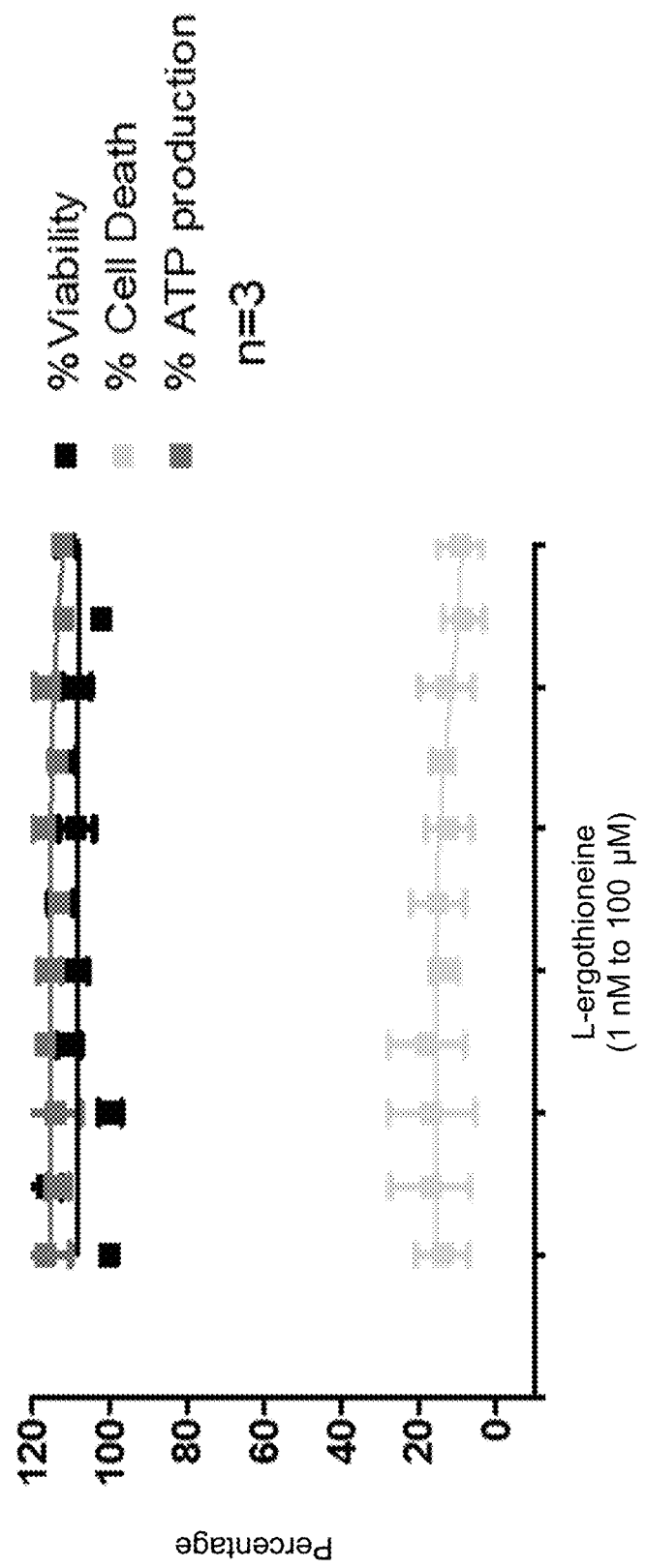

FIG. 6 shows the effect of L-ergothioneine on sebocyte cell viability, cell death, and ATP metabolism (referred to as "ATP production").

FIG. 7 is a dose-response map showing the effect of CBD and niacinamide concentration on percent luminescence reduction, as a proxy measurement for ATP metabolism.

Figure 8A:
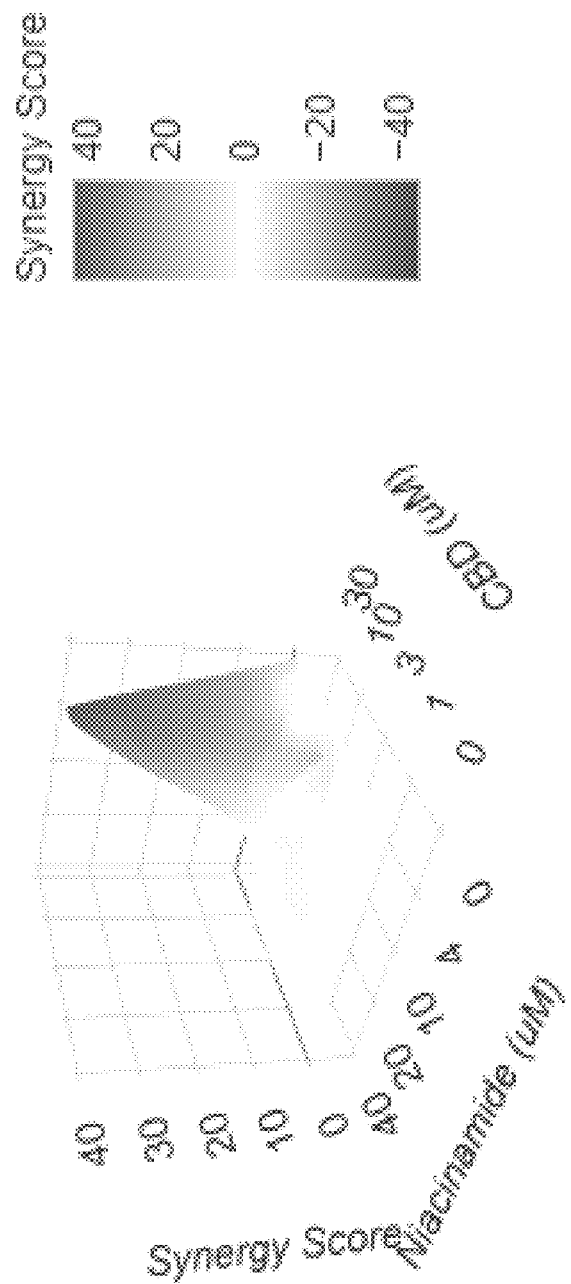
Figure 8B:
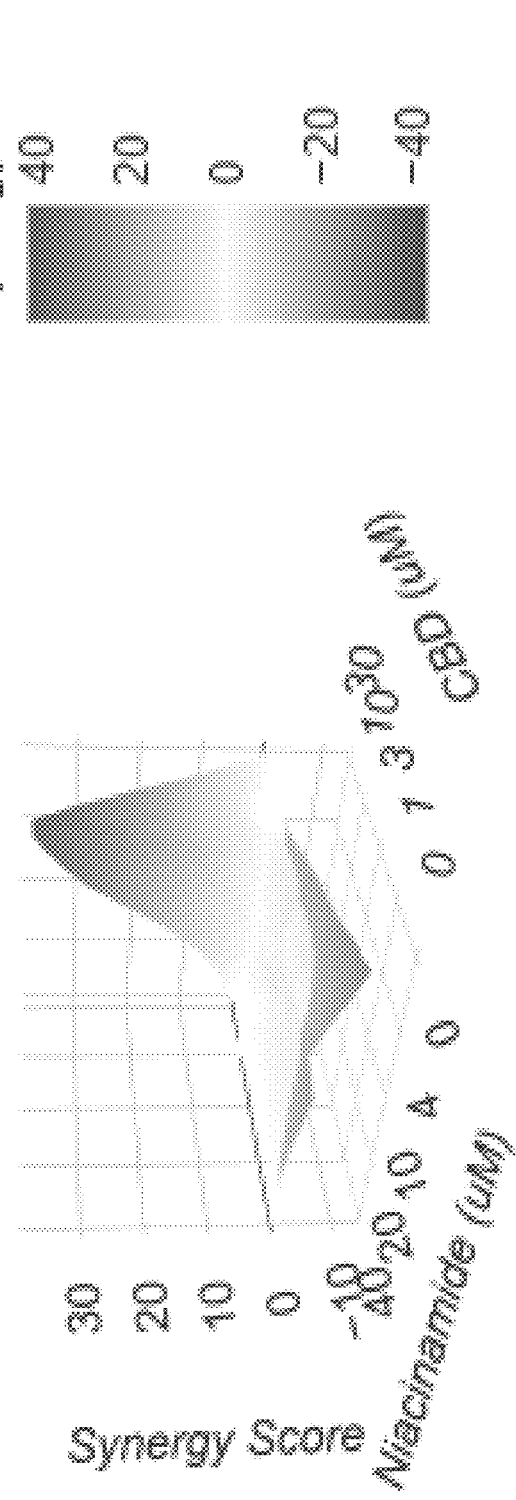
Figure 8C:
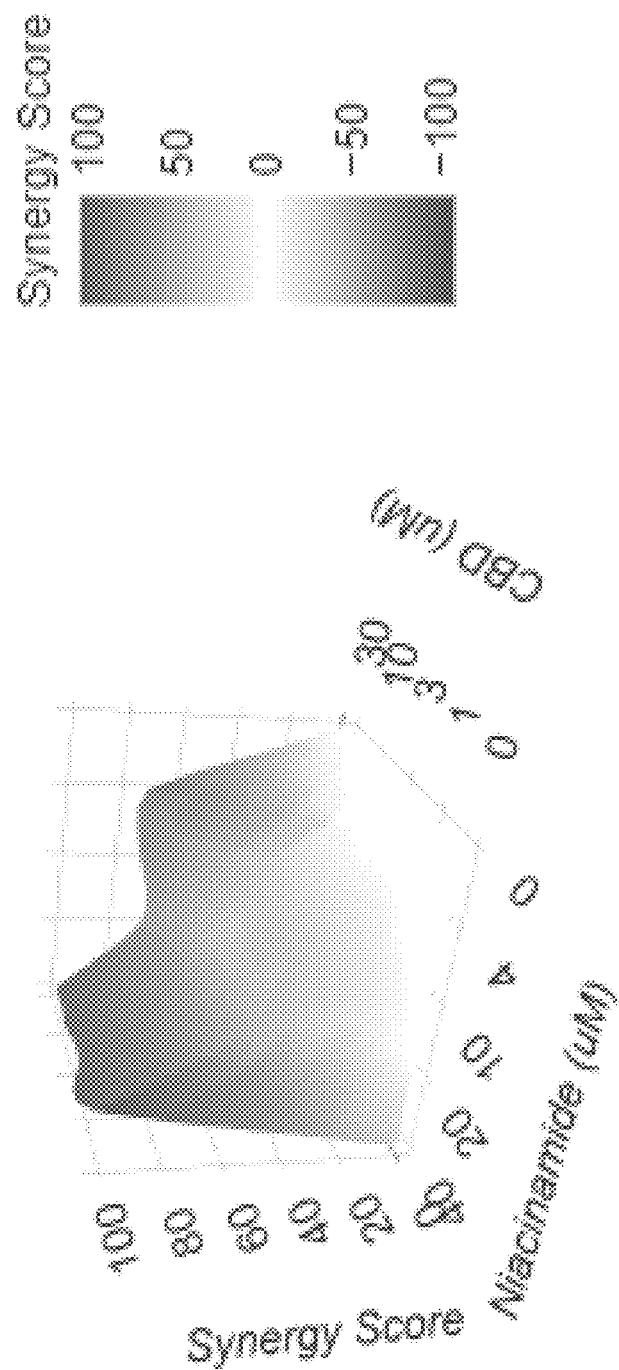
Figure 8D:
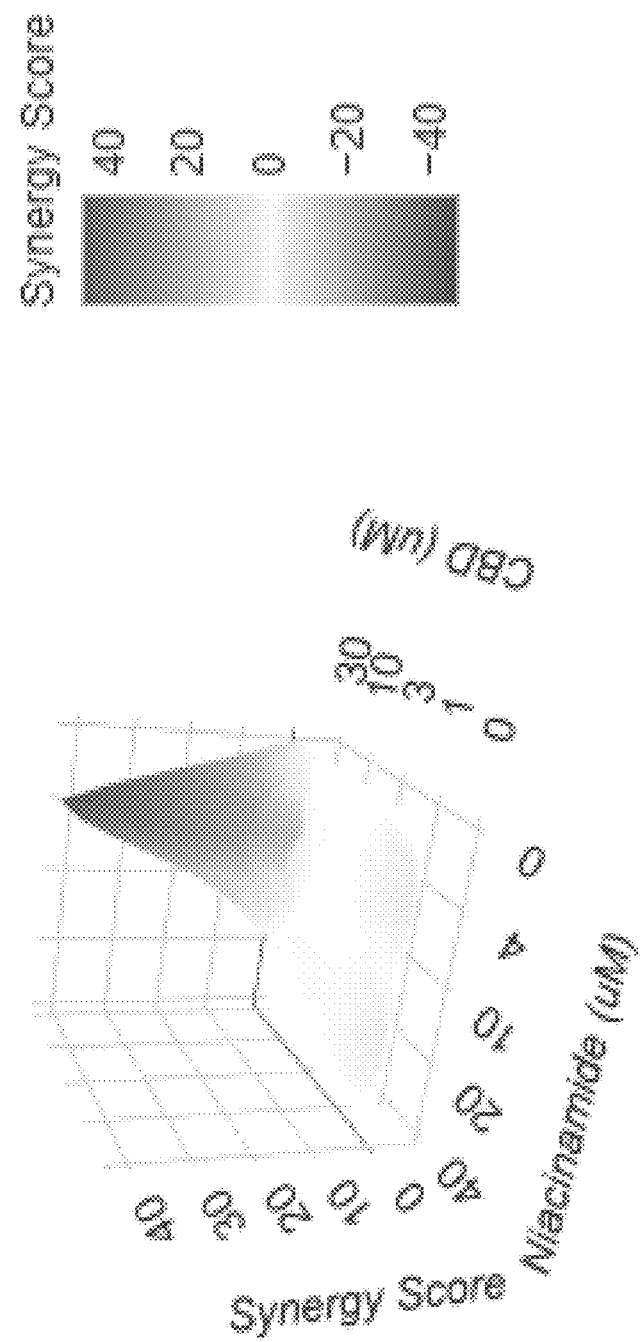

FIGS. 8A-D show a plot of CBD and niacinamide concentration versus synergy. FIG. 8A is a plot of CBD and niacinamide versus ZIP synergy score. FIG. 8B is a plot of CBD and niacinamide versus HSA synergy score. FIG. 8C is a plot of CBD and niacinamide versus Loewe synergy score. FIG. 8D is a plot of CBD and niacinamide versus Bliss synergy score.

Figure 9B:
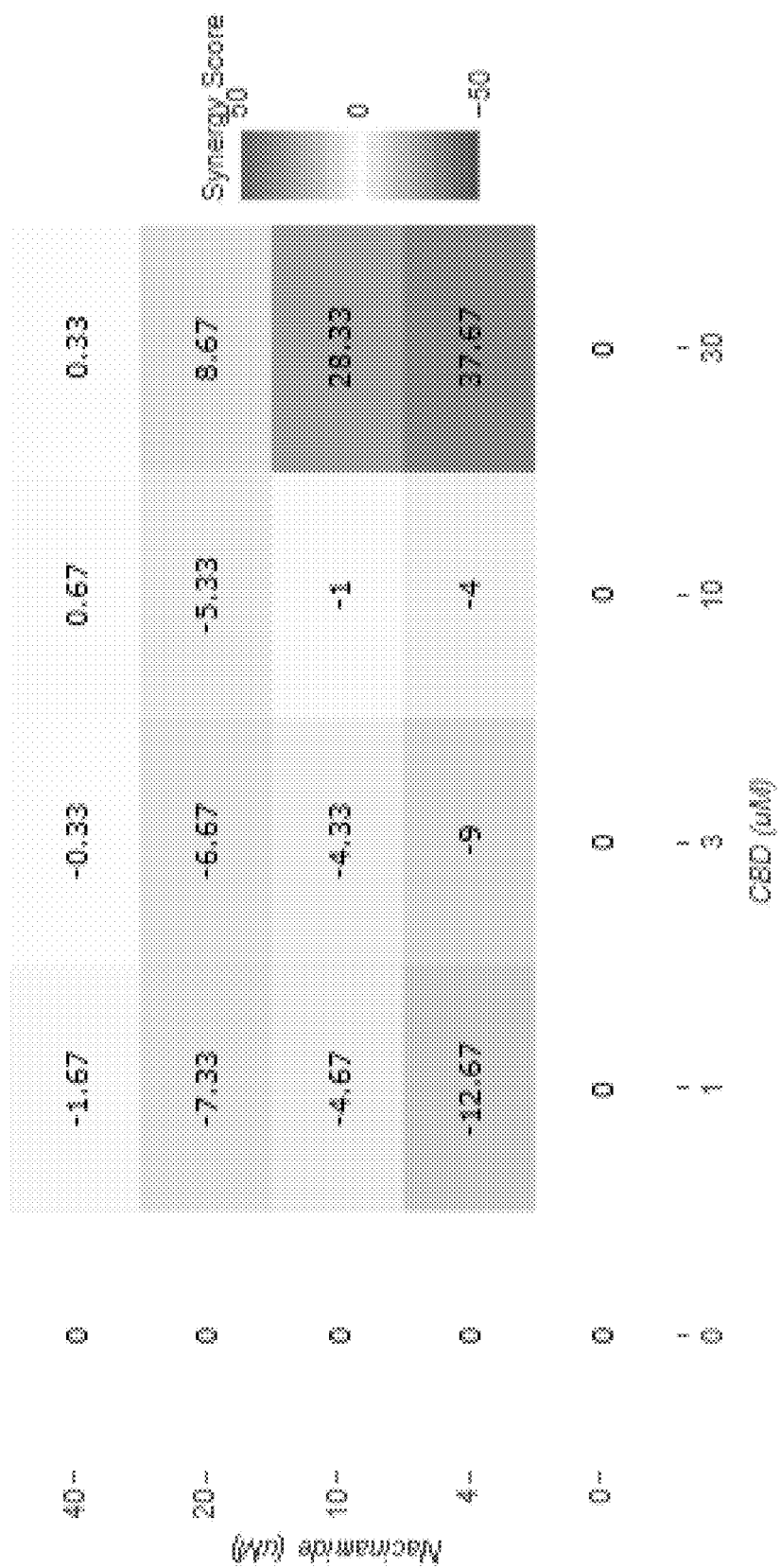
Figure 9C:
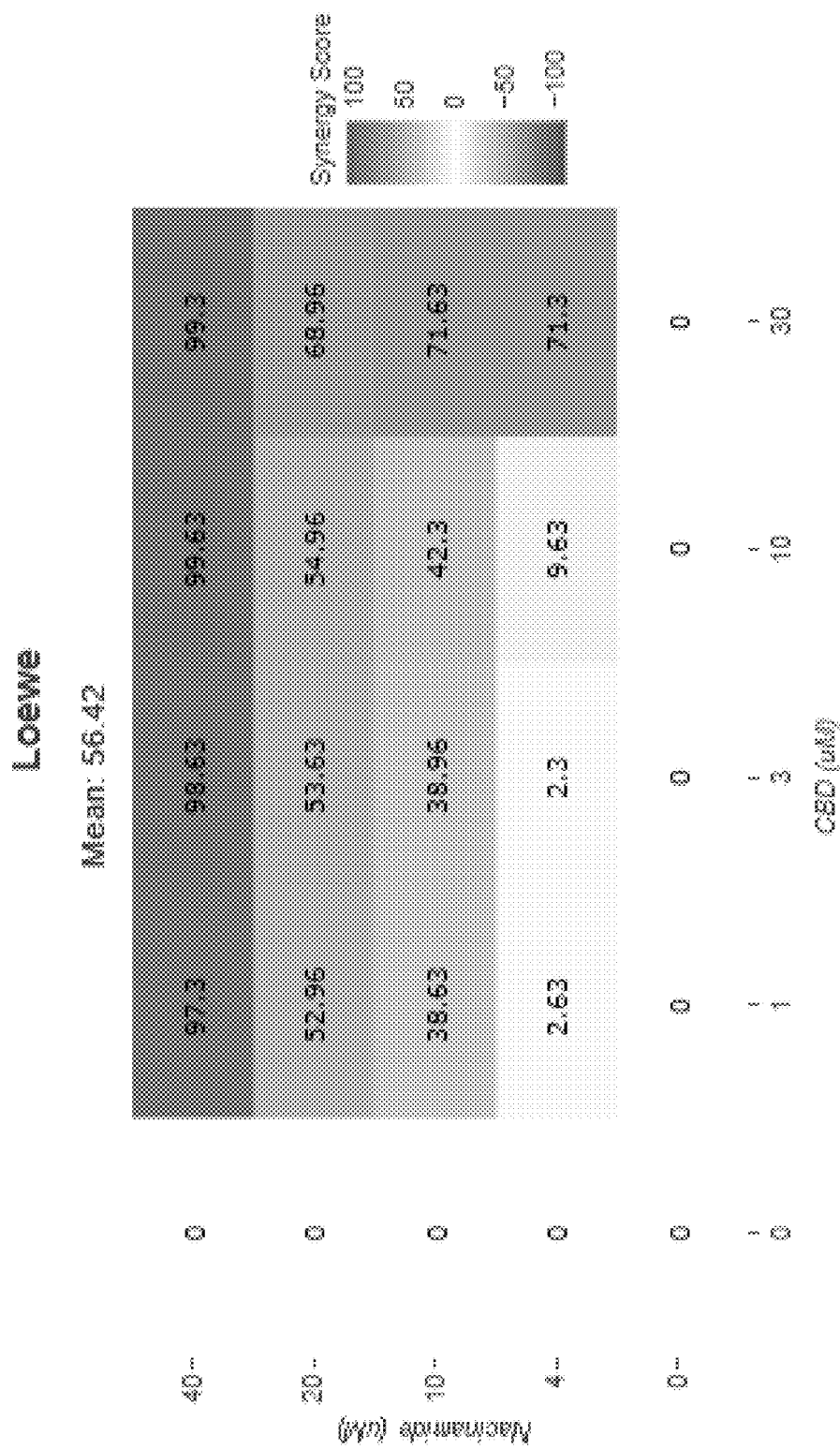

FIGS. 9A-D show heat maps of synergy scores at various CBD and niacinamide concentrations. FIG. 9A is a heat map of ZIP synergy scores for various CBD and niacinamide concentrations. FIG. 9B is a heat map of HSA synergy scores for various CBD and niacinamide concentrations. FIG. 9C is a heat map of Loewe synergy scores for various CBD and niacinamide concentrations. FIG. 9D is a heat map of Bliss synergy scores for various CBD and niacinamide concentrations.

Figure 10B:
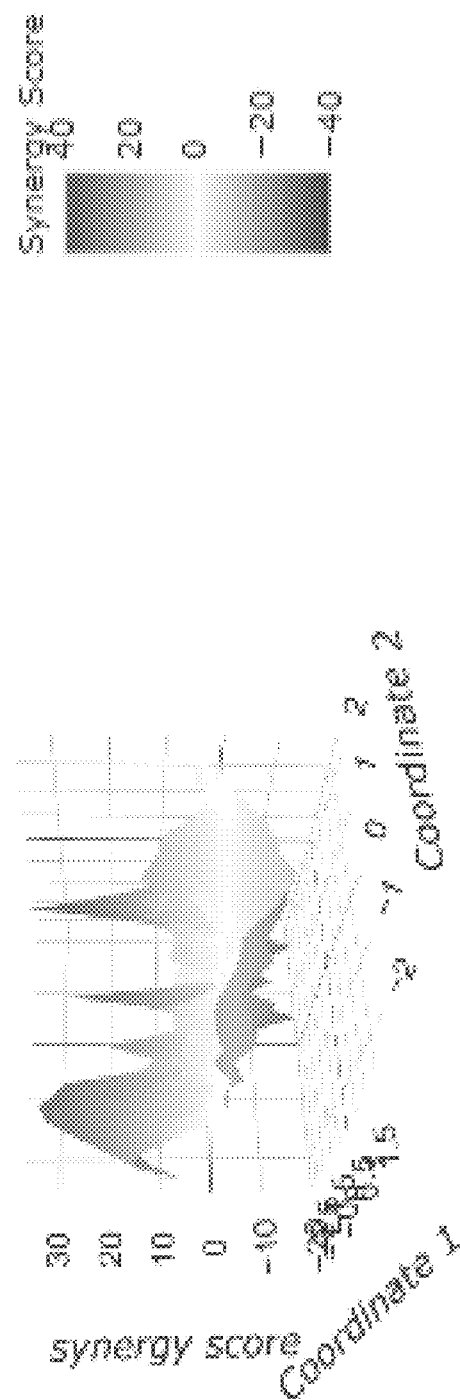
Figure 10C:
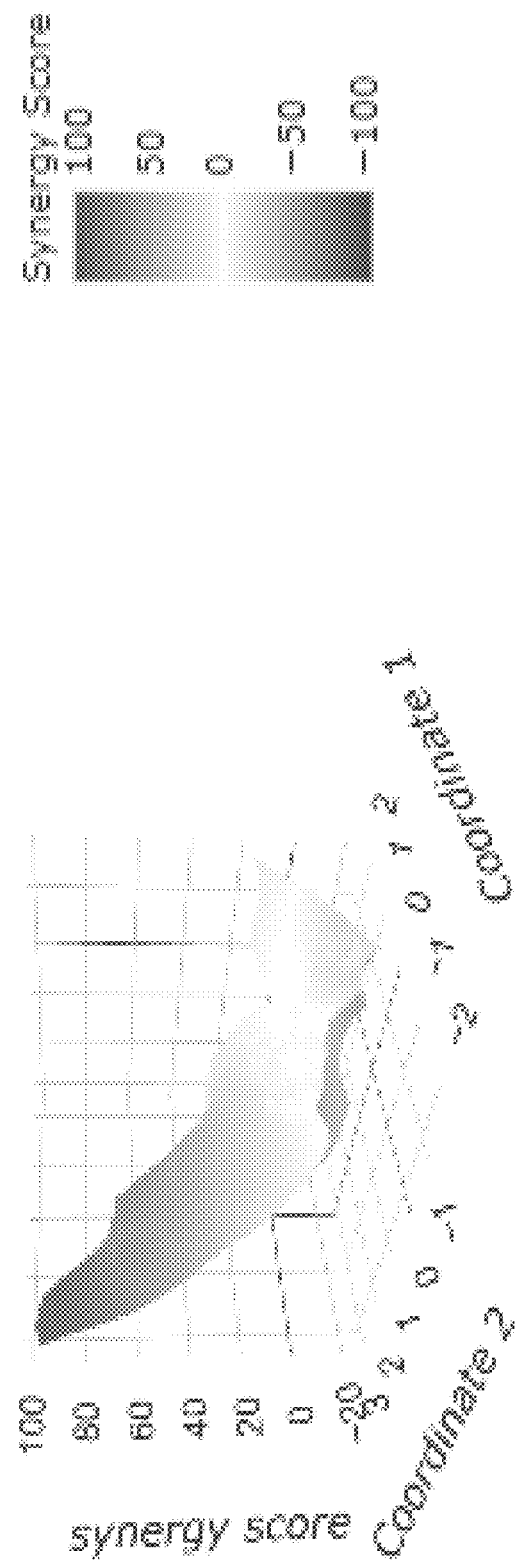
Figure 10D:
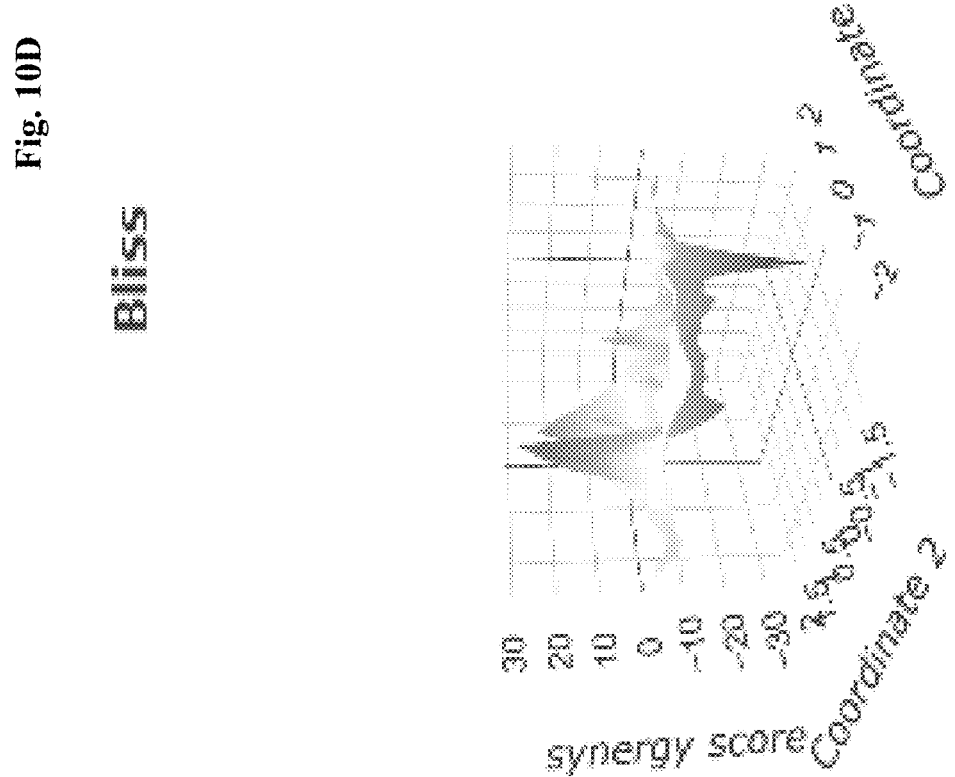

FIGS. 10A-D show plots of the synergy associated with a composition containing CBD, niacinamide, and urolithin A. FIG. 10A is a plot of the ZIP synergy score. FIG. 10B is a plot of the HSA synergy score. FIG. 10C is a plot of the Loewe synergy score. FIG. 10D is a plot of the Bliss synergy score.

Figure 11:
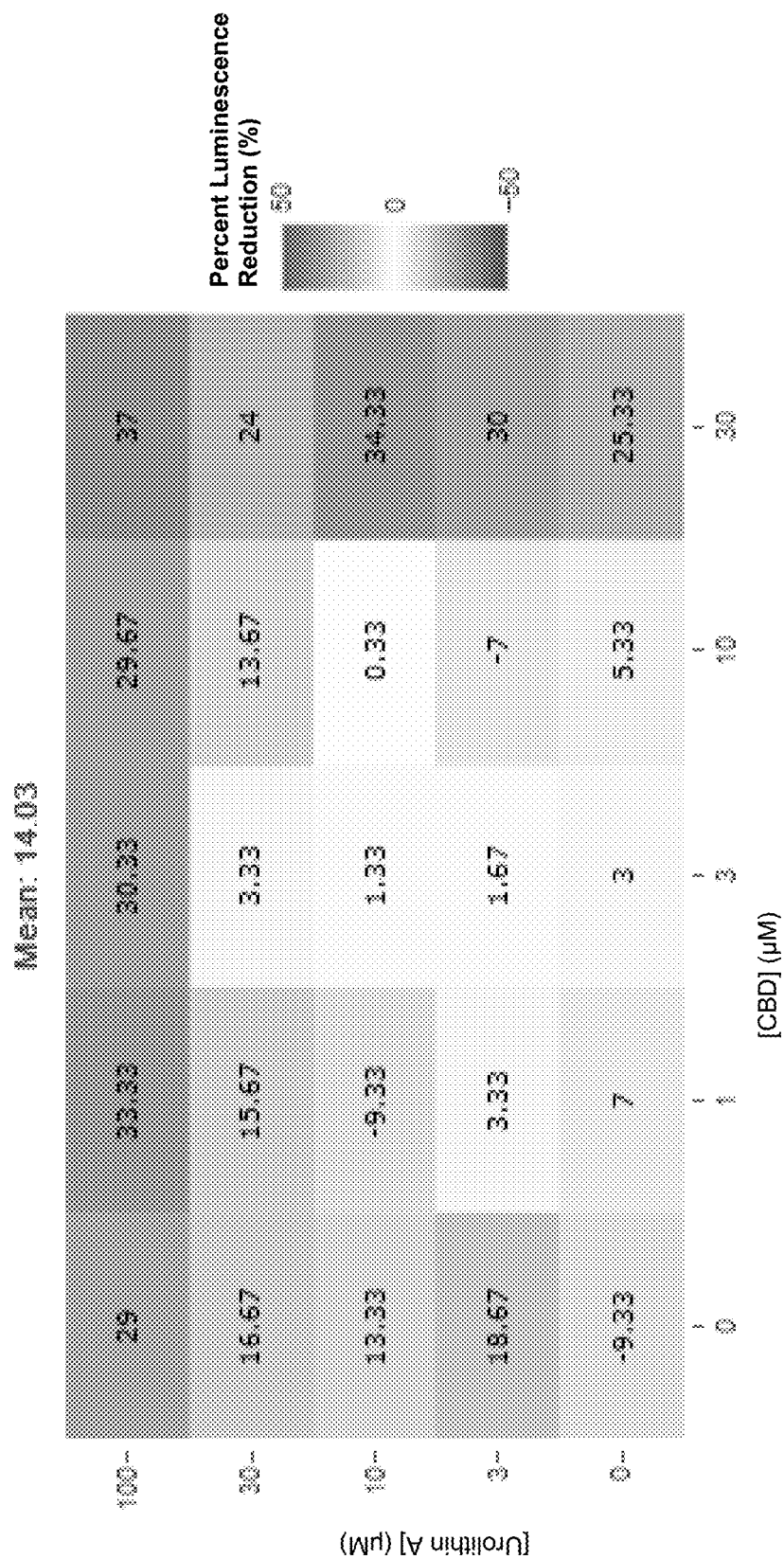

FIG. 11 is a dose-response map showing the effect of CBD and urolithin A concentration on percent luminescence reduction.

Figure 12B:
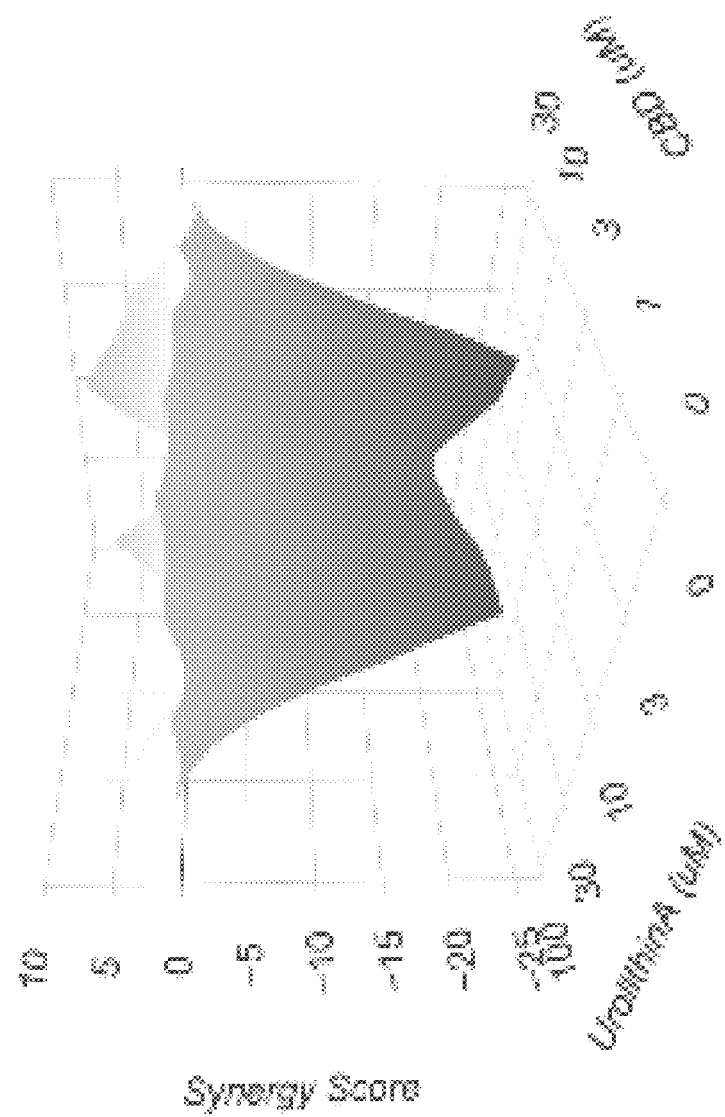
Figure 12C:
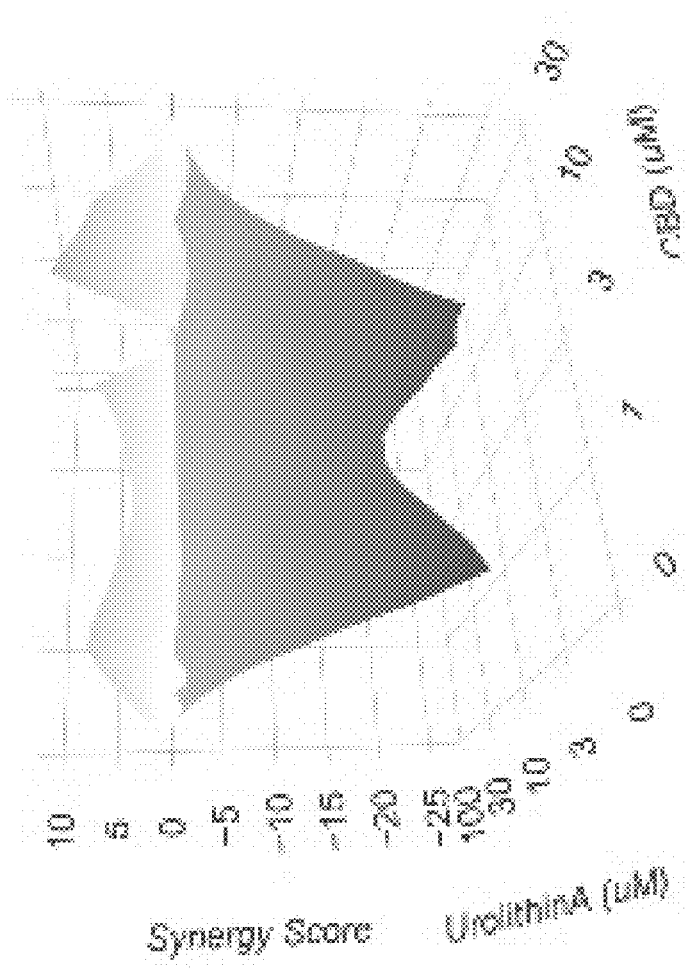

FIGS. 12A-D show a plot of CBD and urolithin A concentration versus synergy. FIG. 12A is a plot of CBD and urolithin A concentration versus ZIP synergy score. FIG. 12B is a plot of CBD and urolithin A concentration versus HSA synergy score. FIG. 12C is a plot of CBD and urolithin A concentration versus Loewe synergy score. FIG. 12D is a plot of CBD and urolithin A concentration versus Bliss synergy score.

Figure 13C:
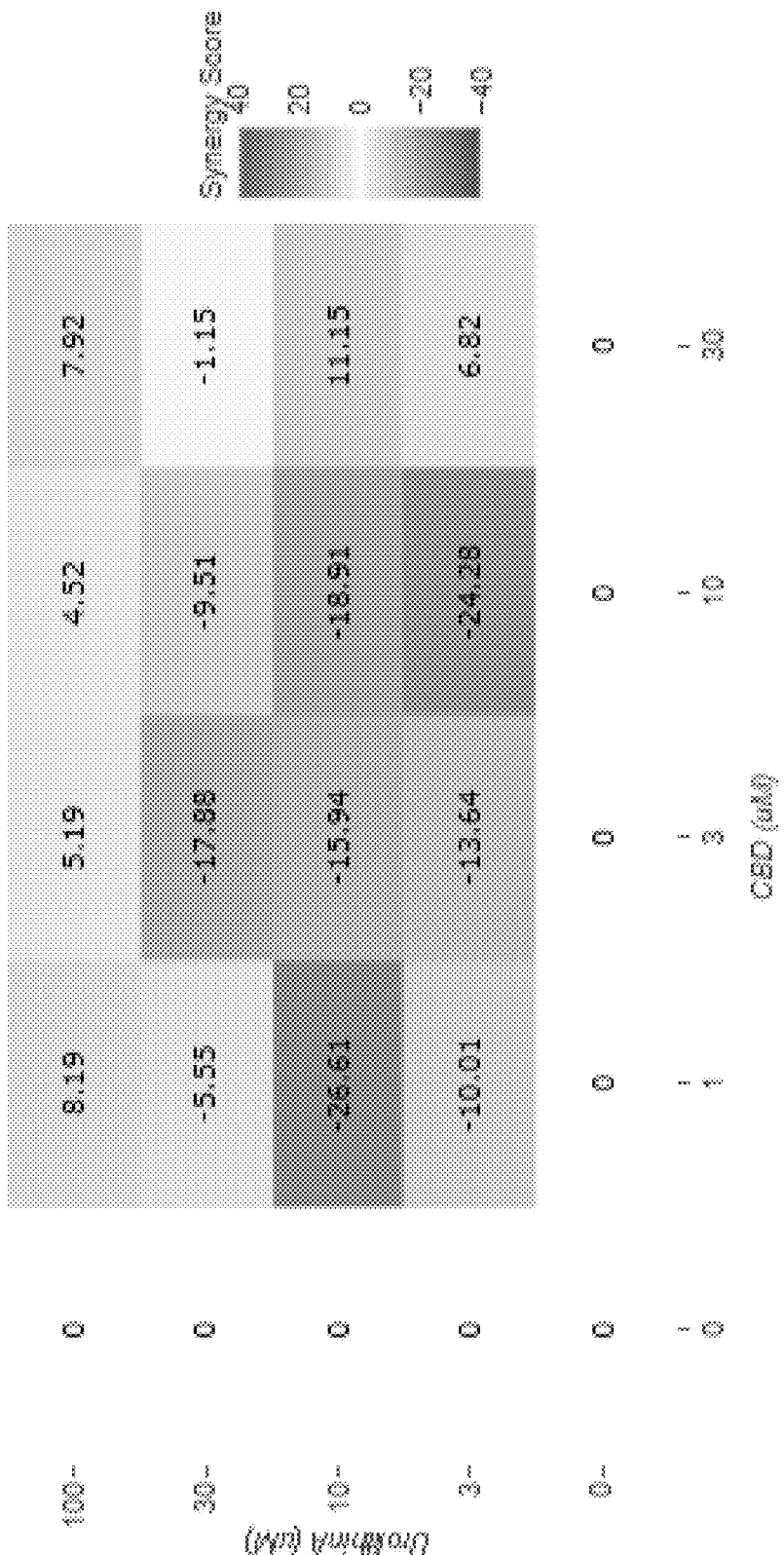

FIGS. 13A-D show heat maps of synergy scores at various CBD and urolithin A concentrations. FIG. 13A is a heat map of ZIP synergy scores for various CBD and urolithin A concentrations. FIG. 13B is a heat map of HSA synergy scores for various CBD and urolithin A concentrations. FIG. 13C is a heat map of Loewe synergy scores for various CBD and urolithin A concentrations. FIG. 13D is a heat map of Bliss synergy scores for various CBD and urolithin A concentrations.

Figure 14:
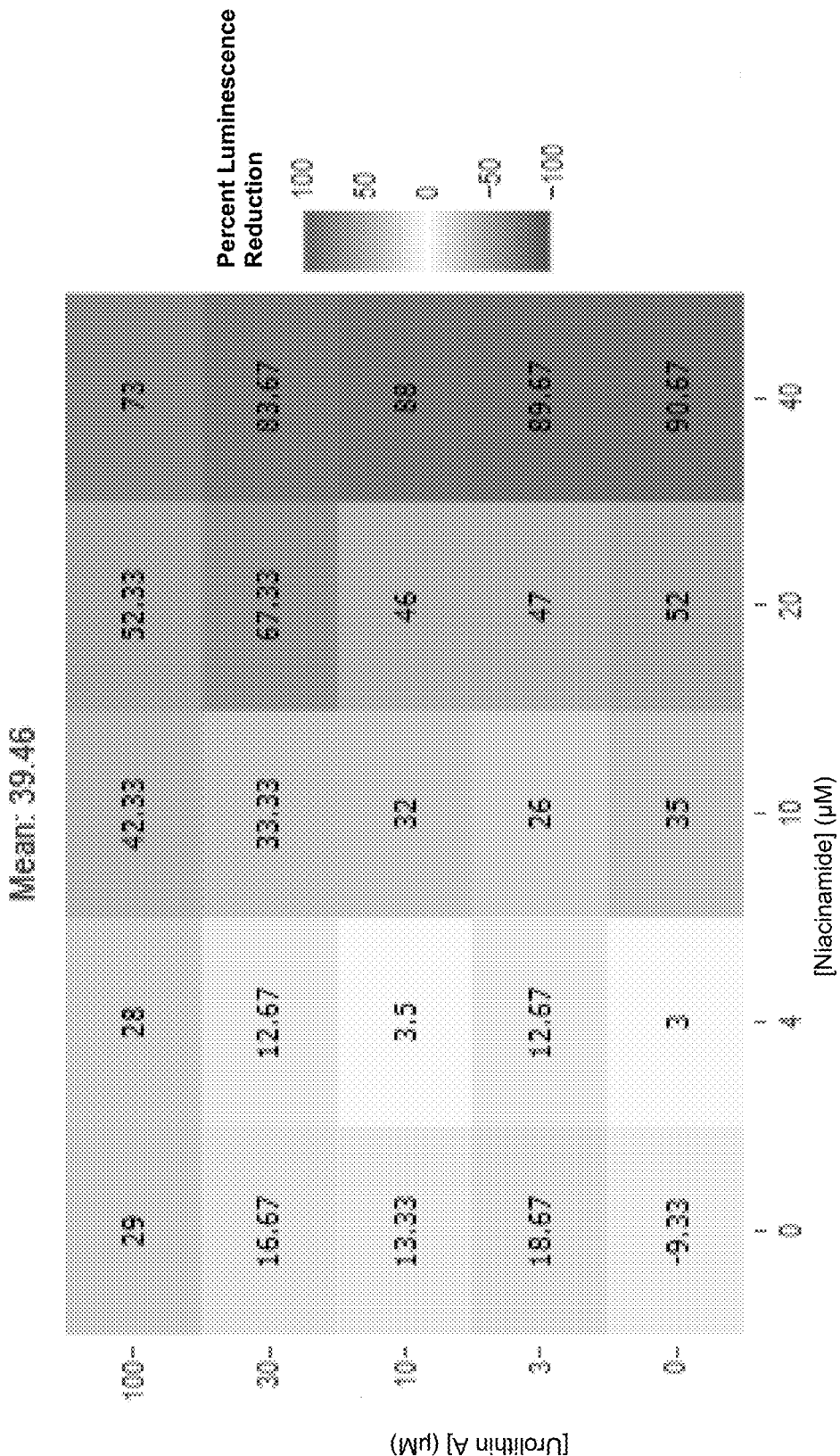

FIG. 14 is a dose-response map showing the effect of niacinamide and urolithin A concentration on percent luminescence reduction.

Figure 15A:
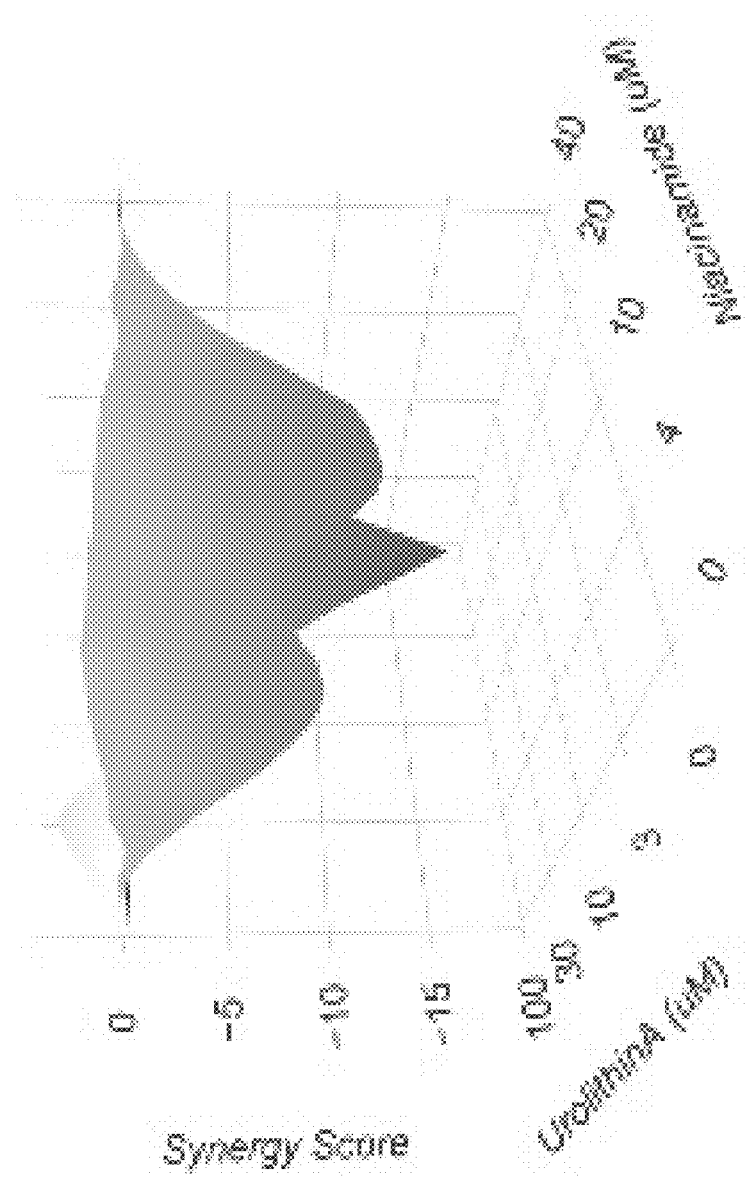
Figure 15B:
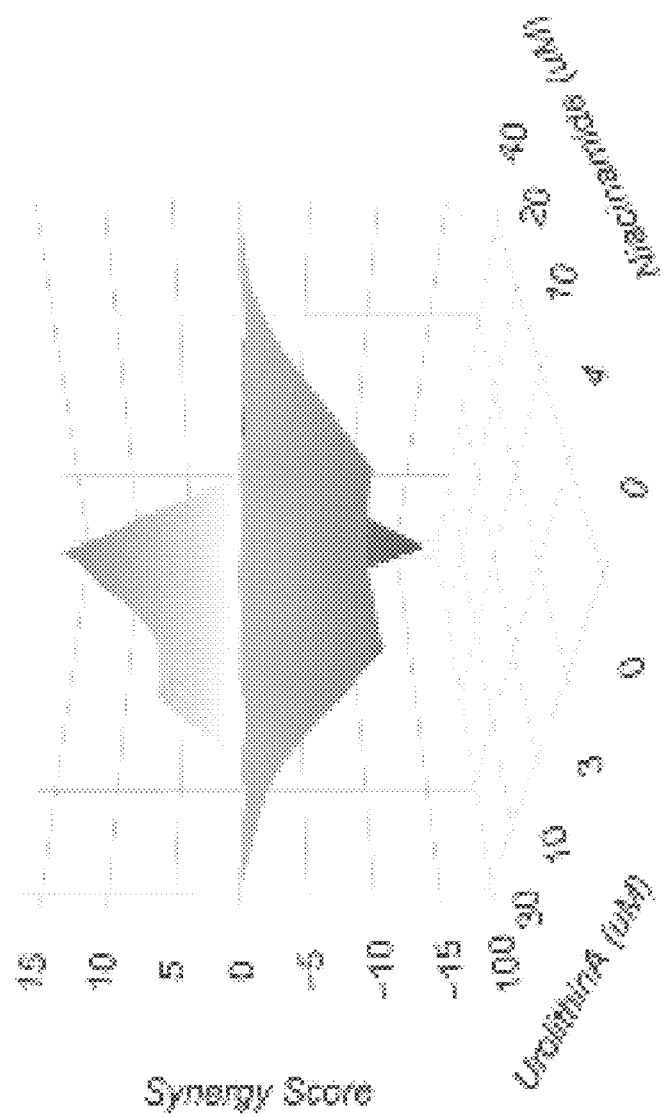
Figure 15C:
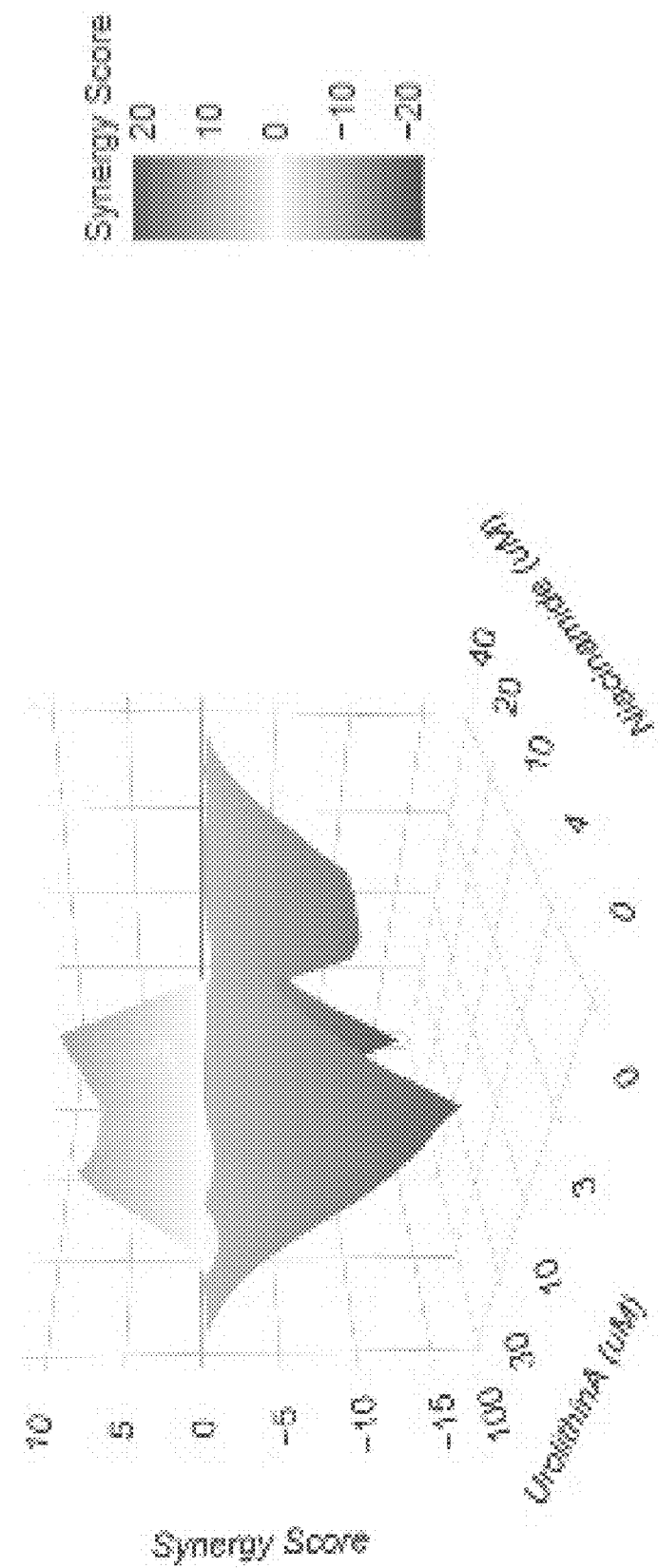
Figure 15D:
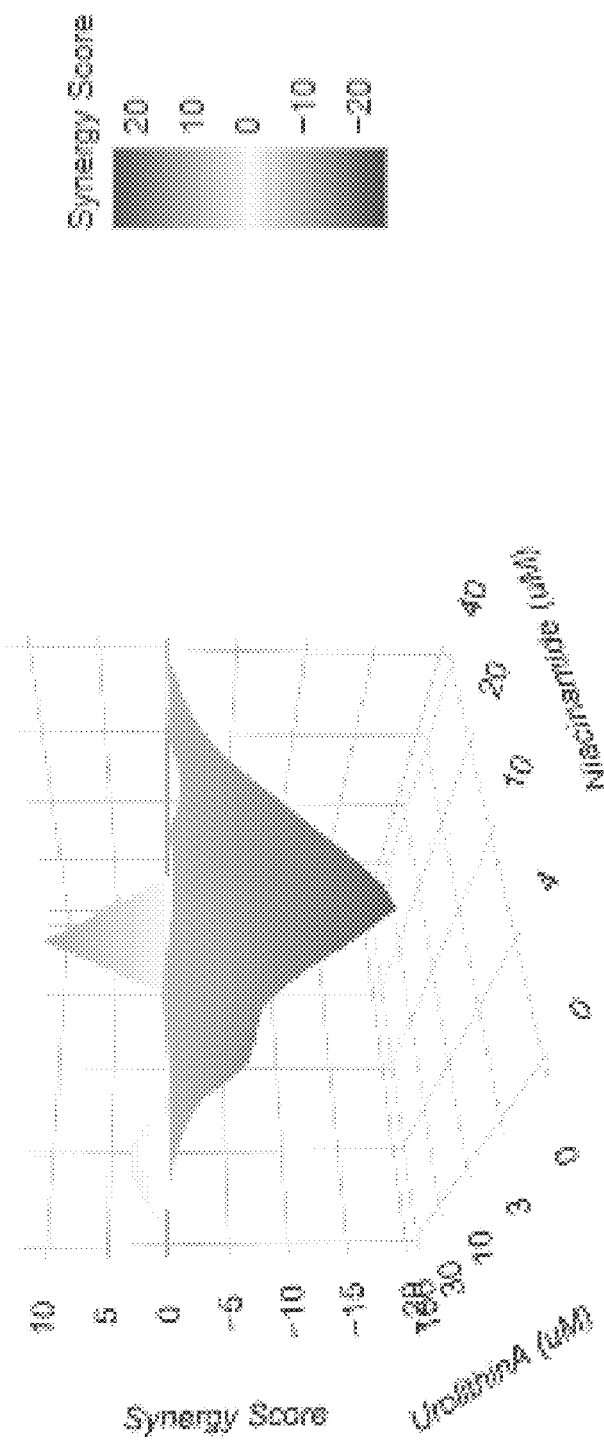

FIGS. 15A-D show a plot of niacinamide and urolithin A concentration versus synergy. FIG. 15A is a plot of niacinamide and urolithin A concentration versus ZIP synergy score. FIG. 15B is a plot of niacinamide and urolithin A concentration versus HSA synergy score. FIG. 15C is a plot of niacinamide and urolithin A concentration versus Loewe synergy score. FIG. 15D is a plot of niacinamide and urolithin A concentration versus Bliss synergy score.

Figure 16A:
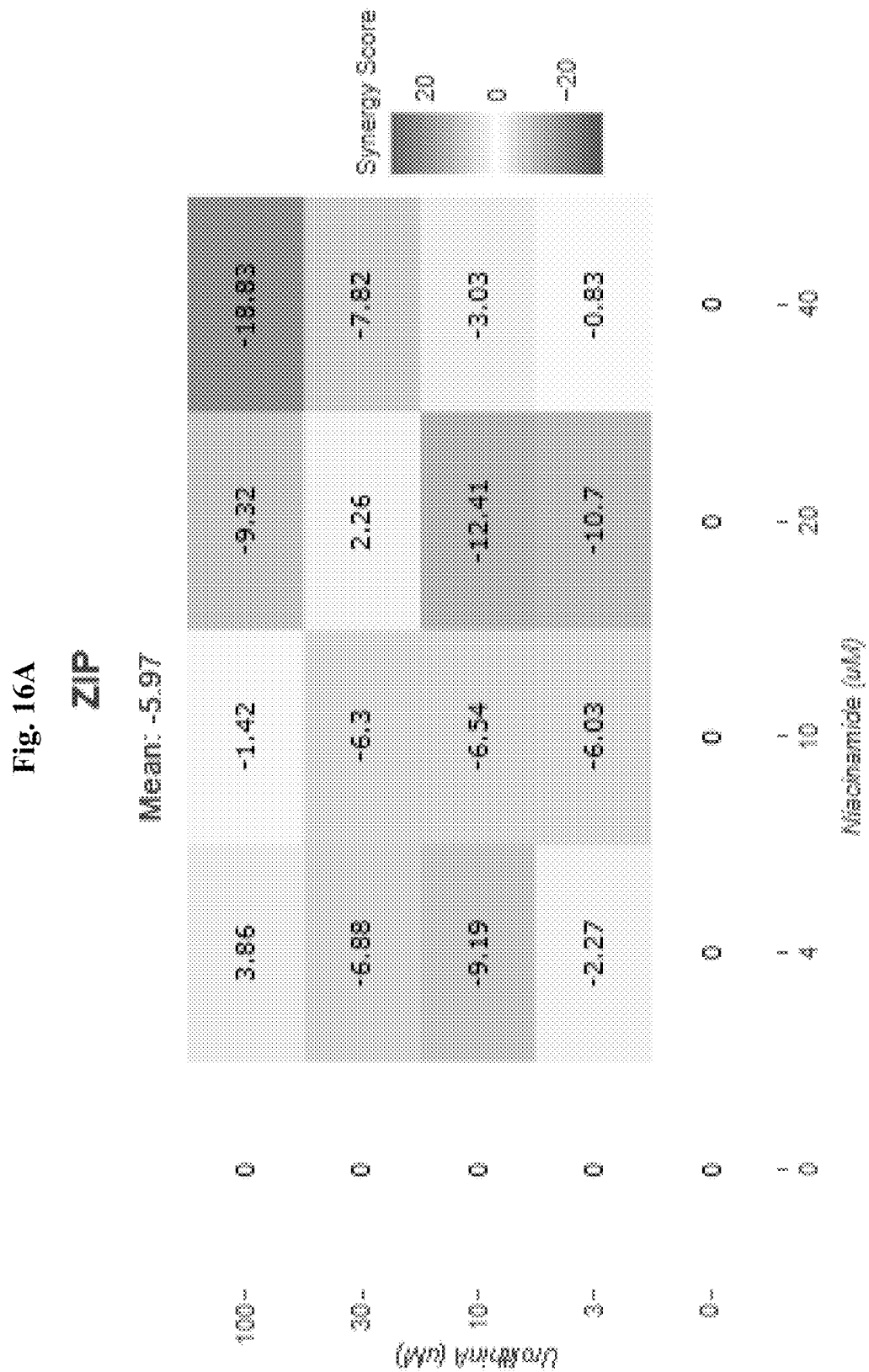

FIGS. 16A-D show heat maps of synergy scores at various niacinamide and urolithin A concentrations. FIG. 16A is a heat map of ZIP synergy scores for various niacinamide and urolithin A concentrations. FIG. 16B is a heat map of HSA synergy scores for various niacinamide and urolithin A concentrations. FIG. 16C is a heat map of Loewe synergy scores for various niacinamide and urolithin A concentrations. FIG. 16D is a heat map of Bliss synergy scores for various niacinamide and urolithin A concentrations.

DETAILED DESCRIPTION OF THE INVENTION

Definitions

As used herein, the verb "comprise" is used in this description and in the claims and its conjugations are used in its non-limiting sense to mean that items following the word are included, but items not specifically mentioned are not excluded.

As used herein, the term "about" refers to plus or minus 10% of the referenced number unless otherwise stated or otherwise evident by the context, and except where such a range would exceed 100% of a possible value, or fall below 0% of a possible value, such as less than 0% content of an ingredient, or more than 100% of the total contents of a composition. For example, reference to an absolute content of a particular cannabinoid of "about 1%" by weight means that that cannabinoid can be present at any amount ranging from 0.9% to 1.1% content by weight.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

The International Code of Zoological Nomenclature defines rank, in the nomenclatural sense, as the level, for nomenclatural purposes, of a taxon in a taxonomic hierarchy (e.g., all families are for nomenclatural purposes at the same rank, which lies between superfamily and subfamily). While somewhat arbitrary, there are seven main ranks defined by the international nomenclature codes: kingdom, phylum/division, class, order, family, genus, and species.

As used herein, "potential cannabinoid content" refers to the theoretical maximum of decarboxylated cannabinoid content, plus converted contents of acidic versions of the same cannabinoid. For example, in some embodiments, THCA can be converted to active THC using the formula: THCA×0.877=THC. When using this approach, the maximum THC for the sample is: THCmax=(THCA×0.877)+THC. This method has been validated according to the principles of the International Conference on Harmonization. Similarly, CBDA can be converted to active CBD and the yield is determined using the yield formula: CBDA×0.877=CBD. The maximum CBD for the sample is: CBDmax=(CBDA×0.877)+CBD.

CBD used in the present disclosure can be from any source, including chemically synthesized CBD, biosynthetically produced CBD (such as that produced by an engineered yeast), or CBD obtained from a plant, such as a *Cannabis* extract. CBD extracts can contain between 1% w/w to 100% w/w CBD. In some embodiments, pure CBD is utilized in the compositions of the disclosure.

THC used in the present disclosure can be from any source, including chemically synthesized THC, biosynthetically produced THC (such as that produced by an engineered yeast), or THC obtained from a plant, such as a *Cannabis* extract. THC extracts can contain between 1% w/w to 100% w/w THC. In some embodiments, pure THC is utilized in the compositions of the disclosure. Other cannabinoids of the present disclosure may similarly be obtained from any source.

As used herein, the term "skin" refers to any of the layers of the skin, including the epidermis, dermis, and hypodermis. The epidermis has five sub-layers, including the stratum corneum, stratum lucidum, stratum *granulosum*, stratum *spinosum*, and stratum basale, which are listed from the outermost sub-layer to the innermost sub-layer. For example, the stratum corneum is the skin's surface.

As used herein, the term "topical composition" refers to any formulation that is applied to the skin. In some embodiments, the disclosure describes "topical application" of the topical composition. As defined herein, "topical application" is application of a topical composition to the skin (e.g., by applying and gently rubbing into skin surface).

Various concentration expressions, including volume concentrations, weight concentrations, and mass concentrations, are utilized to describe the percentage of a component in a solution. Volume concentration has units of % v/v, where v/v is volume per volume. If a solution contains 5% v/v of a component, 5 mL of the component is in a total solution of 100 mL. Weight concentration of a solution is expressed as % w/w, where w/w is weight per weight. If a solution contains 30% w/w of sodium chloride, the solution contains 30 g of sodium chloride and 70 g of solvent and or other components. Mass concentration of a solution is expressed as % w/v, where w/v is weight per volume. If 1 g of sodium chloride is dissolved in a solution with a total volume of 100 mL, a 1% w/v sodium chloride solution has been made.

As used herein, the term "mitochondrial ATP deficit disorder" refers to a disease or disorder that is wholly or partially caused by mitochondrial dysfunction, for example, a dermatological concern. The term dermatological concern refers to any concern that affects the skin, including, but not limited to, acne, psoriasis, eczema, rosacea, ichthyosis, vitiligo, seborrheic dermatitis, actinic keratosis, stretch mark, wrinkles, fine lines, carbuncle, aging, and cellulitis. In some embodiments, these dermatological conditions are caused by viruses, such as SARS-CoV-2. In some embodiments, mitochondrial ATP deficit disorders are characterized by their reduced ATP metabolism in a cell.

In some embodiments, dermatological concerns cause physical and mental discomfort, disturbance and psychological distress, including neurological concerns, sexual dysfunction, and pain. In some embodiments, the compositions described herein improve and/or prevent one or more symptoms of a dermatological concern. Symptoms include comedones, papules, pustules, cysts, blemishes, nodules, lesions, or pimples, pre-emergent pimples, blackheads, wrinkles, fine lines, stretch marks, and/or whiteheads. See FIG. 5

As used herein, the term "acne" refers to a skin disorder which leads to clogged pores and the formation of inflammatory or non-inflammatory lesions on the skin. Acne lesions may be comedones, papules, pustules, cysts, blemishes, nodules, lesions, or pimples, pre-emergent pimples, blackheads, and/or whiteheads. See FIG. 5

As used herein, a "therapeutically effective amount" refers to the minimum amount of an agent or composition required to result in a particular physiological effect (e.g., an amount required to increase, activate, enhance, decrease, or inhibit a particular physiological effect).

As used herein, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "treat" or "treating" means one or more of relieving, alleviating, delaying, reducing, reversing, improving, or managing at least one symptom of a disease, disorder, or concern in a subject. The term "treating" may also mean one or more of preventing, arresting, delaying the onset (i.e., the period prior to clinical manifestation of the condition), reducing the risk of developing or worsening a disease, disorder, or concern, or a reduction in visible symptoms from a disease, disorder, or concern. Examples of concerns include the mitochondrial ATP deficit disorders described throughout this disclosure, pain, dermatological concerns, neurological concerns, sexual dysfunction, and psychological concerns.

As used herein, a "disease" is a state of health of a subject wherein the subject cannot maintain homeostasis. In some embodiments, a subject with a disease does not maintain optimal homeostasis between mitochondria derived from ATP-producing wild type mtDNA and incompetent mitochondria derived from mutant mtDNA (i.e. the highest achievable output of ATP), and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. As used herein, a condition means any disorder, disease, or symptom that does not necessarily have a defined etiology or cause.

As used herein, a "concern" is any disease, disorder, condition, symptom, or imperfection (for example, a skin concern) that distresses a subject.

As used herein, a "cofactor" refers to a non-protein compound that is required for an enzyme to function. References to "redox cofactor" indicate a cofactor for pyruvate dehydrogenase. For example, the enzyme pyruvate dehydrogenase requires the following cofactors: thiamine pyrophosphate (TPP), lipoamide, flavin adenine dinucleotide, nicotinamide adenine dinucleotide, coenzyme A, and a magnesium ion ($Mg^{2+}$). Non-limiting examples of cofactors are found throughout this disclosure. Cofactors may be metal enzymes, vitamins, coenzymes, or prosthetic groups. The term "precursor" in reference to a cofactor refers to any compound that may be converted to a cofactor. For example, niacinamide (also known as "nicotinamide") is the precursor of nicotinamide adenine dinucleotide (NAD).

As used herein, an "antioxidant" refers to a substance that inhibits oxidation.

As used herein, a "mitophagy stimulant" refers to a substance that stimulates (increases) mitophagy. The term "mitophagy" refers to the process of removal of dysfunctional or damaged mitochondria from a cell.

As used herein, an increase in "ATP metabolism" refers to increased ATP usage by the cell. In some embodiments, increased ATP usage has an commensurate increase in ATP production, as the mitochondria feed the cell's needs.

As used herein, the term "synergistic" as it refers to a composition of the disclosure, refers to a composition that exhibits an effect (y) that is in excess of the predicted effect of the composition as calculated by a reference model. In some embodiments, a synergistic effect is calculated using the Synergyfinder web application. The following reference describes the Synergyfinder web application in detail and is incorporated by reference herein in its entirety: Ianevski, A.; He, L.; Aittokallio, T.; Tang, J. SynergyFinder: A Web Application for Analyzing Drug Combination Dose-Response Matrix Data Bioinformatics 2017, 33 (15), 2413-2415.

In some embodiments, the reference model is a "simple deduction model." The simple deduction model determines that a composition exhibits a synergistic effect if the observed effect is greater than the effect predicted from the sum of the effects of the individual components. The synergistic effect according to the deduction model may be calculated using the following equation: y=Observed effect of composition−(sum of expected effect of individual active ingredient components). If y is greater than zero, the composition exhibits a synergistic effect. The synergy percentage adjusted model may also be calculated. The equation for the synergy percentage adjusted is: observed effect of the composition−additive inhibition value. The additive inhibition value for a composition containing two components (e.g., A and B) may be calculated according to the following equation: (Expected effect of component A)+((1−expected effect of component A)×expected effect of component B)/100.

In some embodiments, the reference model is "Highest Single Agent" (HSA). The HSA model states that the expected combination effect equals to the higher effect of individual drugs: $y_{HSA}=\max(y_1,y_2)$. The following reference describes this model in detail and is incorporated by reference herein in its entirety: Berenbaum, M. C. (1989). What is synergy? Pharmacol. Rev., 41(2):93-141.

In some embodiments, the reference model is the Loewe additivity model. This model defines the expected effect $y_{LOEWE}$ as if a drug was combined with itself. the Loewe additivity model considers the dose-response curves of individual drugs. The expected effect $y_{LOEWE}$ must satisfy $$\frac{x_1}{x_{LOEWE}^1} + \frac{x_2}{x_{LOEWE}^2} = 1,$$

where $x_1$ and $x_2$ and $x_{LOEWE}^1$ and $x_{LOEWE}^2$ are the doses of component 1 1 and component 2 alone that produce $y_{LOEWE}$. Using 4-parameter log-logistic (4PL) curves to describe dose-response curves the following parametric form of previous equation is derived:

$$\frac{x_1}{m_1\left(\frac{y_{LOEWE}-E_{min}^1}{E_{max}^1-y_{LOEWE}}\right)^{\frac{1}{\lambda_1}}} + \frac{x_2}{m_2\left(\frac{y_{LOEWE}-E_{min}^2}{E_{max}^2-y_{LOEWE}}\right)^{\frac{1}{\lambda_2}}},$$

where $E_{min}$, $E_{max} \in [0,1]$ are minimal and maximal effects of each component, $m_{1,2}$ are the doses of components that produce the midpoint effect $E_{min}+E_{max}$, also known as relative $EC_{50}$ or $IC_{50}$, and $\lambda_{1,2}$ ($\lambda>0$) are the shape parameters for indicating the sigmoidicity or slope of dose-response curves. A numerical nonlinear softer can be then used to determine $y_{LOEWE}$ for $x_1$ and $x_2$. The Loewe additivity model is described in detail in the following reference, which is incorporated by reference herein in its entirety: Loewe, S. (1953). The problem of synergism and antagonism of combined drugs. Arzneimit-telforschung, 3(4285-290.

In some embodiments, the reference model is the Bliss model. The Bliss model is described in detail in the following reference, which is incorporated by reference herein in its entirety: Bliss, C. I. (1939). The toxicity of poisons applied jointly 1. Annals of Applied Biology, 26(3):585-615. Bliss assumes a stochastic process in which two components exert their effects independently, and the expected combination effect can be calculated based on the probability of independent events as: $y_{BLISS}=y_1+y_2-y_1\times y_2$.

In some embodiments, the reference model is the Zero Interaction Potency (ZIP) model. The ZIP model is described in detail in the following reference, which is incorporated by reference herein in its entirety: Yadav, B., Wennerberg, K., Aittokallio, T., and Tang, J. (2015). Searching for Drug Synergy in Complex Dose-Response Landscapes Using an Interaction Potency Model. Comput Struct Biotechnol J, 13:504-513. ZIP calculates the expected effect of two components under the assumption that they do not potentiate each other:

$$y_{ZIP} = \frac{\left(\frac{x_1}{m_1}\right)^{\lambda_1}}{\left(1+\frac{x_1}{m_1}\right)^{\lambda_1}} + \frac{\left(\frac{x_2}{m_2}\right)^{\lambda_2}}{\left(1+\frac{x_2}{m_2}\right)^{\lambda_2}} - \frac{\left(\frac{x_1}{m_1}\right)^{\lambda_1}}{\left(1+\frac{x_1}{m_1}\right)^{\lambda_1}} \cdot \frac{\left(\frac{x_2}{m_2}\right)^{\lambda_2}}{\left(1+\frac{x_2}{m_2}\right)^{\lambda_2}}$$

Compositions

In some embodiments, the present disclosure provides compositions comprising a cannabinoid and a redox cofactor or precursor thereof, and optionally an antioxidant and/or a mitophagy stimulant.

In some embodiments, the compositions comprise an active ingredient portion. In some embodiments, the active ingredient portion consists of a cannabinoid and a cofactor or precursor thereof. In some embodiments, the active ingredient portion consists of a cannabinoid, a cofactor or precursor thereof, and an antioxidant. In some embodiments, the active ingredient portion consists of a cannabinoid, a cofactor or precursor thereof, and a mitophagy stimulant. In some embodiments, the active ingredient portion consists of a cannabinoid, a cofactor or precursor thereof, an antioxidant, and a mitophagy stimulant. Active ingredient portions may be discussed in binary terms that simply indicate which cannabinoid, cofactor or precursor thereof, antioxidant, or mitophagy stimulant, is present. Active ingredient portions may also indicate the individual contents of each ingredient, for example, by indicating the relative content of one ingredient compared to the other ingredients (e.g., by weight or by moles) in the active ingredient portion. For example, the relative content of cannabinoid in an active ingredient portion containing 5 mg of cannabinoid, 5 mg of cofactor or precursor thereof, 5 mg of antioxidant, and 5 mg of a mitophagy stimulant is 25% by weight of the active ingredient portion. As another example, the relative content of cannabinoid in an active ingredient portion containing 5

Mole of cannabinoid, 5 Mole of cofactor or precursor thereof, 5 Mole of antioxidant, and 10 Mole of a mitophagy stimulant is 20% mol/mol of the active ingredient portion. In some embodiments, the relative content (e.g., weight or moles) of one ingredient compared to another ingredient is expressed as a ratio of the amount of one ingredient compared to the amount of the other ingredient. For example, an active ingredient portion containing 5 mg of cannabinoid and 5 mg of antioxidant has a cannabinoid: antioxidant ratio of 1:1 by weight.

Active ingredient portions may also indicate the content of an ingredient in absolute terms. For example, one may refer to an active ingredient portion as having 5 mg cannabinoid and 5 mg antioxidant.

Active ingredient portions may also indicate the content of an ingredient in relation to the weight of the entire composition. For example, a 100 mg composition having 5 mg cannabinoid has 5% w/w cannabinoid within the total composition.

In some embodiments, in addition to the aforementioned ingredients, the compositions provided herein contain one or more additional ingredients. In some embodiments, a vehicle is used to deliver the pharmaceutically compositions to the skin. In some embodiments, the compositions are incorporated into products as described throughout this disclosure. In some embodiments, the compositions are for the treatment of mitochondrial ATP deficit disorders (e.g. acne). In some embodiments, the compositions increase ATP metabolism.

Cannabinoids

In some embodiments, the compositions described herein contain one or more cannabinoids. Non-limiting examples of cannabinoids include cannabidiol (CBD), cannabinol (CBN), cannabigerol (CBG), cannabichromene (CBC), cannabicyclol (CBL), cannabivarin (CBV), Tetrahydrocannabivarin (THCV), cannabidivarin (CBDV), cannabichromevarin (CBCV), cannabigerovarin (CBGV), cannabigerol monomethyl ether (CBGM), tetrahydrocannabinol (THC), cannabidiolic acid (CBDA), tetrahydrocannabinolic acid (THCA), cannabichromenic acid (CBCA), cannabigerolic acid (CBGA), tetrahydrocannabivarin acid (THCVA), and cannabidivarinic acid (CBDVA). In some embodiments, the cannabinoid comprises CBD. In some embodiments, the cannabinoid comprises THC. In some embodiments, the cannabinoid comprises CBD and THC. Additional combinations of cannabinoids are envisioned in Table A. An "x" in the table refers to the presence of a particular cannabinoid in a composition.

TABLE A

Combinations of Cannabinoids

| Composition | CBD | THC | THCV | CBG | CBC |
|---|---|---|---|---|---|
| 1 | x | x | x | x | x |
| 2 | x | x | x | x |   |
| 3 | x | x | x |   | x |
| 4 | x | x |   | x | x |
| 5 | x |   | x | x | x |
| 6 |   | x | x | x | x |
| 7 | x | x | x |   |   |
| 8 | x | x |   | x |   |
| 9 | x | x |   |   | x |
| 10 | x |   | x | x |   |
| 11 | x |   | x |   | x |
| 12 | x |   |   | x | x |
| 13 |   | x | x | x |   |
| 14 |   | x |   | x | x |
| 15 |   |   | x | x | x |

TABLE A-continued

Combinations of Cannabinoids

| Composition | CBD | THC | THCV | CBG | CBC |
|---|---|---|---|---|---|
| 16 | x | x |   |   |   |
| 17 | x |   | x |   |   |
| 18 | x |   |   | x |   |
| 19 | x |   |   |   | x |
| 20 |   | x | x |   |   |
| 21 |   | x |   | x |   |
| 22 |   | x |   |   | x |
| 23 |   |   | x | x |   |
| 24 |   |   | x |   | x |
| 25 |   |   |   | x | x |
| 26 | x |   |   |   |   |
| 27 |   | x |   |   |   |
| 28 |   |   | x |   |   |
| 29 |   |   |   | x |   |
| 30 |   |   |   |   | x |

In some embodiments, the compositions comprise CBD ($C_{21}H_{30}O_2$; molecular weight=314.5 g/mol) and/or THC ($C_{21}H_{30}O_2$; molecular weight=314.5 g/mol). In some embodiments, CBD and/or THC modulate the efficiency of mitochondria and/or ATP metabolism. In some embodiments, CBD and/or THC modulate eicosanoid and/or endocannabinoid systems associated with mitochondrial conditions and/or hormesis. In some embodiments, CBD and/or THC have anti-inflammatory properties. In some embodiments, the presence of a cannabinoid (e.g. CBD and/or THC) within the compositions described herein cause an improvement in oxidative-phosphorylation. In some embodiments, the improvement in oxidative-phosphorylation leads to augmented cellular ATP production and/or metabolism. In some embodiments, the presence of more than one cannabinoid causes a synergistic improvement in oxidative-phosphorylation. In some embodiments, the cannabinoid modifies the pharmacological location and outcome In some embodiments, CBD and THC work synergistically to improve oxidative-phosphorylation.

In some embodiments, cannabinoids, such as CBD and/or THC are extracted from *Cannabis* plants to form an extract. Non-limiting examples of *Cannabis* plants include *Cannabis sativa, Cannabis indica*, or *Cannabis ruderalis*. In some embodiments, cannabinoids, such as CBD and/or THC, are extracted from hybrid varieties of *Cannabis*. Cannabinoids, such as CBD and/or THC, are extracted from *Cannabis* plants according to known methods in the art. Non-limiting extraction methods include sonication, heating under reflux, soxhlet extraction, solid-phase micro-extraction, supercritical-fluid extraction, pressurized-liquid extraction, microwave-assisted extraction, solid-phase extraction, and surfactant-mediated techniques. In some embodiments, the steps for extraction include, but are not limited to, pre-washing, drying of plant parts or freeze drying, and grinding to obtain homogenous extracted plant samples.

In some embodiments, cannabinoids, such as CBD and/or THC, are extracted using an alcohol-based extraction. In some embodiments, cannabinoids, such as CBD and/or THC, are extracted with ethanol. In some embodiments, cannabinoids, such as cannabidiol and/or THC are extracted with butanol. In some embodiments, cannabinoids, such as cannabidiol and/or THC are obtained using a supercritical carbon dioxide based extraction. Methods for extraction of CBD and/or THC from *Cannabis* plants are described in the following patent documents which are incorporated by reference in their entirety herein: U.S. Pat. No. 7,344,736 (issued Mar. 18, 2008), U.S. Publication No. 2019/0231833

A1, (published Aug. 1, 2019), International Publication No. 2019/020738 (published Jan. 31, 2019), International Publication No. 2004/016277 A1 (published Feb. 26, 2004), and U.S. Publication No. 2019/0160393 A1 (published May 30, 2019).

In some embodiments, an extract of cannabinoids is subjected to winterization, filtration, vaporization, distillation, chromatography, supercritical or subcritical extraction, short path distillation to remove undesirable elements. In some embodiments, cannabinoids are separated from each other by differences in boiling point. For example, CBD and THC are separated from each other by a difference in boiling point.

In some embodiments, the compositions described herein contain one or more of a CBD extract or a THC extract. As used herein, a "CBD extract" contains CBD, and a "THC extract" contains THC. In some embodiments, a CBD extract contains from about 1% w/w to about 100% w/w of CBD, including all subranges and ranges therebetween. For example, in some embodiments, the CBD extract contains about 1 w/w CBD, or about 2% w/w CBD, or about 3% w/w CBD, or about 4% w/w CBD, or about 5 w/w CBD, or about 10% w/w CBD, or about 20% w/w CBD, or about 30% w/w CBD, or about 40% w/w CBD, or about 50 w/w CBD, or about 60% w/w CBD, or about 70% w/w CBD, or about 80% w/w CBD, or about 90% w/w CBD, or about 95 w/w CBD, or about 96% w/w CBD, or about 97% w/w CBD, or about 98% w/w CBD, or about 99% w/w CBD, or about 100% w/w CBD, including all subranges and ranges therebetween. In some embodiments, the CBD extract contains at least about 1% w/w CBD, or at least about 2% w/w CBD, or at least about 3% w/w CBD, or at least about 4% w/w CBD, or at least about 5% w/w CBD, or at least about 10% w/w CBD, or at least about 20% w/w CBD, or at least about 30% w/w CBD, or at least about 40% w/w CBD, or at least about 50% w/w CBD, or at least about 60% w/w CBD, or at least about 70% w/w CBD, or at least about 80% w/w CBD, or at least about 90% w/w CBD, or at least about 95% w/w CBD, or at least about 96% w/w CBD, or at least about 97% w/w CBD, or at least about 98% w/w CBD, or at least about 99% w/w CBD, or at least about 100% w/w CBD. In some embodiments, a THC extract contains from about 1% w/w to about 100% w/w of THC, including all subranges and ranges therebetween.

In some embodiments, the THC extract contains about 1% w/w THC, or about 2% w/w THC, or about 3% w/w THC, or about 4% w/w THC, or about 5 w/w THC, or about 10% w/w THC, or about 20% w/w THC, or about 30% w/w THC, or about 40% w/w THC, or about 50 w/w THC, or about 60% w/w THC, or about 70% w/w THC, or about 80% w/w THC, or about 90% w/w THC, or about 95 w/w THC, or about 96% w/w THC, or about 97% w/w THC, or about 98% w/w THC, or about 99% w/w THC, or about 100% w/w THC, including all subranges and ranges therebetween. In some embodiments, the THC extract contains at least about 1% w/w THC, or at least about 2% w/w THC, or at least about 3% w/w THC, or at least about 4% w/w THC, or at least about 5% w/w THC, or at least about 10% w/w THC, or at least about 20% w/w THC, or at least about 30% w/w THC, or at least about 40% w/w THC, or at least about 50% w/w THC, or at least about 60% w/w THC, or at least about 70% w/w THC, or at least about 80% w/w THC, or at least about 90% w/w THC, or at least about 95% w/w THC, or at least about 96% w/w THC, or at least about 97% w/w THC, or at least about 98% w/w THC, or at least about 99% w/w THC, or at least about 100% w/w THC.

In some embodiments, the CBD extract and/or THC extract contains one or more other cannabinoids. Other cannabinoids have been described throughout this disclosure. In some embodiments, the other cannabinoid is THC. Thus, in some embodiments, the CBD extract contains THC or the THC extract may contain CBD. In some embodiments, the CBD and/or THC extract contains from about 0.1% w/w to about 90% w/w of another cannabinoid, including all subranges and ranges therebetween. In some embodiments, the CBD extract and/or THC extract contains from about 0.1% w/w to about 5% w/w of another cannabinoid, including all subranges and ranges therebetween. In some embodiments, the CBD extract and/or THC extract contains from about 5% w/w to about 15% w/w of another cannabinoid, including all subranges and ranges therebetween. In some embodiments, the CBD extract and/or THC extract contains from about 15% w/w to about 30% w/w of another cannabinoid including all subranges and ranges therebetween. In some embodiments, the CBD extract and/or THC extract contains from about 30% w/w to about 50% w/w of another cannabinoid including all subranges and ranges therebetween. In some embodiments, the CBD extract and/or THC extract contains from 50% w/w to about 75% w/w of another cannabinoid including all subranges and ranges therebetween. In some embodiments, the CBD extract and/or THC extract contains from about 75% w/w to about 90% w/w of another cannabinoid including all subranges and ranges therebetween.

For example, in some embodiments, the CBD and/or THC extract contains about 0.1% w/w, about 0.5% w/w, about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, or about 90% w/w of another cannabinoid, including subranges and ranges therebetween.

In some embodiments, the CBD and/or THC extract contains at least about 0.1% w/w, at least about 0.5% w/w, at least about 1% w/w, at least about 2% w/w, at least about 3% w/w, at least about 4% w/w, at least about 5% w/w, at least about 6% w/w, at least about 7% w/w, at least about 8% w/w, at least about 9% w/w, at least about 10% w/w, at least about 11% w/w, at least about 12% w/w, at least about 13% w/w, at least about 14% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, at least about 80% w/w, at least about 85% w/w, or at least about 90% w/w of another cannabinoid, including all values and ranges thereof.

In some embodiments, a CBD extract or synthetic CBD is pure CBD. In some embodiments, pure CBD contains from about 95% w/w to about 100% w/w of CBD. In some embodiments, pure CBD contains about 95% w/w, or about 96% w/w, or about 97% w/w, or about 98% w/w, or about 99% w/w, or about 100% w/w CBD. In some embodiments, a THC extract or synthetic THC is pure THC. In some embodiments, pure THC contains from about 80% w/w to about 100% w/w of THC. In some embodiments, pure THC contains about 80% w/w, or about 85% w/w, or about 90% w/w, or about 95% w/w, or about 96% w/w, or about 97% w/w, or about 98% w/w, or about 99% w/w, or about 100% w/w THC.

In some embodiments, CBD and/or THC is produced synthetically. Synthetic CBD and/or THC has the same or similar therapeutic effects as naturally occurring CBD and/or THC when administered to the subjects. Patent documents, such as U.S. Publication No. 2019/0031601 (published Jan. 31, 2019), U.S. Pat. No. 9,447,019 (issued Sep. 20, 2016), and U.S. Publication No. 2015/0320698 (published Nov. 12, 2015), which describe synthetic cannabinoids are incorporated by reference herein in their entirety.

In some embodiments, the compositions described herein comprise CBD analogs, CBD salts, modified CBD, propyl cannabinoids (CBDv), THC analogs, THC salts, THC variants, and modified THC.

Non-limiting examples of THC variants include $\Delta^9$-THC-$C_5$, $\Delta^9$-THC-$C_4$, $\Delta^9$-THCV-$C_3$, $\Delta^9$-THCO-$C_1$, $\Delta^9$-THCA-$C_5$ A, $\Delta^9$-THCA-$C_5$ B, $\Delta^9$-THCA-$C_4$ A, $\Delta^9$-THCA-$C_4$ B, $\Delta^9$-THCVA-$C_3$ A, $\Delta^9$-THCOA-$C_1$ A, $\Delta^9$-THCOA-$C_1$ B, $\Delta^8$-THC-$C_5$, $\Delta^8$-THCA-$C_5$ A, (−)-cis-$\Delta^9$-THC-$C_5$.

Methods for cannabinoid synthesis, such as CBD and/or THC synthesis are described in the following patent documents, which are incorporated by reference in their entirety herein: EP Publication No. 2578561 A1 (published Apr. 10, 2013), U.S. Publication No. 2017/0008868 A1 (published Aug. 28, 2018), U.S. Publication No. 2007/0072939 A1 (published Mar. 29, 2007). In some embodiments, CBD and/or THC is produced in microorganisms. Methods for producing CBD and/or THC in microorganisms are described in U.S. Publication No. 2019/0078168 (published Mar. 14, 2019), U.S. Publication No. 2016/0010126 A1 (published Jan. 14, 2016) and International Publication No. 2017/139496 (published Aug. 17, 2016), which are incorporated by reference in their entireties, herein. In some embodiments, CBD is obtained from commercial sources such as Bluebird Botanicals, CBDistillery®, or ExtractLabs®.

In some embodiments, the CBD extract and/or THC extract contains one or more terpenes. Non-limiting examples of terpenes include alpha-cedrene, alpha-humulene, alpha-pinene, alpha-terpinene, beta-myrcene, beta-pinene, borneol, camphene, camphor, caryophyllene oxide, cedrol, alpha-bisabolol, alpha-phellandrene, isopulegol, cis-nerolidol, β-carene, fenchyl alcohol, hexahydrothymol, eucalyptol, isoborneol, farnesene, fenchone, gamma-terpinene, geraniol, geranyl acetate, humulene, guaiol, limonene, linalool, nerol, ocimene, alpha-phellandrene, pulegone, sabinene, sabinene hydrate, terpineol, terpinolene, trans-caryophyllene, β-caryophyllene, trans-nerolidol, and valencene.

In some embodiments, the compositions of the disclosure contain cannabidiolic acid (CBDA) in addition to CBD. In some embodiments, CBDA is converted to CBD by decarboxylation according to the reaction below:

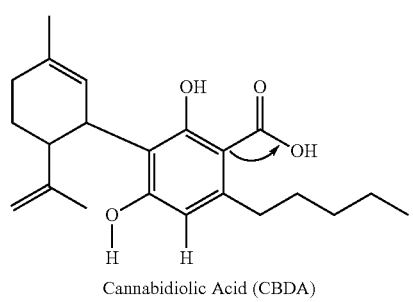

Cannabidiolic Acid (CBDA)

Decarboxylation

Cannabidiol (CBD)

In some embodiments, CBD is obtained from CBDA by heating CBDA to temperatures above 190° F.

In some embodiments, the compositions of the disclosure contain tetrahydrocannabinolic acid (THCA) in addition to THC. In some embodiments, THCA is converted to THC by decarboxylation according to the reaction below:

$\Delta^9$-tetrahydrocannabinolic acid (THCA)

decarboxylation $\Delta^9$-tetrahydrocannabinol (THC)

In some embodiments, THC is obtained from THCA by heating THCA to temperatures above 200° F.

The high lipophilicity of CBD and THC (structures shown below) makes delivery

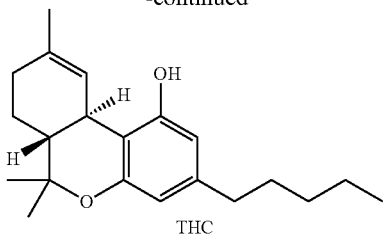

THC of these compounds to the skin challenging.

In some embodiments, the compositions described in the present disclosure allow accumulation of cannabinoids, such as CBD and/or THC, in the skin. In other words, the compositions described herein increase bioavailability of cannabinoids, such as CBD and/or THC, in the skin.

Cofactors

In some embodiments, the compositions further comprise a cofactor or precursor thereof. In some embodiments, a cofactor precursor is used in lieu of a cofactor. In some embodiments, a cofactor precursor is more stable than a cofactor. For example, the cofactor precursor of nicotinamide adenine dinucleotide (NAD+/NADH), niacinamide, is more stable than NADH. In some embodiments, a cofactor precursor of a composition converts to a cofactor after administration. In some embodiments, a cofactor precursor is used in excess.

In some embodiments, the compositions comprise 1, 2, 3, 4, 5, 6, 7, 8, 9, 10, 11, 12, 13, 14, 15, 16, 17, 18, 19, or 20 cofactors or precursors thereof.

Figure 2:
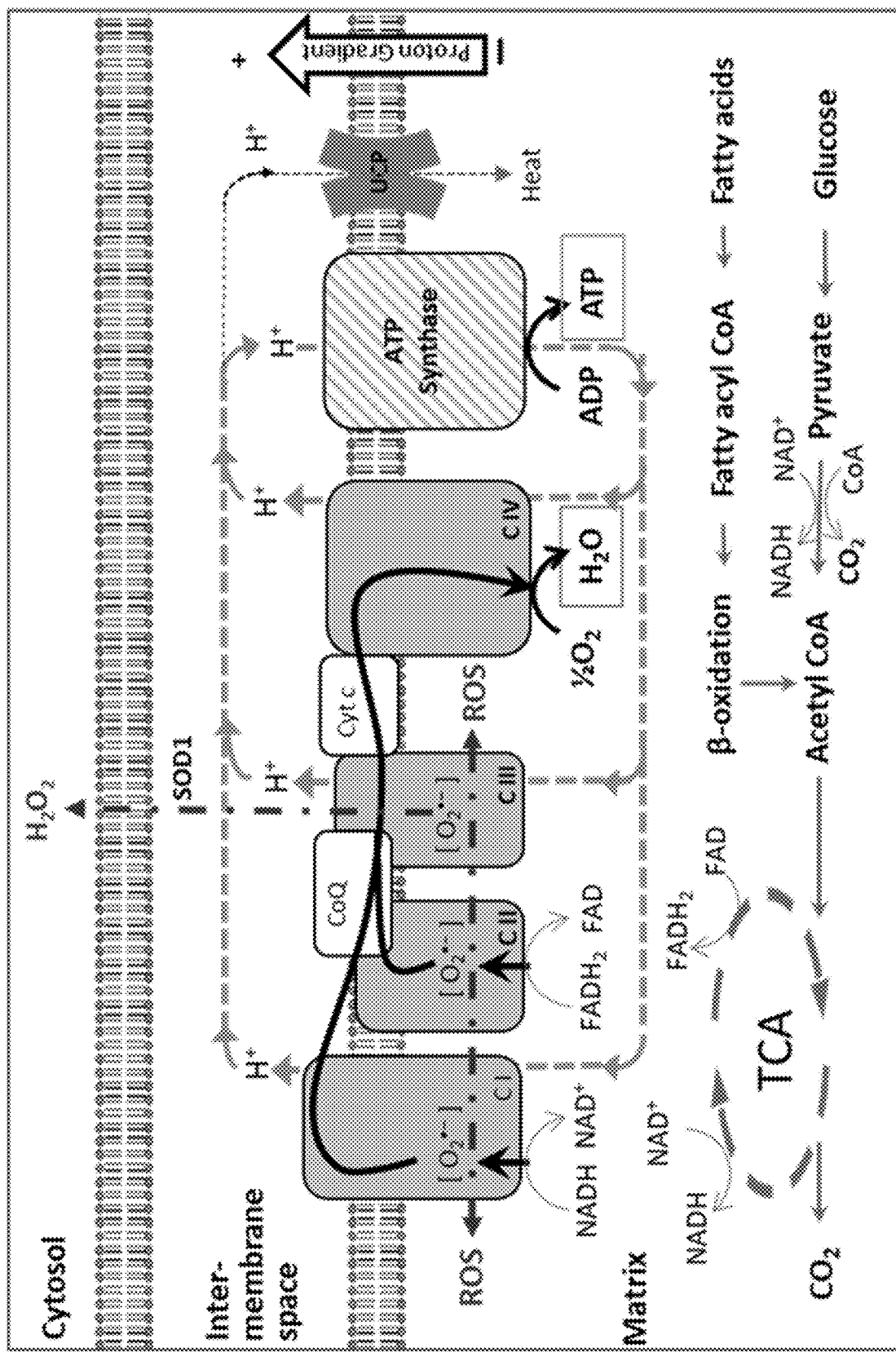
FIG. 2 describes the mitochondrial infrastructure involved in the synthesis of ATP and ROS from a common $O_2 \cdot^-$ radical. ATP synthesis is fundamentally dependent on electron flow in the inner membrane electron transport chain (ETC) energized by the conversion of $^1O_2$ to $H_2O$: $2H^+ + 2e^- + \frac{1}{2}O_2 \rightarrow H_2O$, $\Delta G = -418$ kJ/mol in the mitochondrial matrix. The flow of protons through co-located inner-membrane ATP-synthase provides a charge gradient used to synthesize ATP from ADP. The transfer of electrons from the ETC to the matrix by three nicotinamide adenine dinucleotide (NADH/NAD$^+$) and one flavin adenine dinucleotide (FADH$_2$/FAD) redox cofactors is therefore the most critical component in ATP generation.

In some embodiments, a cofactor or precursor thereof facilitates or is involved in mitochondrial metabolic processes, for example, the tricarboxylic acid cycle (TCA) or the electron transport chain (ETC) (FIG. 2C). In some embodiments, a cofactor or precursor thereof facilitates the transfer of electrons from the inner mitochondrial matrix of the ETC to the mitochondrial matrix of the TCA. In some embodiments, the cofactor or precursor thereof is a TCA/ETC cofactor or precursor thereof. As used herein, a TCA/ETC cofactor or precursor thereof facilitates the TCA and ETC cycles.

In some embodiments, the one or more cofactors is a redox cofactor or precursor thereof. The term "redox cofactor" indicates a cofactor or precursor thereof for pyruvate dehydrogenase. For example, the enzyme pyruvate dehydrogenase requires the following cofactors: thiamine pyrophosphate (TPP), lipoamide, flavin adenine dinucleotide, nicotinamide adenine dinucleotide, coenzyme A, and a magnesium ion ($Mg^{2+}$).

In some embodiments, the cofactor or precursor thereof is a recyclable entity. In some embodiments, the one or more cofactors is not an antioxidant. In some embodiments, a cofactor or precursor thereof does not serve as an antioxidant silencer of reactive oxygen species leaked from non-mitochondrial sources.

In some embodiments, the one or more cofactors or precursors thereof is selected from nicotinamide adenine dinucleotide, Flavin adenine dinucleotide ($FADH_2$), Flavin adenine dinucleotide phosphate, alpha-lipoic acid, acetyl-l-carnitine, niacinamide (vitamin B3), nicotinamide adenine dinucleotide phosphate (NADPH), thiamine, riboflavin, niacin, pyridoxine, cyanocobalamin, biotin, folic acid, pantothenic acid, vitamin C, thiamine pyrophosphate, flavin mononucleotide, pyridoxal phosphate, doexyadenoxylcobalamin, methylcobalamin, tetrahydrofolate, and coenzyme A.

In some embodiments, the cofactor or precursor thereof is riboflavin.

In some embodiments, the cofactor or precursor thereof comprises nicotinamide. In some embodiments, the cofactor or precursor thereof is nicotinamide adenine dinucleotide phosphate.

In some embodiments, the cofactor involved in electron transfer in the electron transport chain is derived from a cofactor precursor. In some embodiments, the cofactor precursor converts to a cofactor via biosynthetic routes known to a person of skill in the art. In some embodiments, the cofactor precursor is a vitamin, such as vitamin B1, B2, B6, B12, niacin, folic acid, or vitamin C.

In some embodiments, the cofactor precursor is niacinamide. Niacinamide also known as "nicotinamide" is the precursor of nicotinamide adenine dinucleotide. The structure of niacinamide ($C_6H_6N_2O$) is shown below. Niacinamide has a molecular weight of 122.1 g/mol. 100% conversion of 1 g of niacinamide to NADH would provide 5.4 g of NADH.

Niacinamide

Antioxidants

In some embodiments, the compositions comprise an antioxidant. Antioxidants are substances that inhibit oxidation. In some embodiments, the compositions comprise about 1, 2, 3, 4, 5, 6, 7, 8, 9, 10, 11, 12, 13, 14, 15, 16, 17, 18, 19, or 20 antioxidants.

In some embodiments, the antioxidant scavenges for non-mitochondrial reactive oxygen species. In some embodiments, the antioxidant sequesters reactive oxygen species that cause mitochondrial damage. In some embodiments, the antioxidant does not sequester $O_2 \cdot^-$ that is required for ATP production. In some embodiments, the antioxidant does not sequester the $O_2 \cdot^-$ that is required to maintain the mitochondrial function necessary for ATP production.

In some embodiments, the antioxidant obeys Lipinski's rule of five (e.g., the antioxidant has a molecular mass of less than 500 g/mol, has no more than 5 hydrogen bond donors, no more than 10 hydrogen bond acceptors, and an octanol-water partition coefficient log P not greater than 5). Lipinski's rules are described in detail in the following references, which are incorporated by reference herein in their entirety: *Adv Drug Deliv Rev.* 2016 Jun. 1; 101: 89-98.; Lipinski et al. *Adv. Drug Deliv. Rev.* 2001; 46:3-26; and Lipinski C A. *J. Pharmacology. Toxicol. Methods.* 2000; 44:235-249.

In some embodiments, the antioxidant does not obey Lipinski's rule of five.

In some embodiments, the antioxidant does not affect normal mitochondria function.

In some embodiments, the antioxidant has a standard redox potential of about −0.06 V. In some embodiments, the antioxidant has a standard redox potential of less than or equal to about −0.06 V. In some embodiments, the antioxidant has a standard redox potential of between about −0.03 V and about −0.2 V, including all subranges and ranges therebetween. In some embodiments, the antioxidant has a standard redox potential of between about −0.03 V and about −0.1 V, including all subranges and ranges therebetween. In some embodiments, the antioxidant has a standard redox potential of between about −0.2 V and about −0.32 V, including all subranges and ranges therebetween. For example, in some embodiments, an antioxidant has a standard redox potential of about −0.03 V, about −0.04 V, about −0.05 V, about −0.06V, about −0.07 V, about −0.08 V, about −0.09 V, about −0.1 V, about −0.11 V, about −0.12 V, about −0.13 V, about −0.14 V, about −0.15 V, about −0.16 V, about −0.16 V, about −0.17 V, about −0.18 V, about −0.19 V, about −0.2 V, about −0.21 V, about −0.22 V, about −0.23 V, about −0.24 V, about −0.25 V, about −0.26 V, about −0.26 V, about −0.27 V, about −0.28 V, about −0.29 V, about −0.3 V, about −0.31 V, about −0.32 V, about −0.33 V, about −0.34 V, about −0.35 V, about −0.36 V, about −0.37 V, about −0.38 V, about −0.39 V, about −0.4 V, about −0.41 V, about −0.42 V, about −0.43 V, about −0.44 V, about −0.45V, about −0.46 V, about −0.47 V, about −0.48 V, about −0.49 V, or about −0.5V. In some embodiments, redox potential is measured with a potentiometer, an oxidation-reduction potential electrode, expressing a redox-active fluorescent protein such as a green fluorescent protein to report redox potential, or surface-enhanced Raman spectroscopy. Additional techniques are described in the following article which is incorporated by reference herein in its entirety: Jiang et al. Nanoscale, 2014, 6, 12104-12110.

In some embodiments, the antioxidant has an octanol-water partition coefficient (log P) that is less than or equal to 5. In some embodiments, the antioxidant has an octanol-water partition coefficient (log P) that is less than or equal to 5, less than or equal to 4, less than or equal to 3, less than or equal to 2, less than or equal to 1, less than or equal to 0, less than or equal to −0.1, less than or equal to −0.2, less than or equal to −0.3, less than or equal to −0.4, less than or equal to −0.5, less than or equal to −0.6, less than or equal to −0.7, less than or equal to −0.8, less than or equal to −0.9, less than or equal to −1, less than or equal to −1.1, less than or equal to −1.2, less than or equal to −1.3, less than or equal to −1.4, less than or equal to −1.5, less than or equal to −1.6, less than or equal to −1.7, less than or equal to −1.8, less than or equal to −1.9, less than or equal to −2, less than or equal to −2.1, less than or equal to −2.2, less than or equal to −2.3, less than or equal to −2.4, less than or equal to −2.5, less than or equal to −2.6, less than or equal to −2.7, less than or equal to −2.8, less than or equal to −2.9, less than or equal to −3, less than or equal to −3.1, less than or equal to −3.2, less than or equal to −3.3, less than or equal to −3.4, less than or equal to −3.5, less than or equal to −3.6, less than or equal to −3.7, less than or equal to −3.8, less than or equal to −3.9, or less than or equal to −4. In some embodiments, the antioxidant has a log P of about −0.27. In some embodiments, the antioxidant has a log P of about −4. In some embodiments, the antioxidant has a log P of less than about −0.27. In some embodiments, the antioxidant has a log P of less than about −4. Multiple methods for determining a molecule's octanol-water partition coefficient are described in the following reference, which is hereby incorporated by reference in its entirety: Bannan et al. *J Chem Theory Comput.* 2016 Aug. 9; 12(8): 4015-4024; Viswanadhan et al. *J. Chem. Inf. Comput. Sci.*, 1989, 29, 163-172. In some embodiments, the molecule's octanol-water partition coefficient is calculated using ALOGPS2.1. ALOGSPS2.1 is described in the following article which is incorporated by reference herein in its entirety: Tetko et al., *J. Chem. Inf. Comput. Sci.*, 2002, 42, 1136-45.

Non-limiting examples of antioxidants that can be used in the compositions of the present invention include acetyl cysteine, ascorbic acid polypeptide, ascorbyl dipalmitate, ascorbyl methylsilanol pectinate, ascorbyl palmitate, ascorbyl stearate, butated hydroxyanisole (BHA), butylated hydroxytoluene (BHT), t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical antioxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, tris(nonylphenyl)phosphite, diethylhexyl syringylidene malonate, vitamin E, diisopropyl vanidene malonate, tocopherol, plant extracts (rosemary, sage, and oregano), carotenoids, amino acids, terpenoids, polyols, flavonoids, phytoalexin, ascorbic acid, lipoic acid, melatonin, coenzyme Q, sodium benzoate, imidazole, vitamin A, methylparaben, propylparaben, ethylenediaminetetraacetic acid (EDTA), L-ergothioneine, a triphenyldecylphosphonium adduct, or an $H_2S$ donor, such as $AP_{123}$ or $AP_{39}$.

In some embodiments, the antioxidant is butylated hydroxytolune (BHT) or butylated hydroxy anisole (BHA). The structure of BHT and BHA are below:

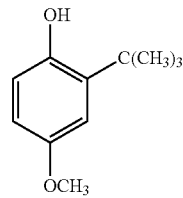 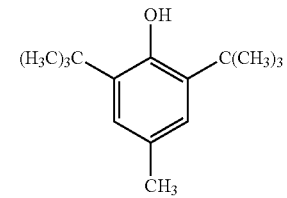

Chemical Formula: $C_{11}H_{16}O_2$
Butylated hydroxy anisole (BHA)

Chemical Formula: $C_{15}H_{24}O$
Butylated hydroxy toluene (BHT)

In some embodiments, the antioxidant is tert-Butylhydroquinone (TBHQ). In some embodiments, the antioxidant is pyrogallol. In some embodiments, the antioxidant is propylgallate. In some embodiments, the antioxidant is N,N'-Di-sec-butyl-p-phenylenediamine. In some embodiments, the antioxidant is coenzyme $Q_{10}$. Co-enzyme $Q_{10}$ has a molecular weight of 863.4 g/mol.

In some embodiments, the antioxidant is astaxanthin, ellagic acid, picrocrocin, lycopene, lutein/zeaxanthin, lutein, zeaxanthin, quercetin, vitamin C, IP-6, beta-carotene, epicatechin, ECGC-epigallocatechin gallate, safranal, proanthocyanidins, resveratrol, vitamin E, melatonin, or mitoQ.

The structures of many of the aforementioned antioxidants are found below.

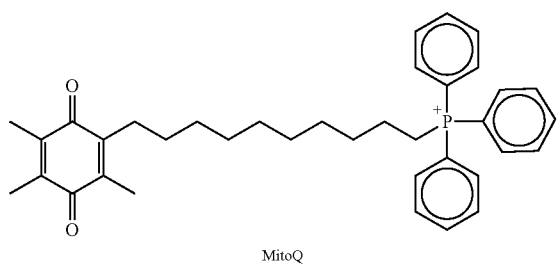
MitoQ

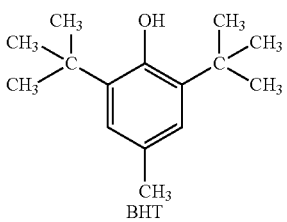
BHT

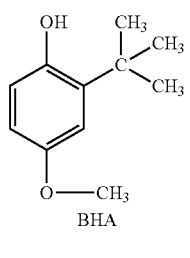
BHA

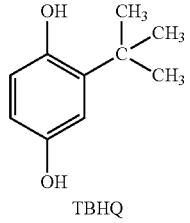
TBHQ

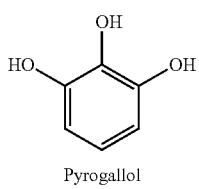
Pyrogallol

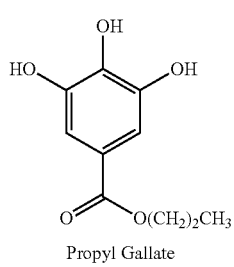
Propyl Gallate

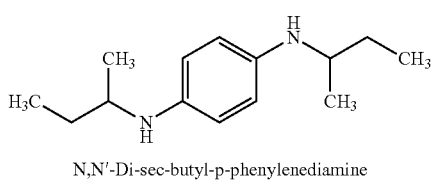
N,N'-Di-sec-butyl-p-phenylenediamine

-continued

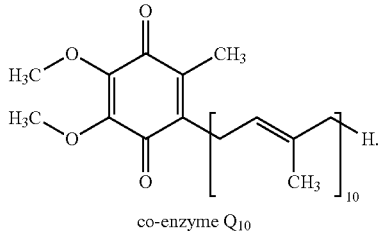
co-enzyme Q₁₀

(a) In some embodiments, the antioxidant is L-ergothioneine. The structure of L-ergothioneine ($C_9H_{15}N_3O_2S$) is below. The molecular weight of L-ergothioneine is 229.3 g/mol.

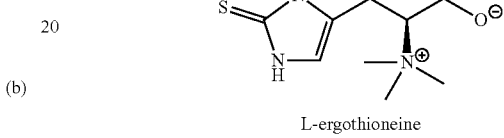
L-ergothioneine (b) In some embodiments, the antioxidant comprises sulfur. In some embodiments, the antioxidant comprises a thiol group. In some embodiments, the antioxidant is a $H_2S$ donor, such as $AP_{123}$ or $AP_{39}$. The molecular structures of $AP_{123}$ and $AP_{39}$ are described in the following publication which is incorporated by reference herein in its entirety: Gero et al. Pharmacol Res. 2016 November; 113(Pt A): 186-198.

(c) In some embodiments, the antioxidant is an amino acid. In some embodiments, the antioxidant is an L-amino acid. In some embodiments, the antioxidant is a D-amino acid. Non-limiting examples of amino acids are histidine, isoleucine, leucine, lysine, methionine, phenylalanine, threonine, tryptophan, valine, arginine, cysteine, glutamine, glycine, proline, tyrosine, alanine, aspartic acid, asparagine, glutamic acid, serine, selenocysteine, pyrrolysine, taurine, and homocysteine.

(d) Mitophagy Stimulant

In some embodiments, the compositions comprise a mitophagy stimulant. A "mitophagy stimulant" refers to a substance that stimulates (increases) mitophagy. The term "mitophagy" refers to the process of removal of dysfunctional or damaged mitochondria from a cell. In some embodiments, a mitophagy stimulant stimulates and assists with the disposal of unhealthy mitochondria. In some embodiments, a mitophagy stimulant assists with the clearance of mitochondria debris. In some embodiments, a mitophagy stimulant clears mitochondria debris from the matrix cristae. In some embodiments, the mitophagy stimulant prevents poor clearance of mitochondrial debris from the cristae of the mitochondrial matrix. In some embodiments, the mitophagy stimulant causes autophagic elimination of mitochondria. In some embodiments, the mitophagy stimulant promotes mitochondrial ATP production. In some embodiments, the mitophagy stimulator is an indirect apoptosis modulator.

In some embodiments, the mitophagy stimulant is urolithin A.

In some embodiments, a mitophagy stimulant is a metabolite of an ellagic acid or ellagitannin. Geraniin, which is isolated from *Geranium thunbergii*, is one example of an ellagitannin. Metabolites of geraniin include ellagic acid, corilagin, gallic acid, brevifolincarboxylic acid, urolithin M3, urolithin M4, urolithin C, urolithin M7, urolithin M5, urolithin M6, urolithin C, and urolithin A. In some embodiments, the mitophagy stimulant is a metabolite of geraniin, including any of the aforementioned metabolites. In some embodiments, the mitophagy stimulant is a urolithin. In some embodiments, the urolithin is selected from urolithin A (also referred to as "urolithin M1"), urolithin B, urolithin C (also referred to as "urolithin M2"), urolithin E, urolithin M7, urolithin M5, urolithin D, isourolithin A, urolithin M4, urolithin M6, urolithin M3, and isourolithin B.

In some embodiments, the mitophagy stimulant is urolithin A (3,8-dihydroxybenzo[c]chromen-6-one). The structure of urolithin A ($C_{13}H_8O_4$) is below. Urolithin A has a molecular weight of 228.2 g/mol.

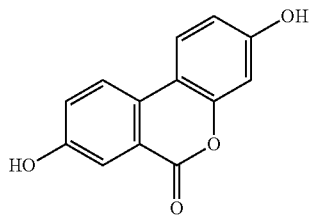 [SMILES: O=c1oc2cc(O)ccc2c2ccc(O)cc12]

A mitophagy stimulant is an example of a "mitophagy modulator". A mitophagy modulator is any substance that affects mitophagy. In some embodiments, the compositions comprise a mitophagy modulator. In some embodiments, a mitophagy modulator is a benzo-coumarin or a dibenzo-α-pyrone. In some embodiments, the benzo-coumarin is selected from 6H-benzo[c]chromen-6-one, 2H-benzo[h]chromen-2-one, 3H-benzo[f]chromen-3-one, and 2H-benzo[g]chromen-2-one. In some embodiments, the dibenzo-α-pyrone is selected from altenuene, isoaltenuene, 2-epialtenuene, 3-epialtenuene, neoaltenuene, dehydroaltenuene A, dehydroaltenuene B, alternariol, alternariol 9-methyl ether, alternariol 9-methyl ether-3-O-sulfate, alternariol 9-O-sulfate, 4-hydroxyalternariol 9-methyl ether, altertenuol, graphislactone A, graphislactone B, graphislactone C, graphislactone E, graphislactone F, graphislactone F, graphislactone, G, graphislactone H, graphislactone D, palmariol A, and palmariol B.

Additional Ingredients

The compositions of the present disclosure can also include none of, any one of, any combination of, or all of the following additional ingredients: other anti-acne ingredients, water, a chelating agent, a UV absorption agent, a moisturizing agent, lilac stem cells, an SRC inhibitor, an avenanthramide, Xperse® 401, licorice, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or more of these additional ingredients. U.S. Pat. No. 9,814,670 (issued Nov. 14, 2017) describes many of these ingredients and is incorporated by reference in its entirety herein.

In some embodiments, the compositions of the disclosure contain water.

Anti-Acne Ingredients

In some embodiments, the compositions of the disclosure contain an anti-acne ingredient. In some embodiments, the anti-acne ingredient includes, but is not limited to, comedolytics (which help keratinization and thus prevent clogged pores), antibiotics (which generally target the acne-causing bacterium *Propionibacterium acnes* or *P. acnes*), and anti-inflammatory compounds (which have a direct effect on inflammation independent of any comedolytic or antibiotic effects). Non-limiting examples of comedolytics include alpha hydroxy acids (e.g., glycolic acid, lactic acid, and salicylic acid), retinoids (e.g., tretinoin and isotretinoin), and saturated dicarboxylic acids (e.g., suberic acid, azelaic acid, and sebacic acid). Non-limiting examples of antibiotics include cephalosporins (e.g., cefoxitin, ceftazidime, and cefepime), lincosamides (e.g., clindamycin and lincomycin), macrolides (e.g., erythromycin and azithromycin), pleuromutillins (e.g., retapamulin), metal complexes (e.g., zinc pyrithione, zinc methoxazole, and zinc sulfathiazole), penicillins (e.g., amoxicillin, ampicillin, and carbenicillin), fluoroquinolones (e.g., ciprofloxacin, clinafloxacin, ofloxacin, and trovafloxacin), retinoids (e.g., tretinoin), saturated dicarboxylic acids (e.g., suberic acid, azelaic acid, and sebacic acid), sulfonamides (e.g., sulfamethizole, sulfamethoxazole, sulfisoxazole), sulfones (e.g., dapsone or diaminodiphenyl sulfone), and tetracyclines (e.g., doxycycline and minocycline). Non-limiting examples of an anti-inflammatory compound include lincosamides (e.g., clindamycin and lincomycin), niacinamide (also known as nicotinamide and pyridine-3-corboxamide), retinoids (e.g., tretinoin), and saturated dicarboxylic acids (e.g., suberic acid, azelaic acid, and sebacic acid). For example, anti-acne compounds include azelaic acid, clindamycin, niacinamide, tretinoin, and zinc pyrithione, or a pharmaceutically acceptable salt thereof.

In some embodiments, the anti-acne ingredient is lilac stem cells. In some embodiments, the lilac stem cells are from any species within the genus *Syringa*. In some embodiments, the lilac stem cells are from any one of the following plants: *Syringa vulgaris, Syringa persica, Syringa velutina, Syringa reflexa, Syringa josikaea, Syringa microphylla, Syringa chinensis, Syringa emodi, Syringa josikaea, Syringa komarowii, Syringa oblata, Syringa pinetorum, Syringa pubescens, Syringa reticulate, Syringa tomentella,* or *Syringa villosa*. In some embodiments, lilac stem cells comprise maltodextrin and *Syringa vulgaris* (Lilac) Leaf Cell Culture Extract (e.g. Dermasyr 10™ by Croda).

Zinc Oxide and Titanium Dioxide in
Caprylic/Capric Triglyceride (Xperse® 401)

In some embodiments, the compositions described herein comprise zinc oxide and titanium dioxide in caprylic/capric triglyceride (Xperse® 401). In some embodiments, zinc oxide and titanium dioxide in caprylic/capric triglyceride provides UV protection. In some embodiments, zinc oxide and titanium dioxide in caprylic/capric triglyceride is a broad-band UVA/UVB blocker. In some embodiments, zinc oxide and titanium dioxide in caprylic/capric triglyceride decreases red spots on the skin associated with acne or scars from acne.

Retinoids

In some embodiments, the compositions described herein comprise a retinoid. In some embodiments, the retinoid is selected from the group consisting of retinol, retinal, tretinoin, isotretinoin, alitretinoin, etretinate, acitretin, adapalene, bexarotene, and tazarotene.

Avenanthramides

In some embodiments, the compositions described herein comprise avenanthramides. In some embodiments, the avenanthramides are from oats (*Avena sativa*), white cabbage butterfly eggs (*Pieris brassicae* and *Pieris rapae*), or fungus-infected carnation (*Dianthus* caryophyllus). In some embodiments, the avenanthramides are an extract of one or more of *Avena sativa, Pieris brassicae, Pieris rapae*, or *Dianthus* caryophyllus. In some embodiments, the avenanthramides are synthetic. In some embodiments, the avenanthramides are conjugates of a phenylpropanoid with anthranilic acid or 5-hydroxyanthranilic acid.

In some embodiments, the avenanthramides are from oats. In some embodiments, the avenanthramide is SymCalmin® by Symrise. In some embodiments, the avenanthramide is Dihydroavenanthramide D.

In some embodiments, avenanthramides are antioxidants. In some embodiments, avenanthramides prevent or treat itching. In some embodiments, avenanthramides are antihistamines.

Polyolprepolymer-2

In some embodiments, the compositions described herein comprise polyolprepolymer-2 (PP2). In some embodiments, PP2 improves delivery and/or deposition of one or more ingredients of the composition, wherein the ingredients are selected from an antioxidant, a mitophagy modulator, a cannabinoid, and a cofactor or precursor thereof.

Licorice

In some embodiments, the compositions of the disclosure contain licorice. In some embodiments, licorice (*Glycrrhiza glabra*) is used as a demulcent and/or as a coating agent. In some embodiments, licorice is used as an anti-inflammatory. In some embodiments, licorice is used as an anti-pigment. As used herein, an "anti-pigment" reduces dark spots. In some embodiments, the licorice is deglychrrhizinated licorice (DGL).

Chelating Agents

In some embodiments, the compositions of the disclosure contain chelating agents. Non-limiting examples of chelating agents include disodium ethylenediaminetetraacetic acid (EDTA) and tetrasodium EDTA.

UV Absorption Agents

In some embodiments, the compositions of the present disclosure include UV absorption agents. UV absorption agents include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis-diethylamino hydroxybenzoyl benzoate, bis benzoxazoylphenyl ethylhexylimino-triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl-4-methoxycinnamate. Non-limiting examples of physical sunblocks include, kaolin, talc, petrolatum and metal oxides (e.g., titanium dioxide and zinc oxide).

Emollients

In some embodiments, the compositions of the disclosure contain one or more emollients. Emollients are lubricating ingredients that make the skin soft and smooth and help the skin to retain moisture. Non-limiting examples of emollients include vegetable oils, mineral oils, shea butter, cocoa butter, petrolatum, cholesterol, silicone, and animal oils (including emu, mink, and lanolin).

Moisturizing Agent

In some embodiments, the compositions of the disclosure contain moisturizing agents. Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe-barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, *Matricaria* (*Chamomilla recutita*) oil, methyl glucose sesquistearate, methylsilanol PCA, mineral oil, mink oil, *Mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinol palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dukis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

Preservatives

In some embodiments, the compositions of the disclosure contain preservatives. Non-limiting examples of preservatives include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid and salts thereof, thimerosal, potassium sorbate, or combinations thereof. In some embodiments, paraben is not included in the formulations of the disclosure.

Thickening Agents

In some embodiments, the compositions of the disclosure contain thickening agents. Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture thereof.

Non-limiting examples of additional thickening agents that can be used in the context of the present invention include carboxylic acid polymers, cross-linked polyacrylate polymers, polyacrylamide polymers, polysaccharides, and gums. Examples of carboxylic acid polymers include cross-linked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid cross-linked with allyl ethers of sucrose or pentaerythritol (e.g., Carbopol™ 900 series from B. F. Goodrich).

Non-limiting examples of cross-linked polyacrylate polymers include cationic and nonionic polymers. Examples are described in U.S. Pat. Nos. 5,100,660; 4,849,484; 4,835,206; 4,628,078; 4,599,379, each of which is incorporated by reference in its entirety herein.

Non-limiting examples of polyacrylamide polymers (including nonionic polyacrylamide polymers including substituted branched or unbranched polymers) include polyacrylamide, iso-paraffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *Sclerotium* gum, sodium carboxymethyl dextran, sodium carrageenan, tragacanth gum, xanthan gum, and mixtures thereof.

Silicone Containing Compounds

In some embodiments, the compositions of the disclosure contain a silicone containing compound. In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present disclosure include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present disclosure include those available from General Electric Co., Silicone Products Div., Waterford, N.Y. and SWS Silicones Div. of Stauffer Chemical Co., Adrian, Mich.

Essential Oils

In some embodiments, the compositions of the disclosure contain essential oils. Essential oils include oils derived from herbs, flowers, trees, and other plants. Such oils are typically present as tiny droplets between the plant's cells, and can be extracted by several method known to those of skill in the art (e.g., steam distilled, enfleurage (extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° C. to 240° C. and densities ranging from about 0.759 g/mL to about 1.096 g/mL.

Essential oils typically are named by the plant from which the oil is found. For example, rose oil or peppermint oil are derived from rose or peppermint plants, respectively. Non-limiting examples of essential oils that can be used in the context of the present invention include sesame oil, *Macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, *geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

Carrier Oils

In some embodiments, the compositions of the disclosure contain carrier oils. Carrier oils are used to dilute essential oils so they can be applied to the skin without side effects. Non-limiting examples of carrier oils include coconut oil (*Cocus nucifera*), black cumin seed oil (*Nigella sativa*), jojoba oil (*Simmondsia chinensis*), evening primrose oil *Oenothera biennis*), rose hip oil (*Rosa mosqueta*), Aloe (*Aloe vera*), and grapeseed oil (*Vitus vinifera*). In some embodiments, *Aloe vera* is used as a carrier oil.

Structuring Agents

In some embodiments, the compositions of the disclosure contain structuring agents. Structuring agents, in certain aspects, assist in providing rheological characteristics, which contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

Vitamins and Minerals

In some embodiments, the compositions of the disclosure contain one or more vitamins, minerals, or amino acids. Non-limiting examples of vitamins include vitamin A, ascorbic acid (vitamin C), vitamin D, vitamin E, vitamin K, thiamine, riboflavin, niacin, pantothenic acid, pyridoxine, biotin, folate, cobalamin, and cyanocobalamin. Non-limiting examples of minerals that can be included in the compositions of the present invention include antimony, barium, beryllium, bismuth, boron, bromine, calcium, carbon, cerium, cesium, chloride, chromium, cobalt, copper, dysprosium, erbium, europium, fluorine, gadolinium, gallium, germanium, gold, hafnium, holmium, indium, iodine, iridium, iron, lantharum, lithium, magnesium, manganese, molybdenum, neodymium, nickel, niobium, osmium, palladium phosphorus, platinum, potassium, paresodymium, rhenium, rhodium, rubidium, ruthenium, samarium, sodium, selenium, silicon, silver, sodium, strontium, sulfur, tantalum, thallium, thorium, tellurium, terbium, thulium, tin, titanium, tungsten, ytterbium, yttrium, zinc, and zirconium. Any soluble salt of these minerals suitable for inclusion edible products can be used, for example, calcium carbonate, calcium citrate, calcium malate, calcium-citrate-malate, calcium gluconate, magnesium citrate, magnesium gluconate, magnesium sulfate, zinc chloride, zinc sulfate, potassium iodide, and copper sulfate.

In some embodiments, the compositions of the disclosure include amino acids. Non-limiting examples of amino acids include alanine, glutamic acid, glycine, histidine, isoleucine, leucine, methionine, phenylalanine, serine, threonine, tryptophan, valine, aspartic acid, arginine, asparagine, glutamine, proline, cysteine, and lysine.

In some embodiments, the compositions of the disclosure contain retinoids. Retinoids have shown promise in the treatment of aging, burns, scaling, and dermatitis. Non-limiting examples of retinoids include retinol, tretinoin, adapalene, tazarotene, alitretinoin, isortetinoin, retinyl palmitate, retinaldehyde, and bexarotene.

Pharmaceutical Ingredients

In some embodiments, the compositions of the disclosure contain pharmaceutical ingredients. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including difluoromethylonithine (DFMO) and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, eye drop actives, animal therapeutics, wound treatment agents, and wound healing agents.

In some embodiments, the pharmaceutical ingredient is a steroid. Non-limiting examples of steroids include dexamethasone, dexamethasone acetate, dexamethasone sodium phosphate, cortisone, cortisone acetate, hydrocortisone, hydrocortisone acetate, hydrocortisone cypionate, sodium hydrocortisone phosphate, prednisol hydrochloroneone acetate, prednisol acetate Prednisolone, Prednisolone Sodium Phosphate, Prednisolone Tebutate, Prednisolone Pivalate, Triamcinolone, Triamcinolone Acetonide, Triamcinolone Hexacetonide, Triamcinolone Diacetate, Methylprednisolone Acetate, Sodium Methodotassium Sodium Methionate, Sodium Methionate Diploate betamethasone, betamethasone, disodium phosphate of vetamethasone, sodium phosphate of vetamethasone, betamethasone acetate, disodium phosphate of betamethasone, chloroprednisone acetate, corticosterone, deoxycorticosterone, deoxycorticosterone acetate, deoxymethyrostaone deoxyketol ester, fludrocortisone, fludrocortisone acetate, dichlorisone acetate, fluorohydrocortisone, fluorometolone, fluprednisolone, parametasona, parametasona acetate, androsterone, fluoxymesterone, aldosterone, methandrostenolone, methyrostenedione, methyldostentaone testosterone, testosterone, testosterone equonates testosterone, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone hydroxyprogesterone, hydroxyprogesterone acetate, normethisterone, pregnenolone, progesterone, ethinyl estradiol, mestranol, dimethisterone, etisterone, ethinodiol diacetate, norethindrone, norethindrone acetate, norethisterone, fluocinolone acetonide, flurandrenolone, succinate hydrocortisone succinate, methylprednisolone sodium, prednisolone sodium phosphate, triamcinolone acetonide, sodium hydroxydione, spironolactone, oxandrolone, oxymetholone, prometholone, testosterone cypionate, testosterone phenylacetate, estradiol cypionate and noretynodrel.

Additional Ingredients

In some embodiments, the compositions comprise an ingredient with anti-mite properties. In some embodiments, the ingredient with anti-mite properties is comprised in a lotion or cream. Non-limiting examples of compounds that have anti-mite properties include permethrin or permethrin cream, lindane or lindane lotion, crotamiton, precipitated sulfur 6% in petrolatum, benzyl benzoate, albendazole, and ivermectin.

In some embodiments, the compositions comprise an ingredient with anti-yeast properties. In some embodiments, the ingredient with anti-yeast properties is comprised in a lotion or cream. Non-limiting examples of compounds that have anti-yeast properties include lcotrimazole, miconazole, tioconazole, terconazole, butoconazole, fluconazole, ketoconazole, tioconazole, boric acid, clotrimazole, nystatin, itraconazole, and sulfanilamide.

In some embodiments, the compositions comprise an ingredient that affects keratinocyte growth. In some embodiments, the ingredient that affects keratinocyte growth is piperonylic acid and keratinocyte growth factor.

In some embodiments, the compositions comprise an ingredient that affects melanin production. In some embodiments, the ingredient that affects melanin production is a skin-lightening compound, such as kojic acid or arbutin. In some embodiments, the ingredient that affects melanin production is a forskolin (*Coleus forskohlii*) extract. In some embodiments, the compositions comprise melanin.

In some embodiments, the compositions comprise an ingredient that affects sebum production. In some embodiments, the ingredient that affects sebum production is testosterone, 5-testosterone, 5-androstene-317diol, oestrogens, an antiandrogen, such as cyproterone acetate and spironolactone, a vitamin-A derivative, such as isotretinoin, progesterone, medroxyprogesterone, levonorgestrel, a phenothiazine, such as chlorpromazine, co-pyrindiol, or ethinyl estradiol.

In some embodiments, the compositions comprise an ingredient that affects fibroblast stimulation. In some embodiments, the ingredient that affects fibroblast stimulation is a human leukocyte antigen (HLA)-II molecule, transforming growth factor-β1 (TGF-β1), transforming growth factor-β2 (TGF-β2), transforming growth factor-β3 (TGF-β3), or interleukin-6 (IL-6).

In some embodiments, the compositions comprise an ingredient that affects angiogenesis. In some embodiments, the ingredient that affects angiogenesis comprises transforming growth factor α (TGF-α), transforming growth factor-β (TGF-β), basic-FGF (b-FGF), angiostatin, endostatin, and platelet-derived endothelial cell growth factor (PDGF). In some embodiments, the compositions comprise an ingredient that affects neural receptors of pain and/or itch. In some embodiments, the ingredient that affects neural receptors of pain and/or itch is a cyclooxygenase inhibitor, serotonin, thymic stromal lymphopoietin (TSLP), interleukin-33 (IL-33), histamine, proteases, interleukin-4 (IL-4), interleukin-13 (IL-13), and interleukin-31 (IL-31). Non-limiting examples of cyclooxygenase inhibitors include aspirin, ibuprofen, naproxen, rofecoxib, celecoxib, valdecoxib, lumiracoxib, etoricoxib, and parecoxib.

Vehicles

In some embodiments, the active ingredients and additional ingredients are mixed with a vehicle. A vehicle facilitates the delivery of an ingredient of the skin composition to the skin. In some embodiments, a vehicle is selected from the group consisting of liposome, nanosome, emulsion, microemulsion, nanocapsules, solid lipid nanoparticles, and nanocrystals.

In some embodiments, the vehicle is a liposome. Liposomes are vesicular structures, which have an aqueous core enclosed by a lipid bilayer. In some embodiments, liposomes contain phospholipids or fatty acids. In some embodiments, liposomes range in size from 15 nm in diameter to several micrometers in diameter. In some embodiments, liposomes exhibit a unilamellar structure or a multilamellar structure. Liposomes facilitate the continuous supply of active ingredients or additional ingredients to cells over a sustained period of time.

In some embodiments, the vehicle is a nanosome. Nanosomes are liposomes with a particle size of between about 20 nm to about 600 nm. In some embodiments, the nanosomes of the disclosure have a particle size of about 20 nm, or about 30 nm, or about 40 nm, or about 50 nm, or about 60 nm, or about 70 nm, or about 80 nm, or about 90 nm, or about 100 nm, or about 200 nm, or about 300 nm, or about 400 nm, or about 500 nm, or about 600 nm. A representative methods for preparing liposomes is found in International Publication No. 2008/010241 (published Jan. 24, 2008), which is incorporated by reference herein, in its entirety.

In some embodiments, the vehicle is an emulsion. An emulsion is a dispersed system containing at least two immiscible liquid phases, one of which is dispersed in the form of small droplets throughout the other, and an emulsifying agent to improve the stability of the system. Non-limiting examples of emulsifying agents include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

In some embodiments, emulsions are classified according to the droplet size of the liquids present in the emulsions. Nanoemulsions are systems containing droplets with particle sizes from 10 to 1000 nm. Microemulsions are systems containing droplets with particle sizes from about 5 nm to about 100 nm. McClements, which is incorporated by reference herein in its entirety, discusses characteristics of nanoemulsions and microemulsions (McClements. 2012, Soft Matter 8(6):1719-1729). Macroemulsions are systems containing droplets with average particle sizes between about 10 µm and about 1000 µm. In some embodiments, the emulsion is selected from the group consisting of water-in-oil, oil-in-water, silicone-in-water, and water-in-silicone. In some embodiments, the emulsion is a multiple emulsion system, such as water-in-oil-in-water, oil-in-water-in-oil, and oil-in-water-in-silicone. The name of the emulsion indicates the identities of the immiscible phases.

In some embodiments, "oil" signifies the oil phase of an emulsion. Non-limiting examples of oils which may be utilized within the oil phase include hydrocarbon oils of animal origin and hydrocarbon oils of vegetable origin. Non-limiting examples of hydrocarbon oils of vegetable origin include liquid triglycerides of fatty acids comprising 4 to 10 carbon atoms such as triglycerides of heptanoic or octanoic acids or also, for example, sunflower, corn, and soy, pumpkin, grape seeds, sesame, hazelnut, apricot, *Macadamia*, arara, sunflower, castor, avocado, and triglycerides of caprylic/capric acids. In some embodiments, the oil phase of the emulsion contains from about 10% w/w to about 90% w/w. In some embodiments, the oil phase of the emulsion is about 5% w/w, or about 10% w/w, or about 15% w/w, or about 20% w/w, or about 25% w/w, or about 30% w/w, or about 35% w/w, or about 40% w/w, or about 45% w/w, or about 50% w/w, or about 55% w/w, or about 60% w/w, or about 65% w/w, or about 70% w/w, or about 75% w/w, or about 80% w/w, or about 85% w/w, or about 90% w/w.

In some embodiments, the oil phase of an emulsion is used to solubilize a cannabinoid.

In some embodiments, "water" signifies the water phase of an emulsion. In some embodiments, the water phase of the emulsion contains from about 10% w/w to about 90% w/w. In some embodiments, the water phase of the emulsion is about 5% w/w, or about 10% w/w, or about 15% w/w, or about 20% w/w, or about 25% w/w, or about 30% w/w, or about 35% w/w, or about 40% w/w, or about 45% w/w, or about 50% w/w, or about 55% w/w, or about 60% w/w, or about 65% w/w, or about 70% w/w, or about 75% w/w, or about 80% w/w, or about 85% w/w, or about 90% w/w.

In some embodiments, the vehicle of the compositions of the disclosure is an oil-in-water emulsion. In some embodiments, the vehicle comprises PP2.

Exemplary Compositions of the Disclosure and Products Containing the Same

In some embodiments, any of the compositions described herein may be incorporated into a product. Non-limiting examples of products include, but are not limited to, serums, face serums, anti-aging creams, shampoo, conditioner, leave in conditioner, hairspray, lubricant, sexual health products, cleansers, toners, spot treatment, vaginal treatments, suppositories, enemas, hemorrhoid treatments, moisturizers, moisturizing creams, sunscreen products, sunless skin tanning products, skin benefit creams and lotions, softeners, day lotions, gels, ointments, foundations, night creams, eye creams, acne cleaners, acne toners, acne spot treatments, acne day moisturizer, acne night moisturizer, acne day and night moisturizer, patches, perfumes, toners, astringents, pimple patches, face creams, cleansers, face masks, masks, sheet masks, make-up products, such as lipstick, foundation, eye shadow, eye liner, lip liner, soap, facial and body soap, baby lotions, baby oils, baby shampoos, powders, wet wipes, deodorants, douches, or other known products or applications. In some embodiments, the product is a cleanser, toner, spot treatment, day/night moisturizer, or sunscreen.

Exemplary compositions of the disclosure are found in Tables B and C. Table D shows the active ingredient portion of exemplary compositions. Tables E, F, G, H, and I show additional exemplary compositions. In some embodiments, the compositions comprise an active ingredient portion as detailed in Table B or Table D. In some embodiments, the composition is any one of the compositions of Tables B-I or of Examples 1 or 3.

TABLE B

Composition of active ingredient portion of exemplary products

| Product | Cannabinoid (e.g. CBD) (mg/mL) | Cofactor or precursor thereof (e.g. Niacinamide) (mg/mL) | Antioxidant (e.g. L-ergothioneine) (mg/mL) |
| --- | --- | --- | --- |
| CBD Acne Cleanser | 0.42 | 10 | 1 |
| CBD Acne Toner | 2.25 | 20 | 1 |
| CBD Acne Spot Treatment | 6.75 | 30 | 10 |
| CBD Acne Day Night Moisturizer | 3.97 | 20 | 10 |
| CBD Morning SPF 30 | 3.97 | 20 | 10 |

TABLE C

Exemplary products comprising compositions of the disclosure

| Product | Cannabinoid (e.g. CBD) (mg/mL) | Salicylic Acid (mg/mL) | PP2 (mg/mL) | Cofactor or precursor thereof (e.g. Niacinamide) (mg/mL) | Antioxidant (e.g. L-ergothioneine) (mg/mL) | Licorice | Xperse ® 401 (mg/mL) |
| --- | --- | --- | --- | --- | --- | --- | --- |
| CBD Acne Cleanser | 0.42 | 10 | 0.1 | 10 | 1 | — | — |
| CBD Acne Toner | 2.25 | 15 | 0.1 | 20 | 1 | 2 | — |
| CBD Acne Spot Treatment | 6.75 | 15 | 30 | 30 | 10 | 2 | — |
| CBD Acne Day/Night Moisturizer | 3.97 | 15 | 30 | 20 | 10 | 2 | — |
| CBD Morning SPF 30 | 3.97 | — | 20 | 20 | 10 | — | 260 |

TABLE D

Composition of active ingredient portion of exemplary products

| Product | Cannabinoid (e.g. CBD) (% w/w) | Cofactor or precursor thereof (e.g. Niacinamide) (% w/w) | Antioxidant (e.g. L-ergothioneine) (% w/w) |
|---|---|---|---|
| CBD Acne Cleanser | 4.76 | 95.23 | .0048 |
| CBD Acne Pads | 2.91 | 48.66 | 48.44 |
| CBD Acne Spot Treatment | 19.20 | 80.79 | 0.01 |
| CBD Acne Day/Night Moisturizer | 17.29 | 89.69 | 0.02 |
| CBD Morning SPF 30 | 17.35 | 82.63 | 0.02 |

TABLE E

Composition of CBD Acne Cleanser Product

| Ingredient | Amount (% w/w) |
|---|---|
| cannabidiol | 0.05 |
| niacinamide | 1 |
| ergothioneine | 0.00005 |
| acrylates crosspolymer-4 | 0.96 |
| calcium gluconate | 0.01 |
| cocamidopropyl betaine | 4.5 |
| cocamidopropyl hydroxysltaine | 2.45 |
| coco-glucoside | 4.4 |
| EDTA | 0.00625 |
| essential oils | 0.2 |
| gluconolactone | 0.74 |
| glycerin | 3.501 |
| poly(C20-28 olefin) | 0.3125 |
| polysorbate 20 | 0.24625 |
| PPG-12/SMDI Copolymer | 0.01 |
| salicylic acid | 1.5 |
| sodium benzoate | 0.25 |
| sodium C14-16 olefin sulfonate | 10 |
| sodium chloride | 1.05 |
| sodium hydroxide | 0.0752 |
| tetrasodium glutamate diacetate | 0.047 |
| water | 68.69175 |

TABLE F

Composition of CBD Acne Pads Product

| Ingredient | Amount (% w/w) |
|---|---|
| cannabidiol | 0.12 |
| niacinamide | 2.0091 |
| ergothioneine | 2 |
| amylopectin | 0.0003 |
| calcium gluconate | 0.01 |
| citric acid | 0.0014 |
| dextrin | 0.0003 |
| dipotassium glycyrrhizate | 0.05 |
| essential oils | 0.1 |
| gluconolactone | 0.74 |
| panthenol | 0.0926 |
| pentylene glycol | 3 |
| polydextrose | 0.0003 |
| polysorbate 20 | 0.985 |
| PPG-12/SMDI copolymer | 0.01 |
| salicylic acid | 1.5 |
| sodium benzoate | 0.25 |
| sodium hydroxide | 0.0002 |
| tetrasodium glutamate diacetate | 0.047 |
| water | 89.0838 |

TABLE G

Composition of CBD Acne Spot Treatment Product

| Ingredient | Amount (% w/w) |
|---|---|
| cannabidiol | 0.715 |
| niacinamide | 3.0088 |
| ergothioneine | 0.0005 |
| amylopectin | 0.0004 |
| caprylhydroxamic acid | 0.16 |
| caprylyl glycol | 0.72 |
| cetearyl alcohol | 1.5 |
| cetearyl olivate | 2.4 |
| dextrin | 0.0004 |
| dipotassium glycyrrhizate | 0.2 |
| essential oils | 0.2 |
| ethoxydiglycol | 2 |
| glyceryl caprylate | 1 |
| hydroxyethylcellulose | 0.7 |
| pentylene glycol | 4 |
| polydextrose | 0.0004 |
| PPG-12/SMDI copolymer | 3 |
| propanediol | 3.12 |
| salicylic acid | 2 |
| sclerotium gum | 0.5 |
| sorbitan olivate | 1.6 |
| water | 73.1745 |

TABLE H

Composition of CBD Day/Night Moisturizer Product

| Ingredient | Amount (% w/w) |
|---|---|
| cannabidiol | 0.42 |
| niacinamide | 2.0091 |
| ergothioneine | 0.0005 |
| aloe barbadensis leaf juice | 0.01 |
| amylopectin | 0.0003 |
| caprylhydroxamic acid | 0.15 |
| caprylic/capric triglyceride | 4.5 |
| cetearyl alcohol | 2 |
| cetearyl olivate | 1.8 |
| citric acid | 0.2 |
| dextrin | 0.0003 |
| dipotassium glycyrrhizate | 0.2 |
| essential oils | 0.3 |
| glycerin | 0.225 |
| glyceryl caprylate | 1.425 |
| hydroxyethyl acrylate/sodium acryloyldimethyl taurate copolymer | 1.7 |
| pentylene glycol | 3 |
| polydextrose | 0.0003 |
| polysorbate 60 | 0.08 |
| PPG-12/SMDI Copolymer | 3 |
| salicylic acid | 1.5 |
| silica | 1 |
| sodium hyaluronate | 0.01 |
| sorbitan isostearate | 0.14 |
| sorbitan olivate | 1.2 |
| squalane | 2 |
| water | 73.1295 |

TABLE I

Composition of CBD Morning SPF30

| Ingredient | Amount (% w/w) |
| --- | --- |
| cannabidiol | 0.42 |
| niacinamide | 2 |
| ergothioneine | 0.0005 |
| alumina | 0.91 |
| bisabolol | 0.1988 |
| caprylhydroxamic acid | 0.16 |
| caprylic/capric triglyceride | 9.1 |
| caprylyl glycol | 0.72 |
| cetearyl alcohol | 2 |
| dipotassium glycyrrhizate | 0.2 |
| essential oils | 0.4 |
| glycerin | 2.991 |
| hydroxyethyl acrylate/sodium acryloyldimethyl taurate copolymer | 0.17 |
| pentylene glycol | 3 |
| polyhydroxystearic acid | 1.3 |
| polyolprepolymer 2 | 2 |
| polysorbate 60 | 0.008 |
| propanediol | 1.12 |
| silica | 2 |
| sodium hyaluronate | 0.02 |
| sodium hydroxide | 0.0002 |
| sorbitan isostearate | 0.014 |
| steareth-2 | 3 |
| steareth-21 | 2 |
| stearic acid | 0.91 |
| tetrasodium glutamate diacetate | 0.047 |
| titanium dioxide | 5.98 |
| tocopherol | 0.0018 |
| tridecane | 1.7682 |
| triethoxycaprylylsilane | 0.26 |
| undecane | 4.23 |
| water | 45.1293 |
| xanthan gum | 0.4 |
| zinc oxide | 7.54 |
| Zingiber officinale (ginger) root extract | 0.0012 |

In some embodiments, a composition listed in any one of Tables B-I or in Examples 1 or 3 comprises CBD THC, THCV, CBC, CBG, individually or in combination, in lieu of CBD. In some embodiments, a composition listed in any one of Tables B-I or in Examples 1 or 3 comprises lilac stem cells, for example, Dermasyr 10™. In some embodiments, a composition listed in any one of Tables B-I or in Examples 1 or 3 comprises avenanthramides.

In some embodiments, provided herein is a composition comprising all the ingredients of Formulation K (Table 3 of Example 1). In some embodiments, provided herein is a composition comprising all the ingredients of Formulation L (Table 4 of Example 1). In some embodiments, provided herein is a composition comprising all the ingredients of Formulation M (Table 5 of Example 1). In some embodiments, provided herein is a composition comprising all the ingredients of Formulation N (Table 6 of Example 1). In some embodiments, provided herein is a composition comprising all the ingredients of Formulation O (Table 7 of Example 1). In some embodiments, provided herein is a composition comprising all the ingredients of Formulation U (Table 9 of Example 1). In some embodiments, provided herein is a composition comprising all the ingredients of Formulation V (Table 9 of Example 1). In some embodiments, provided herein is a composition comprising all the ingredients of Formulation W (Table 9 of Example 1). In some embodiments, provided herein is a composition comprising all the ingredients of Formulation X (Table 9 of Example 1). In some embodiments, provided herein is a composition comprising all the ingredients of Formulation Y (Table 9 of Example 1).

In some embodiments, the compositions of the present disclosure are incorporated into products or alternative formulations at up to about 50% w/w. In some embodiments, the compositions of the present disclosure are incorporated into products or alternative formulations at up to about 100% w/w. In some embodiments, the compositions of the disclosure are incorporated into products or alternative formulations at up to about 0.1% w/w, up to about 0.2% w/w, up to about 0.3% w/w, up to about 0.4% w/w, up to about 0.5% w/w, up to about 0.6% w/w, up to about 0.7% w/w, up to about 0.8% w/w, up to about 0.9% w/w, up to about 1.0% w/w, up to about 1.1% w/w, up to about 1.2% w/w, up to about 1.3% w/w, up to about 1.4% w/w, up to about 1.5% w/w, up to about 1.6% w/w, up to about 1.7% w/w, up to about 1.8% w/w, up to about 1.9% w/w, up to about 2.0% w/w, up to about 2.5% w/w, up to about 3.0% w/w, up to about 3.5% w/w, up to about 4.0% w/w, up to about 4.5% w/w, or up to about 5.0% w/w, up to about 6.0% w/w, up to about 7.0% w/w, up to about 8.0% w/w, up to about 9.0% w/w, up to about 10% w/w, up to about 15% w/w, up to about 20% w/w, up to about 25% w/w, up to about 30% w/w, up to about 35% w/w, up to about 35% w/w, up to about 40% w/w, up to about 45% w/w, or up to about 50% w/w, including all values and ranges in between.

In some embodiments, a composition of the disclosure is incorporated into a cleanser. In some embodiments, the cleanser exfoliates the skin. In some embodiments, the cleanser contains antibiotics. In some embodiments, a cleanser unclogs pores, reduces the size of existing blackheads, and slows or stops the formation of new blackheads. In some embodiments, cleansers counter free radical damage. In some embodiments, a cleanser rinses clean without leaving residue behind. In some embodiments, a cleanser removes excess oil. In some embodiments, a cleanser cleanses skin of impurities. In some embodiments, after cleansing with a cleanser, skin feels deeply cleaned. In some embodiments, a cleanser is gentle and non-irritating. In some embodiments, the cleanser feels calming on the skin. In some embodiments, the cleanser cleans skin without stripping away natural moisture. In some embodiments, the cleanser does not cause the formation of acne (e.g., breakouts). In some embodiments, the cleanser increases hydration. In some embodiments, the cleanser feels refreshing. In some embodiments, after applying the cleanser, the skin feels comfortable and supple. In some embodiments, after applying the cleanser, the skin does not feel tight. In some embodiments, after applying the cleanser, the skin looks and feels clearer. In some embodiments, after applying the cleanser, the pores look and feel unclogged.

In some embodiments, a composition of the disclosure is incorporated into a toner. In some embodiments, a toner removes the last traces of pore-clogging dirt, debris, and/or makeup that cleansers might not catch. In some embodiments, a toner gently removes excess oil. In some embodiments, a toner contains soothing botanicals or moisturizers.

In some embodiments, a composition of the disclosure is incorporated into a spot treatment. Spot treatments are applied directly on the acne. In some embodiments, spot treatment helps reduce redness, swelling, and pain directly at the spot of the acne.

In some embodiments, a composition of the disclosure is incorporated into a moisturizer. In some embodiments, the moisturizer is oil free. As used herein, an oil-free formulation contains less than 5% w/w of oil.

In some embodiments, a composition of the disclosure is incorporated into a sunscreen. In some embodiments, the sunscreen is lightweight. Lightweight sunscreens feel lighter on the skin. In some embodiments, lightweight sunscreens are absorbed more quickly than non-light weight sunscreens. In some embodiments, a lightweight sunscreen is oil free. In some embodiments, the sunscreen is oil free. In some embodiments, the sunscreen is non-comedogenic. In some embodiments, the sunscreen is SPF 8 or above, for example SPF 8, SPF 15, SPF 25, SPF 30, SPF 40, SPF 50, or higher.

In some embodiments, the compositions comprise from about 0.01 milligrams (mg) to about 100 mg of cannabinoid, about 0.5 mg to about 100 mg cofactor or precursor thereof, and about 0.1 mg and 100 mg antioxidant per milliliter of composition, including all ranges and subranges therebetween. In some embodiments, the compositions comprise about 0.42 milligrams (mg) cannabinoid, about 10 mg cofactor or precursor thereof, and about 1 mg antioxidant per milliliter of composition. In some embodiments, the compositions comprise about 2.3 milligrams (mg) cannabinoid, about 20 mg cofactor or precursor thereof, and about 1 mg antioxidant per milliliter of composition. In some embodiments, the compositions comprise about 6.8 milligrams (mg) cannabinoid, about 30 mg cofactor or precursor thereof, and about 10 mg antioxidant per milliliter of composition. In some embodiments, the compositions comprise about 4 milligrams (mg) cannabinoid, about 2 mg cofactor or precursor thereof, and about 10 mg antioxidant per milliliter of composition. In some embodiments, the compositions comprise from about 0.01 milligrams (mg) to about 10 mg of cannabinoid and about 0.5 mg to about 50 mg cofactor or precursor thereof per milliliter of composition. In some embodiments, the compositions comprise about 0.42 milligrams (mg) cannabinoid and about 10 mg cofactor or precursor thereof per milliliter of composition. In some embodiments, the compositions comprise about 2.3 milligrams (mg) cannabinoid and about 20 mg cofactor or precursor thereof per milliliter of composition. In some embodiments, the compositions comprise about 6.8 milligrams (mg) cannabinoid and about 30 mg cofactor or precursor thereof per milliliter of composition. In some embodiments, the compositions comprise about 4 milligrams (mg) cannabinoid, about 2 mg cofactor or precursor thereof, and about 10 mg antioxidant per milliliter of composition.

In some embodiments, the compositions comprise from about 0.1 millimoles (mmol) to about 250 mmol of cannabinoid, about 1 mmol to about 300 mmol cofactor or precursor thereof, and about 1 mmol and about 100 mmol antioxidant per liter of composition.

In some embodiments, the compositions comprise a cannabinoid (e.g., CBD) and a cofactor or precursor thereof (e.g., niacinamide) at a molar ratio of between about 50:1 and about 1:80. In some embodiments, the compositions comprise a cannabinoid (e.g., CBD) and a cofactor or precursor thereof (e.g., niacinamide) at a molar ratio of between about 2:1 and about 10:1. In some embodiments, the compositions comprise a cannabinoid (e.g., CBD) and a cofactor or precursor thereof (e.g., niacinamide) at a molar ratio of between about 3:1 and about 10:1. In some embodiments, the compositions comprise a cannabinoid (e.g., CBD) and a cofactor or precursor thereof (e.g., niacinamide) at a molar ratio of between about 1:10 and about 1:55. In some embodiments, the compositions comprise a cannabinoid (e.g., CBD) and a cofactor or precursor thereof (e.g., niacinamide) at a molar ratio of between about 1:10 and about 1:15. In some embodiments, the compositions comprise a cannabinoid (e.g., CBD) and a cofactor or precursor thereof (e.g., niacinamide) at a molar ratio of about 50:1, about 49:1, about 48:1, about 47:1, about 46:1, about 45:1, about 44:1, about 43:1, about 42:1, about 41:1, about 40:1, about 39:1, about 38:1, about 37:1, about 36:1, about 35:1, about 34:1, about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1.5:1, about 1:1, about 1:1.5 about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, about 1:40, about 1:41, about 1:42, about 1:43, about 1:44, about 1:45, about 1:46, about 1:47, about 1:48, about 1:49, about 1:50, about 1:51, about 1:52, about 1:53, about 1:54, about 1:55, about 1:56, about 1:57, about 1:58, about 1:59, about 1:60, about 1:61, about 1:62, about 1:63, about 1:64, about 1:65, about 1:66, about 1:67, about 1:68, about 1:69, about 1:70, about 1:71, about 1:72, about 1:73, about 1:74, about 1:75, about 1:76, about 1:77, about 1:78, about 1:79, about 1:80, about including all ranges and subranges therebetween.

In some embodiments, the compositions comprise a cannabinoid (e.g., CBD) and a mitophagy stimulant (e.g., urolithin A) at a molar ratio of between about 50:1 and about 1:80. In some embodiments, the compositions comprise a cannabinoid (e.g., CBD) and a mitophagy stimulant (e.g., urolithin A) at a molar ratio of between about 1:10 and about 10:1. In some embodiments, the compositions comprise a cannabinoid (e.g., CBD) and a mitophagy stimulant (e.g., urolithin A) at a molar ratio of between about 1:3 and about 10:1. In some embodiments, the compositions comprise a cannabinoid (e.g., CBD) and a mitophagy stimulant (e.g., urolithin A) at a molar ratio of about 50:1, about 49:1, about 48:1, about 47:1, about 46:1, about 45:1, about 44:1, about 43:1, about 42:1, about 41:1, about 40:1, about 39:1, about 38:1, about 37:1, about 36:1, about 35:1, about 34:1, about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 1.5:1, about 1:1, about 1:1.5 about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, about 1:40, about 1:41, about 1:42, about 1:43, about 1:44, about 1:45, about 1:46, about 1:47, about 1:48, about 1:49, about 1:50, about 1:51, about 1:52, about 1:53, about 1:54, about 1:55, about 1:56, about 1:57, about 1:58, about 1:59, about 1:60, about 1:61, about 1:62, about 1:63, about 1:64, about 1:65, about 1:66, about 1:67, about 1:68, about 1:69, about 1:70, about 1:71, about 1:72, about 1:73, about 1:74, about 1:75, about 1:76, about 1:77, about 1:78, about 1:79, about 1:80, about including all ranges and subranges therebetween.

In some embodiments, the compositions comprise CBD and niacinamide. In some embodiments, the compositions comprise CBD, niacinamide, and L-ergothioneine. In some embodiments, the compositions comprise CBD, niacinamide, L-ergothioneine, and urolithin A. In some embodiments, CBD in the previous embodiments or subsequent embodiments is replaced with any cannabinoid or cannabinoid combination of this disclosure, including those of Table A.

In some embodiments, a composition of the disclosure comprises about 0.01% to about 1% of cannabinoid (e.g., a single cannabinoid such as CBD, or combination of cannabinoids) by weight of the composition. In some embodiments, a composition of the disclosure comprises from about 0.1% to about 99% cannabinoid (e.g., a single cannabinoid such as CBD, or combination of cannabinoids) by weight of the composition. In some embodiments, a compositions of the disclosure contains from about 0% to about 75% cannabinoid (e.g., a single cannabinoid such as CBD, or combination of cannabinoids) by weight of the composition. In some embodiments, compositions of the disclosure contain from about 0.01% to about 75% cannabinoid (e.g., a single cannabinoid such as CBD, or combination of cannabinoids) by weight of the composition. In some embodiments, the cannabinoid is an extract. For example, in some embodiments, a composition of the disclosure comprises about 0.01%, about 0.05%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 21%, about 22%, about 23%, about 24%, about 25%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% cannabinoid (e.g., a single cannabinoid such as CBD, or combination of cannabinoids) by weight of the composition, including any range or subrange therebetween.

In some embodiments, a composition comprises at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% cannabinoid (e.g., a single cannabinoid such as CBD, or combination of cannabinoids), by weight of the composition.

In some embodiments, the composition comprises up to about 35 cannabinoid (e.g., a single cannabinoid such as CBD, or combination of cannabinoids), by weight of the composition.

In some embodiments, the active ingredient portion of a composition of the disclosure comprises from about 0.1% to about 99% cannabinoid (e.g., a single cannabinoid such as CBD, or combination of cannabinoids) by weight of the active ingredient portion of the composition. In some embodiments, the active ingredient portion of a composition of the disclosure comprises about 1% to about 10% of cannabinoid (e.g., a single cannabinoid such as CBD, or combination of cannabinoids) by weight of the active ingredient portion. In some embodiments, the active ingredient portion of a composition of the disclosure comprises about 15% to about 25% of cannabinoid. For example, in some embodiments, active ingredient portion of a composition of the disclosure comprises about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 21%, about 22%, about 23%, about 24%, about 25%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% of cannabinoids by weight of the active ingredient portion, including any range or subrange therebetween.

In some embodiments, the active ingredient portion of a composition comprises at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% cannabinoid (e.g., a single cannabinoid such as CBD, or combination of cannabinoids), by weight of the active ingredient portion.

In some embodiments, the active ingredient portion of a composition of the disclosure comprises about 19.2% of cannabinoid (e.g., a single cannabinoid such as CBD, or combination of cannabinoids), by weight of the active ingredient portion. In some embodiments, the active ingredient portion of a composition of the disclosure comprises about 2.9% of cannabinoid (e.g., a single cannabinoid such as CBD, or combination of cannabinoids), by weight of the active ingredient portion. In some embodiments, the active ingredient portion of a composition of the disclosure comprises about 4.8% of cannabinoid (e.g., a single cannabinoid such as CBD, or combination of cannabinoids), by weight of the active ingredient portion. In some embodiments, the active ingredient portion of a composition of the disclosure comprises about 17.3% of cannabinoid (e.g., a single cannabinoid such as CBD, or combination of cannabinoids), by weight of the active ingredient portion. In some embodiments, the active ingredient portion of a composition of the disclosure comprises about 17.4% of cannabinoid (e.g., a single cannabinoid such as CBD, or combination of cannabinoids), by weight of the active ingredient portion.

In some embodiments, the compositions of the disclosure comprise from about 0.01 milligrams (mg) to about 10 milligrams of cannabinoid (e.g., a single cannabinoid such as CBD, or combination of cannabinoids) per milliliter (mL) of composition. For example, in some embodiments, the compositions comprise about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.15 mg, about 0.20 mg, about 0.25 mg, about 0.30 mg, about 0.35 mg, about 0.40 mg, about 0.45 mg, about 0.5 mg, about 0.55 mg, about 0.60 mg, about 0.65 mg, about 0.70 mg, about 0.75 mg, about 0.80 mg, about 0.85 mg, about 0.90 mg, about 0.95 mg, about 1.0 mg, about 1.5 mg, about 2.0 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, or about 10.0 mg of cannabinoid (e.g., a single cannabinoid such as CBD, or combination of cannabinoids) per mL of composition, including all ranges and values in between. In some embodiments, the compositions of the disclosure comprise about 0.42 mg of cannabinoid (e.g., a single cannabinoid such as CBD, or combination of cannabinoids) per mL of composition. In some embodiments, the compositions of the disclosure comprise about 2.3 mg of cannabinoid (e.g., a single cannabinoid such as CBD, or combination of cannabinoids) per mL of composition. In some embodiments, the compositions of the disclosure comprise about 6.8 mg of cannabinoid (e.g., a single cannabinoid such as CBD, or combination of cannabinoids) per mL of composition. In some embodiments, the compositions of the disclosure comprise about 4 mg of cannabinoid (e.g., a single cannabinoid such as CBD, or combination of cannabinoids) per mL of composition.

In some embodiments, the compositions of the disclosure comprise from about 1 micromolar (µM) to about 32 millimolar (mM) of cannabinoid (e.g., a single cannabinoid such as CBD, or combination of cannabinoids). In some embodiments, the compositions of the disclosure comprise from about 0.1 mM to about 32 mM of cannabinoid (e.g., a single cannabinoid such as CBD, or combination of cannabinoids). In some embodiments, the compositions comprise between about 1 µM and about 40 µM cannabinoid (e.g., a single cannabinoid such as CBD, or combination of cannabinoids). In some embodiments, the compositions comprise between about 1 µM and about 30 µM cannabinoid (e.g., a single cannabinoid such as CBD, or combination of cannabinoids). For example, in some embodiments, the compositions of the disclosure comprise about 1 µM, about 2 µM, about 3 µM, about 4 µM, about 5 µM, about 6 µM, about 7 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 31 µM, about 32 µM, about 33 µM, about 34 µM, about 35 µM, about 36 µM, about 37 µM, about 38 µM, about 39 µM, about 40 µM, about 41 µM, about 42 µM, about 43 µM, about 44 µM, about 45 µM, about 46 µM, about 47 µM, about 48 µM, about 49 µM, about 50 µM, about 51 µM, about 52 µM, about 53 µM, about 54 µM, about 55 µM, about 56 µM, about 57 µM, about 58 µM, about 59 µM, about 60 µM, about 61 µM, about 62 µM, about 63 µM, about 64 µM, about 65 µM, about 66 µM, about 67 µM, about 68 µM, about 69 µM, about 70 µM, about 71 µM, about 72 µM, about 73 µM, about 74 µM, about 75 µM, about 76 µM, about 77 µM, about 78 µM, about 79 µM, about 80 µM, about 81 µM, about 82 µM, about 83 µM, about 84 µM, about 85 µM, about 86 µM, about 87 µM, about 88 µM, about 89 µM, about 90 µM, about 91 µM, about 92 µM, about 93 µM, about 94 µM, about 95 µM, about 96 µM, about 97 µM, about 98 µM, about 99 µM, about 100 µM (0.1 mM), about 0.2 mM, about 0.3 mM, about 0.4 mM, about 0.5 mM, about 0.6 mM, about 0.7 mM, about 0.8 mM, about 0.9 mM, about 1 mM, about 1.1 mM, about 1.2 mM, about 1.3 mM, about 1.4 mM, about 1.5 mM, about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, about 10 mM, about 10.5 mM, about 11 mM, about 11.5 mM, about 12 mM, about 12.5 mM, about 13 mM, about 13.5 mM, about 14 mM, about 14.5 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, or about 400 mM of cannabinoid (e.g., a single cannabinoid such as CBD, or combination of cannabinoids), including all values and ranges in between. In some embodiments, the compositions of the disclosure comprise about 1.3 mM of cannabinoid (e.g., a single cannabinoid such as CBD, or combination of cannabinoids). In some embodiments, the compositions of the disclosure comprise about 7.1 mM of cannabinoid (e.g., a single cannabinoid such as CBD, or combination of cannabinoids). In some embodiments, the compositions of the disclosure comprise about 21 mM of cannabinoid (e.g., a single cannabinoid such as CBD, or combination of cannabinoids). In some embodiments, the compositions of the disclosure comprise about 12.6 mM of cannabinoid (e.g., a single cannabinoid such as CBD, or combination of cannabinoids). In some embodiments, the compositions comprise about 1 µM cannabinoid (e.g., a single cannabinoid such as CBD, or combination of cannabinoids). In some embodiments, the compositions comprise about 3 µM cannabinoid (e.g., a single cannabinoid such as CBD, or combination of cannabinoids). In some embodiments, the compositions comprise about 10 µM cannabinoid (e.g., a single cannabinoid such as CBD, or combination of cannabinoids). In some embodiments, the compositions comprise about 30 µM cannabinoid (e.g., a single cannabinoid such as CBD, or combination of cannabinoids).

In some embodiments, the compositions of the disclosure comprise at least about 1 µM, at least about 2 µM, at least about 3 µM, at least about 4 µM, at least about 5 µM, at least about 6 µM, at least about 7 µM, at least about 8 µM, at least about 9 µM, at least about 10 µM, at least about 11 µM, at least about 12 µM, at least about 13 µM, at least about 14 µM, at least about 15 µM, at least about 16 µM, at least about 17 µM, at least about 18 µM, at least about 19 µM, at least about 20 µM, at least about 21 µM, at least about 22 µM, at least about 23 µM, at least about 24 µM, at least about 25 µM, at least about 26 µM, at least about 27 µM, at least about 28 nM, at least about 29 µM, at least about 30 µM, at least about 31 µM, at least about 32 µM, at least about 33 µM, at least about 34 µM, at least about 35 µM, at least about 36 µM, at least about 37 µM, at least about 38 µM, at least about 39 µM, at least about 40 µM, at least about 41 µM, at least about 42 µM, at least about 43 µM, at least about 44 µM, at least about 45 µM, at least about 46 µM, at least about 47 µM, at least about 48 at least about 49 µM, at least about 50 µM, at least about 51 µM, at least about 52 µM, at least about 53 µM, at least about 54 µM, at least about 55 µM, at least about 56 µM, at least about 57 µM, at least about 58 µM, at least about 59 µM, at least about 60 µM, at least about 61 µM, at least about 62 µM, at least about 63 µM, at least about 64 µM, at least about 65 µM, at least about 66 µM, at least about 67 µM, at least about 68 µM, at least about 69 µM, at least about 70 µM, at least about 71 µM, at least about 72 µM, at least about 73 µM, at least about 74 µM, at least about 75 µM, at least about 76 µM, at least about 77 µM, at least about 78 µM, at least about 79 µM, at least about 80 µM, at least about 81 µM, at least about 82 µM, at least about 83 µM, at least about 84 µM, at least about 85 µM, at least about 86 µM, at least about 87 µM, at least about 88 µM, at least about 89 µM, at least about 90 µM, at least about 91 µM, at least about 92 µM, at least about 93 µM, at least about 94 µM, at least about 95 µM, at least about 96 µM, at least about 97 µM, at least about 98 µM, at least about 99 µM, at least about 100 µM (0.1 mM), at least about 0.2 mM, at least about 0.3 mM, at least about 0.4 mM, at least about 0.5 mM, at least about 0.6 mM, at least about 0.7 mM, at least about 0.8 mM, at least about 0.9 mM, at least about 1 mM, at least about 1.1 mM, at least about 1.2 mM, at least about 1.3 mM, at least about 1.4 mM, at least about 1.5 mM, at least about 2 mM, at least about 2.5 mM, at least about 3 mM, at least about 3.5 mM, at least about 4 mM, at least about 4.5 mM, at least about 5 mM, at least about 5.5 mM, at least about 6 mM, at least about 6.5 mM, at least about 7 mM, at least about 7.5 mM, at least about 8 mM, at least about 8.5 mM, at least about 9 mM, at least about 9.5 mM, at least about 10 mM, at least about 10.5 mM, at least about 11 mM, at least about 11.5 mM, at least about 12 mM, at least about 12.5 mM, at least about 13 mM, at least about 13.5 mM, at least about 14 mM, at least about 14.5 mM, at least about 15 mM, at least about 16 mM, at least about 17 mM, at least about 18 mM, at least about 19 mM, at least about 20 mM, at least about 21 mM, at least about 22 mM, at least about 23 mM, at least about 24 mM, at least about 25 mM, at least about 26 mM, at least about 27 mM, at least about 28 mM, at least about 29 mM, at least about 30 mM, at least about 31 mM, or at least about 32 mM, at least about 40 mM, at least about 50 mM, at least about 60 mM, at least about 70 mM, at least about 80 mM, at least about 90 mM, at least about 100 mM, at least about 110 mM, at least about 120 mM, at least about 130 mM, at least about 140 mM, at least about 150 mM, at least about 160 mM, at least about 170 mM, at least about 180 mM, at least about 190 mM, at least about 200 mM, at least about 210 mM, at least about 220 mM, at least about 230 mM, at least about 240 mM, at least about 250 mM, at least about 260 mM, at least about 270 mM, at least about 280 mM, at least about 290 mM, at least about 300 mM, at least about 310 mM, at least about 320 mM, at least about 330 mM, at least about 340 mM, at least about 350 mM, at least about 360 mM, at least about 370 mM, at least about 380 mM, at least about 390 mM, or at least about 400 mM of cannabinoid (e.g., a single cannabinoid such as CBD, or combination of cannabinoids). In some embodiments, the compositions of the disclosure comprise at least about 1.3 mM of cannabinoid (e.g., a single cannabinoid such as CBD, or combination of cannabinoids). In some embodiments, the compositions of the disclosure comprise at least about 7.1 mM of cannabinoid (e.g., a single cannabinoid such as CBD, or combination of cannabinoids). In some embodiments, the compositions of the disclosure comprise at least about 21 mM of cannabinoid (e.g., a single cannabinoid such as CBD, or combination of cannabinoids). In some embodiments, the compositions of the disclosure comprise at least about 12.6 mM of cannabinoid (e.g., a single cannabinoid such as CBD, or combination of cannabinoids). In some embodiments, the compositions comprise at least about 1 µM cannabinoid (e.g., a single cannabinoid such as CBD, or combination of cannabinoids). In some embodiments, the compositions comprise at least about 3 µM cannabinoid (e.g., a single cannabinoid such as CBD, or combination of cannabinoids). In some embodiments, the compositions comprise at least about 10 µM cannabinoid (e.g., a single cannabinoid such as CBD, or combination of cannabinoids). In some embodiments, the compositions comprise at least about 30 µM cannabinoid (e.g., a single cannabinoid such as CBD, or combination of cannabinoids).

In some embodiments, the compositions of the disclosure contain THC and CBD. In some embodiments, the compositions contain a weight ratio of THC to CBD from about 1:100 to about 100:1, for example about 1:99, about 5:95, about 10:90, about 15:85, about 20:80, about 25:75, about 30:70, about 40:60, about 45:55, about 50:50, about 55:45, about 60:40, about 65:35, about 70:30, about 75:25, about 80:20, about 85:15, about 90:10, about 95:5, or about 99:1.

In some embodiments, the compositions comprise between about 0.01 mg about 10 mg of CBD and between about 0.01 mg and about 10 mg of THC per milliliter of composition. In some embodiments, the compositions comprise between about 0.1 mmol and about 10 mmol of CBD and between about 0.1 mmol and about 10 mmol of THC per milliliter of composition.

In some embodiments, the compositions comprise from about 0.01% w/w to about 20% w/w of terpenes. For example, in some embodiments, the compositions comprise about 0.01% w/w, about 0.02% w/w, about 0.03% w/w, about 0.04% w/w, about 0.05 w/w, about 0.06% w/w, about 0.07% w/w, about 0.08% w/w, about 0.09% w/w, about 0.1% w/w, about 0.2% w/w, about 0.3% w/w, about 0.4% w/w, about 0.5 w/w, about 0.6% w/w, about 0.7% w/w, about 0.8% w/w, about 0.9% w/w, about 1.0% w/w, about 2% w/w, about 3% w/w, about 4% w/w, about 5 w/w, about 6% w/w, about 7% w/w, about 8% w/w, about 9% w/w, about 10% w/w, about 11 w/w, about 12% w/w, about 13% w/w, about 14% w/w, about 15 w/w, about 16% w/w, about 17% w/w, about 18% w/w, about 19% w/w, or about 20% w/w of terpenes by weight of the total composition. In some embodiments, the compositions comprise at least about 0.01% w/w, at least about 0.02% w/w, at least about 0.03% w/w, at least about 0.04% w/w, at least about 0.05% w/w, at least about 0.06% w/w, at least about 0.07% w/w, at least about 0.08% w/w, at least about 0.09% w/w, at least about 0.1% w/w, at least about 0.2% w/w, at least about 0.3% w/w, at least about 0.4% w/w, at least about 0.5% w/w, at least about 0.6% w/w, at least about 0.7% w/w, at least about 0.8% w/w, at least about 0.9% w/w, at least about 1.0% w/w, at least about 2% w/w, at least about 3% w/w, at least about 4% w/w, at least about 5% w/w, at least about 6% w/w, at least about 7% w/w, at least about 8% w/w, at least about 9% w/w, at least about 10% w/w, at least about 11% w/w, at least about 12% w/w, at least about 13% w/w, at least about 14% w/w, at least about 15% w/w, at least about 16% w/w, at least about 17% w/w, at least about 18% w/w, at least about 19% w/w, or at least about 20% w/w of terpenes by weight of the total composition.

In some embodiments, the compositions described herein comprise between about 0.01% and 99% cofactor or precursor thereof (e.g., niacinamide) by weight of the composition. In some embodiments, the compositions described herein comprise between about 0.01% and 5% cofactor or precursor thereof (e.g., niacinamide) by weight of the composition. In some embodiments, the compositions comprise between about 1% and 3% cofactor or precursor thereof (e.g., niacinamide) by weight of the composition. For example, the compositions comprise about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 3.5%, about 4.0%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% cofactor or precursor thereof (e.g., niacinamide) by weight of the composition, including all ranges and subranges therebetween.

In some embodiments, the compositions comprise about 1% cofactor or precursor thereof (e.g., niacinamide) by weight of the composition. In some embodiments, the compositions comprise about 2% cofactor or precursor thereof (e.g., niacinamide) by weight of the composition. In some embodiments, the compositions comprise about 3% cofactor or precursor thereof (e.g., niacinamide) by weight of the composition.

In some embodiments, the compositions comprise at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.5%, at least about 2.0%, at least about 2.5%, at least about 3.0%, at least about 3.5%, at least about 4.0%, at least about 4.5%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% cofactor or precursor thereof (e.g., niacinamide) by weight of the composition.

In some embodiments, the compositions comprise at least about 1% cofactor or precursor thereof (e.g., niacinamide) by weight of the composition. In some embodiments, the compositions comprise at least about 2% cofactor or precursor thereof (e.g., niacinamide) by weight of the composition. In some embodiments, the compositions comprise at least about 3% cofactor or precursor thereof (e.g., niacinamide) by weight of the composition.

In some embodiments, the active ingredient portion of a composition of the disclosure comprises about 0.01% to about 99% of cofactor or precursor (e.g., niacinamide) thereof by weight of the active ingredient portion including all subranges and ranges therebetween. In some embodiments, the active ingredient portion of a composition of the disclosure comprises about 30% to about 98% of cofactor or precursor thereof (e.g., niacinamide) by weight of the active ingredient portion including all subranges and ranges therebetween. In some embodiments, the active ingredient portion of a composition of the disclosure comprises about 75% to about 98% of cofactor or precursor thereof (e.g., niacinamide) by weight of the active ingredient portion including all subranges and ranges therebetween. In some embodiments, the active ingredient portion of a composition of the disclosure comprises about 75% to about 85% of cofactor or precursor thereof (e.g., niacinamide) by weight of the active ingredient portion, including all subranges and ranges therebetween. In some embodiments, the active ingredient portion of a composition of the disclosure comprises about 85% to about 98% of cofactor or precursor thereof (e.g., niacinamide). In some embodiments, the active ingredient portion of a composition of the disclosure comprises about 30% to about 75% of cofactor or precursor thereof (e.g., niacinamide) by weight of the active ingredient portion, including all subranges and ranges therebetween. In some embodiments, the active ingredient portion of a composition of the disclosure comprises about 45% to about 55% of cofactor or precursor thereof (e.g., niacinamide) by weight of the active ingredient portion. For example, in some embodiments, the active ingredient portion of a composition of the disclosure comprises about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 3.5%, about 4.0%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% cofactor or precursor thereof (e.g., niacinamide) by weight of the active ingredient portion, including all subranges and ranges therebetween.

In some embodiments, the active ingredient portion of a composition of the disclosure comprises at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.5%, at least about 2.0%, at least about 2.5%, at least about 3.0%, at least about 3.5%, at least about 4.0%, at least about 4.5%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% cofactor or precursor thereof (e.g., niacinamide) by weight of the active ingredient portion.

In some embodiments, the active ingredient portion of a composition of the disclosure comprises about 81% cofactor or precursor thereof (e.g., niacinamide) by weight of the active ingredient portion. In some embodiments, the active ingredient portion of a composition of the disclosure comprises about 49% cofactor or precursor thereof b (e.g., niacinamide) y weight of the active ingredient portion. In some embodiments, the active ingredient portion of a composition of the disclosure comprises about 95% cofactor or precursor thereof (e.g., niacinamide) by weight of the active ingredient portion. In some embodiments, the active ingredient portion of a composition of the disclosure comprises about 83% cofactor or precursor thereof (e.g., niacinamide) by weight of the active ingredient portion. In some embodiments, the active ingredient portion of a composition of the disclosure comprises at least about 81% cofactor or precursor thereof (e.g., niacinamide) by weight of the active ingredient portion. In some embodiments, the active ingredient portion of a composition of the disclosure comprises at least about 49% cofactor or precursor thereof (e.g., niacinamide) by weight of the active ingredient portion. In some embodiments, the active ingredient portion of a composition of the disclosure comprises at least about 95% cofactor or precursor thereof (e.g., niacinamide) by weight of the active ingredient portion. In some embodiments, the active ingredient portion of a composition of the disclosure comprises at least about 83% cofactor or precursor thereof (e.g., niacinamide) by weight of the active ingredient portion.

In some embodiments, the compositions comprise between about 0.5 mg and about 50 mg of cofactor or precursor thereof (e.g., niacinamide) per milliliter of composition, including all subranges and ranges therebetween. For example, the compositions comprise about 0.5 mg, about 0.5 mg, about 1 mg, about 1.5 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg of cofactor or precursor thereof (e.g., niacinamide) per milliliter of composition, including all subranges and ranges therebetween. In some embodiments, the compositions comprise about 2 mg of cofactor or precursor thereof (e.g., niacinamide) per milliliter of composition. In some embodiments, the compositions comprise about 10 mg of cofactor or precursor thereof (e.g., niacinamide) per milliliter of composition. In some embodiments, the compositions comprise about 20 mg of cofactor or precursor thereof (e.g., niacinamide) per milliliter of composition. In some embodiments, the compositions comprise about 30 mg of cofactor or precursor thereof (e.g., niacinamide) per milliliter of composition.

In some embodiments, the compositions comprise at least about 0.5 mg, at least about 0.75 mg, at least about 1 mg, at least about 1.5 mg, at least about 2 mg, at least about 3 mg, at least about 4 mg, at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, at least about 20 mg, at least about 21 mg, at least about 22 mg, at least about 23 mg, at least about 24 mg, at least about 25 mg, at least about 26 mg, at least about 27 mg, at least about 28 mg, at least about 29 mg, at least about 30 mg, at least about 31 mg, at least about 32 mg, at least about 33 mg, at least about 34 mg, at least about 35 mg, at least about 36 mg, at least about 37 mg, at least about 38 mg, at least about 39 mg, at least about 40 mg, at least about 41 mg, at least about 42 mg, at least about 43 mg, at least about 44 mg, at least about 45 mg, at least about 46 mg, at least about 47 mg, at least about 48 mg, at least about 49 mg, or at least about 50 mg of cofactor or precursor thereof (e.g., niacinamide) per milliliter of composition. In some embodiments, the compositions comprise at least about 2 mg of cofactor or precursor thereof (e.g., niacinamide) per milliliter of composition. In some embodiments, the compositions comprise at least about 10 mg of cofactor or precursor thereof (e.g., niacinamide) per milliliter of composition. In some embodiments, the compositions comprise at least about 20 mg of cofactor or precursor thereof (e.g., niacinamide) per milliliter of composition. In some embodiments, the compositions comprise at least about 30 mg of cofactor or precursor thereof (e.g., niacinamide) per milliliter of composition.

In some embodiments, the compositions comprise between about 1 µM and 300 mM of cofactor or precursor thereof (e.g., niacinamide). In some embodiments, the compositions comprise between about 1 mM and 300 mM of cofactor or precursor thereof (e.g., niacinamide). In some embodiments, the compositions described herein comprise between about 1 µM of cofactor or precursor thereof (e.g., niacinamide) and about 40 µM of cofactor or precursor thereof (e.g., niacinamide). In some embodiments, the compositions described herein comprise between about 4 µM of cofactor or precursor thereof (e.g., niacinamide) and about 40 µM of cofactor or precursor thereof (e.g., niacinamide). For example, in some embodiments, the compositions comprise about 1 µM, about 2 µM, about 3 µM, about 4 µM, about 5 µM, about 6 µM, about 7 µM, about 8 µM, about 9 µM, about 10 µM, about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 31 µM, about 32 µM, about 33 µM, about 34 µM, about 35 µM, about 36 µM, about 37 µM, about 38 µM, about 39 µM, about 40 µM, about 41 µM, about 42 µM, about 43 µM, about 44 µM, about 45 µM, about 46 µM, about 47 µM, about 48 µM, about 49 µM, about 50 µM, about 51 µM, about 52 µM, about 53 µM, about 54 µM, about 55 µM, about 56 µM, about 57 µM, about 58 µM, about 59 µM, about 60 µM, about 61 µM, about 62 µM, about 63 µM, about 64 µM, about 65 µM, about 66 µM, about 67 µM, about 68 µM, about 69 µM, about 70 µM, about 71 µM, about 72 µM, about 73 µM, about 74 µM, about 75 µM, about 76 µM, about 77 µM, about 78 µM, about 79 µM, about 80 µM, about 81 µM, about 82 µM, about 83 µM, about 84 µM, about 85 µM, about 86 µM, about 87 µM, about 88 µM, about 89 µM, about 90 µM, about 91 µM, about 92 µM, about 93 µM, about 94 µM, about 95 µM, about 96 µM, about 97 µM, about 98 µM, about 99 µM, about 100 µM (0.1 mM), about 0.2 mM, about 0.3 mM, about 0.4 mM, about 0.5 mM, about 0.6 mM, about 0.7 mM, about 0.8 mM, about 0.9 mM, 1 mM, about 2 mM, about 4 mM, about 6 mM, about 8 mM, about 10 mM, about 12 mM, about 14 mM, about 16 mM, about 18 mM, about 20 mM, about 22 mM, about 24 mM, about 26 mM, about 28 mM, about 30 mM, about 32 mM, about 34 mM, about 36 mM, about 38 mM, about 40 mM, about 42 mM, about 44 mM, about 46 mM, about 48 mM, about 50 mM, about 52 mM, about 54 mM, about 56 mM, about 58 mM, about 60 mM, about 62 mM, about 64 mM, about 66 mM, about 68 mM, about 70 mM, about 72 mM, about 74 mM, about 76 mM, about 78 mM, about 80 mM, about 82 mM, about 84 mM, about 86 mM, about 88 mM, about 90 mM, about 92 mM, about 94 mM, about 96 mM, about 98 mM, about 100 mM, about 102 mM, about 104 mM, about 106 mM, about 108 mM, about 110 mM, about 112 mM, about 114 mM, about 116 mM, about 118 mM, about 120 mM, about 122 mM, about 124 mM, about 126 mM, about 128 mM, about 130 mM, about 132 mM, about 134 mM, about 136 mM, about 138 mM, about 140 mM, about 142 mM, about 144 mM, about 146 mM, about 148 mM, about 150 mM, about 152 mM, about 154 mM, about 156 mM, about 158 mM, about 160 mM, about 162 mM, about 164 mM, about 166 mM, about 168 mM, about 170 mM, about 172 mM, about 174 mM, about 176 mM, about 178 mM, about 180 mM, about 182 mM, about 184 mM, about 186 mM, about 188 mM, about 190 mM, about 192 mM, about 194 mM, about 196 mM, about 198 mM, about 200 mM, about 202 mM, about 204 mM, about 206 mM, about 208 mM, about 210 mM, about 212 mM, about 214 mM, about 216 mM, about 218 mM, about 220 mM, about 222 mM, about 224 mM, about 226 mM, about 228 mM, about 230 mM, about 232 mM, about 234 mM, about 236 mM, about 238 mM, about 240 mM, about 242 mM, about 244 mM, about 246 mM, about 248 mM, about 250 mM, about 252 mM, about 254 mM, about 256 mM, about 258 mM, about 260 mM, about 262 mM, about 264 mM, about 266 mM, about 268 mM, about 270 mM, about 272 mM, about 274 mM, about 276 mM, about 278 mM, about 280 mM, about 282 mM, about 284 mM, about 286 mM, about 288 mM, about 290 mM, about 292 mM, about 294 mM, about 296 mM, about 298 mM, or about 300 mM of cofactor or precursor thereof (e.g., niacinamide), including all subranges and ranges therebetween. In some embodiments, the compositions comprise about 16.4 mM of cofactor or precursor thereof (e.g., niacinamide). In some embodiments, the compositions comprise about 246 mM of cofactor or precursor thereof (e.g., niacinamide). In some embodiments, the compositions comprise about 164 mM of cofactor or precursor thereof (e.g., niacinamide). In some embodiments, the compositions comprise about 82 mM of cofactor or precursor thereof (e.g., niacinamide). In some embodiments, the compositions described herein comprise about 4 μM of cofactor or precursor thereof (e.g., niacinamide). In some embodiments, the compositions described herein comprise about 10 μM of cofactor or precursor thereof (e.g., niacinamide). In some embodiments, the compositions described herein comprise about 20 μM of cofactor or precursor thereof (e.g., niacinamide). In some embodiments, the compositions described herein comprise about 40 μM of cofactor or precursor thereof (e.g., niacinamide).

In some embodiments, the compositions comprise at least about 1 μM, at least about 2 μM, at least about 3 μM, at least about 4 μM, at least about 5 μM, at least about 6 μM, at least about 7 μM, at least about 8 μM, at least about 9 μM, at least about 10 μM, at least about 11 μM, at least about 12 μM, at least about 13 μM, at least about 14 μM, at least about 15 μM, at least about 16 μM, at least about 17 μM, at least about 18 μM, at least about 19 μM, at least about 20 μM, at least about 21 μM, at least about 22 μM, at least about 23 μM, at least about 24 μM, at least about 25 μM, at least about 26 μM, at least about 27 μM, at least about 28 μM, at least about 29 μM, at least about 30 μM, at least about 31 μM, at least about 32 μM, at least about 33 μM, at least about 34 μM, at least about 35 μM, at least about 36 μM, at least about 37 μM, at least about 38 μM, at least about 39 μM, at least about 40 μM, at least about 41 μM, at least about 42 μM, at least about 43 at least about 44 μM, at least about 45 μM, at least about 46 μM, at least about 47 μM, at least about 48 μM, at least about 49 μM, at least about 50 μM, at least about 51 μM, at least about 52 μM, at least about 53 μM, at least about 54 μM, at least about 55 μM, at least about 56 μM, at least about 57 μM, at least about 58 μM, at least about 59 μM, at least about 60 μM, at least about 61 μM, at least about 62 μM, at least about 63 μM, at least about 64 μM, at least about 65 μM, at least about 66 μM, at least about 67 μM, at least about 68 μM, at least about 69 μM, at least about 70 μM, at least about 71 μM, at least about 72 μM, at least about 73 μM, at least about 74 μM, at least about 75 μM, at least about 76 μM, at least about 77 μM, at least about 78 μM, at least about 79 μM, at least about 80 μM, at least about 81 μM, at least about 82 μM, at least about 83 μM, at least about 84 μM, at least about 85 μM, at least about 86 μM, at least about 87 μM, at least about 88 μM, at least about 89 μM, at least about 90 μM, at least about 91 μM, at least about 92 μM, at least about 93 μM, at least about 94 μM, at least about 95 μM, at least about 96 μM, at least about 97 μM, at least about 98 μM, at least about 99 μM, at least about 100 μM (0.1 mM), at least about 0.2 mM, at least about 0.3 mM, at least about 0.4 mM, at least about 0.5 mM, at least about 0.6 mM, at least about 0.7 mM, at least about 0.8 mM, at least about 0.9 mM, 1 mM, at least about 2 mM, at least about 4 mM, at least about 6 mM, at least about 8 mM, at least about 10 mM, at least about 12 mM, at least about 14 mM, at least about 16 mM, at least about 18 mM, at least about 20 mM, at least about 22 mM, at least about 24 mM, at least about 26 mM, at least about 28 mM, at least about 30 mM, at least about 32 mM, at least about 34 mM, at least about 36 mM, at least about 38 mM, at least about 40 mM, at least about 42 mM, at least about 44 mM, at least about 46 mM, at least about 48 mM, at least about 50 mM, at least about 52 mM, at least about 54 mM, at least about 56 mM, at least about 58 mM, at least about 60 mM, at least about 62 mM, at least about 64 mM, at least about 66 mM, at least about 68 mM, at least about 70 mM, at least about 72 mM, at least about 74 mM, at least about 76 mM, at least about 78 mM, at least about 80 mM, at least about 82 mM, at least about 84 mM, at least about 86 mM, at least about 88 mM, at least about 90 mM, at least about 92 mM, at least about 94 mM, at least about 96 mM, at least about 98 mM, at least about 100 mM, at least about 102 mM, at least about 104 mM, at least about 106 mM, at least about 108 mM, at least about 110 mM, at least about 112 mM, at least about 114 mM, at least about 116 mM, at least about 118 mM, at least about 120 mM, at least about 122 mM, at least about 124 mM, at least about 126 mM, at least about 128 mM, at least about 130 mM, at least about 132 mM, at least about 134 mM, at least about 136 mM, at least about 138 mM, at least about 140 mM, at least about 142 mM, at least about 144 mM, at least about 146 mM, at least about 148 mM, at least about 150 mM, at least about 152 mM, at least about 154 mM, at least about 156 mM, at least about 158 mM, at least about 160 mM, at least about 162 mM, at least about 164 mM, at least about 166 mM, at least about 168 mM, at least about 170 mM, at least about 172 mM, at least about 174 mM, at least about 176 mM, at least about 178 mM, at least about 180 mM, at least about 182 mM, at least about 184 mM, at least about 186 mM, at least about 188 mM, at least about 190 mM, at least about 192 mM, at least about 194 mM, at least about 196 mM, at least about 198 mM, at least about 200 mM, at least about 202 mM, at least about 204 mM, at least about 206 mM, at least about 208 mM, at least about 210 mM, at least about 212 mM, at least about 214 mM, at least about 216 mM, at least about 218 mM, at least about 220 mM, at least about 222 mM, at least about 224 mM, at least about 226 mM, at least about 228 mM, at least about 230 mM, at least about 232 mM, at least about 234 mM, at least about 236 mM, at least about 238 mM, at least about 240 mM, at least about 242 mM, at least about 244 mM, at least about 246 mM, at least about 248 mM, at least about 250 mM, at least about 252 mM, at least about 254 mM, at least about 256 mM, at least about 258 mM, at least about 260 mM, at least about 262 mM, at least about 264 mM, at least about 266 mM, at least about 268 mM, at least about 270 mM, at least about 272 mM, at least about 274 mM, at least about 276 mM, at least about 278 mM, at least about 280 mM, at least about 282 mM, at least about 284 mM, at least about 286 mM, at least about 288 mM, at least about 290 mM, at least about 292 mM, at least about 294 mM, at least about 296 mM, at least about 298 mM, or at least about 300 mM of cofactor or precursor thereof (e.g., niacinamide), including all subranges and ranges therebetween. In some embodiments, the compositions comprise at least about 16.4 mM of cofactor or precursor thereof (e.g., niacinamide). In some embodiments, the compositions comprise at least about 246 mM of cofactor or precursor thereof (e.g., niacinamide). In some embodiments, the compositions comprise at least about 164 mM of cofactor or precursor thereof (e.g., niacinamide). In some embodiments, the compositions comprise at least about 82 mM of cofactor or precursor thereof (e.g., niacinamide). In some embodiments, the compositions described herein comprise at least about 4 μM of cofactor or precursor thereof (e.g., niacinamide). In some embodiments, the compositions described herein comprise at least about 10 μM of cofactor or precursor thereof (e.g., niacinamide). In some embodiments, the compositions described herein comprise at least about 20 μM of cofactor or precursor thereof (e.g., niacinamide). In some embodiments, the compositions described herein comprise at least about 40 μM of cofactor or precursor thereof (e.g., niacinamide).

In some embodiments, the compositions comprise between about 0.00001% w/w and about 5% antioxidant (e.g. L-ergothioneine) by weight of the composition. In some embodiments, the compositions comprise between about 0.0001% and about 5% antioxidant (e.g. L-ergothioneine) by weight of the composition. In some embodiments, the compositions comprise between about 0.01% and about 5% antioxidant (e.g. L-ergothioneine) by weight of the composition. In some embodiments, the compositions comprise between about 0.05% and 1.5% antioxidant (e.g. L-ergothioneine) by weight of the composition, including all subranges and ranges therebetween. In some embodiments, the compositions comprise between about 0.00001% and 0.001% antioxidant (e.g. L-ergothioneine) by weight of the composition, including all subranges and ranges therebetween. In some embodiments, the compositions comprise between about 1.5% w/and 2.5% antioxidant (e.g. L-ergothioneine) by weight of the composition, including all subranges and ranges therebetween. For example, in some embodiments, the compositions disclosed herein comprise about 0.00001%, about 0.00002%, about 0.00003%, about 0.00004%, about 0.00005%, about 0.00006%, about 0.00007%, about 0.00008%, about 0.00009%, about 0.0001%, about 0.0002%, about 0.0003%, about 0.0004%, about 0.0005%, about 0.0006%, about 0.0007%, about 0.0008%, about 0.0009%, about 0.001%, about 0.002%, 0.003%, about 0.004%, about 0.005%, about 0.006%, about 0.007%, about 0.008%, about 0.009%, about 0.01%, about 0.05%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, or about 5.0% antioxidant (e.g. L-ergothioneine) by weight of the composition, including all subranges and ranges therebetween.

In some embodiments, the compositions comprise about 0.1% antioxidant (e.g. L-ergothioneine) by weight of the composition. In some embodiments, the compositions comprise about 1.0% antioxidant (e.g. L-ergothioneine) by weight of the composition. In some embodiments, the compositions comprise about 0.0005% antioxidant by weight of the composition, including all subranges and ranges therebetween. In some embodiments, the compositions comprise about 0.00005% antioxidant by weight of the composition. In some embodiments, the compositions comprise about 2% antioxidant by weight of the composition.

In some embodiments, the compositions disclosed herein comprise at least about 0.00001%, at least about 0.00002%, at least about 0.00003%, at least about 0.00004%, at least about 0.00005%, at least about 0.00006%, at least about 0.00007%, at least about 0.00008%, at least about 0.00009%, at least about 0.0001%, at least about 0.0002%, at least about 0.0003%, at least about 0.0004%, at least about 0.0005%, at least about 0.0006%, at least about 0.0007%, at least about 0.0008%, at least about 0.0009%, at least about 0.001%, at least about 0.002%, 0.003%, at least about 0.004%, at least about 0.005%, at least about 0.006%, at least about 0.007%, at least about 0.008%, at least about 0.009%, at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.0%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.1%, at least about 3.2%, at least about 3.3%, at least about 3.4%, at least about 3.5%, at least about 3.6%, at least about 3.7%, at least about 3.8%, at least about 3.9%, at least about 4.0%, at least about 4.1%, at least about 4.2%, at least about 4.3%, at least about 4.4%, at least about 4.5%, at least about 4.6%, at least about 4.7%, at least about 4.8%, at least about 4.9%, or at least about 5.0% antioxidant (e.g. L-ergothioneine) by weight of the composition, including all subranges and ranges therebetween.

In some embodiments, the active ingredient portion of a composition of the disclosure comprises about 0.001% to about 99% of antioxidant (e.g. L-ergothioneine) by weight of the active ingredient portion, including all subranges and ranges therebetween. In some embodiments, the active ingredient portion of a composition of the disclosure comprises about 0.001% to about 0.03% of antioxidant (e.g. L-ergothioneine) by weight of the active ingredient portion, including all subranges and ranges therebetween. In some embodiments, the active ingredient portion of a composition of the disclosure comprises about 40% to about 60% of antioxidant (e.g. L-ergothioneine) by weight of the active ingredient portion, including all values and ranges therebetween. In some embodiments, the active ingredient portion of a composition of the disclosure comprises about 45% to about 55% of antioxidant (e.g. L-ergothioneine) by weight of the active ingredient portion, including all subranges and ranges therebetween. For example, in some embodiments, the active ingredient portion of a composition of the disclosure comprises about 0.001%, about 0.002%, about 0.003%, about 0.004%, about 0.005%, about 0.006%, about 0.007%, about 0.008%, about 0.009%, about 0.01%, about 0.011, about 0.012%, about 0.013%, about 0.014%, about 0.015%, about 0.016%, about 0.017%, about 0.018%, about 0.019%, about 0.02%, about 0.021%, about 0.022%, about 0.023%, about 0.024%, about 0.025%, about 0.026%, about 0.027%, about 0.028%, about 0.029%, or about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 3.5%, about 4.0%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% antioxidant (e.g. L-ergothioneine) by weight of the active ingredient portion, including all subranges and ranges therebetween.

In some embodiments, the active ingredient portion comprises about 0.01% of antioxidant (e.g. L-ergothioneine) by weight of the active ingredient portion. In some embodiments, the active ingredient portion comprises about 0.005% of antioxidant (e.g. L-ergothioneine) by weight of the active ingredient portion. In some embodiments, the active ingredient portion comprises about 0.02% of antioxidant (e.g. L-ergothioneine) by weight of the active ingredient portion. In some embodiments, the active ingredient portion comprises about 48% of antioxidant (e.g. L-ergothioneine) by weight of the active ingredient portion.

In some embodiments, the active ingredient portion of a composition of the disclosure comprises at least about 0.001%, at least about 0.002%, at least about 0.003%, at least about 0.004%, at least about 0.005%, at least about 0.006%, at least about 0.007%, at least about 0.008%, at least about 0.009%, at least about 0.01%, at least about 0.011, at least about 0.012%, at least about 0.013%, at least about 0.014%, at least about 0.015%, at least about 0.016%, at least about 0.017%, at least about 0.018%, at least about 0.019%, at least about 0.02%, at least about 0.021%, at least about 0.022%, at least about 0.023%, at least about 0.024%, at least about 0.025%, at least about 0.026%, at least about 0.027%, at least about 0.028%, at least about 0.029%, or at least about 0.03%, at least about 0.04%, at least about 0.05%, at least about 0.06%, at least about 0.07%, at least about 0.08%, at least about 0.09%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.5%, at least about 2.0%, at least about 2.5%, at least about 3.0%, at least about 3.5%, at least about 4.0%, at least about 4.5%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% antioxidant (e.g. L-ergothioneine) by weight of the active ingredient portion.

In some embodiments, a composition comprises between about 0.1 mg and about 100 mg of antioxidant (e.g. L-ergothioneine) per milliliter of composition. For example, in some embodiments, the composition comprises about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, or about 100 mg of antioxidant (e.g. L-ergothioneine) per milliliter of composition, including all subranges and ranges therebetween. In some embodiments, a composition comprises about 1 mg of antioxidant (e.g. L-ergothioneine) per milliliter of composition. In some embodiments, a composition comprises about 10 mg of antioxidant (e.g. L-ergothioneine) per milliliter of composition.

In some embodiments, the composition comprises at least about 0.1 mg, at least about 0.2 mg, at least about 0.3 mg, at least about 0.4 mg, at least about 0.5 mg, at least about 0.6 mg, at least about 0.7 mg, at least about 0.8 mg, at least about 0.9 mg, at least about 1 mg, at least about 2 mg, at least about 3 mg, at least about 4 mg, at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, at least about 20 mg, at least about 21 mg, at least about 22 mg, at least about 23 mg, at least about 24 mg, at least about 25 mg, at least about 26 mg, at least about 27 mg, at least about 28 mg, at least about 29 mg, at least about 30 mg, at least about 31 mg, at least about 32 mg, at least about 33 mg, at least about 34 mg, at least about 35 mg, at least about 36 mg, at least about 37 mg, at least about 38 mg, at least about 39 mg, at least about 40 mg, at least about 41 mg, at least about 42 mg, at least about 43 mg, at least about 44 mg, at least about 45 mg, at least about 46 mg, at least about 47 mg, at least about 48 mg, at least about 49 mg, at least about 50 mg, at least about 51 mg, at least about 52 mg, at least about 53 mg, at least about 54 mg, at least about 55 mg, at least about 56 mg, at least about 57 mg, at least about 58 mg, at least about 59 mg, at least about 60 mg, at least about 61 mg, at least about 62 mg, at least about 63 mg, at least about 64 mg, at least about 65 mg, at least about 66 mg, at least about 67 mg, at least about 68 mg, at least about 69 mg, at least about 70 mg, at least about 71 mg, at least about 72 mg, at least about 73 mg, at least about 74 mg, at least about 75 mg, at least about 76 mg, at least about 77 mg, at least about 78 mg, at least about 79 mg, at least about 80 mg, at least about 81 mg, at least about 82 mg, at least about 83 mg, at least about 84 mg, at least about 85 mg, at least about 86 mg, at least about 87 mg, at least about 88 mg, at least about 89 mg, at least about 90 mg, at least about 91 mg, at least about 92 mg, at least about 93 mg, at least about 94 mg, at least about 95 mg, at least about 96 mg, at least about 97 mg, at least about 98 mg, at least about 99 mg, or at least about 100 mg of antioxidant (e.g. L-ergothioneine) per milliliter of composition, including all subranges and ranges therebetween. In some embodiments, a composition comprises at least about 1 mg of antioxidant (e.g. L-ergothioneine) per milliliter of composition. In some embodiments, a composition comprises at least about 10 mg of antioxidant (e.g. L-ergothioneine) per milliliter of composition.

In some embodiments, a composition comprises between about 1 nanomolar (nM) and about 100 mM of antioxidant (e.g. L-ergothioneine). For example, in some embodiments, the composition comprises about 1 nM, about 10 nM, about 20 nM, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 260 nM, about 270 nM, about 280 nM, about 290 nM, about 300 nM, about 310 nM, about 320 nM, about 330 nM, about 340 nM, about 350 nM, about 360 nM, about 370 nM, about 380 nM, about 390 nM, about 400 nM, about 410 nM, about 420 nM, about 430 nM, about 440 nM, about 450 nM, about 460 nM, about 470 nM, about 480 nM, about 490 nM, about 500 nM, about 510 nM, about 520 nM, about 530 nM, about 540 nM, about 550 nM, about 560 nM, about 570 nM, about 580 nM, about 590 nM, about 600 nM, about 610 nM, about 620 nM, about 630 nM, about 640 nM, about 650 nM, about 660 nM, about 670 nM, about 680 nM, about 690 nM, about 700 nM, about 710 nM, about 720 nM, about 730 nM, about 740 nM, about 750 nM, about 760 nM, about 770 nM, about 780 nM, about 790 nM, about 800 nM, about 810 nM, about 820 nM, about 830 nM, about 840 nM, about 850 nM, about 860 nM, about 870 nM, about 880 nM, about 890 nM, about 900 nM, about 910 nM, about 920 nM, about 930 nM, about 940 nM, about 950 nM, about 960 nM, about 970 nM, about 980 nM, about 990 nM, about 1000 nM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 51 mM, about 52 mM, about 53 mM, about 54 mM, about 55 mM, about 56 mM, about 57 mM, about 58 mM, about 59 mM, about 60 mM, about 61 mM, about 62 mM, about 63 mM, about 64 mM, about 65 mM, about 66 mM, about 67 mM, about 68 mM, about 69 mM, about 70 mM, about 71 mM, about 72 mM, about 73 mM, about 74 mM, about 75 mM, about 76 mM, about 77 mM, about 78 mM, about 79 mM, about 80 mM, about 81 mM, about 82 mM, about 83 mM, about 84 mM, about 85 mM, about 86 mM, about 87 mM, about 88 mM, about 89 mM, about 90 mM, about 91 mM, about 92 mM, about 93 mM, about 94 mM, about 95 mM, about 96 mM, about 97 mM, about 98 mM, about 99 mM, or about 100 mM of antioxidant (e.g. L-ergothioneine), including all subranges and ranges therebetween. In some embodiments, a composition comprises about 4.4 mM of antioxidant (e.g. L-ergothioneine). In some embodiments, a composition comprises about 44 mM of antioxidant (e.g. L-ergothioneine).

In some embodiments, the composition comprises at least about 1 nM, at least about 10 nM, at least about 20 nM, at least about 30 nM, at least about 40 nM, at least about 50 nM, at least about 60 nM, at least about 70 nM, at least about 80 nM, at least about 90 nM, at least about 100 nM, at least about 110 nM, at least about 120 nM, at least about 130 nM, at least about 140 nM, at least about 150 nM, at least about 160 nM, at least about 170 nM, at least about 180 nM, at least about 190 nM, at least about 200 nM, at least about 210 nM, at least about 220 nM, at least about 230 nM, at least about 240 nM, at least about 250 nM, at least about 260 nM, at least about 270 nM, at least about 280 nM, at least about 290 nM, at least about 300 nM, at least about 310 nM, at least about 320 nM, at least about 330 nM, at least about 340 nM, at least about 350 nM, at least about 360 nM, at least about 370 nM, at least about 380 nM, at least about 390 nM, at least about 400 nM, at least about 410 nM, at least about 420 nM, at least about 430 nM, at least about 440 nM, at least about 450 nM, at least about 460 nM, at least about 470 nM, at least about 480 nM, at least about 490 nM, at least about 500 nM, at least about 510 nM, at least about 520 nM, at least about 530 nM, at least about 540 nM, at least about 550 nM, at least about 560 nM, at least about 570 nM, at least about 580 nM, at least about 590 nM, at least about 600 nM, at least about 610 nM, at least about 620 nM, at least about 630 nM, at least about 640 nM, at least about 650 nM, at least about 660 nM, at least about 670 nM, at least about 680 nM, at least about 690 nM, at least about 700 nM, at least about 710 nM, at least about 720 nM, at least about 730 nM, at least about 740 nM, at least about 750 nM, at least about 760 nM, at least about 770 nM, at least about 780 nM, at least about 790 nM, at least about 800 nM, at least about 810 nM, at least about 820 nM, at least about 830 nM, at least about 840 nM, at least about 850 nM, at least about 860 nM, at least about 870 nM, at least about 880 nM, at least about 890 nM, at least about 900 nM, at least about 910 nM, at least about 920 nM, at least about 930 nM, at least about 940 nM, at least about 950 nM, at least about 960 nM, at least about 970 nM, at least about 980 nM, at least about 990 nM, at least about 1000 nM, at least about 1 mM, at least about 2 mM, at least about 3 mM, at least about 4 mM, at least about 5 mM, at least about 6 mM, at least about 7 mM, at least about 8 mM, at least about 9 mM, at least about 10 mM, at least about 11 mM, at least about 12 mM, at least about 13 mM, at least about 14 mM, at least about 15 mM, at least about 16 mM, at least about 17 mM, at least about 18 mM, at least about 19 mM, at least about 20 mM, at least about 21 mM, at least about 22 mM, at least about 23 mM, at least about 24 mM, at least about 25 mM, at least about 26 mM, at least about 27 mM, at least about 28 mM, at least about 29 mM, at least about 30 mM, at least about 31 mM, at least about 32 mM, at least about 33 mM, at least about 34 mM, at least about 35 mM, at least about 36 mM, at least about 37 mM, at least about 38 mM, at least about 39 mM, at least about 40 mM, at least about 41 mM, at least about 42 mM, at least about 43 mM, at least about 44 mM, at least about 45 mM, at least about 46 mM, at least about 47 mM, at least about 48 mM, at least about 49 mM, at least about 50 mM, at least about 51 mM, at least about 52 mM, at least about 53 mM, at least about 54 mM, at least about 55 mM, at least about 56 mM, at least about 57 mM, at least about 58 mM, at least about 59 mM, at least about 60 mM, at least about 61 mM, at least about 62 mM, at least about 63 mM, at least about 64 mM, at least about 65 mM, at least about 66 mM, at least about 67 mM, at least about 68 mM, at least about 69 mM, at least about 70 mM, at least about 71 mM, at least about 72 mM, at least about 73 mM, at least about 74 mM, at least about 75 mM, at least about 76 mM, at least about 77 mM, at least about 78 mM, at least about 79 mM, at least about 80 mM, at least about 81 mM, at least about 82 mM, at least about 83 mM, at least about 84 mM, at least about 85 mM, at least about 86 mM, at least about 87 mM, at least about 88 mM, at least about 89 mM, at least about 90 mM, at least about 91 mM, at least about 92 mM, at least about 93 mM, at least about 94 mM, at least about 95 mM, at least about 96 mM, at least about 97 mM, at least about 98 mM, at least about 99 mM, or at least about 100 mM of antioxidant (e.g. L-ergothioneine).

The following paragraphs provide exemplary amounts of mitophagy stimulants used in the compositions of the disclosure. Compositions comprising a mitophagy modulator may comprise any of the exemplary amounts described for mitophagy stimulants herein.

In some embodiments, the compositions of the disclosure contain between about 0.01% to about 99% of a mitophagy stimulant (e.g., urolithin A) by weight of the composition. In some embodiments, the compositions of the disclosure contain between about 0.01% to about 20% of a mitophagy stimulant (e.g., urolithin A) by weight of the composition.

For example, in some embodiments, the compositions of the disclosure contain about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% mitophagy stimulant (e.g., urolithin A) by weight of the composition. In some embodiments, the compositions comprise about 1% mitophagy stimulant (e.g., urolithin A) by weight of the composition.

In some embodiments, the compositions of the disclosure contain at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.5%, at least about 2.0%, at least about 2.5%, at least about 3.0%, at least about 3.5%, at least about 4.0%, at least about 4.5%, at least about 5.0%, at least about 5.5%, at least about 6.0%, at least about 6.5%, at least about 7.0%, at least about 7.5%, at least about 8.0%, at least about 8.5%, at least about 9.0%, at least about 9.5%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% mitophagy stimulant (e.g., urolithin A) by weight of the composition. In some embodiments, the compositions comprise at least about 1% mitophagy stimulant (e.g., urolithin A) by weight of the composition.

In some embodiments, the compositions of the disclosure comprise between about 0.01 milligrams (mg) and 200 mg of mitophagy stimulant (e.g., urolithin A) per milliliter of composition. For example, in some embodiments, the compositions comprise about 0.01 mg, about 0.05 mg, about 0.1 mg, about 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 101 mg, about 102 mg, about 103 mg, about 104 mg, about 105 mg, about 106 mg, about 107 mg, about 108 mg, about 109 mg, about 110 mg, about 111 mg, about 112 mg, about 113 mg, about 114 mg, about 115 mg, about 116 mg, about 117 mg, about 118 mg, about 119 mg, about 120 mg, about 121 mg, about 122 mg, about 123 mg, about 124 mg, about 125 mg, about 126 mg, about 127 mg, about 128 mg, about 129 mg, about 130 mg, about 131 mg, about 132 mg, about 133 mg, about 134 mg, about 135 mg, about 136 mg, about 137 mg, about 138 mg, about 139 mg, about 140 mg, about 141 mg, about 142 mg, about 143 mg, about 144 mg, about 145 mg, about 146 mg, about 147 mg, about 148 mg, about 149 mg, about 150 mg, about 151 mg, about 152 mg, about 153 mg, about 154 mg, about 155 mg, about 156 mg, about 157 mg, about 158 mg, about 159 mg, about 160 mg, about 161 mg, about 162 mg, about 163 mg, about 164 mg, about 165 mg, about 166 mg, about 167 mg, about 168 mg, about 169 mg, about 170 mg, about 171 mg, about 172 mg, about 173 mg, about 174 mg, about 175 mg, about 176 mg, about 177 mg, about 178 mg, about 179 mg, about 180 mg, about 181 mg, about 182 mg, about 183 mg, about 184 mg, about 185 mg, about 186 mg, about 187 mg, about 188 mg, about 189 mg, about 190 mg, about 191 mg, about 192 mg, about 193 mg, about 194 mg, about 195 mg, about 196 mg, about 197 mg, about 198 mg, about 199 mg, or about 200 mg of mitophagy stimulant (e.g., urolithin A) per milliliter of composition. In some embodiments, a composition comprises 100 mg of mitophagy stimulant (e.g., urolithin A) per milliliter of composition.

In some embodiments, the compositions comprise at least about 0.01 mg, at least about 0.05 mg, at least about 0.1 mg, at least about 0.15 mg, at least about 0.2 mg, at least about 0.25 mg, at least about 0.3 mg, at least about 0.35 mg, at least about 0.4 mg, at least about 0.45 mg, at least about 0.5 mg, at least about 0.55 mg, at least about 0.6 mg, at least about 0.65 mg, at least about 0.7 mg, at least about 0.75 mg, at least about 0.8 mg, at least about 0.85 mg, at least about 0.9 mg, at least about 0.95 mg, at least about 1 mg, at least about 1.5 mg, at least about 2 mg, at least about 2.5 mg, at least about 3 mg, at least about 3.5 mg, at least about 4 mg, at least about 4.5 mg, at least about 5 mg, at least about 5.5 mg, at least about 6 mg, at least about 6.5 mg, at least about 7 mg, at least about 7.5 mg, at least about 8 mg, at least about 8.5 mg, at least about 9 mg, at least about 9.5 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, at least about 20 mg, at least about 21 mg, at least about 22 mg, at least about 23 mg, at least about 24 mg, at least about 25 mg, at least about 26 mg, at least about 27 mg, at least about 28 mg, at least about 29 mg, at least about 30 mg, at least about 31 mg, at least about 32 mg, at least about 33 mg, at least about 34 mg, at least about 35 mg, at least about 36 mg, at least about 37 mg, at least about 38 mg, at least about 39 mg, at least about 40 mg, at least about 41 mg, at least about 42 mg, at least about 43 mg, at least about 44 mg, at least about 45 mg, at least about 46 mg, at least about 47 mg, at least about 48 mg, at least about 49 mg, at least about 50 mg, at least about 51 mg, at least about 52 mg, at least about 53 mg, at least about 54 mg, at least about 55 mg, at least about 56 mg, at least about 57 mg, at least about 58 mg, at least about 59 mg, at least about 60 mg, at least about 61 mg, at least about 62 mg, at least about 63 mg, at least about 64 mg, at least about 65 mg, at least about 66 mg, at least about 67 mg, at least about 68 mg, at least about 69 mg, at least about 70 mg, at least about 71 mg, at least about 72 mg, at least about 73 mg, at least about 74 mg, at least about 75 mg, at least about 76 mg, at least about 77 mg, at least about 78 mg, at least about 79 mg, at least about 80 mg, at least about 81 mg, at least about 82 mg, at least about 83 mg, at least about 84 mg, at least about 85 mg, at least about 86 mg, at least about 87 mg, at least about 88 mg, at least about 89 mg, at least about 90 mg, at least about 91 mg, at least about 92 mg, at least about 93 mg, at least about 94 mg, at least about 95 mg, at least about 96 mg, at least about 97 mg, at least about 98 mg, at least about 99 mg, at least about 100 mg, at least about 101 mg, at least about 102 mg, at least about 103 mg, at least about 104 mg, at least about 105 mg, at least about 106 mg, at least about 107 mg, at least about 108 mg, at least about 109 mg, at least about 110 mg, at least about 111 mg, at least about 112 mg, at least about 113 mg, at least about 114 mg, at least about 115 mg, at least about 116 mg, at least about 117 mg, at least about 118 mg, at least about 119 mg, at least about 120 mg, at least about 121 mg, at least about 122 mg, at least about 123 mg, at least about 124 mg, at least about 125 mg, at least about 126 mg, at least about 127 mg, at least about 128 mg, at least about 129 mg, at least about 130 mg, at least about 131 mg, at least about 132 mg, at least about 133 mg, at least about 134 mg, at least about 135 mg, at least about 136 mg, at least about 137 mg, at least about 138 mg, at least about 139 mg, at least about 140 mg, at least about 141 mg, at least about 142 mg, at least about 143 mg, at least about 144 mg, at least about 145 mg, at least about 146 mg, at least about 147 mg, at least about 148 mg, at least about 149 mg, at least about 150 mg, at least about 151 mg, at least about 152 mg, at least about 153 mg, at least about 154 mg, at least about 155 mg, at least about 156 mg, at least about 157 mg, at least about 158 mg, at least about 159 mg, at least about 160 mg, at least about 161 mg, at least about 162 mg, at least about 163 mg, at least about 164 mg, at least about 165 mg, at least about 166 mg, at least about 167 mg, at least about 168 mg, at least about 169 mg, at least about 170 mg, at least about 171 mg, at least about 172 mg, at least about 173 mg, at least about 174 mg, at least about 175 mg, at least about 176 mg, at least about 177 mg, at least about 178 mg, at least about 179 mg, at least about 180 mg, at least about 181 mg, at least about 182 mg, at least about 183 mg, at least about 184 mg, at least about 185 mg, at least about 186 mg, at least about 187 mg, at least about 188 mg, at least about 189 mg, at least about 190 mg, at least about 191 mg, at least about 192 mg, at least about 193 mg, at least about 194 mg, at least about 195 mg, at least about 196 mg, at least about 197 mg, at least about 198 mg, at least about 199 mg, or at least about 200 mg of mitophagy stimulant (e.g., urolithin A) per milliliter of composition. In some embodiments, a composition comprises at least about 100 mg of mitophagy stimulant (e.g., urolithin A) per milliliter of composition.

In some embodiments, the compositions of the disclosure comprise between about 1 µM and 10 mM of mitophagy stimulant (e.g., urolithin A). In some embodiments, the compositions of the disclosure comprise between about 0.01 mM and 10 mM of mitophagy stimulant (e.g., urolithin A). For example, in some embodiments, the compositions of the disclosure comprise about 1 µM, about 2 µM, about 3 µM, about 4 µM, about 5 µM, about 6 µM, about 7 µM, about 8 µM, about 9 µM, about 10 µM about 11 µM, about 12 µM, about 13 µM, about 14 µM, about 15 µM, about 16 µM, about 17 µM, about 18 µM, about 19 µM, about 20 µM, about 21 µM, about 22 µM, about 23 µM, about 24 µM, about 25 µM, about 26 µM, about 27 µM, about 28 µM, about 29 µM, about 30 µM, about 31 µM, about 32 µM, about 33 µM, about 34 µM, about 35 µM, about 36 µM, about 37 µM, about 38 µM, about 39 µM, about 40 µM, about 41 µM, about 42 µM, about 43 µM, about 44 µM, about 45 µM, about 46 µM, about 47 µM, about 48 µM, about 49 µM, about 50 µM, about 51 µM, about 52 µM, about 53 µM, about 54 µM, about 55 µM, about 56 µM, about 57 µM, about 58 µM, about 59 µM, about 60 µM, about 61 µM, about 62 µM, about 63 µM, about 64 µM, about 65 µM, about 66 µM, about 67 µM, about 68 µM, about 69 µM, about 70 µM, about 71 µM, about 72 µM, about 73 µM, about 74 µM, about 75 µM, about 76 µM, about 77 µM, about 78 µM, about 79 µM, about 80 µM, about 81 µM, about 82 µM, about 83 µM, about 84 µM, about 85 µM, about 86 µM, about 87 µM, about 88 µM, about 89 µM, about 90 µM, about 91 µM, about 92 µM, about 93 µM, about 94 µM, about 95 µM, about 96 µM, about 97 µM, about 98 µM, about 99 µM, about 100 µM (0.1 mM), about 0.15 mM, about 0.2 mM, about 0.25 mM, about 0.3 mM, about 0.35 mM, about 0.4 mM, about 0.45 mM, about 0.5 mM, about 0.55 mM, about 0.6 mM, about 0.65 mM, about 0.7 mM, about 0.75 mM, about 0.8 mM, about 0.85 mM, about 0.9 mM, about 0.95 mM, about 1 mM, about 1.5 mM, about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, or about 10 mM of mitophagy stimulant (e.g., urolithin A) per liter of composition.

In some embodiments, the compositions comprise about 3 µM mitophagy stimulant (e.g., urolithin A). In some embodiments, the compositions comprise about 10 µM mitophagy stimulant (e.g., urolithin A). In some embodiments, the compositions comprise about 30 µM mitophagy stimulant (e.g., urolithin A). In some embodiments, the compositions comprise about 100 µM mitophagy stimulant (e.g., urolithin A).

in some embodiments, the compositions of the disclosure comprise at least about 1 µM, at least about 2 µM, at least about 3 µM, at least about 4 µM, at least about 5 µM, at least about 6 µM, at least about 7 µM, at least about 8 µM, at least about 9 µM, at least about 10 µM at least about 11 µM, at least about 12 µM, at least about 13 µM, at least about 14 µM, at least about 15 µM, at least about 16 µM, at least about 17 µM, at least about 18 µM, at least about 19 µM, at least about 20 µM, at least about 21 µM, at least about 22 µM, at least about 23 µM, at least about 24 µM, at least about 25 µM, at least about 26 µM, at least about 27 µM, at least about 28 µM, at least about 29 µM, at least about 30 µM, at least about 31 µM, at least about 32 µM, at least about 33 µM, at least about 34 µM, at least about 35 µM, at least about 36 µM, at least about 37 µM, at least about 38 µM, at least about 39 µM, at least about 40 µM, at least about 41 µM, at least about 42 µM, at least about 43 µM, at least about 44 µM, at least about 45 µM, at least about 46 µM, at least about 47 µM, at least about 48 µM, at least about 49 µM, at least about 50 µM, at least about 51 µM, at least about 52 µM, at least about 53 µM, at least about 54 µM, at least about 55 µM, at least about 56 µM, at least about 57 µM, at least about 58 µM, at least about 59 µM, at least about 60 µM, at least about 61 µM, at least about 62 µM, at least about 63 µM, at least about 64 µM, at least about 65 µM, at least about 66 µM, at least about 67 µM, at least about 68 µM, at least about 69 µM, at least about 70 µM, at least about 71 µM, at least about 72 µM, at least about 73 µM, at least about 74 µM, at least about 75 µM, at least about 76 µM, at least about 77 µM, at least about 78 µM, at least about 79 µM, at least about 80 µM, at least about 81 µM, at least about 82 µM, at least about 83 µM, at least about 84 µM, at least about 85 µM, at least about 86 µM, at least about 87 µM, at least about 88 µM, at least about 89 µM, at least about 90 µM, at least about 91 µM, at least about 92 µM, at least about 93 µM, at least about 94 µM, at least about 95 µM, at least about 96 µM, at least about 97 µM, at least about 98 µM, at least about 99 µM, at least about 100 µM (0.1 mM), at least about 0.15 mM, at least about 0.2 mM, at least about 0.25 mM, at least about 0.3 mM, at least about 0.35 mM, at least about 0.4 mM, at least about 0.45 mM, at least about 0.5 mM, at least about 0.55 mM, at least about 0.6 mM, at least about 0.65 mM, at least about 0.7 mM, at least about 0.75 mM, at least about 0.8 mM, at least about 0.85 mM, at least about 0.9 mM, at least about 0.95 mM, at least about 1 mM, at least about 1.5 mM, at least about 2 mM, at least about 2.5 mM, at least about 3 mM, at least about 3.5 mM, at least about 4 mM, at least about 4.5 mM, at least about 5 mM, at least about 5.5 mM, at least about 6 mM, at least about 6.5 mM, at least about 7 mM, at least about 7.5 mM, at least about 8 mM, at least about 8.5 mM, at least about 9 mM, at least about 9.5 mM, or at least about 10 mM of mitophagy stimulant (e.g., urolithin A) per liter of composition.

In some embodiments, the compositions comprise at least about 3 µM mitophagy stimulant (e.g., urolithin A). In some embodiments, the compositions comprise at least about 10

μM mitophagy stimulant (e.g., urolithin A). In some embodiments, the compositions comprise at least about 30 μM mitophagy stimulant (e.g., urolithin A). In some embodiments, the compositions comprise at least about 100 μM mitophagy stimulant (e.g., urolithin A).

In some embodiments, the compositions comprise an anti-acne ingredient (e.g., salicylic acid). In some embodiments, the compositions comprise about 0.005% to about 5% anti-acne ingredient (e.g., salicylic acid) by weight of the composition. In some embodiments, the compositions comprise 0.5% to about 3% anti-acne ingredient (e.g., salicylic acid) by weight of the composition. In some embodiments, the compositions comprise about 1% to about 2% anti-acne ingredient (e.g., salicylic acid) by weight of the composition. For example, in some embodiments, the composition comprises about 0.005%, about 0.01%, about 0.05%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, or about 5.0% anti-acne ingredient (e.g., salicylic acid) by weight of the composition, including all subranges and ranges therebetween. In some embodiments, the compositions provided herein comprise about 1.5% anti-acne ingredient (e.g., salicylic acid) by weight of the composition. In some embodiments, the compositions provided herein comprise about 2.0% anti-acne ingredient (e.g., salicylic acid) by weight of the composition.

In some embodiments, the compositions comprise an anti-acne ingredient (e.g., salicylic acid). In some embodiments, the compositions comprise at least about 0.005% to at least about 5% anti-acne ingredient (e.g., salicylic acid) by weight of the composition. In some embodiments, the compositions comprise 0.5% to at least about 3% anti-acne ingredient (e.g., salicylic acid) by weight of the composition. In some embodiments, the compositions comprise at least about 1% to at least about 2% anti-acne ingredient (e.g., salicylic acid) by weight of the composition. For example, in some embodiments, the composition comprises at least about 0.005%, at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.0%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.1%, at least about 3.2%, at least about 3.3%, at least about 3.4%, at least about 3.5%, at least about 3.6%, at least about 3.7%, at least about 3.8%, at least about 3.9%, at least about 4.0%, at least about 4.1%, at least about 4.2%, at least about 4.3%, at least about 4.4%, at least about 4.5%, at least about 4.6%, at least about 4.7%, at least about 4.8%, at least about 4.9%, or at least about 5.0% anti-acne ingredient (e.g., salicylic acid) by weight of the composition, including all subranges and ranges therebetween. In some embodiments, the compositions provided herein comprise at least about 1.5% anti-acne ingredient (e.g., salicylic acid) by weight of the composition. In some embodiments, the compositions provided herein comprise at least about 2.0% anti-acne ingredient (e.g., salicylic acid) by weight of the composition.

In some embodiments, the compositions comprise between about 1 mg and about 30 mg of anti-acne ingredient (e.g., salicylic acid) per mL of composition, for example, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, or about 30 mg of anti-acne ingredient (e.g., salicylic acid) per mL of composition. In some embodiments, the compositions comprise about 10 mg of anti-acne ingredient (e.g., salicylic acid) per milliliter of composition. In some embodiments, the compositions comprise about 15 mg of anti-acne ingredient (e.g., salicylic acid) per milliliter of composition.

In some embodiments, the compositions comprise at least about 1 mg, at least about 2 mg, at least about 3 mg, at least about 4 mg, at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, at least about 20 mg, at least about 21 mg, at least about 22 mg, at least about 23 mg, at least about 24 mg, at least about 25 mg, at least about 26 mg, at least about 27 mg, at least about 28 mg, at least about 29 mg, or at least about 30 mg of anti-acne ingredient (e.g., salicylic acid) per mL of composition. In some embodiments, the compositions comprise at least about 10 mg of anti-acne ingredient (e.g., salicylic acid) per milliliter of composition. In some embodiments, the compositions comprise at least about 15 mg of anti-acne ingredient (e.g., salicylic acid) per milliliter of composition.

In some embodiments, the compositions comprise between about 0.01% and about 5% lilac stem cells by weight of the composition. For example, in some embodiments, the compositions comprise about 0.01%, about 0.05%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, or about 5.0% lilac cells by weight of the composition. In some embodiments, the compositions comprise about 0.01% lilac cells by weight of the composition. In some embodiments, the compositions comprise about 1% lilac cells by weight of the composition.

In some embodiments, the compositions comprise between at least about 0.01% and at least about 5% lilac stem cells by weight of the composition. For example, in some embodiments, the compositions comprise at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.0%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.1%, at least about 3.2%, at least about 3.3%, at least about 3.4%, at least about 3.5%, at least about 3.6%, at least about 3.7%, at least about 3.8%, at least about 3.9%, at least about 4.0%, at least about 4.1%, at least about 4.2%, at least about 4.3%, at least about 4.4%, at least about 4.5%, at least about 4.6%, at least about 4.7%, at least about 4.8%, at least about 4.9%, or at least about 5.0% lilac cells by weight of the composition. In some embodiments, the compositions comprise at least about 0.01% lilac cells by weight of the composition. In some embodiments, the compositions comprise at least about 1% lilac cells by weight of the composition.

In some embodiments, the compositions described herein comprise between about 0.05% and about 5% avenanthramides by weight of the composition. For example, in some embodiments, the compositions comprise about 0.05%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, or about 5.0% avenanthramides by weight of the composition.

In some embodiments, the compositions comprise at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.0%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.1%, at least about 3.2%, at least about 3.3%, at least about 3.4%, at least about 3.5%, at least about 3.6%, at least about 3.7%, at least about 3.8%, at least about 3.9%, at least about 4.0%, at least about 4.1%, at least about 4.2%, at least about 4.3%, at least about 4.4%, at least about 4.5%, at least about 4.6%, at least about 4.7%, at least about 4.8%, at least about 4.9%, or at least about 5.0% avenanthramides by weight of the composition.

In some embodiments, the compositions comprise about 0.005% and about 5 PP2 by weight of the composition. In some embodiments, the compositions comprise about 1% and about 2% PP2 by weight of the composition. In some embodiments, the compositions comprise about 2% and about 3% PP2 by weight of the composition. In some embodiments, the compositions comprise about 3% and about 4% PP2 by weight of the composition. In some embodiments, the compositions comprise about 4% and about 5% PP2 by weight of the composition. For example, in some embodiments, the compositions comprise about 0.005%, about 0.01%, about 0.05%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, or about 5.0% PP2 by weight of the composition, including all subranges and ranges therebetween. In some embodiments, the compositions provided herein comprise about 0.01% PP2 by weight of the composition.

In some embodiments, the compositions comprise at least about 0.005%, at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.0%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.1%, at least about 3.2%, at least about 3.3%, at least about 3.4%, at least about 3.5%, at least about 3.6%, at least about 3.7%, at least about 3.8%, at least about 3.9%, at least about 4.0%, at least about 4.1%, at least about 4.2%, at least about 4.3%, at least about 4.4%, at least about 4.5%, at least about 4.6%, at least about 4.7%, at least about 4.8%, at least about 4.9%, or at least about 5.0% PP2 by weight of the composition, including all subranges and ranges therebetween. In some embodiments, the compositions provided herein comprise at least about 0.01% PP2 by weight of the composition.

In some embodiments, the compositions described herein comprise between about 0.01 mg and about 50 mg PP2 per milliliter of composition. For example, in some embodiments, the compositions comprise about 0.01 mg, about 0.05 mg, about 0.1 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg PP2 per mL of composition. In some embodiments, the composition comprises about 0.1 mg PP2 per mL of composition. In some embodiments, the composition comprises about 20 mg PP2 per mL of composition. In some embodiments, the composition comprises about 30 mg PP2 per mL of composition.

In some embodiments, the compositions comprise at least about 0.01 mg, at least about 0.05 mg, at least about 0.1 mg, at least about 0.5 mg, at least about 1 mg, at least about 2 mg, at least about 3 mg, at least about 4 mg, at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, at least about 20 mg, at least about 21 mg, at least about 22 mg, at least about 23 mg, at least about 24 mg, at least about 25 mg, at least about 26 mg, at least about 27 mg, at least about 28 mg, at least about 29 mg, at least about 30 mg, at least about 31 mg, at least about 32 mg, at least about 33 mg, at least about 34 mg, at least about 35 mg, at least about 36 mg, at least about 37 mg, at least about 38 mg, at least about 39 mg, at least about 40 mg, at least about 41 mg, at least about 42 mg, at least about 43 mg, at least about 44 mg, at least about 45 mg, at least about 46 mg, at least about 47 mg, at least about 48 mg, at least about 49 mg, or at least about 50 mg PP2 per mL of composition. In some embodiments, the composition comprises at least about 0.1 mg PP2 per mL of composition. In some embodiments, the composition comprises at least about 20 mg PP2 per mL of composition. In some embodiments, the composition comprises at least about 30 mg PP2 per mL of composition.

In some embodiments, the compositions comprise between about 0.1% and about 10% licorice by weight of the composition. For example, in some embodiments, the compositions comprise about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10% licorice by weight of the composition, including all subranges and ranges therebetween. In some embodiments, the compositions comprise at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, or at least about 10% licorice by weight of the composition, including all subranges and ranges therebetween.

In some embodiments, the compositions comprise between about 0.1 mg/mL and about 10 mg/mL licorice. In some embodiments, the compositions comprise about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, or about 10 mg/mL licorice, including all ranges and subranges therebetween.

Methods of Using the Compositions of the Disclosure

In some embodiments, the compositions described herein are used to increase ATP metabolism in a cell. ATP is metabolized when it is converted to adenosine diphosphate (ADP) or adenosine monophosphate (AMP). In some embodiments, the compositions increase ATP metabolism by increasing ATP production by mitochondria. The increased ATP production provides the necessary ATP substrate for ATP metabolism.

In some embodiments, the compositions described herein are used to optimize mitochondrial function and/or ATP output. In some embodiments, the compositions described herein are used to increase the concentration of ATP in one or more organs and/or tissues. In some embodiments, the compositions described herein increase the concentration of ATP in one or more organs and/or tissues. In some embodiments, the organ is the skin. In some embodiments, after treatment with the compositions of the disclosure, the concentration of ATP increases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or more.

In some embodiments, provided herein is a method for increasing ATP metabolism in a cell, comprising: administering to a patient in need thereof a therapeutically effective amount of a composition of the disclosure. In some embodiments, provided herein is a method for increasing ATP metabolism in a cell, comprising contacting the cell with a therapeutically effective amount of a composition of the disclosure. The composition may be any composition described herein. In some embodiments, the composition comprises a cannabinoid and a redox cofactor or precursor thereof. In some embodiments, the composition comprises a cannabinoid, a redox cofactor or precursor thereof, and an antioxidant. In some embodiments, the composition comprises a cannabinoid, a redox cofactor or precursor thereof, and a mitophagy stimulant. In some embodiments, the composition comprises a cannabinoid, a redox cofactor or precursor thereof, an antioxidant, and a mitophagy stimulant. In some embodiments, the compositions described herein increase ATP metabolism in sebocytes.

In some embodiments, the present disclosure provides methods of treating a subject experiencing a mitochondrial ATP deficit disorder comprising administering a therapeutically effective amount of a composition comprising a cannabinoid, an antioxidant, a cofactor or precursor thereof, and optionally comprising a mitophagy modulator.

In some embodiments, the subject is a patient in need thereof. In some embodiments, the patient is a human that is affected by a mitochondrial ATP deficit disorder. In some embodiments, the subject is not suffering from a disease or disorder.

In some embodiments, the subject is a mammal. In some embodiments, the subject is an animal or a human. Non-limiting examples of animals include dogs, cats, wolves, bears, tigers, lions, monkeys, guinea pigs, giraffes, elephants, mice, rats, ferrets, pigs, hamsters, and rabbits. In some embodiments, application of a composition described herein has a favorable benefit/risk ratio.

In some embodiments, the subjects are between about 0 years old and 100 years old, for example, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, or about 100 years old.

In some embodiments, the compositions of the disclosure are applied to subjects undergoing puberty. In some embodiments, the subjects undergoing puberty are between about 9 years and about 18 years old, for example, about 9 years old, about 10 years old, about 11 years old, about 12 years old, about 13 years old, about 14 years old, about 15 years old, about 16 years old, about 17 years old, or about 18 years old.

In some embodiments, the compositions of the disclosure are applied to subjects that are pregnant.

In some embodiments, the compositions of the disclosure are applied to subjects that are not suffering from a disease or disorder. In some embodiments, the compositions of the disclosure are applied for their aesthetic value. In some embodiments, the compositions are utilized to reduce fine lines, decrease wrinkles, improve the symptoms of aging, reduce cellulitis, reduce excess pigmentation, reduce sun damage, reduce freckles, reduce brown spots, decrease redness, increase luminosity, make pigmentation even, increase pigmentation, reduce thinning of the skin or hair, odor, and tighten sagging skin.

In some embodiments, the compositions of the disclosure are used to improve psychological concerns of a subject in need. Psychological concerns include anxiety, stress, bipolar disorder, depression, eating disorders, or obsessive-compulsive disorders.

In some embodiments, a mitochondrial ATP deficit disorder (e.g. a dermatological condition, such as 'acne') is a symptom of a disease such as, intracranial problems, cranial neuropathy, Alzheimer's Disease, and Parkinson's Disease.

In some embodiments, the mitochondrial ATP deficit disorder is caused by a bacterial infection. In some embodiments, the mitochondrial ATP deficit disorder is caused by a viral infection. In some embodiments, the mitochondrial ATP deficit disorder is caused by aging.

In some embodiments, a patient with a mitochondrial ATP deficit disorder has a deficiency in a cofactor. In some embodiments, treating with a composition described herein reverses a cofactor deficiency.

In some embodiments, the compositions provided herein may be used to improve fine lines, wrinkles, sun damage, freckles, brown spots, redness, irritation, itch, flaking, dryness, loss of lubrication, pain, decreased luminosity, uneven pigmentation, increased pigmentation, loss of pigmentation, soreness, thinning, odor, fungal, mite, viral or bacterial infestations, cellulite, sagging skin, laxity, excess sebum, sore muscles, psoriasis, eczema, rosacea, ichthyosis, vitiligo, hives, seborrheic dermatitis, actinic keratosis, carbuncle, sexual dysfunction, aging, cellulitis, a pigmentary disorder, excess pigmentation, aging, actinic damage, decreased hydration, decreased barrier function.

In some embodiments, the compositions are used prophylactically. In some embodiments, the compositions are used prophylactically to prevent an ATP deficit. In some embodiments, the ATP deficit is caused by a mitochondrial ATP deficit disorder.

Figure 1:
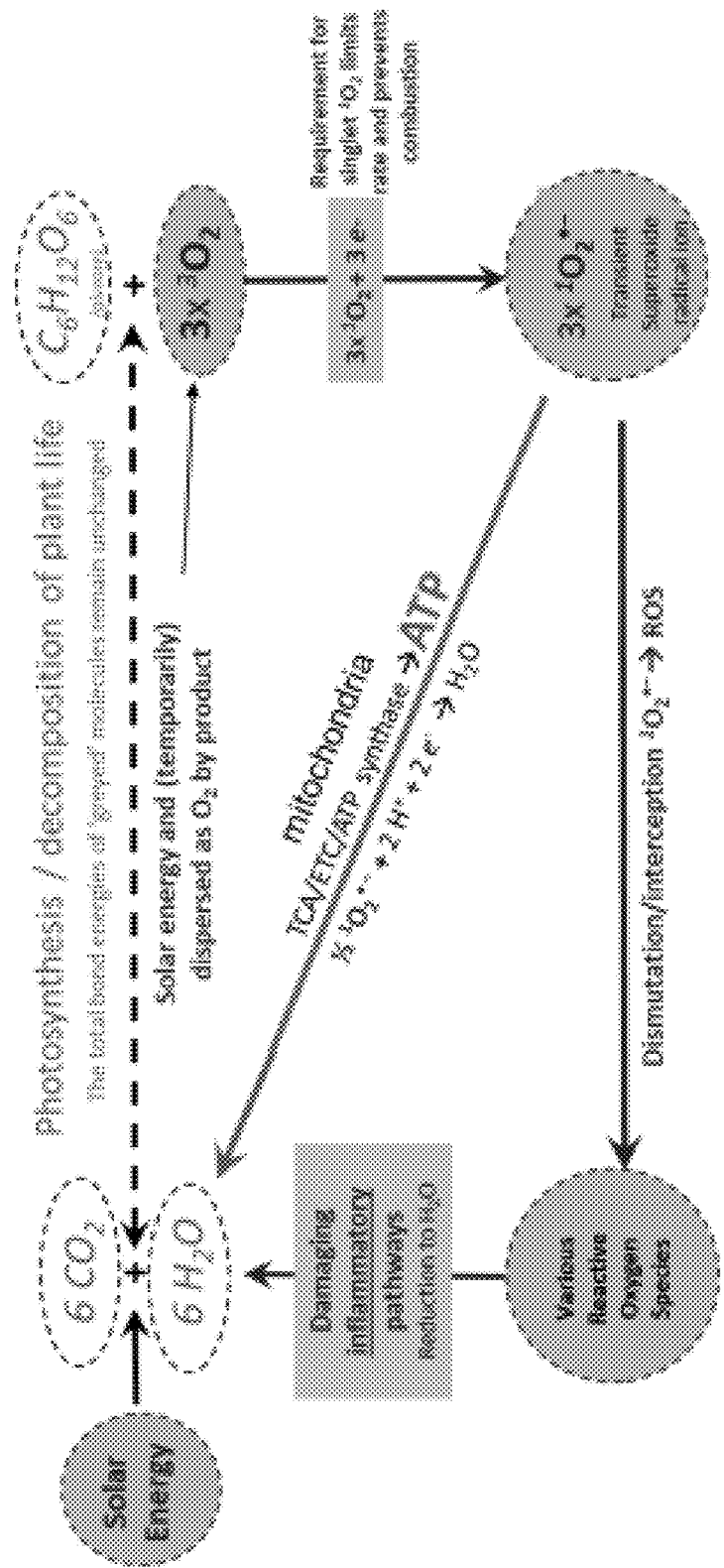
FIG. 1 illustrates the acquisition and disposal of solar-derived energy and identifies changing the balance between alternate routes of disposal of the obligatory rate-limiting superoxide ion $O_2 \cdot^-$. Open circles describe a notional pre-life state of $CO_2$ and $H_2O$ being energized by the sun to photosynthesise an exemplar 'carbohydrate (glucose.). The loss of the $O_2$ by-product into a largely nitrogen atmosphere prevents the ready reversal of the glucose synthesis process. However, over time (a 'lifetime') atmospheric $O_2$ and the many ROS species derived from it will return result on the reversion of the photosynthetic products to $CO_2$ and $H_2O$. Overall, the total bond energies of the starting materials ($CO_2$ and $H_2O$) and their carbon-based photosynthetic products remain equal (a futile cycle) and the solar energy is temporarily transformed into $O_2$ and thence to reactive oxygen species, ROS* (Shaded circles). When the $O_2$ content of the atmosphere become high enough, animal life becomes possible because of the ability of the mitochondrion (an organelle derived from a primitive bacterium) to transform corrosive oxygen-based energy into carbon compatible energy in the form of ATP, thus endowing a primitive animal cell with the energy required to be mobile and exercise a level of self-determination, such as consolidating into large multicell entities with functionally differentiated cells. Notable points are that ATP production occurs at the expense of ROS production and vice versa, thus low ATP and damaging oxidative stress are inversely related.

Restricted ATP availability arising from mitochondrial dysfunction underlies various idiosyncratic pathological conditions. Usually these will show an inflammatory component arising from automatic elevation of ROS levels (see FIG. 1). Temporary ATP insufficiencies can be encountered during short-term physiological changes (e.g. adolescence, during menstrual cycles, illness etc.). Progressive reduction of ATP availability occurs with increasing age, due to the long-term accumulation within the otherwise wild-type mtDNA complement of ROS-damaged mtDNA which remains replicable but translates to incompetent or poorly competent mitochondria. In a similar manner, a minor proportion of a maternally inherited incompetent mutant mtDNA within the wild type can be triggered to undergo a degree of preferential replication and translation. In this case the accumulation of deficient mitochondria is more rapid, more extensive, and more devastating than the effects of aging. However, wild type mitochondria in whatever proportion the exist, respond normally to internal and external mitochondrial and human signaling and chemical intervention.

Figure 3C:
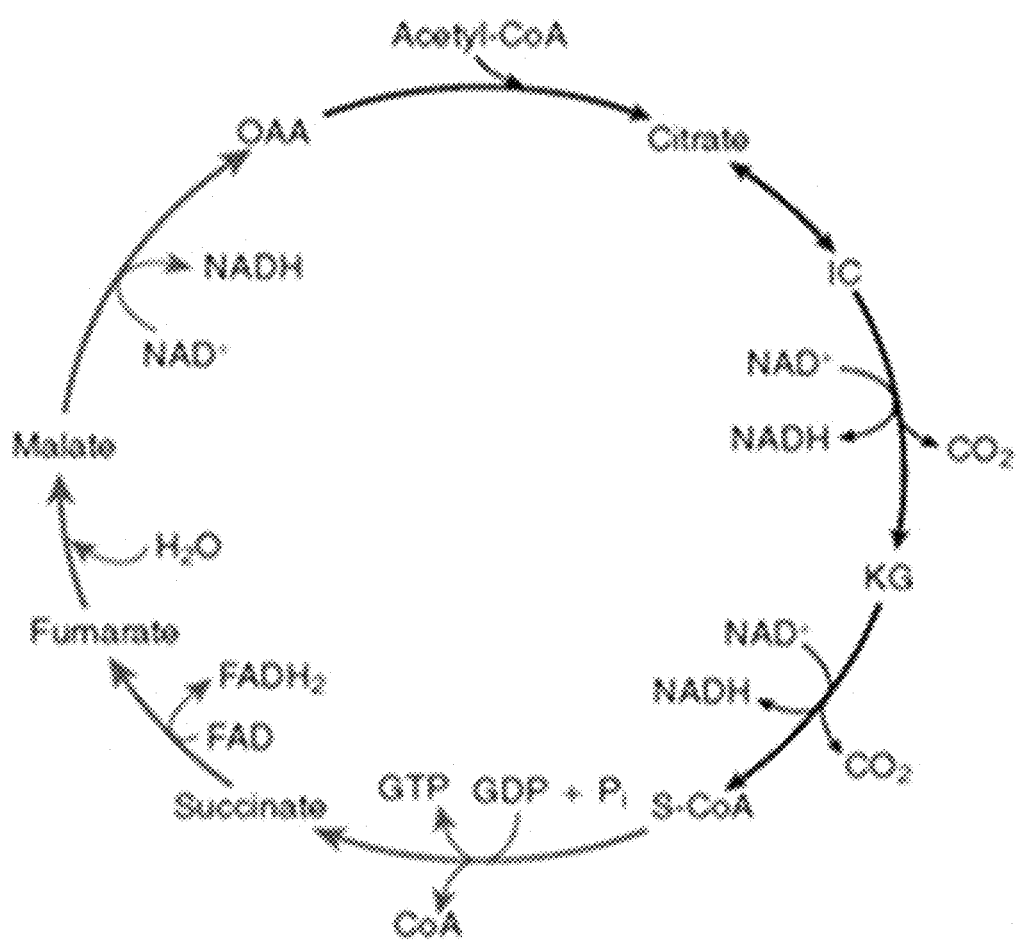
FIG. 3C is a schematic of the TCA cycle. Restricted ATP availability arising from mitochondrial dysfunction underlies various idiosyncratic pathological conditions. Usually these will show an inflammatory component arising from automatic elevation of ROS levels (FIG. 1). Temporary ATP insufficiencies can be encountered during short-term physiological changes (e.g. adolescence, during menstrual cycles, illness etc.).

In a different situation, all (or practically all) mitochondria in the cell complement derive from wild-type mtDNA and produce competent mitochondria, but ATP output is subnormal. In this case, associated mitochondrial mechanisms and systems normally purposed to extrinsically enable support and optimize the core TCA/ETC/ATP-synthase mediated ATP production process (FIG. 3), may be dysfunctional. Commonly sub-optimal performance is due to an alternative fate for the $O_2{\cdot}^-$ radical ion by dismutation or radical transfer with bystanders, leading to 'reactive oxygen species' (ROS), including hydrogen peroxide ($H_2O_2$), peroxide, superoxide, and hydroxyl radicals (OH·). These can cause damage to mitochondria beyond normal diurnal repairable limits, damage mtDNA hindering faithful replication or cause ATP to fall to levels insufficient to support timely apoptosis and mitochondria renewal, or efficient mitophagy to remove the mitochondrial debris from cristae that prevents efficient mitochondrial processing.

In some embodiments, the compositions described herein restore hormesis, the state in which oxidative stress, a disturbance in the balance between the production of $O_2{\cdot}^-$ and antioxidant defenses, is minimal and ATP output is maximal. In a normal, healthy, well-exercised individual this position is just short of the point of oxidative stress and is almost exclusively controlled by human systems set to deal with local varying ATP demands. Treatments will therefore be effective in all humans, including those carrying aberrant mtDNA, particularly when the level of aberrant mtDNA in the mitochondrial population is low.

In some embodiments, administering the compositions described herein improve the health of a subject's mitochondria. Healthy mitochondria adapt to environmental changes, repair damage invoked by ROS, degrade and/or sequester ROS, and maintain cellular mitochondrial homeostasis. Healthy mitochondria also detect the need for mitochondrial renewal and trigger apoptosis, so that old mitochondria can be replaced by new mitochondria. In some embodiments, before administering a composition described herein, a subject has unhealthy mitochondria. Non-limiting examples of characteristics of unhealthy mitochondria include:
 (a) mitochondria that do not adapt to environmental changes;
 (b) mitochondria that do not repair damage invoked by ROS;
 (c) mitochondria that do not degrade and/or sequester excessive ROS;
 (d) mitochondria that do not maintain optimal mitochondrial ATP output;
 (e) mitochondria that do not detect the need for mitochondria renewal;
 (f) mitochondria that do not trigger timely apoptosis of old mitochondria; and
 (g) mitochondria that cannot support the clearance of apoptosis debris by mitophagy In some embodiments, before administering of a composition described herein, a subject has healthy mitochondria. Non-limiting examples of healthy mitochondria include:
 (a) mitochondria that adapt to environmental changes;
 (b) mitochondria that repair damage invoked by ROS;
 (c) mitochondria that degrade and/or sequester ROS;

(d) mitochondria that maintain mitochondrial optimal homeostasis;
(e) mitochondria that detect the need for mitochondria renewal; and
(f) mitochondria that trigger apoptosis of old mitochondria.
(g) mitochondria that can support their own mitophagy In some embodiments, before administering a composition of the disclosure, a subject has cells that are undergoing oxidative stress.

In some embodiments, after administering a composition of the disclosure, the oxidative stress of a subject's cells decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95, or about 100% compared to prior to administering of a composition. In some embodiments, the reduction in oxidative stress is quantitated by measuring reactive oxygen species in a cell by for example, flow cytometry, microscopy, or enzyme-linked immunosorbent assay (ELISA). In some embodiments, a reduction in oxidative stress is quantitated by measuring a decrease in DNA and/or RNA damage, for example, by quantitating levels of the marker of DNA damage, 8-hydroxydeoxyguanosine (8-OHdG). In some embodiments, a reduction in oxidative stress is quantitated by measuring a decrease in lipid peroxidation, for example, by quantitating levels of a lipid marker of oxidative stress. In some embodiments, a reduction in oxidative stress is quantitated by measuring the concentration of ATP in a cell. Non-limiting lipid measures of oxidative stress include malondialdehyde, lipid hydroperoxide (LPO), 4-hydroxy-trans-2-nonenoic acid (4-HNA), 8-isoprostane, and oxidized low-density lipoproteins (LDL).

In some embodiments, the present disclosure provides methods of treating a subject experiencing a dermatological concern or preventing a subject from experiencing a dermatological concern comprising administering an effective amount of a composition comprising a cannabinoid, an antioxidant, a cofactor or precursor thereof, and optionally comprising a mitophagy modulator.

In some embodiments, the dermatological concern is selected from acne, psoriasis, eczema, rosacea, ichthyosis, vitiligo, seborrheic dermatitis, actinic keratosis, stretch mark, wrinkles, fine lines, carbuncle, hives, aging, and cellulitis. In some embodiments, the dermatological concern is acne. In some embodiments, the compositions of the disclosure are used to treat an acne lesion. In some embodiments, a composition of the disclosure is used to treat a symptom of a dermatological concern, including blemishes, nodules, lesions, wrinkles, fine lines, stretch marks, zits, papule, pimples, pre-emergent pimples, blackheads, hives, and/or whiteheads.

In some embodiments, the compositions are used to regulate visible, tactile, or visible and tactile discontinuities in the skin. In some embodiments, the discontinuities are associated with aging. In some embodiments, the discontinuities are associated with puberty. Non-limiting examples of discontinuities include acne, fine lines, wrinkles, dark spots, burns, stretch marks, and enlarged pores. In some embodiments, the compositions of the disclosure are used to treat psoriasis, dermatitis, sunburn, and rosacea.

In some embodiments, the compositions are used to reduce one or more symptoms associated with aging. Non-limiting examples of symptoms associated with aging include loss of elasticity in skin, dryness, itchiness, fine lines, thinning skin, and wrinkles. In some embodiments, the compositions are used for firming of the skin.

In some embodiments, the compositions are used to treat hypopigmentation. In some embodiments, the compositions are used to treat hyperpigmentation.

In some embodiments, the compositions are used to treat stretch marks. In some embodiments, the compositions are used to treat thinning skin.

In some embodiments, the compositions of the disclosure are used to treat subjects with non-inflammatory acne, also known as comedones, (e.g., blackheads and white heads). In other embodiments, the acne is inflammatory acne (e.g., papules, pustules, nodules, and cysts). In still other embodiments, the acne is a combination of non-inflammatory acne and inflammatory acne.

In some embodiments, the compositions of the disclosure are utilized to treat subjects with mild, moderate, or severe acne. When a subject has several comedones but very few papules and pustules, then the subject has mild acne. If a subject has a mix of comedones and several inflamed papules and pustules existing together, the acne is mild to moderate acne. If a subject also has some nodules along with papules and pustules, the acne is moderate acne. Deep cysts or any type of acne that leaves behind permanent pitted or saucer-shaped scars is categorized as severe acne.

In some embodiments, the compositions of the disclosure are anti-bacterial, anti-inflammatory, antioxidants, or combinations thereof. In some embodiments, the compositions of the disclosure are anti-inflammatory. In some embodiments, the compositions of the disclosure are antioxidants. In some embodiments, the compositions of the disclosure are anti-bacterial. In some embodiments, the compositions of the disclosure are antioxidants and anti-inflammatory. In some embodiments, the compositions of the disclosure are antioxidants and anti-bacterial. In some embodiments, the compositions of the disclosure are anti-bacterial and anti-inflammatory.

In some embodiments, the compositions of the disclosure are applied for hydration of the skin. In some embodiments, the compositions of the disclosure are used as a sunblock. In some embodiments, the compositions of the disclosure are utilized to prevent photo-aging. In some embodiments, the compositions of the disclosure are utilized to repair skin cells. In some embodiments, the compositions of the disclosure are used to protect skin from external factors. In some embodiments, the compositions of the disclosure are used for eye care. In some embodiments, the compositions of the disclosure are used to reduce fine lines or wrinkles near the eyes.

In some embodiments, the compositions of the disclosure are applied to subjects for psychological reasons. In some embodiments, the compositions described herein improve one's appearance. In some embodiments, the compositions described herein disguise a dermatological concern.

In some embodiments, the compositions of the disclosure are applied to subjects with dry skin, oily skin, sensitive skin, or skin that is both oily and dry.

In some embodiments, the compositions are administered intranasally, orally, parenterally, or topically. In some embodiments, the compositions are topical compositions. In some embodiments, the compositions are applied topically to a subject's skin. In some embodiments, the compositions are applied via depot injection. In some embodiments, the compositions are applied via depot injection to the membrane of the brain.

In some embodiments, the compositions of the disclosure are applied to the epidermis. In some embodiments, the compositions of the disclosure penetrate and absorb the dermis. In some embodiments, the compositions of the disclosure penetrate and are absorbed by the hypodermis. In some embodiments, the compositions of the disclosure penetrate and are absorbed by fat. In some embodiments, the compositions of the disclosure penetrate and are absorbed by muscles.

In some embodiments, the compositions of the disclosure are applied to the face, the forehead, nose, cheeks, ears, eyes, eye mucosa, scalp, hands, neck, décolleté, scalp, paw, hand, palm, arm, leg, foot, sole, chest, breast, back, abdomen, buttock, vulva, eyelid, nipples, penis, scrotum, anus, hair, nails, mucosal membranes, skin, or any other areas of a subject. In some embodiments, the compositions of the disclosure are applied to the lips. In some embodiments, the compositions of the disclosure are applied into the ears as ear drops. In some embodiments, the composition is applied to the whole body.

In some embodiments, the compositions of the disclosure are applied directly at the site of the acne, for example, on the blemish, nodule, cyst, lesion, zit, pimple, pre-emergent pimple, blackhead, hive, whitehead, papule, or postule (see FIG. 5).

In some embodiments, the compositions are applied as a product of the disclosure, described above. In some embodiments, the compositions are applied for an extended period for an aesthetic, preventive, prophylactic, or therapeutic benefit (i.e. a "leave-on" composition). In some embodiments, the leave-on composition is left on the skin for a period of at least 1 minute, or at least 2 minutes, or at least 3 minutes, or at least 4 minutes, or at least 5 minutes, or at least 6 minutes, or at least 7 minutes, or at least 8 minutes, or at least 9 minutes, or at least 10 minutes, or at least 15 minutes, or at least 20 minutes, or at least 25 minutes, or at least 30 minutes, or at least 45 minutes, or at least 1 hour, or at least 12 hours, or up to 24 hours, including all values and ranges in between.

In some embodiments, the compositions are applied one or more times per day. In some embodiments, the compositions are applied once per day. In some embodiments, the compositions are applied twice a day, or three times a day, or four time a day, or more. In some embodiments, the compositions are applied every other day, or every third day, or every fourth day, or every fifth day, or every sixth day, once per week, once per month, once per six months, or once per year.

In some embodiments, a composition's effect of treating a mitochondrial ATP deficit disorder lasts for about 1 day, about 1 week, about 2 weeks, about 3 weeks, about 4 weeks, about 5 weeks, about 1 month, about 2 months, about 3 months, about 4 months, about 5 months, about 6 months, about 7 months, about 8 months, about 9 months, about 10 months, about 11 months, about 1 year, or more. In some embodiments, a composition's effect of boosting ATP lasts for about 1 day, about 1 week, about 2 weeks, about 3 weeks, about 4 weeks, about 5 weeks, about 1 month, about 2 months, about 3 months, about 4 months, about 5 months, about 6 months, about 7 months, about 8 months, about 9 months, about 10 months, about 11 months, about 1 year, or more.

In some embodiments, a subject treated with the compositions of the disclosure experiences an improvement in a dermatological concern. In some embodiments, the improvement in a dermatological concern is quantified using any one of the following methods:

(a) creation and use of a portal (e.g., through the internet), which allows secure examination of high-resolution photographs;
(b) remote examination of high-resolution photographs;
(c) in person examination by a qualified grader;
(d) evaluating a symptom by counting and/or measuring;
(e) quantitating the quality of life of the subject; or
(f) collecting a statement from a subject on the effect of the composition on the subject's concerns or symptoms thereof.

In some embodiments, when a subject is treated with the compositions of the disclosure, the subject exhibits a reduction in acne compared to pre-treatment of about 5%, or about 10%, or about 15%, or about 20%, or about 25%, or about 30%, or about 35%, or about 40%, or about 45%, or about 50%, or about 55%, or about 60%, or about 65%, or about 70%, or about 75%, or about 80%, or about 85%, or about 90%, or about 95%, or more.

In some embodiments, a subject treated with the compositions of the disclosure experiences an improvement in acne. In some embodiments, the improvement in acne is quantified using any one of the following methods:

(a) creation and use of a portal (e.g., through the internet), which allows secure examination of high-resolution photographs;
(b) remote examination of high-resolution photographs;
(c) in person examination by a qualified grader;
(d) counting the number of acne lesions;
(e) counting the type of acne lesions;
(f) measuring the size of acne lesions;
(g) quantitating the quality of life of the subject,
(h) quantifying the amount of scarring as result of acne; or
(i) quantifying the amount of red or brown discoloration caused by acne.

In some embodiments, after application of a therapeutically effective amount of a composition to the acne, the reduction in acne occurs within 1 minute, 5 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 1 day, 2 days, 3 days, 4 days, 5 days, 6 days, 7 days, 8 days, 9 days, 10 days, 11 days, 12 days, 13 days, or 14 days.

In some embodiments, the number of acne lesions decreases after treatment with a therapeutically effective amount of a composition of the disclosure. In some embodiments, the number of acne lesions decreases by about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 lesions.

In some embodiments, after treatment with a therapeutically effective amount of a composition of the disclosure, the number of acne lesions decreases by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more.

In some embodiments, after treatment with a therapeutically effective amount of a composition of the disclosure, the size of at least one acne lesion decreases by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more.

In some embodiments, after treatment with a therapeutically effective amount of a composition of the disclosure, the number of red spots decreases by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more.

In some embodiments, after treatment with a therapeutically effective amount of a composition of the disclosure, the number of brown spots decreases by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more.

In some embodiments, after treatment with a therapeutically effective amount of a composition of the disclosure, scarring as a result of acne decreases by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more.

In some embodiments, after treatment with a therapeutically effective amount of a composition of the disclosure, a subject's quality of life improves according to the acne-specific Quality of Life Questionnaire. A higher score on the acne-specific Quality of Life Questionnaire is associated with higher impairment in quality of life as a result of acne. In some embodiments, after treatment with the compositions of the disclosure, a subject's score on the acne-specific Quality of Life Questionnaire decreases by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more.

EXAMPLES

Example 1. Preparation of Formulations Containing a Cannabinoid, a Cofactor or Precursor Thereof, and an Antioxidant Formulations containing a cannabinoid, a cofactor or precursor thereof, and an antioxidant are prepared. The cannabinoid within the formulations is CBD, THC, CBG, THCV, CBC, or combinations thereof. The cofactor or precursor thereof within the formulations is niacinamide. The antioxidant within the formulations is L-ergothioneine. The mitophagy stimulant is urolithin A. Exemplary formulations are shown in Tables 1-10.

TABLE 1

Exemplary Formulations containing a cannabinoid, cofactor or precursor thereof, and an antioxidant

| Ingredient | Formulation A | Formulation B | Formulation C | Formulation D | Formulation E |
|---|---|---|---|---|---|
| Cannabinoid | 0.42 mg/mL | 2.25 mg/mL | 6.75 mg/mL | 4 mg/mL | 4 mg/mL |
| Cofactor or precursor thereof | 10 mg/mL | 20 mg/mL | 30 mg/mL | 20 mg/mL | 20 mg/mL |
| Antioxidant | 1 mg/mL | 1 mg/mL | 10 mg/mL | 10 mg/mL | 10 mg/mL |

TABLE 2

Active Ingredient Portion of Formulations containing a cannabinoid, cofactor or precursor thereof, and an antioxidant

| Formulation | Cannabinoid (e.g. CBD) (% w/w) | Cofactor or precursor thereof (e.g. Niacinamide) (% w/w) | Antioxidant (e.g. L-ergothioneine) (% w/w) |
|---|---|---|---|
| Formulation F | 4.76 | 95.23 | .0048 |
| Formulation G | 2.91 | 48.66 | 48.44 |
| Formulation H | 19.20 | 80.79 | 0.01 |
| Formulation I | 17.29 | 89.69 | 0.02 |
| Formulation J | 17.35 | 82.63 | 0.02 |

TABLE 3

Exemplary Formulation K containing a cannabinoid, cofactor or precursor thereof, and an antioxidant

| Ingredient | Amount (% w/w) |
|---|---|
| cannabidiol | 0.05 |
| niacinamide | 1 |
| ergothioneine | 0.00005 |
| acrylates crosspolymer-4 | 0.96 |
| calcium gluconate | 0.01 |
| cocamidopropyl betaine | 4.5 |
| cocamidopropyl hydroxysltaine | 2.45 |
| coco-glucoside | 4.4 |
| EDTA | 0.00625 |
| essential oils | 0.2 |
| gluconolactone | 0.74 |
| glycerin | 3.501 |
| poly(C20-28 olefin) | 0.3125 |
| polysorbate 20 | 0.24625 |
| PPG-12/SMDI Copolymer | 0.01 |
| salicylic acid | 1.5 |
| sodium benzoate | 0.25 |
| sodium C14-16 olefin sulfonate | 10 |
| sodium chloride | 1.05 |
| sodium hydroxide | 0.0752 |
| tetrasodium glutamate diacetate | 0.047 |
| water | 68.69175 |

TABLE 4

Exemplary Formulation L containing a cannabinoid, cofactor or precursor thereof, and an antioxidant

| Ingredient | Amount (% w/w) |
|---|---|
| cannabidiol | 0.12 |
| niacinamide | 2.0091 |
| ergothioneine | 2 |
| amylopectin | 0.0003 |
| calcium gluconate | 0.01 |
| citric acid | 0.0014 |

TABLE 4-continued

Exemplary Formulation L containing a cannabinoid, cofactor or precursor thereof, and an antioxidant

| Ingredient | Amount (% w/w) |
| --- | --- |
| dextrin | 0.0003 |
| dipotassium glycyrrhizate | 0.05 |
| essential oils | 0.1 |
| gluconolactone | 0.74 |
| panthenol | 0.0926 |
| pentylene glycol | 3 |
| polydextrose | 0.0003 |
| polysorbate 20 | 0.985 |
| PPG-12/SMDI copolymer | 0.01 |
| salicylic acid | 1.5 |
| sodium benzoate | 0.25 |
| sodium hydroxide | 0.0002 |
| tetrasodium glutamate diacetate | 0.047 |
| water | 89.0838 |

TABLE 5

Exemplary Formulation M containing a cannabinoid, cofactor or precursor thereof, and an antioxidant

| Ingredient | Amount (% w/w) |
| --- | --- |
| cannabidiol | 0.715 |
| niacinamide | 3.0088 |
| ergothioneine | 0.0005 |
| amylopectin | 0.0004 |
| caprylhydroxamic acid | 0.16 |
| caprylyl glycol | 0.72 |
| cetearyl alcohol | 1.5 |
| cetearyl olivate | 2.4 |
| dextrin | 0.0004 |
| dipotassium glycyrrhizate | 0.2 |
| essential oils | 0.2 |
| ethoxydiglycol | 2 |
| glyceryl caprylate | 1 |
| hydroxyethylcellulose | 0.7 |
| pentylene glycol | 4 |
| polydextrose | 0.0004 |
| PPG-12/SMDI copolymer | 3 |
| propanediol | 3.12 |
| salicylic acid | 2 |
| sclerotium gum | 0.5 |
| sorbitan olivate | 1.6 |
| water | 73.1745 |

TABLE 6

Exemplary Formulation N containing a cannabinoid, cofactor or precursor thereof, and an antioxidant

| Ingredient | Amount (% w/w) |
| --- | --- |
| cannabidiol | 0.42 |
| niacinamide | 2.0091 |
| ergothioneine | 0.0005 |
| aloe barbadensis leaf juice | 0.01 |
| amylopectin | 0.0003 |
| caprylhydroxamic acid | 0.15 |
| caprylic/capric triglyceride | 4.5 |
| cetearyl alcohol | 2 |
| cetearyl olivate | 1.8 |
| citric acid | 0.2 |
| dextrin | 0.0003 |
| dipotassium glycyrrhizate | 0.2 |
| essential oils | 0.3 |
| glycerin | 0.225 |
| glyceryl caprylate | 1.425 |
| hydroxyethyl acrylate/sodium acryloyldimethyl taurate copolymer | 1.7 |

TABLE 6-continued

Exemplary Formulation N containing a cannabinoid, cofactor or precursor thereof, and an antioxidant

| Ingredient | Amount (% w/w) |
| --- | --- |
| pentylene glycol | 3 |
| polydextrose | 0.0003 |
| polysorbate 60 | 0.08 |
| PPG-12/SMDI Copolymer | 3 |
| salicylic acid | 1.5 |
| silica | 1 |
| sodium hyaluronate | 0.01 |
| sorbitan isostearate | 0.14 |
| sorbitan olivate | 1.2 |
| squalane | 2 |
| water | 73.1295 |

TABLE 7

Exemplary Formulation O containing a cannabinoid, cofactor or precursor thereof, and an antioxidant

| Ingredient | Amount (% w/w) |
| --- | --- |
| cannabidiol | 0.42 |
| niacinamide | 2 |
| ergothioneine | 0.0005 |
| alumina | 0.91 |
| bisabolol | 0.1988 |
| caprylhydroxamic acid | 0.16 |
| caprylic/capric triglyceride | 9.1 |
| caprylyl glycol | 0.72 |
| cetearyl alcohol | 2 |
| dipotassium glycyrrhizate | 0.2 |
| essential oils | 0.4 |
| glycerin | 2.991 |
| hydroxyethyl acrylate/sodium acryloyldimethyl taurate copolymer | 0.17 |
| pentylene glycol | 3 |
| polyhydroxystearic acid | 1.3 |
| polyolprepolymer 2 | 2 |
| polysorbate 60 | 0.008 |
| propanediol | 1.12 |
| silica | 2 |
| sodium hyaluronate | 0.02 |
| sodium hydroxide | 0.0002 |
| sorbitan isostearate | 0.014 |
| steareth-2 | 3 |
| steareth-21 | 2 |
| stearic acid | 0.91 |
| tetrasodium glutamate diacetate | 0.047 |
| titanium dioxide | 5.98 |
| tocopherol | 0.0018 |
| tridecane | 1.7682 |
| triethoxycaprylylsilane | 0.26 |
| undecane | 4.23 |
| water | 45.1293 |
| xanthan gum | 0.4 |
| zinc oxide | 7.54 |
| Zingiber officinale (ginger) root extract | 0.0012 |

Formulations that contain a mitophagy stimulant in addition to a cannabinoid, a cofactor or precursor thereof, and an antioxidant are also prepared. The cannabinoid within the formulations is CBD, THC, CBG, THCV, CBC, or combinations thereof. The cofactor or precursor thereof within the formulations is niacinamide. The antioxidant within the formulations is L-ergothioneine. The mitophagy stimulant within the formulations is urolithin A. Exemplary formulations are shown in Table 8.

TABLE 8

Exemplary Formulations containing a cannabinoid, cofactor or precursor thereof, an antioxidant, and a mitophagy modulator

| Ingredient | Formulation P | Formulation Q | Formulation R | Formulation S | Formulation T |
|---|---|---|---|---|---|
| Cannabinoid | 0.42 mg/mL | 2.25 mg/mL | 6.75 mg/mL | 4 mg/mL | 4 mg/mL |
| Cofactor or precursor thereof | 10 mg/mL | 20 mg/mL | 30 mg/mL | 20 mg/mL | 20 mg/mL |
| Antioxidant | 1 mg/mL | 1 mg/mL | 10 mg/mL | 10 mg/mL | 10 mg/mL |
| Mitophagy Stimulant | 1% w/w | 1% w/w | 1% w/w | 1% w/w | 1% w/w |

Additional formulations containing salicylic acid, PP2, licorice, and Xperse®401 are prepared. Exemplary formulations are shown in Table 9.

TABLE 9

Exemplary Formulations containing a cannabinoid, cofactor or precursor thereof, an antioxidant, and one or more of salicylic acid, PP2, licorice, and Xperse ® 401

| Ingredient | Formulation U | Formulation V | Formulation W | Formulation X | Formulation Y |
|---|---|---|---|---|---|
| Cannabinoid | 0.42 mg/mL | 2.25 mg/mL | 6.75 mg/mL | 4 mg/mL | 4 mg/mL |
| Cofactor or precursor thereof | 10 mg/mL | 20 mg/mL | 30 mg/mL | 20 mg/mL | 20 mg/mL |
| Antioxidant | 1 mg/mL | 1 mg/mL | 10 mg/mL | 10 mg/mL | 10 mg/mL |
| Salicylic Acid | 10 mg/mL | 15 mg/mL | 15 mg/mL | 15 mg/mL | — |
| PP2 | 0.1 mg/mL | 0.1 mg/mL | 30 mg/mL | 30 mg/mL | 20 mg/mL |
| Licorice | — | 2 mg/mL | 2 mg/mL | 2 mg/mL | — |
| Xperse ® 401 | — | — | — | — | 260 mg/mL |

Additional formulations containing salicylic acid, PP2, licorice, Xperse®401, and a mitophagy stimulant are prepared. Exemplary formulations are shown in Table 10.

TABLE 10

Exemplary Formulations containing a cannabinoid, cofactor or precursor thereof, an antioxidant, a mitophagy modulator, and one or more of salicylic acid, PP2, licorice, and Xperse ® 401

| Ingredient | Formulation Z | Formulation AA | Formulation BB | Formulation CC | Formulation DD |
|---|---|---|---|---|---|
| Cannabinoid | 0.42 mg/mL | 2.25 mg/mL | 6.75 mg/mL | 4 mg/mL | 4 mg/mL |
| Cofactor or precursor thereof | 10 mg/mL | 20 mg/mL | 30 mg/mL | 20 mg/mL | 20 mg/mL |
| Antioxidant | 1 mg/mL | 1 mg/mL | 10 mg/mL | 10 mg/mL | 10 mg/mL |
| Salicylic Acid | 10 mg/mL | 15 mg/mL | 15 mg/mL | 15 mg/mL | — |
| PP2 | 0.1 mg/mL | 0.1 mg/mL | 30 mg/mL | 30 mg/mL | 20 mg/mL |
| Licorice | — | 2 mg/mL | 2 mg/mL | 2 mg/mL | — |
| Xperse ® 401 | — | — | — | — | 260 mg/mL |
| Mitophagy Stimulant | 1% w/w | 1% w/w | 1% w/w | 1% w/w | 1% w/w |

Each of the formulations described in Tables 1-10 is incorporated into an acne cleanser, a cleanser, a toner, an acne toner, a spot treatment, an acne spot treatment, a day/night moisturizer, an acne day/night moisturizer, a morning sunscreen, a face cream, and a sunscreen.

Example 2. Evaluating Synergies of Disclosed Compositions on the Increase of ATP Metabolism The ability of various combinations of ingredients to increase ATP metabolism is evaluated via a sebocyte assay according to the following protocol. Immortalized human sebaceous gland cell lines (sebocytes) are a well-established model for studying acne. Primary human sebocytes Batch #13140680) were obtained from Celprogen™ and grown according to manufacturer's instructions. The cells were seeded at a concentration of 5000 cells per cm$^2$ in a tissue culture treated flask and incubated at 37° C. in a humidified incubator in the presence of 5% $CO_2$ (all subsequent incubations were subject to these conditions). At 60-80% confluency, cells were passaged by detaching cells using TrypLE™ Express (Sigma). Cells were seeded in a black 96-well half area plate at a concentration of 5000 cells per well and allowed to equilibrate overnight at 37° C.

Sebocytes were incubated with compositions comprising CBD, niacinamide, urolithin A, or combination thereof. Various concentrations of CBD (0 µM, 1 µM, 3 µM, 10 µM, 30 µM), niacinamide (0 µM, 4 µM, 10 µM, 20 µM, 40 µM), and urolithin A (0 µM, 3 µM, 10 µM, 30 µM, 100 µM) were evaluated in triplicate. The ability of each composition to increase ATP metabolism was determined using a luminescence assay (Celltiter-Glo™) according to manufacturer's instructions. Initial experiments (not shown) confirmed that the aforementioned ingredient concentrations provided luminescence values within the linear range of the CellTiter-Glo® assay and did not cause deleterious levels of sebocyte cell death.

Table 11 reports the percent luminescence reductions for cells treated with each composition compared to cells that are not administered a composition of the disclosure. This value is calculated using the formula: (1−(treatment luminescence/control luminescence))*100. The luminescence measurements in this assay are proportional to the number of metabolically active cells in a sample. Cells that are metabolically active (e.g., have functioning mitochondria) consume ATP and convert luciferin to oxyluciferin. If a first cell population exhibits a percent luminescence reduction of 50 and a second cell population exhibits a percent luminescence reduction of 20, the first cell population's cells are more metabolically active than the second cell population's cells, because they consumed more ATP in the same period of time.

TABLE 11

Percent luminescence reductions for compositions containing CBD, niacinamide, urolithin A, or combinations thereof.

| [CBD] (µM) | [Niacinamide] (µM) | [Urolithin A] (µM) | % Luminescence Reduction | | |
|---|---|---|---|---|---|
| | | | Repeat 1 | Repeat 2 | Repeat 3 |
| 0 | 0 | 0 | n/a | n/a | n/a |
| 1 | 0 | 0 | n/a | 5 | 9 |
| 3 | 0 | 0 | 10 | 10 | −11 |
| 10 | 0 | 0 | 6 | 12 | −2 |
| 30 | 0 | 0 | 28 | 36 | 12 |
| 0 | 0 | 3 | 34 | 13 | 9 |
| 1 | 0 | 3 | 5 | 8 | −3 |
| 3 | 0 | 3 | 8 | 7 | −10 |
| 10 | 0 | 3 | n/a | n/a | −7 |
| 30 | 0 | 3 | 32 | 29 | 29 |
| 0 | 0 | 10 | 20 | 15 | 5 |
| 1 | 0 | 10 | −11 | 3 | −20 |
| 3 | 0 | 10 | 5 | 14 | −15 |
| 10 | 0 | 10 | 9 | 5 | −13 |
| 30 | 0 | 10 | 48 | 48 | 7 |
| 0 | 0 | 30 | 15 | 17 | 18 |
| 1 | 0 | 30 | 50 | 26 | −29 |
| 3 | 0 | 30 | 25 | 18 | −33 |
| 10 | 0 | 30 | 40 | 22 | −21 |
| 30 | 0 | 30 | 33 | 43 | −4 |
| 0 | 0 | 100 | 25 | 35 | 27 |
| 1 | 0 | 100 | 37 | 30 | 33 |
| 3 | 0 | 100 | 33 | 35 | 23 |
| 10 | 0 | 100 | 36 | 24 | 29 |
| 30 | 0 | 100 | 42 | 50 | 19 |
| 0 | 4 | 0 | 4 | 11 | −6 |
| 1 | 4 | 0 | −6 | 2 | −13 |
| 3 | 4 | 0 | −12 | 5 | −11 |
| 10 | 4 | 0 | 2 | 18 | −16 |
| 30 | 4 | 0 | 51 | 90 | 48 |
| 0 | 4 | 3 | 45 | 2 | −9 |
| 1 | 4 | 3 | 4 | 14 | 8 |
| 3 | 4 | 3 | 5 | 29 | 2 |

TABLE 11-continued

Percent luminescence reductions for compositions containing CBD, niacinamide, urolithin A, or combinations thereof.

| [CBD] (µM) | [Niacinamide] (µM) | [Urolithin A] (µM) | % Luminescence Reduction | | |
|---|---|---|---|---|---|
| | | | Repeat 1 | Repeat 2 | Repeat 3 |
| 10 | 4 | 3 | 13 | 18 | 24 |
| 30 | 4 | 3 | 52 | 55 | 50 |
| 0 | 4 | 10 | n/a | 10 | −3 |
| 1 | 4 | 10 | −6 | 14 | 4 |
| 3 | 4 | 10 | −7 | 5 | 10 |
| 10 | 4 | 10 | −1 | 14 | 24 |
| 30 | 4 | 10 | 34 | 59 | 90 |
| 0 | 4 | 30 | 10 | 17 | 11 |
| 1 | 4 | 30 | 11 | 25 | 80 |
| 3 | 4 | 30 | 13 | 25 | 26 |
| 10 | 4 | 30 | 13 | 29 | 26 |
| 30 | 4 | 30 | 45 | 63 | 27 |
| 0 | 4 | 100 | 31 | 35 | 18 |
| 1 | 4 | 100 | 33 | 32 | 32 |
| 3 | 4 | 100 | 42 | 45 | 27 |
| 10 | 4 | 100 | 58 | 40 | 27 |
| 30 | 4 | 100 | 63 | 79 | 86 |
| 0 | 10 | 0 | 39 | 37 | 29 |
| 1 | 10 | 0 | 30 | 35 | 26 |
| 3 | 10 | 0 | 29 | 33 | 30 |
| 10 | 10 | 0 | 35 | 44 | 23 |
| 30 | 10 | 0 | 65 | 70 | 55 |
| 0 | 10 | 3 | 25 | 32 | 21 |
| 1 | 10 | 3 | 35 | 2 | 33 |
| 3 | 10 | 3 | −1 | 11 | 28 |
| 10 | 10 | 3 | 44 | 11 | 24 |
| 30 | 10 | 3 | 47 | 59 | 45 |
| 0 | 10 | 10 | 26 | 36 | 34 |
| 1 | 10 | 10 | 34 | 31 | 33 |
| 3 | 10 | 10 | 33 | 30 | 33 |
| 10 | 10 | 10 | 29 | 21 | 33 |
| 30 | 10 | 10 | 49 | 55 | 51 |
| 0 | 10 | 30 | 24 | 42 | 34 |
| 1 | 10 | 30 | 37 | 38 | 51 |
| 3 | 10 | 30 | 37 | 36 | 41 |
| 10 | 10 | 30 | 39 | 40 | 38 |
| 30 | 10 | 30 | 54 | 57 | 37 |
| 0 | 10 | 100 | 40 | 47 | 40 |
| 1 | 10 | 100 | 50 | 47 | 46 |
| 3 | 10 | 100 | 42 | 46 | 45 |
| 10 | 10 | 100 | 51 | 39 | 38 |
| 30 | 10 | 100 | 57 | 56 | 53 |
| 0 | 20 | 0 | 49 | 54 | 53 |
| 1 | 20 | 0 | 46 | 49 | 39 |
| 3 | 20 | 0 | 49 | 45 | 42 |
| 10 | 20 | 0 | 47 | 45 | 48 |
| 30 | 20 | 0 | 61 | 58 | 63 |
| 0 | 20 | 3 | 46 | 51 | 44 |
| 1 | 20 | 3 | 51 | 57 | 46 |
| 3 | 20 | 3 | 52 | 54 | 46 |
| 10 | 20 | 3 | 57 | 66 | 56 |
| 30 | 20 | 3 | 66 | 81 | 49 |
| 0 | 20 | 10 | 46 | 49 | 43 |
| 1 | 20 | 10 | 50 | 44 | 47 |
| 3 | 20 | 10 | 52 | 54 | 51 |
| 10 | 20 | 10 | 50 | 59 | 53 |
| 30 | 20 | 10 | 62 | 69 | 71 |
| 0 | 20 | 30 | 99 | 52 | 51 |
| 1 | 20 | 30 | 58 | 63 | 50 |
| 3 | 20 | 30 | 48 | 60 | 55 |
| 10 | 20 | 30 | 48 | 56 | 50 |
| 30 | 20 | 30 | 50 | 56 | 51 |
| 0 | 20 | 100 | 53 | 64 | 40 |
| 1 | 20 | 100 | 54 | 58 | 55 |
| 3 | 20 | 100 | 67 | 57 | 51 |
| 10 | 20 | 100 | 63 | 61 | 54 |
| 30 | 20 | 100 | 58 | 58 | 58 |
| 0 | 40 | 0 | 90 | 92 | 90 |
| 1 | 40 | 0 | 86 | 91 | 90 |
| 3 | 40 | 0 | 87 | 92 | 92 |
| 10 | 40 | 0 | 83 | 99 | 92 |
| 30 | 40 | 0 | 85 | 96 | 92 |
| 0 | 40 | 3 | 88 | 91 | 90 |

TABLE 11-continued

Percent luminescence reductions for compositions containing
CBD, niacinamide, urolithin A, or combinations thereof.

| [CBD] | [Niacinamide] | [Urolithin A] | % Luminescence Reduction | | |
|---|---|---|---|---|---|
| (μM) | (μM) | (μM) | Repeat 1 | Repeat 2 | Repeat 3 |
| 1 | 40 | 3 | 86 | 83 | 89 |
| 3 | 40 | 3 | 87 | 79 | 90 |
| 10 | 40 | 3 | 90 | 85 | 82 |
| 30 | 40 | 3 | 89 | 97 | 92 |
| 0 | 40 | 10 | 85 | 90 | 89 |
| 1 | 40 | 10 | 81 | 89 | 87 |
| 3 | 40 | 10 | 84 | 90 | 97 |
| 10 | 40 | 10 | 85 | 91 | 97 |
| 30 | 40 | 10 | 82 | 92 | 90 |
| 0 | 40 | 30 | 80 | 87 | 84 |
| 1 | 40 | 30 | 88 | 91 | 61 |
| 3 | 40 | 30 | 84 | 88 | 76 |
| 10 | 40 | 30 | 85 | 92 | 78 |
| 30 | 40 | 30 | 80 | 88 | 84 |
| 0 | 40 | 100 | 71 | 83 | 65 |
| 1 | 40 | 100 | 76 | 85 | 78 |
| 3 | 40 | 100 | 76 | 85 | 75 |
| 10 | 40 | 100 | 81 | 85 | 79 |
| 30 | 40 | 100 | 86 | 86 | 79 | n/a indicates failure of the assay to detect luminescence.

The ability of the ingredients of each composition to synergistically increased ATP metabolism was evaluated. Various reference models were utilized to determine the synergy, including the simple deduction model, percentage adjusted synergy, the HSA model, the Bliss model, the Loewe additivity model, and the ZIP model.

As demonstrated in Examples 2A-2D, compositions containing CBD and niacinamide or CBD, niacinamide, and urolithin A synergistically increased ATP metabolism, but compositions containing CBD and urolithin A or urolithin A and niacinamide did not, and in many instances resulted in reductions in ATP metabolism. Certain concentrations of CBD and niacinamide were particularly synergistic (e.g., 30 μM CBD with 4 μM or 10 μM niacinamide).

These assays also tested the ability of the antioxidant L-ergothioneine at concentrations ranging from 1 nM to 100 μM to affect skin cell viability and influence mitochondrial function. L-ergothioneine is an antioxidant that does not affect normal mitochondrial function. FIG. 6 shows that cells treated with L-ergothioneine retain viability and ATP metabolism throughout the tested concentration range. These characteristics show that inclusion of L-ergothioneine in a dermatological formulation is safe and that L-ergothioneine will not interfere with niacinamide's ability to increase ATP metabolism.

Example 2A. Compositions Containing Niacinamide and CBD Synergistically Increase ATP Metabolism Compositions containing niacinamide and CBD synergistically increased ATP metabolism beyond what was expected for a combination of the individual ingredients (Table 12). In particular, compositions containing 30 μM CBD with 10 μM or 4 μM of niacinamide were synergistic, as indicated by synergy scores calculated using the simple deduction model, percent adjusted synergy, the HSA model, the Bliss model, the Loewe additivity model, and the ZIP model (FIGS. 8A-D, FIGS. 9A-D). FIG. 7 shows the effect of CBD and niacinamide concentration on percent luminescence reduction.

Example 2B. Compositions Containing Niacinamide, CBD, and Urolithin a Synergistically Increase ATP Metabolism Compositions containing CBD, niacinamide, and urolithin A improved ATP metabolism beyond what was expected for a combination of the individual ingredients (Table 13). In particular, compositions containing 30 μM CBD with 10 μM or 4 μM of niacinamide were synergistic, as indicated by synergy scores calculated using the simple deduction model, the HSA model, the Bliss model, the Loewe additivity model, and the ZIP model (FIGS. 10A-D).

Example 2C. Compositions Containing CBD and Urolithin a do not Synergistically Increase ATP Metabolism Compositions containing CBD and urolithin A but without niacinamide do not synergistically increase ATP metabolism beyond what was expected for a combination of the individual ingredients (Table 14), as indicated by synergy scores calculated using the simple deduction model, percent adjusted synergy, the HSA model, the Bliss model, the Loewe additivity model, and the ZIP model (FIGS. 12A-D, FIGS. 13A-D). FIG. 11 shows the effect of CBD and urolithin A concentration on percent luminescence reduction.

Example 2D. Compositions Containing Niacinamide and Urolithin a do not Synergistically Increase ATP Metabolism Compositions containing niacinamide and urolithin A but without CBD do not synergistically increase ATP metabolism beyond what was expected for a combination of the individual ingredients (Table 15), as indicated by synergy scores calculated using the simple deduction model, percent adjusted synergy, the HSA model, the Bliss model, the Loewe additivity model, and the ZIP model (FIGS. 15A-D, FIGS. 16A-D). FIG. 14 shows the effect of niacinamide and urolithin A concentration on percent luminescence reduction.

TABLE 12

Synergistic effect of niacinamide and CBD

| [CBD] μM | [Niacinamide] μM | Average Luminescence Reduction of Combination | Luminescence Reduction of CBD Alone | Luminescence Reduction of Niacinamide Alone | Simple Reduction Model | Synergy Percentage Adjusted | Additive Inhibition Value | ZIP Model | HSA model | Loewe Model | Bliss Model |
|---|---|---|---|---|---|---|---|---|---|---|---|
| 30.0 | 4.0 | 63.0 | 25.3 | 3.0 | 34.7 | 35.4 | 27.6 | 39.6 | 37.7 | 71.3 | 42.2 |
| 30.0 | 10.0 | 63.3 | 25.3 | 35.0 | 3.0 | 11.9 | 51.5 | 9.2 | 1.3 | 5.2 | 5.6 |
| 10.0 | 10.0 | 34.0 | 5.3 | 35.0 | -6.3 | -4.5 | 38.5 | 14.7 | 4.3 | 8.2 | 5.5 |
| 1.0 | 10.0 | 30.3 | 7.0 | 35.0 | -11.7 | -9.2 | 39.6 | 6.7 | -4.7 | 38.6 | -3.6 |
| 1.0 | 4.0 | -5.7 | 7.0 | 3.0 | -15.7 | -15.5 | 9.8 | 4.0 | -12.7 | 2.6 | -7.0 |

TABLE 12-continued

Synergistic effect of niacinamide and CBD

| [CBD] µM | [Niacinamide] µM | Average Luminescence Reduction of Combination | Luminescence Reduction of CBD Alone | Luminescence Reduction of Niacinamide Alone | Simple Reduction Model | Synergy Percentage Adjusted | Additive Inhibition Value | ZIP Model | HSA model | Loewe Model | Bliss Model |
|---|---|---|---|---|---|---|---|---|---|---|---|
| 30.0 | 20.0 | 60.7 | 25.3 | 52.0 | −16.7 | −3.5 | 64.2 | 3.6 | 8.7 | 69.0 | −0.1 |
| 3.0 | 10.0 | 30.7 | 3.0 | 35.0 | −7.3 | −6.3 | 37.0 | 3.4 | −4.3 | 39.0 | −0.4 |
| 10.0 | 40.0 | 91.3 | 5.3 | 90.7 | −4.7 | 0.2 | 91.2 | 0.9 | 0.7 | 99.6 | 1.0 |
| 3.0 | 40.0 | 90.3 | 3.0 | 90.7 | −3.3 | −0.6 | 90.9 | 0.9 | −0.3 | 98.6 | 0.2 |
| 1.0 | 40.0 | 89.0 | 7.0 | 90.7 | −8.7 | −2.3 | 91.3 | 0.6 | −1.7 | 97.3 | −1.5 |
| 3.0 | 4.0 | −6.0 | 3.0 | 3.0 | −12.0 | −11.9 | 5.9 | −1.4 | −9.0 | 2.3 | −3.1 |
| 30.0 | 40.0 | 91.0 | 25.3 | 90.7 | −25.0 | −2.0 | 93.0 | −3.0 | 0.3 | 99.3 | −1.4 |
| 1.0 | 20.0 | 44.7 | 7.0 | 52.0 | −14.3 | −10.7 | 55.4 | −3.7 | −7.3 | 53.0 | −6.5 |
| 3.0 | 20.0 | 45.3 | 3.0 | 52.0 | −9.7 | −8.1 | 53.4 | −5.1 | −6.7 | 53.6 | −3.8 |
| 10.0 | 4.0 | 1.3 | 5.3 | 3.0 | −7.0 | −6.8 | 8.2 | −5.3 | −4.0 | 9.6 | 1.7 |
| 10.0 | 20.0 | 46.7 | 5.3 | 52.0 | −10.7 | −7.9 | 54.6 | −5.3 | −5.3 | 55.0 | −3.7 |
| 30.0 | 4.0 | 63.0 | 25.3 | 3.0 | 34.7 | 35.4 | 27.6 | 39.6 | 37.7 | 71.3 | 42.2 |

TABLE 13

Synergistic effect of niacinamide, CBD, and urolithin A

| [CBD] µM | [Niacin-amide] µM | [Uro-lithin A] µM | Average Luminescence Reduction of Combination | Luminescence Reduction of CBD Alone | Luminescence Reduction of Niacinamide Alone | Luminescence Reduction of Urolithin A Alone | Simple Deduction Model | ZIP Model | HSA model | Loewe Model | Bliss Model |
|---|---|---|---|---|---|---|---|---|---|---|---|
| 30.0 | 4.0 | 100.0 | 76.0 | 25.3 | 3.0 | 29.0 | 18.7 | 25.9 | 47.0 | 45.0 | 27.4 |
| 30.0 | 4.0 | 10.0 | 61.0 | 25.3 | 3.0 | 13.3 | 19.3 | 17.7 | 35.7 | 31.9 | 23.8 |
| 30.0 | 4.0 | 3.0 | 52.3 | 25.3 | 3.0 | 18.7 | 5.3 | 15.0 | 27.0 | 23.3 | 11.2 |
| 1.0 | 4.0 | 30.0 | 38.7 | 7.0 | 3.0 | 16.7 | 12.0 | 5.8 | 22.0 | 15.5 | 13.8 |
| 1.0 | 4.0 | 100.0 | 32.3 | 7.0 | 3.0 | 29.0 | −6.7 | 3.8 | 3.3 | 5.2 | −3.6 |
| 3.0 | 4.0 | 100.0 | 38.0 | 3.0 | 3.0 | 29.0 | 3.0 | 2.6 | 9.0 | 10.9 | 4.8 |
| 30.0 | 4.0 | 30.0 | 45.0 | 25.3 | 3.0 | 16.7 | 0.0 | 2.6 | 19.7 | 15.9 | 5.4 |
| 10.0 | 4.0 | 100.0 | 41.7 | 5.3 | 3.0 | 29.0 | 4.3 | 2.2 | 12.7 | 14.6 | 6.9 |
| 30.0 | 10.0 | 10.0 | 51.7 | 25.3 | 35.0 | 13.3 | −22.0 | 0.1 | 16.7 | 10.8 | −6.3 |
| 30.0 | 10.0 | 3.0 | 50.3 | 25.3 | 35.0 | 18.7 | −28.7 | −0.1 | 15.3 | 9.4 | −10.2 |
| 30.0 | 10.0 | 100.0 | 55.3 | 25.3 | 35.0 | 29.0 | −34.0 | −0.5 | 20.3 | 14.4 | −10.2 |
| 30.0 | 40.0 | 3.0 | 92.7 | 25.3 | 90.7 | 18.7 | −42.0 | −1.9 | 2.0 | 2.6 | −1.7 |
| 1.0 | 10.0 | 100.0 | 47.7 | 7.0 | 35.0 | 29.0 | −23.3 | −1.9 | 12.7 | 14.7 | −9.4 |
| 3.0 | 40.0 | 10.0 | 90.3 | 3.0 | 90.7 | 13.3 | −16.7 | −2.0 | −0.3 | 0.3 | −1.8 |
| 1.0 | 10.0 | 30.0 | 42.0 | 7.0 | 35.0 | 16.7 | −16.7 | −2.0 | 7.0 | 11.0 | −7.6 |
| 3.0 | 40.0 | 3.0 | 85.3 | 3.0 | 90.7 | 18.7 | −27.0 | −3.0 | −5.3 | −4.7 | −7.3 |
| 10.0 | 40.0 | 10.0 | 91.0 | 5.3 | 90.7 | 13.3 | −18.3 | −3.1 | 0.3 | 0.9 | −1.3 |
| 1.0 | 40.0 | 3.0 | 86.0 | 7.0 | 90.7 | 18.7 | −30.3 | −3.6 | −4.7 | −4.1 | −6.9 |

TABLE 14

No synergistic effect between CBD and urolithin A

| [CBD] µM | [Urolithin A] µM | Average Luminescence Reduction of Combination | Luminescence Reduction of CBD Alone | Luminescence Reduction of Urolithin A Alone | Simple Deduction Model | Synergy Percentage Adjusted | Additive Inhibition Value | ZIP Model | HSA model | Loewe Model | Bliss Model |
|---|---|---|---|---|---|---|---|---|---|---|---|
| 1.0 | 100.0 | 33.3 | 7.0 | 29.0 | −2.7 | −0.6 | 34.0 | 14.7 | 4.3 | 8.2 | 5.5 |
| 3.0 | 100.0 | 30.3 | 3.0 | 29.0 | −1.7 | −0.8 | 31.1 | 9.2 | 1.3 | 5.2 | 5.6 |
| 1.0 | 3.0 | 3.3 | 7.0 | 18.7 | −22.3 | −21.0 | 24.4 | 4.5 | −15.3 | −10.0 | −14.0 |
| 30.0 | 10.0 | 34.3 | 25.3 | 13.3 | −4.3 | −1.0 | 35.3 | 3.6 | 9.0 | 11.2 | 5.1 |
| 1.0 | 30.0 | 15.7 | 7.0 | 16.7 | −8.0 | −6.8 | 22.5 | 3.1 | −1.0 | −5.5 | 0.4 |
| 10.0 | 100.0 | 29.7 | 5.3 | 29.0 | −4.7 | −3.1 | 32.8 | 2.7 | 0.7 | 4.5 | 3.2 |
| 30.0 | 100.0 | 37.0 | 25.3 | 29.0 | −17.3 | −10.0 | 47.0 | 0.5 | 8.0 | 7.9 | −5.0 |
| 30.0 | 3.0 | 30.0 | 25.3 | 18.7 | −14.0 | −9.3 | 39.3 | −0.4 | 4.7 | 6.8 | −3.6 |
| 3.0 | 3.0 | 1.7 | 3.0 | 18.7 | −20.0 | −19.4 | 21.1 | −1.5 | −17.0 | −13.6 | −12.1 |
| 1.0 | 10.0 | −9.3 | 7.0 | 13.3 | −29.7 | −28.7 | 19.4 | −5.5 | −22.7 | −26.7 | −21.2 |
| 30.0 | 30.0 | 24.0 | 25.3 | 16.7 | −18.0 | −13.8 | 37.8 | −5.8 | −1.3 | −1.1 | −8.0 |
| 3.0 | 10.0 | 1.3 | 3.0 | 13.3 | −15.0 | −14.6 | 15.9 | −7.2 | −12.0 | −15.9 | −6.8 |
| 10.0 | 30.0 | 13.7 | 5.3 | 16.7 | −8.3 | −7.4 | 21.1 | −8.6 | −3.0 | −9.5 | −0.1 |

TABLE 14-continued

No synergistic effect between CBD and urolithin A

| [CBD] μM | [Urolithin A] μM | Average Luminescence Reduction of Combination | Luminescence Reduction of CBD Alone | Luminescence Reduction of Urolithin A Alone | Simple Deduction Model | Synergy Percentage Adjusted | Additive Inhibition Value | ZIP Model | HSA model | Loewe Model | Bliss Model |
|---|---|---|---|---|---|---|---|---|---|---|---|
| 3.0 | 30.0 | 3.3 | 3.0 | 16.7 | −16.3 | −15.8 | 19.2 | −8.9 | −13.3 | −17.9 | −8.3 |
| 10.0 | 3.0 | −7.0 | 5.3 | 18.7 | −31.0 | −30.0 | 23.0 | −10.8 | −25.7 | −24.3 | −22.8 |
| 10.0 | 10.0 | 0.3 | 5.3 | 13.3 | −18.3 | −17.6 | 18.0 | −13.6 | −13.0 | −18.9 | −10.0 |

TABLE 15

No synergistic effect between niacinamide and urolithin A

| [Niacinamide] μM | [Urolithin A] μM | Average Luminescence Reduction of Combination | Luminescence Reduction of Niacinamide Alone | Luminescence Reduction of Urolithin A Alone | Simple Deduction Model | Synergy Percentage Adjusted | Additive Inhibition Value | ZIP Model | HSA model | Loewe Model | Bliss Model |
|---|---|---|---|---|---|---|---|---|---|---|---|
| 4.0 | 100.0 | 28.0 | 3.0 | 29.0 | −4.0 | −3.1 | 31.0 | 3.9 | −1.0 | 0.9 | 3.3 |
| 20.0 | 30.0 | 67.3 | 52.0 | 16.7 | −1.3 | 7.3 | 60.0 | 2.3 | 15.3 | 10.7 | 11.1 |
| 40.0 | 3.0 | 89.7 | 90.7 | 18.7 | −19.7 | −2.7 | 92.4 | −0.8 | −1.0 | −0.4 | −2.0 |
| 10.0 | 100.0 | 42.3 | 35.0 | 29.0 | −21.7 | −11.5 | 53.9 | −1.4 | 7.3 | 9.3 | −7.2 |
| 4.0 | 3.0 | 12.7 | 3.0 | 18.7 | −9.0 | −8.4 | 21.1 | −2.3 | −6.0 | −4.6 | −1.1 |
| 40.0 | 10.0 | 88.0 | 90.7 | 13.3 | −16.0 | −3.9 | 91.9 | −3.0 | −2.7 | −2.1 | −3.2 |
| 10.0 | 3.0 | 26.0 | 35.0 | 18.7 | −27.7 | −21.1 | 47.1 | −6.0 | −9.0 | −3.1 | −16.2 |
| 10.0 | 30.0 | 33.3 | 35.0 | 16.7 | −18.3 | −12.5 | 45.8 | −6.3 | −1.7 | 2.3 | −7.4 |
| 10.0 | 10.0 | 32.0 | 35.0 | 13.3 | −16.3 | −11.7 | 43.7 | −6.5 | −3.0 | 2.9 | −6.4 |
| 4.0 | 30.0 | 12.7 | 3.0 | 16.7 | −7.0 | −6.5 | 19.2 | −6.9 | −4.0 | −10.5 | 1.0 |
| 40.0 | 30.0 | 83.7 | 90.7 | 16.7 | −23.7 | −8.6 | 92.2 | −7.8 | −7.0 | −6.4 | −7.8 |
| 4.0 | 10.0 | 3.5 | 3.0 | 13.3 | −12.8 | −12.4 | 15.9 | −9.2 | −9.8 | −15.7 | −4.6 |
| 20.0 | 100.0 | 52.3 | 52.0 | 29.0 | −28.7 | −13.6 | 65.9 | −9.3 | 0.3 | −4.3 | −10.4 |
| 20.0 | 3.0 | 47.0 | 52.0 | 18.7 | −23.7 | −14.0 | 61.0 | −10.7 | −5.0 | −9.6 | −10.3 |
| 20.0 | 10.0 | 46.0 | 52.0 | 13.3 | −19.3 | −12.4 | 58.4 | −12.4 | −6.0 | −10.6 | −8.5 |
| 40.0 | 100.0 | 73.0 | 90.7 | 29.0 | −46.7 | −20.4 | 93.4 | −18.8 | −17.7 | −17.1 | −19.8 |

Example 3. In Cell Study of Ability of Formulations Comprising a Cannabinoid, a Cofactor or Precursor Thereof, an Antioxidant; and a Mitophagy Modulator to Treat Acne (Prophetic)

The ability of the formulations from Example 1 or Tables 17-19 (e.g., formulations which comprise a cannabinoid (e.g., CBD), an antioxidant (e.g. L-ergothioneine), a cofactor (e.g. niacinamide), a mitophagy modulator (e.g. urolithin A), or any combination thereof), to treat acne, is measured. Control formulations comprising individual components of the formulations of Example 1 and combinations thereof are also evaluated. Exemplary control formulations are described in Table 16.

TABLE 16

Exemplary Control Formulations

| Control Formulation | Cannabinoid | Cofactor or precursor thereof | Antioxidant | Mitophagy modulator |
|---|---|---|---|---|
| 1 | x | | | |
| 2 | | x | | |
| 3 | | | x | |
| 4 | | | | x |
| 5 | x | x | | |
| 6 | x | | x | |
| 7 | x | | | x |
| 8 | | x | x | |
| 9 | | x | | x |
| 10 | | | x | x |

TABLE 16-continued

Exemplary Control Formulations

| Control Formulation | Cannabinoid | Cofactor or precursor thereof | Antioxidant | Mitophagy modulator |
|---|---|---|---|---|
| 11 | x | x | x | |
| 12 | x | | x | x |
| 13 | x | x | | x |
| 14 | | x | x | x |

An x under any of "Cannabinoid," "Cofactor or precursor thereof," "antioxidant," or "mitophagy modulator" indicates the presence of the ingredient in the control formulation.

Exemplary experimental compositions are described in Example 1 and also in Tables 17-19 below.

TABLE 17

Exemplary Compositions

| Ingredient | Concentration |
|---|---|
| Cannabinoid (e.g. CBD) | 0.010 mg/ml |
| Mitophagy Modulator (e.g. Urolithin A) | 0.0023 mg/mL-0.0091 mg/mL |
| Antioxidant (e.g. L-ergothioneine) | $2.3 \times 10^{-7}$ mg/mL-$2.3 \times 10^{-1}$ mg/mL |
| Cofactor (e.g. Niacinamide) | 0.12 mg/mL-1.2 mg/mL |

TABLE 18

Exemplary Compositions

| Ingredient | Concentration |
|---|---|
| Cannabinoid (e.g. CBD) | 10 µg/mL |
| Mitophagy Modulator (e.g. Urolithin A) | 10 µM-40 µM |
| Antioxidant (e.g. L-ergothioneine) | 1 nM-1 mM |
| Cofactor (e.g. Niacinamide) | 1 mM-10 mM |

TABLE 19

Exemplary Compositions

| Ingredient | Concentration |
|---|---|
| Cannabinoid (i.e. CBD) | 0 µM, 1 µM, 3 µM, 10 µM, 30 µM |
| Mitophagy Modulator (i.e. Urolithin A) | 0 µM, 3 µM, 10 µM, 30 µM, 100 µM |
| Cofactor (i.e. Niacinamide) | 0 µM, 4 µM, 10 µM, 20 µM, 40 µM |

Sebocyte Assay:

Immortalized human sebaceous gland cell lines (sebocytes) are a well-established model for studying acne. Human sebocytes are obtained, for example, from Celprogen®. Primary human sebocytes (Cellprogen, Batch #13140680) are grown according to manufacturer's instruction using Celprogen®'s proprietary cell consumables. Cells are seeded at a concentration of 5000 cells per cm² in a tissue culture treated flask and incubated at 37° C. in a humidified incubator in the presence of 5% $CO_2$ (all subsequent incubations were subject to these conditions). At 60-80% confluency cells are passaged by detaching cells using TrypLE™ Express (Sigma). Cells are seeded in a black 96-well half area plate at a concentration of 5000 cells per well and allowed to equilibrate overnight at 37° C. Compositions comprising a cannabinoid (i.e., CBD), a mitophagy modulator (i.e., urolithin A), a cofactor (i.e., niacinamide), or a combination thereof are incubated with sebocytes for 24 hours (see compositions in Example 1, control formulations of Table 16, and Tables 17-19). The ability of each composition to increase ATP metabolism is determined using a luminescence assay (Celltiter-Glo™) according to manufacturer's instructions.

The results of this study will support the use of the formulations of Example 1 and 2 as a treatment for acne, psoriasis, eczema, rosacea, ichthyosis, vitiligo, seborrheic dermatitis, actinic keratosis, stretch mark, wrinkles, fine lines, carbuncle, aging, and cellulitis.

Alternative endpoints that are used to assess the effect of the formulations in Tables 16-19, and Example 1 on the mitochondrial health of sebocytes include cell viability, ATP production, apoptosis, necrosis, oxygen consumption rate, glycolysis, membrane potential, mitophagy, the amount of reactive oxygen species, oxygen consumption rate, the amount of inflammation, markers of apoptosis, including DNA fragmentation (capsase dependent apoptosis), mitochondrial membrane potential, and annexin V binding to phosphatidylserine. Additionally, the ability of the formulations in Tables 16-19, and Example 1 to reduce lipid accumulation is evaluated. The effect of the formulations on cell proliferation are evaluated. The toxicity and ability of the formulations to cause necrosis is also evaluated. An AlamarBlue™ assay is conducted to evaluate mitochondrial activity of each formulation. Note that although the tables above list CBD as the example cannabinoid, various cannabinoids and combinations of cannabinoids as disclosed in Table A of this disclosure will be tested in the formulations above.

Example 4. Method of Treating Acne (Prophetic)

The ability of the formulations described in Examples 1-3 to treat acne is measured in the study described below:

Table 20 describes a screening tool used to recruit participants into the study. Each potential recruit is asked questions of Table 20, and participants are selected according to the criteria in column 3 of Table 20.

TABLE 20

Screening Tool

| Question | Answer Choice | Selection Criteria |
|---|---|---|
| Please indicate your gender. | (a) male, (b) female | Recruit 80 % female, 20 % male |
| Please indicate your age | [write an age] | Only select respondents that are 18-30 |
| Have you done any of the following in the past six (6) months, or currently? Please select all that apply. | (a) smoked cigarettes, (b) received a chemical peel, microdermabrasion, Botox, restylane or any other type of idjection, (c) used any prescription skin products, (d) are pregnant or lactating, (e) none of the above | Do not select if respondent chooses A, B, C, or D |
| Are you under a doctor's care for a medical skin condition for your skin, i.e., Rosacea, psoriasis, eczema, severe acne, etc.? | (a) Yes, (b) No | Donot choose respondents that select (a). |

TABLE 20-continued

Screening Tool

| Question | Answer Choice | Selection Criteria |
|---|---|---|
| Have you undergone cosmetic surgery on the face within the last 10 years? | (a) Yes, (b) No | Do not choose respondents that select (a). |
| Do you have a known history of allergies to cosmetics products OR skincare products containing CBD? | (a) Yes, (b) No, (c) I don't know | Do not choose respondents that select (a) or (c) |
| How would you describe your facial skin? Select one. | (a) very dry, (b) dry, (c) normal, (d) combination, (e) oily, (f) very oily | Do not choose respondents that select (a) |
| How would you describe the shade of your skin. (See Fig. 4) | (a) very fair, (b) fair, (c) medium, (d) olive, (e) brown, (f) black | Recruit all respondents |
| How would you describe your facial skin sensitivity on a scale of 1-10 with 1 being not sensitive at all and 10 being extremely sensitive? | (a) 1, (b) 2, (c) 3, (d) 4, (e) 5, (f) 6, (g) 7, (h) 8, (i) 9, (j) 10 | Recruit respondents that select (a)-(f) |
| Are you suffering from visible facial acne right now? | (a) yes, severe acne, (b) moderate acne, (c) mild acne, (d) no | Do not choose respondents that select (a) or (d) |
| Are you currently using a prescription acne medication? | (a) yes, (b) no | Do not choose respondents that select (a). |
| Are you currently using a topical skin care treatment regimen to try to calm or heal your acne? If yes, what regimen? | (a) yes, (b) no | Do not choose respondents that select (a) |
| When you have active acne flare-ups, how long does your acne last? | (a) I feel like I always have acne flare-ups /continually, (b) a week to a month, (c) about a week, (d) it's gone in a day | Do not choose respondents that select (d) |
| What type of acne do you experience? | (a) chronic acne, (b) stress acne, (c) hormonal/menstruation acne, (d) perimenopausal acne, (e) cystic acne, (f) sports-induced acne, (g) face mask-induced acne, (h) pollution-induced acne, (i) oily skin-induced acne, (j) acne caused by a medication I am required to take, (k) diet related acne, (l) cosmetic-induced acne (clogged pores), (m) I don't know/not sure | Do not choose respondents that select (e) |
| Please look at the chart of FIG. 5. What types of acne bumps do you experience on a regular basis? | (a) blackheads, (b) whiteheads, (c) papules, (d) pustules, (e) nodules, (f) cysts | Do not choose respondents that select (f) |

Application of Formulation:

The formulations described in Example 1 or 2 are applied to an area that contains acne. As negative controls, formulations which lack one or more of a cannabinoid, an antioxidant, a cofactor or precursor thereof, a mitophagy modulator, licorice, Xperse® 401, PP2, and salicylic acid are utilized. Photographs before treatment and every day after treatment, in person examination by a qualified grader, a count of the number of acne lesions, a count of the type of acne lesions, measurement of size of the acne lesions, and quantification of the quality of life of the subject are used to determine the efficacy of the formulations for treating acne.

Self Assessments:

Each participant evaluates satisfaction with the composition's reduction of lesions, effect on the appearance of the skin, hydration of the skin, dryness of the skin, and other symptoms, as described in Table 21.

TABLE 21

Self-Assessment Questionnaire

| ASSESSMENT: Please rate your level of agreement with the following statements as they relate to your use of the formulations. | Strongly Agree | Agree | Disagree | Strongly Disagree |
|---|---|---|---|---|
| Blemishes look calmer | | | | |
| Blemishes appear smoother | | | | |
| Blemishes feel calmer | | | | |
| Skin feels smoother | | | | |
| Blemishes appear less red | | | | |
| Blemishes are less intense | | | | |
| Blemishes are less painful | | | | |
| Blemishes are smaller | | | | |
| Skin appears less distressed | | | | |
| Skin looks clearer | | | | |
| Blemishes are less inflamed | | | | |
| Skin appears less red | | | | |

TABLE 21-continued

Self-Assessment Questionnaire

| ASSESSMENT: Please rate your level of agreement with the following statements as they relate to your use of the formulations. | Strongly Agree | Agree | Disagree | Strongly Disagree |
|---|---|---|---|---|
| Skin is soothed | | | | |
| Blemishes became flatter | | | | |
| Blemishes were healed | | | | |
| Blemishes were significantly reduced in size | | | | |
| Blemishes were significantly reduced in intensity | | | | |
| Blemishes were eliminated | | | | |
| My skin's appearance has improved | | | | |
| Blemishes did not reoccur | | | | |
| This is the best treatment for acne I have ever used | | | | |
| Works on even stubborn acne | | | | |
| I would replace my current acne treatment with these products | | | | |
| This is a painless solution for acne | | | | |
| Fastest acne treatment I've used | | | | |
| I did not think I could get results like this without going to a dermatologist | | | | |
| Please tell us more about your experience using this trio of acne fighting products [open-ended] | Asked each self-assessment interval but only required on Day 28 | | | |

Participants are also asked the following questions:
1) On a scale from 1 to 5, how effective were these products at meeting your facial skin concerns? 1-5 with 1 being Not Effective and 5 being Very Effective
2) On a scale from 1 to 5, how happy were you with the results from these products?
1-5 with 1 being Not Very Happy and 5 being Very Happy
3) How likely would you be to purchase this product trio? Very likely, Somewhat likely, Somewhat unlikely, or Very unlikely?
4) How many stars would you rate this product trio with 5 being the best possible rating? 5 stars, 4 stars, 3 stars, 2 stars, or 1 star?
5) How likely are you to recommend this product trio to a friend/family member? Very likely, Somewhat likely, Somewhat unlikely, or Very unlikely?

Similar experiments are used to evaluate the effect of the formulations on psoriasis, eczema, rosacea, ichthyosis, vitiligo, seborrheic dermatitis, actinic keratosis, stretch mark, wrinkles, fine lines, carbuncle, aging, and cellulitis.

Example 5. Evaluation of Antioxidant's Ability to Affect ATP Metabolism (Prophetic)

The effect of antioxidant selection on a compositions effect on ATP metabolism is evaluated. The antioxidant in any of the compositions described in Example 1 and in Tables 17-19 is substituted with any one of the following antioxidants: antioxidants that do not affect normal mitochondria function, antioxidants that do not affect mitochondrial processing, antioxidants that do enter the mitochondria, but do not affect mitochondrial processing, antioxidants with a molecular weight greater than 500 g/mol, antioxidants with a molecular weight between 200 g/mol and 500 g/mol, antioxidants with a molecular weight of less than 200 g/mol, antioxidants with a standard redox potential between –0.2 V and –0.32 V, antioxidants with a redox potential of –0.06 V, antioxidants with a redox potential of –0.06 V or lower, antioxidants with greater than 5 hydrogen bond donors, antioxidants containing more than 10 hydrogen bond acceptors, and antioxidants with an octanol-water partition coefficient (log P) that exceeds 5. The endpoints described in Examples 3 and 4 are also evaluated. The ability of L-ergothioneine to affect ATP metabolism is compared to the aforementioned antioxidants.

Examples of antioxidants that are evaluated include L-ergothioneine, butylated hydroxytolune (BHT), butylated hydroxy anisole (BHA), tert-Butylhydroquinone (TBHQ), pyrogallol, propylgallate, N,N'-Di-sec-butyl-p-phenylenediamine, coenzyme $Q_{10}$, astaxanthin, ellagic acid, picrocrocin, lycopene, lutein/zeaxanthin, lutein, zeaxanthin, quercetin, vitamin C, IP-6, beta-carotene, epicatechin, ECGC-epigallocatechin gallate, safranal, proanthocyanidins, resveratrol, vitamin E, melatonin, mitoQ, acetyl cysteine, ascorbic acid polypeptide, ascorbyl dipalmitate, ascorbyl methylsilanol pectinate, ascorbyl palmitate, ascorbyl stearate, butated hydroxyanisole (BHA), butylated hydroxytoluene (BHT), t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical antioxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, tris(nonylphenyl)phosphite, diethylhexyl syringylidene malonate, vitamin E, diisopropyl vanidene malonate, tocopherol, plant extracts (rosemary, sage, and oregano), carotenoids, amino acids, terpenoids, polyols, flavonoids, phytoalexin, ascorbic acid, lipoic acid, melatonin, coenzyme Q, sodium benzoate, imidazole, vitamin A, methylparaben, propylparaben, ethylenediaminetetraacetic acid (EDTA), L-ergothioneine, a triphenyldecylphosphonium adduct, or an $H_2S$ donor, such as $AP_{123}$ or $AP_{39}$.

Numbered Embodiments of the Disclosure

Notwithstanding the appended claims, the disclosure sets forth the following numbered embodiments:
1. A composition, comprising:
   a. a cannabinoid; and
   b. a redox cofactor or precursor thereof.
1.1 The composition of embodiment 1, comprising:
   c. an antioxidant.
1.2 The composition of embodiment 1 or 1.1, comprising:
   d. a mitophagy stimulant.
2. The composition of any one of embodiments 1-1.2, wherein the composition is effective at treating a dermatological mitochondrial ATP deficit disorder or concern.
2.1 The composition of any one of embodiments 1-2, wherein the composition increases ATP metabolism in sebocyte cells.

3. The composition of any one of embodiments 1-2.1, wherein the composition is capable of treating acne.
4. The composition of any one of embodiments 1-3, wherein the cannabinoid comprises cannabidiol (CBD).
5. The composition of any one of embodiments 1-4, wherein the cannabinoid comprises is delta 9 tetrahydrocannabinol (THC).
6. The composition of any one of embodiments 1-3, wherein the cannabinoid comprises CBD and THC.
7. The composition of any one of embodiments 1-6, wherein the composition comprises a cannabinoid selected from the group consisting of cannabidiol (CBD), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM), Tetrahydrocannabinol (THC), cannabidiolic acid (CBDA), tetrahydrocannabinolic acid (THCA), Cannabichromenic acid (CBCA), cannabigerolic acid (CBGA), tetrahydrocannabivarin acid (THCVA), cannabidivarinic acid (CBDVA), and any combinations thereof.
8. The composition of any one of embodiments 1-6, wherein the cofactor or precursor thereof is involved in the mitochondrial electron transfer chain.
9. The composition of any one of embodiments 1-8, wherein the cofactor or precursor thereof comprises niacinamide.
10. The composition of any one of embodiments 1-9, wherein the antioxidant does not affect ATP homeostasis of cells.
11. The composition of any one of embodiments 1-10, wherein the antioxidant is selected from the group consisting of: L-ergothioneine, butylated hydroxytolune (BHT), butylated hydroxy anisole (BHA), tert-Butylhydroquinone (TBHQ), pyrogallol, propylgallate, N,N'-Di-sec-butyl-p-phenylenediamine, coenzyme $Q_{10}$, astaxanthin, ellagic acid, picrocrocin, lycopene, lutein/zeaxanthin, lutein, zeaxanthin, quercetin, vitamin C, IP-6, beta-carotene, epicatechin, ECGC-epigallocatechin gallate, safranal, proanthocyanidins, resveratrol, vitamin E, melatonin, and mitoQ.
12. The composition of any one of embodiments 1-11, wherein the antioxidant is an amino acid.
13. The composition of any one of embodiments 1-12, wherein the antioxidant is L-ergothioneine.
14. The composition of any one of embodiments 1.2-13, wherein the mitophagy stimulant is selected from the group consisting of urolithin A, urolithin B, urolithin C, urolithin E, urolithin M7, urolithin M5, urolithin D, isourolithin A, urolithin M4, urolithin M6, urolithin M3, and isourolithin B.
15. The composition of any one of embodiments 1.2-13, wherein the mitophagy stimulant is a metabolite of an ellagic acid or ellagitannin.
16. The composition of any one of embodiments 1.2-13, wherein the mitophagy stimulant is a urolithin.
17. The composition of any one of embodiment 1.2-13, wherein the mitophagy stimulant is urolithin A.
17.1 The composition of any one of embodiments 1-17, wherein the cannabinoid is CBD, and wherein the cofactor or precursor thereof is niacinamide.
17.2 The composition of embodiment 17.1, wherein the CBD and niacinamide are at a molar ratio between 2:1 to 10:1.
17.3 The composition of embodiment 17.1, wherein the CBD and niacinamide are at a molar ratio between 3:1 to 10:1.
17.4 The composition of embodiment 17.1, wherein the CBD and niacinamide are at a molar ratio between 1:10 to 1:55.
17.5 The composition of embodiment 17.1, wherein the CBD and niacinamide are at a molar ratio of 1:10 to 1:15.
17.6 The composition of any one of embodiments 17.1-17.3, wherein the CBD and urolithin are at a molar ratio of 1:10 to 10:1.
17.7 The composition of any one of embodiments 17.1-17.3, wherein the CBD and urolithin are at a molar ratio of 1:3 to 10:1.
18. The composition of any one of embodiments 1-17, wherein the cannabinoid is CBD, the cofactor or precursor thereof is niacinamide, and the antioxidant is L-ergothioneine.
18.1 The composition of embodiment 18, wherein the CBD and niacinamide are at a molar ratio between 2:1 to 10:1.
18.2 The composition of embodiment 18, wherein the CBD and niacinamide are at a molar ratio between 3:1 to 10:1.
18.3 The composition of embodiment 18, wherein the CBD and niacinamide are at a molar ratio between 1:10 to 1:55.
18.4 The composition of embodiment 18, wherein the CBD and niacinamide are at a molar ratio of 1:10 to 1:15.
18.5 The composition of any one of embodiments 18-18.2, wherein the CBD and urolithin are at a molar ratio of 1:10 to 10:1.
18.6 The composition of any one of embodiments 18-18.2, wherein the CBD and urolithin are at a molar ratio of 1:3 to 10:1.
19. The composition of any one of embodiments 1-17, wherein the cannabinoid is THC, the cofactor or precursor thereof is niacinamide, and the antioxidant is L-ergothioneine.
20. The composition of any one of embodiments 1-17, wherein the cannabinoid is CBD and THC, the cofactor or precursor thereof is niacinamide, and the antioxidant is L-ergothioneine.
21. The composition of any one of embodiments 1-17, wherein the cannabinoid is CBD, the cofactor or precursor thereof is niacinamide, the antioxidant is L-ergothioneine, and the mitophagy stimulant is present and is urolithin A.
22. The composition of any one of embodiments 1-17, wherein the cannabinoid is THC, the cofactor or precursor thereof is niacinamide, the antioxidant is L-ergothioneine, and the mitophagy stimulant is present and is urolithin A.
23. The composition of any one of embodiments 1-17, wherein the cannabinoid is a mixture of CBD and THC, the cofactor or precursor thereof is niacinamide, the antioxidant is L-ergothioneine, and the mitophagy stimulant is present and is urolithin A.
24. The composition of any one of embodiments 1-17 and 18.3-18.4, comprising about 0.01 milligrams (mg) to about 10 mg of cannabinoid, about 0.5 mg to about 50 mg cofactor or precursor thereof, and about 0.1 mg and 100 mg antioxidant per milliliter of composition.

25. The composition of embodiment 24, wherein the cannabinoid is CBD, the cofactor or precursor thereof is niacinamide, and the antioxidant is L-ergothioneine.
26. The composition of embodiment 24, wherein the cannabinoid is CBD, the cofactor or precursor thereof is niacinamide, the antioxidant is L-ergothioneine, and the mitophagy stimulant is present and is urolithin A.
27. The composition of any one of embodiments 1-17 and 18.3-18.4, comprising about 0.42 mg cannabinoid, about 10 mg cofactor or precursor thereof, and about 1 mg antioxidant per milliliter of composition.
28. The composition of embodiment 27, wherein the cannabinoid is CBD, the cofactor or precursor thereof is niacinamide, and the antioxidant is L-ergothioneine.
29. The composition of embodiment 27, wherein the cannabinoid is CBD, the cofactor or precursor thereof is niacinamide, the antioxidant is L-ergothioneine, and the mitophagy stimulant is present and is urolithin A.
30. The composition of any one of embodiments 1-17 and 18.3-18.4, comprising about 2.3 mg cannabinoid, about 20 mg cofactor or precursor thereof, and about 1 mg antioxidant per milliliter of composition.
31. The composition of embodiment 30, wherein the cannabinoid is CBD, the cofactor or precursor thereof is niacinamide, and the antioxidant is L-ergothioneine.
32. The composition of embodiment 30, wherein the cannabinoid is CBD, the cofactor or precursor thereof is niacinamide, the antioxidant is L-ergothioneine, and the mitophagy stimulant is present and is urolithin A.
33. The composition of any one of embodiments 1-17 and 18.3-18.4, comprising about 6.8 mg cannabinoid, about 30 mg cofactor or precursor thereof, and about 10 mg antioxidant per milliliter of composition.
34. The composition of embodiment 33, wherein the cannabinoid is CBD, the cofactor or precursor thereof is niacinamide, and the antioxidant is L-ergothioneine.
35. The composition of embodiment 33, wherein the cannabinoid is CBD, the cofactor or precursor thereof is niacinamide, the antioxidant is L-ergothioneine, and the mitophagy stimulant is present and is urolithin A.
36. The composition of any one of embodiments 1-17 and 18.3-18.4, comprising about 4 mg cannabinoid, about 2 mg cofactor or precursor thereof, and about 10 mg antioxidant per milliliter of composition.
37. The composition of embodiment 36, wherein the cannabinoid is CBD, the cofactor or precursor thereof is niacinamide, and the antioxidant is L-ergothioneine.
38. The composition of embodiment 36, wherein the cannabinoid is CBD, the cofactor or precursor thereof is niacinamide, the antioxidant is L-ergothioneine, and the mitophagy stimulant is present and is urolithin A.
39. The composition of any one of embodiments 1-38, comprising an additional ingredient selected from the group consisting of an avenanthramide, lilac stem cells, and salicylic acid.
40. A method for increasing ATP metabolism in a cell, comprising: administering to a patient in need thereof, a therapeutically effective amount of a composition comprising:
  a. a cannabinoid; and
  b. a redox cofactor or precursor thereof.
40.1 A method for increasing ATP metabolism in a cell, comprising: contacting the cell with a therapeutically effective amount of a composition comprising:
  a. a cannabinoid; and
  b. a redox cofactor or precursor thereof.
40.2 The method of any one of embodiments 40 or 40.1, comprising;
  c. an antioxidant.
40.3 The method of any one of embodiments 40-40.2, comprising
  d. a mitophagy stimulant.
41. The method of any one of embodiments 40-40.3, wherein the patient suffers from a dermatological concern.
42. The method of embodiment 41, wherein the dermatological concern is selected from the group consisting of: acne, psoriasis, eczema, rosacea, ichthyosis, vitiligo, hives, seborrheic dermatitis, actinic keratosis, carbuncle, and cellulitis.
43. The method of embodiment 41, wherein the dermatological concern is acne.
44. The method of any one of embodiments 40-43, wherein the cannabinoid is cannabidiol (CBD).
45. The method of any one of embodiments 40-43, wherein the cannabinoid is delta 9 tetrahydrocannabinol (THC).
46. The method of any one of embodiments 40-45, wherein the cannabinoid comprises CBD and THC.
47. The method of any one of embodiments 40-46, wherein the composition comprises a cannabinoid selected from the group consisting of cannabidiol (CBD), Cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM), Tetrahydrocannabinol (THC), cannabidiolic acid (CBDA), tetrahydrocannabinolic acid (THCA), Cannabichromenic acid (CBCA), cannabigerolic acid (CBGA), tetrahydrocannabivarin acid (THCVA), cannabidivarinic acid (CBDVA), and any combinations thereof.
48. The method of any one of embodiments 40-47, wherein the cofactor or precursor thereof is involved in the mitochondrial electron transfer chain.
49. The method of any one of embodiments 40-48, wherein the cofactor or precursor thereof is niacinamide.
50. The method of any one of embodiments 40-49, wherein the antioxidant does not affect ATP homeostasis of cells.
51. The method of any one of embodiments 40-50, wherein the antioxidant is selected from the group consisting of: L-ergothioneine, butylated hydroxytolune (BHT), butylated hydroxy anisole (BHA), tert-Butylhydroquinone (TBHQ), pyrogallol, propylgallate, N,N'-Di-sec-butyl-p-phenylenediamine, coenzyme $Q_{10}$, astaxanthin, ellagic acid, picrocrocin, lycopene, lutein/zeaxanthin, lutein, zeaxanthin, quercetin, vitamin C, IP-6, beta-carotene, epicatechin, ECGC-epigallocatechin gallate, safranal, proanthocyanidins, resveratrol, vitamin E, melatonin, and mitoQ.
52. The method of any one of embodiments 40-51, wherein the antioxidant is an amino acid.
53. The method of any one of embodiments 40-52, wherein the antioxidant is L-ergothioneine.
55. The method of any one of embodiments 40-53, wherein the mitophagy stimulant is selected from the group consisting of urolithin A, urolithin B, urolithin C, urolithin E, urolithin M7, urolithin M5, urolithin D, isourolithin A, urolithin M4, urolithin M6, urolithin M3, and isourolithin B.

56. The method of any one of embodiments 40-55, wherein the mitophagy stimulant is a metabolite of an ellagic acid or ellagitannin.
57. The method of any one of embodiments 40-56, wherein the mitophagy stimulant is a urolithin.
58. The method of any one of embodiments 40-57, wherein the mitophagy modulator is urolithin A.
58.1 The composition of any one of embodiments 40-58, wherein the cannabinoid is CBD, and wherein the cofactor or precursor thereof is niacinamide.
58.2 The method of embodiment 58.1, wherein the CBD and niacinamide are at a molar ratio between 2:1 to 10:1.
58.3 The method of embodiment 58.1, wherein the CBD and niacinamide are at a molar ratio between 3:1 to 10:1.
58.4 The method of embodiment 58.1, wherein the CBD and niacinamide are at a molar ratio between 1:10 to 1:55.
58.5 The method of embodiment 58.1, wherein the CBD and niacinamide are at a molar ratio of 1:10 to 1:15.
58.6 The method of any one of embodiments 58.1-58.3, wherein the CBD and urolithin are at a molar ratio of 1:10 to 10:1.
58.7 The method of any one of embodiments 58.1-58.3, wherein the CBD and urolithin are at a molar ratio of 1:3 to 10:1.
59. The method of any one of embodiments 40-58, wherein the cannabinoid is CBD, the cofactor or precursor thereof is niacinamide, and the antioxidant is L-ergothioneine.
59.1 The composition of embodiment 59, wherein the CBD and niacinamide are at a molar ratio between 2:1 to 10:1.
59.2 The composition of embodiment 59, wherein the CBD and niacinamide are at a molar ratio between 3:1 to 10:1.
59.3 The composition of embodiment 59, wherein the CBD and niacinamide are at a molar ratio between 1:10 to 1:55.
59.4 The composition of embodiment 59, wherein the CBD and niacinamide are at a molar ratio of 1:10 to 1:15.
59.5 The method of any one of embodiments 59-58.2, wherein the CBD and urolithin are at a molar ratio of 1:10 to 10:1.
59.6 The method of any one of embodiments 59-59.2, wherein the CBD and urolithin are at a molar ratio of 1:3 to 10:1.
60. The method of any one of embodiments 40-58, wherein the cannabinoid is THC, the cofactor or precursor thereof is niacinamide, and the antioxidant is L-ergothioneine.
61. The method of any one of embodiments 40-58, wherein the cannabinoid is CBD and THC, the cofactor or precursor thereof is niacinamide, and the antioxidant is L-ergothioneine.
62. The method of any one of embodiments 40-58, wherein the cannabinoid is CBD, the cofactor or precursor thereof is niacinamide, the antioxidant is L-ergothioneine, and the mitophagy stimulant is present and is urolithin A.
63. The method of any one of embodiments 40-58, wherein the cannabinoid is THC, the cofactor or precursor thereof is niacinamide, the antioxidant is L-ergothioneine, and the mitophagy stimulant is present and is urolithin A.
64. The method of any one of embodiments 40-58, wherein the cannabinoid is CBD and THC, the cofactor or precursor thereof is niacinamide, the antioxidant is L-ergothioneine, and the mitophagy stimulant is present and is urolithin A.
65. The method of any one of embodiments 40-58 and 59.3-59.4, comprising about 0.01 milligrams (mg) to about 10 mg of cannabinoid, about 0.5 mg to about 50 mg cofactor or precursor thereof, and about 0.1 mg and 100 mg antioxidant per milliliter of composition.
66. The method of embodiment 65, wherein the cannabinoid is CBD, the cofactor or precursor thereof is niacinamide, and the antioxidant is L-ergothioneine.
67. The method of embodiment 65, wherein the cannabinoid is CBD, the cofactor or precursor thereof is niacinamide, the antioxidant is L-ergothioneine, and the mitophagy stimulant is present and is urolithin A.
68. The method of any one of embodiments 40-58 and 59.3-59.4, comprising about 0.42 mg cannabinoid, about 10 mg cofactor or precursor thereof, and about 1 mg antioxidant per milliliter of composition.
69. The method of embodiment 68, wherein the cannabinoid is CBD, the cofactor or precursor thereof is niacinamide, and the antioxidant is L-ergothioneine.
70. The method of embodiment 68, wherein the cannabinoid is CBD, the cofactor or precursor thereof is niacinamide, the antioxidant is L-ergothioneine, and the mitophagy stimulant is present and is urolithin A.
71. The method of any one of embodiments 40-58 and 59.3-59.4, comprising about 2.3 mg cannabinoid, about 20 mg cofactor or precursor thereof, and about 1 mg antioxidant per milliliter of composition.
72. The method of embodiment 71, wherein the cannabinoid is CBD, the cofactor or precursor thereof is niacinamide, and the antioxidant is L-ergothioneine.
73. The method of embodiment 71, wherein the cannabinoid is CBD, the cofactor or precursor thereof is niacinamide, the antioxidant is L-ergothioneine, and the mitophagy stimulant is present and is urolithin A.
74. The method of any one of embodiments 40-58 and 59.3-59.4, comprising about 6.8 mg cannabinoid, about 30 mg cofactor or precursor thereof, and about 10 mg antioxidant per milliliter of composition.
75. The method of embodiment 74, wherein the cannabinoid is CBD, the cofactor or precursor thereof is niacinamide, and the antioxidant is L-ergothioneine.
76. The method of embodiment 74, wherein the cannabinoid is CBD, the cofactor or precursor thereof is niacinamide, the antioxidant is L-ergothioneine, and the mitophagy stimulant is present and is urolithin A.
77. The method of any one of embodiments 40-58 and 59.3-59.4, comprising about 4 mg cannabinoid, about 2 mg cofactor or precursor thereof, and about 10 mg antioxidant per milliliter of composition.
78. The method of embodiment 77, wherein the cannabinoid is CBD, the cofactor or precursor thereof is niacinamide, and the antioxidant is L-ergothioneine.
79. The method of embodiment 77, wherein the cannabinoid is CBD, the cofactor or precursor thereof is niacinamide, the antioxidant is L-ergothioneine, and the mitophagy stimulant is present and is urolithin A.
80. The method of any one of embodiments 40-79, wherein the composition comprises an additional ingredient selected from the group consisting of an avenanthramide, lilac stem cells, and salicylic acid.

81. The method of any one of embodiments 40-80, comprising applying the composition to skin of a patient.
82. The method of any one of embodiments 40-81, comprising applying the composition to acne.
83. The composition of any one of embodiments 1-39, wherein the composition is incorporated into a product selected from the group consisting of an acne cleanser, an acne toner, an acne spot treatment, an acne day/night moisturizer, and a sunscreen.
84. A composition comprising all the ingredients of Formulation K.
85. A composition comprising all the ingredients of Formulation L.
86. A composition comprising all the ingredients of Formulation M.
87. A composition comprising all the ingredients of Formulation N.
88. A composition comprising all the ingredients of Formulation O.
89. A composition comprising all the ingredients of Formulation U.
90. A composition comprising all the ingredients of Formulation V.
91. A composition comprising all the ingredients of Formulation W.
92. A composition comprising all the ingredients of Formulation X.
93. A composition comprising all the ingredients of Formulation Y.
94. A composition comprising all the ingredients of Formulation Z.
95. A composition comprising all the ingredients of Formulation AA.
96. A composition comprising all the ingredients of Formulation BB.
97. A composition comprising all the ingredients of Formulation CC.
98. A composition comprising all the ingredients of Formulation DD.
99. A method for increasing ATP metabolism in a cell, comprising exposing a cell to the composition from any one of embodiments 1-39 or 84-98.
100. A method of treating acne, comprising applying to skin of a patient in need thereof, a therapeutically effective amount of the composition from any one of embodiments 1-39 or 84-98.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following Claims define the scope of the disclosure and that methods and structures within the scope of these claims and their equivalents be covered thereby.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:

1. A composition, comprising:
   (a) between 3-30 µM cannabidiol (CBD);
   (b) between 4-40 µM niacinamide; and
   (c) between 30-100 µM urolithin A.
2. The composition of claim 1, further comprising an antioxidant.
3. A method for increasing ATP metabolism in a cell comprising applying the composition of claim 1 to skin of a patient.
4. The composition of claim 2, wherein the antioxidant is L-ergothioneine.
5. The method of claim 3, wherein the skin of the patient exhibits acne.

* * * * *